US012617778B2

(12) United States Patent
Lee et al.

(10) Patent No.: US 12,617,778 B2
(45) Date of Patent: May 5, 2026

(54) HETEROCYCLIC COMPOUND, ORGANIC LIGHT-EMITTING ELEMENT COMPRISING SAME, COMPOSITION FOR ORGANIC LAYER OF ORGANIC LIGHT-EMITTING ELEMENT, AND METHOD FOR PRODUCING ORGANIC LIGHT-EMITTING ELEMENT

(71) Applicant: LT MATERIALS CO., LTD., Yongin-si (KR)

(72) Inventors: Yong-Hui Lee, Yongin-si (KR); Jun-Tae Mo, Yongin-si (KR); Dong-Jun Kim, Yongin-si (KR)

(73) Assignee: LT MATERIALS CO., LTD., Yongin-si (KR)

( * ) Notice: Subject to any disclaimer, the term of this patent is extended or adjusted under 35 U.S.C. 154(b) by 1011 days.

(21) Appl. No.: 17/774,352

(22) PCT Filed: Dec. 21, 2020

(86) PCT No.: PCT/KR2020/018832
§ 371 (c)(1),
(2) Date: May 4, 2022

(87) PCT Pub. No.: WO2021/133016
PCT Pub. Date: Jul. 1, 2021

(65) Prior Publication Data

US 2022/0411411 A1 Dec. 29, 2022

(30) Foreign Application Priority Data

Dec. 26, 2019 (KR) ........................ 10-2019-0174983

(51) Int. Cl.

| | |
|---|---|
| ***H01L 51/54*** | (2006.01) |
| ***C07D 405/04*** | (2006.01) |
| ***C07D 405/14*** | (2006.01) |
| ***C07D 409/14*** | (2006.01) |
| ***C07D 487/04*** | (2006.01) |
| ***C07D 491/048*** | (2006.01) |
| ***C07D 493/04*** | (2006.01) |
| ***C07D 495/04*** | (2006.01) |
| ***H10K 71/16*** | (2023.01) |
| ***H10K 85/60*** | (2023.01) |
| *H10K 71/00* | (2023.01) |

(52) U.S. Cl.
CPC ......... *C07D 405/14* (2013.01); *C07D 405/04* (2013.01); *C07D 409/14* (2013.01); *C07D 487/04* (2013.01); *C07D 491/048* (2013.01); *C07D 493/04* (2013.01); *C07D 495/04* (2013.01); *H10K 71/164* (2023.02); *H10K 85/631* (2023.02); *H10K 85/654* (2023.02); *H10K 85/657* (2023.02); *H10K 85/6572* (2023.02); *H10K 85/6574* (2023.02); *H10K 85/6576* (2023.02); *H10K 71/00* (2023.02)

(58) Field of Classification Search
None
See application file for complete search history.

(56) References Cited

U.S. PATENT DOCUMENTS

| | | | | |
|---|---|---|---|---|
| 2012/0138914 | A1* | 6/2012 | Kawamura .......... | C07D 307/79 257/E51.026 |
| 2015/0115239 | A1 | 4/2015 | Pflumm et al. | |
| 2017/0237017 | A1 | 8/2017 | Parham et al. | |
| 2017/0279056 | A1* | 9/2017 | Kim ..................... | H10K 85/654 |
| 2019/0185411 | A1 | 6/2019 | Lee et al. | |
| 2019/0237680 | A1 | 8/2019 | Kim et al. | |
| 2020/0111969 | A1 | 4/2020 | No et al. | |
| 2020/0136058 | A1 | 4/2020 | Kim et al. | |
| 2021/0013411 | A1 | 1/2021 | Mo et al. | |

FOREIGN PATENT DOCUMENTS

| | | | |
|---|---|---|---|
| KR | 10-2018-0109747 | A | 10/2018 |
| KR | 10-2018-0109748 | A | 10/2018 |
| KR | 10-1943428 | B1 | 1/2019 |
| KR | 10-2019-0120985 | A | 10/2019 |
| WO | WO 2013/135352 | A1 | 9/2013 |
| WO | WO 2016/023608 | A1 | 2/2016 |
| WO | WO 2019/212290 | A1 | 11/2019 |

OTHER PUBLICATIONS

Partial Supplementary European Search Report for European Application No. 20908347.6, dated Nov. 9, 2023.
International Search Report for PCT/KR2020/018832 mailed on Jun. 9, 2021.

* cited by examiner

*Primary Examiner* — Andrew K Bohaty
(74) *Attorney, Agent, or Firm* — NKL LAW; Jae Youn Kim

(57) ABSTRACT

The present specification provides a heterocyclic compound represented by Chemical Formula 1, an organic light emitting device comprising the same, a composition for an organic material layer of an organic light emitting device, and a method for manufacturing an organic light emitting device.

11 Claims, 2 Drawing Sheets

【FIG. 1】
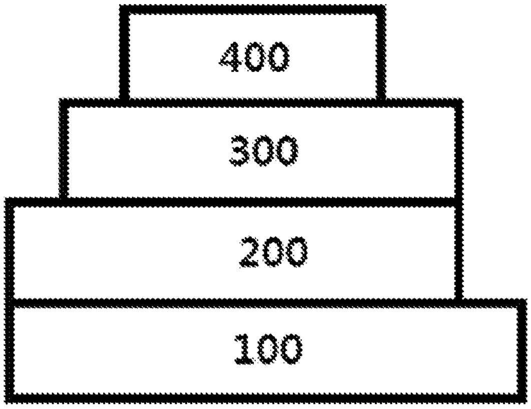
【FIG. 2】
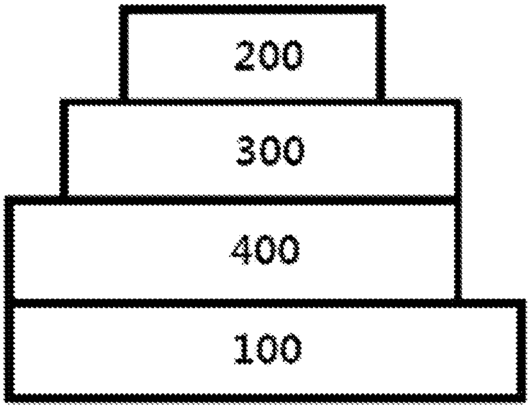

【FIG. 3】
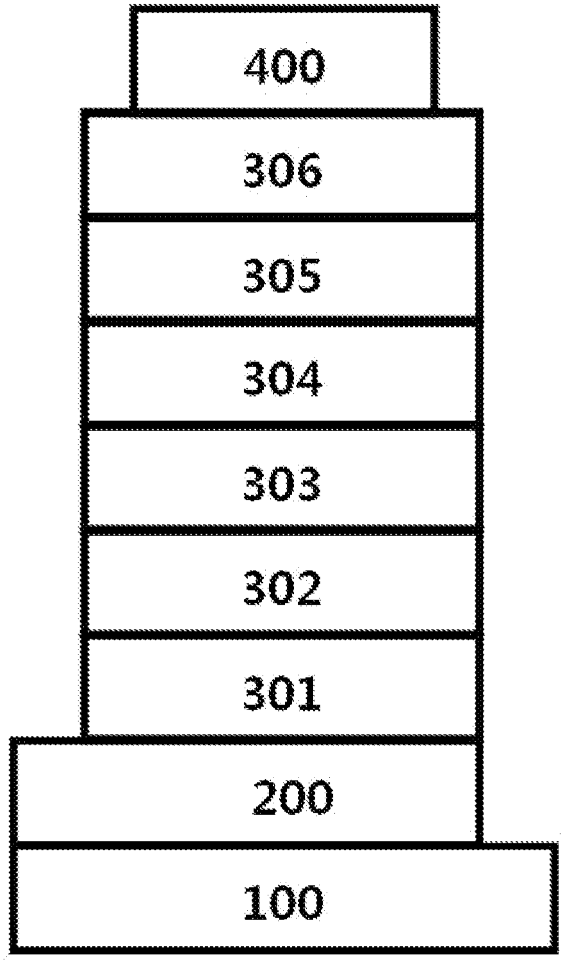

HETEROCYCLIC COMPOUND, ORGANIC LIGHT-EMITTING ELEMENT COMPRISING SAME, COMPOSITION FOR ORGANIC LAYER OF ORGANIC LIGHT-EMITTING ELEMENT, AND METHOD FOR PRODUCING ORGANIC LIGHT-EMITTING ELEMENT

TECHNICAL FIELD

This application claims priority to and the benefits of Korean Patent Application No. 10-2019-0174983, filed with the Korean Intellectual Property Office on Dec. 26, 2019, the entire contents of which are incorporated herein by reference.

The present specification relates to a heterocyclic compound, an organic light emitting device comprising the same, a composition for an organic material layer of an organic light emitting device, and a method for manufacturing an organic light emitting device.

BACKGROUND ART

An organic electroluminescent device is one type of self-emissive display devices, and has an advantage of having a wide viewing angle, and a high response speed as well as having an excellent contrast.

An organic light emitting device has a structure disposing an organic thin film between two electrodes. When a voltage is applied to an organic light emitting device having such a structure, electrons and holes injected from the two electrodes bind and pair in the organic thin film, and light emits as these annihilate. The organic thin film may be formed in a single layer or a multilayer as necessary.

A material of the organic thin film may have a light emitting function as necessary. For example, as a material of the organic thin film, compounds capable of forming a light emitting layer themselves alone may be used, or compounds capable of performing a role of a host or a dopant of a host-dopant-based light emitting layer may also be used. In addition thereto, compounds capable of performing roles of hole injection, hole transfer, electron blocking, hole blocking, electron transfer, electron injection and the like may also be used as a material of the organic thin film.

Development of an organic thin film material has been continuously required for enhancing performance, lifetime or efficiency of an organic light emitting device.

Studies on an organic light emitting device comprising a compound capable of satisfying conditions required for materials usable in an organic light emitting device, for example, satisfying proper energy level, electrochemical stability, thermal stability and the like, and having a chemical structure capable of performing various roles required in an organic light emitting device depending on substituents have been required.

PRIOR ART DOCUMENTS

Patent Documents

U.S. Pat. No. 4,356,429

DISCLOSURE

Technical Problem

The present application relates to a heterocyclic compound, an organic light emitting device comprising the same, a composition for an organic material layer of an organic light emitting device, and a method for manufacturing an organic light emitting device.

Technical Solution

One embodiment of the present application provides a heterocyclic compound represented by the following Chemical Formula 1.

[Chemical Formula 1]

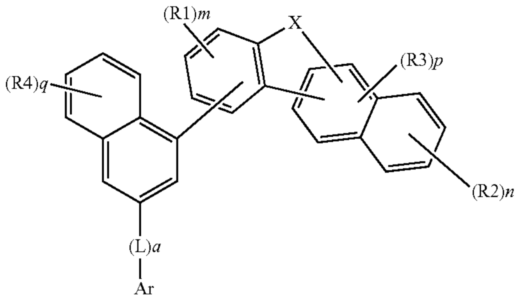

In Chemical Formula 1,

X is O; or S,

L is a direct bond; a substituted or unsubstituted C6 to C60 arylene group; or a substituted or unsubstituted C2 to C60 heteroarylene group, R1 to R4 are the same as or different from each other, and each independently selected from the group consisting of hydrogen; deuterium; halogen; a cyano group; a substituted or unsubstituted C1 to C60 alkyl group; a substituted or unsubstituted C2 to C60 alkenyl group; a substituted or unsubstituted C2 to C60 alkynyl group; a substituted or unsubstituted C1 to C60 alkoxy group; a substituted or unsubstituted C3 to C60 cycloalkyl group; a substituted or unsubstituted C2 to C60 heterocycloalkyl group; a substituted or unsubstituted C6 to C60 aryl group; a substituted or unsubstituted C2 to C60 heteroaryl group; —P(=O)RR'; —SiRR'R" and —NRR', or two or more groups adjacent to each other bond to each other to form a substituted or unsubstituted C6 to C60 aliphatic or aromatic hydrocarbon ring or a substituted or unsubstituted C2 to C60 aliphatic or aromatic heteroring, q and n are the same as or different from each other, and are each an integer of 0 to 4, m is an integer of 0 to 3, p is an integer of 0 to 2, a is an integer of 0 to 4, and Ar is represented by any one of the following Chemical Formula 1-1 to Chemical Formula 1-6,

[Chemical Formula 1-1]

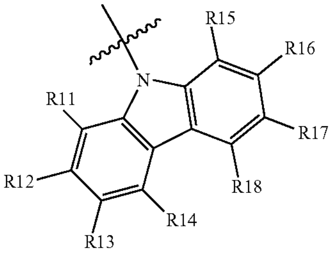

-continued

[Chemical Formula 1-2]

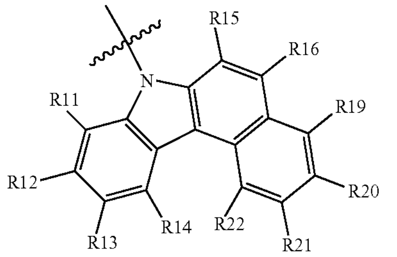

[Chemical Formula 1-3]

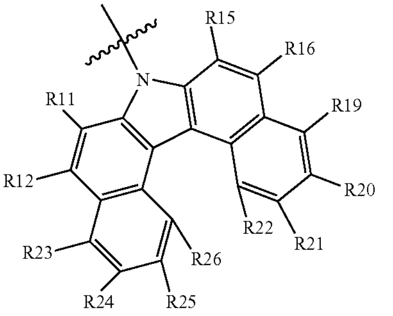

[Chemical Formula 1-4]

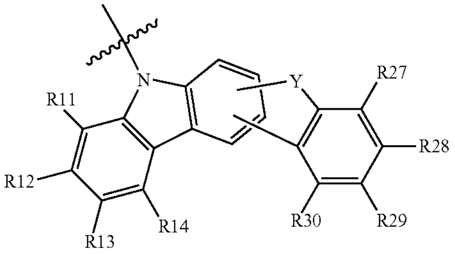

[Chemical Formula 1-5]

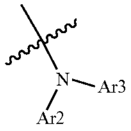

[Chemical Formula 1-6]

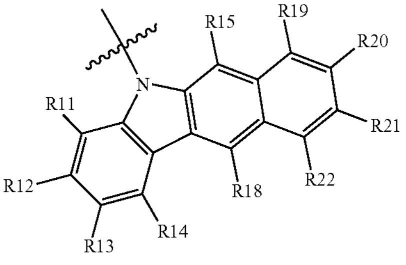

in Chemical Formulae 1-1 to 1-6,

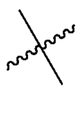

means a position linked to L of Chemical Formula 1,

R11 to R30 are the same as or different from each other, and each independently selected from the group consisting of hydrogen; deuterium; a substituted or unsubstituted C1 to C60 alkyl group; a substituted or unsubstituted C6 to C60 aryl group; a substituted or unsubstituted C2 to C60 heteroaryl group; —P(═O)RR'; —SiRR'R" and —NRR', Ar2 and Ar3 are the same as or different from each other, and each independently a substituted or unsubstituted C6 to C60 aryl group; or a substituted or unsubstituted C2 to C60 heteroaryl group, Y is O; S; NRa; or CRbRc, and R, R', R" and Ra to Rc are the same as or different from each other, and each independently a substituted or unsubstituted C1 to C60 alkyl group; a substituted or unsubstituted C6 to C60 aryl group; or a substituted or unsubstituted C2 to C60 heteroaryl group.

In addition, one embodiment of the present application provides an organic light emitting device comprising a first electrode; a second electrode provided opposite to the first electrode; and one or more organic material layers provided between the first electrode and the second electrode, wherein one or more layers of the organic material layers comprise the heterocyclic compound represented by Chemical Formula 1.

In the organic light emitting device provided in one embodiment of the present application, the organic material layer comprising the heterocyclic compound of Chemical Formula 1 further comprises a heterocyclic compound represented by the following Chemical Formula 7.

[Chemical Formula 7]

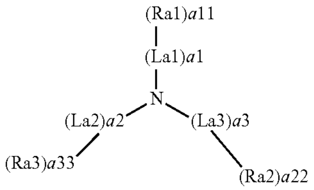

In Chemical Formula 7,

La1 to La3 are the same as or different from each other, and each independently a direct bond; a substituted or unsubstituted C6 to C60 arylene group; or a substituted or unsubstituted C2 to C60 heteroarylene group, Ra1 is a substituted or unsubstituted C6 to C60 aryl group, Ra2 and Ra3 are the same as or different from each other, and each independently selected from the group consisting of hydrogen; deuterium; halogen; a cyano group; a substituted or unsubstituted C1 to C60 alkyl group; a substituted or unsubstituted C2 to C60 alkenyl group; a substituted or unsubstituted C2 to C60 alkynyl group; a substituted or unsubstituted C1 to C60 alkoxy group; a substituted or unsubstituted C3 to C60 cycloalkyl group; a substituted or unsubstituted C2 to C60 heterocycloalkyl group; a substituted or unsubstituted C6 to C60 aryl group; a substituted or unsubstituted C2 to C60 heteroaryl group; and —NRR', or two or more groups adjacent to each other bond to each other to form a substituted or unsubstituted C6 to C60 aliphatic or aromatic hydrocarbon ring or a substituted or unsubstituted C2 to C60 aliphatic or aromatic heteroring, R and R' are the same as or different from each other, and each independently a substituted or unsubstituted C1 to C60 alkyl group; a substituted or unsubstituted C6 to C60 aryl group; or a substituted or unsubstituted C2 to C60 heteroaryl group, a1 to a3 are an integer of 0 to 4, a11, a22 and a33 are an integer of 1 to 6, and when a1 to a3, a11, a22 and a33 are 2 or greater, substituents in the parentheses are the same as or different from each other.

In addition, another embodiment of the present application provides a composition for an organic material layer of an organic light emitting device, the composition comprising the heterocyclic compound represented by Chemical Formula 1 and the heterocyclic compound represented by Chemical Formula 7.

Lastly, one embodiment of the present application provides a method for manufacturing an organic light emitting device, the method comprising preparing a substrate; forming a first electrode on the substrate; forming one or more organic material layers on the first electrode; and forming a second electrode on the organic material layer, wherein the forming of organic material layers comprises forming one or more organic material layers using the composition for an organic material layer according to one embodiment of the present application.

Advantageous Effects

A compound described in the present specification can be used as a material of an organic material layer of an organic light emitting device. In the organic light emitting device, the compound is capable of performing a role of a hole injection material, a hole transfer material, a light emitting material, an electron transfer material, an electron injection material or the like. Particularly, the compound can be used as a light emitting material of the organic light emitting device. For example, the compound can be used alone as a light emitting material, or two of the compounds can be used together as a light emitting material, and can be used as a host material of a light emitting layer.

Particularly, the heterocyclic compound of Chemical Formula 1 according to one embodiment of the present application has the molecular weight readily controlled, has properties of enhancing thermal stability when included in an organic light emitting device later by having enhanced thermal stability when having a substituent, and has properties of lowering a driving voltage and enhancing light emission efficiency when included in an organic light emitting device later by readily controlling an energy level through expansion of conjugation.

DESCRIPTION OF DRAWINGS

FIG. 1 to FIG. 3 are diagrams each schematically illustrating a lamination structure of an organic light emitting device according to one embodiment of the present application.

REFERENCE NUMERAL

100: Substrate
200: Anode
300: Organic Material Layer
301: Hole Injection Layer
302: Hole Transfer Layer
303: Light Emitting Layer
304: Hole Blocking Layer
305: Electron Transfer Layer
306: Electron Injection Layer
400: Cathode

MODE FOR DISCLOSURE

Hereinafter, the present application will be described in detail.

In the present specification, a "case of a substituent being not indicated in a chemical formula or compound structure" means that a hydrogen atom bonds to a carbon atom. However, since deuterium ($^2H$) is an isotope of hydrogen, some hydrogen atoms may be deuterium.

In one embodiment of the present application, a "case of a substituent being not indicated in a chemical formula or compound structure" may mean that positions that may come as a substituent may all be hydrogen or deuterium. In other words, since deuterium is an isotope of hydrogen, some hydrogen atoms may be deuterium that is an isotope, and herein, a content of the deuterium may be from 0% to 100%.

In one embodiment of the present application, in a "case of a substituent being not indicated in a chemical formula or compound structure", hydrogen and deuterium may be mixed in compounds when deuterium is not explicitly excluded such as a deuterium content being 0% or a hydrogen content being 100%. In other words, an expression of "substituent X is hydrogen" does not exclude deuterium such as a hydrogen content being 100% or a deuterium content being 0%, and therefore, may mean a state in which hydrogen and deuterium are mixed.

In one embodiment of the present application, deuterium is one of isotopes of hydrogen, is an element having deuteron formed with one proton and one neutron as a nucleus, and may be expressed as hydrogen-2, and the elemental symbol may also be written as D or 2H.

In one embodiment of the present application, an isotope means an atom with the same atomic number (Z) but with a different mass number (A), and may also be interpreted as an element with the same number of protons but with a different number of neutrons.

In one embodiment of the present application, a meaning of a content T % of a specific substituent may be defined as T2/T1×100=T % when the total number of substituents that a basic compound may have is defined as T1, and the number of specific substituents among these is defined as T2.

In other words, in one example, having a deuterium content of 20% in a phenyl group represented by

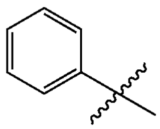 [SMILES: *c1ccccc1]

means that the total number of substituents that the phenyl group may have is 5 (T1 in the formula), and the number of deuterium among these is 1 (T2 in the formula). In other words, having a deuterium content of 20% in a phenyl group may be represented by the following structural formulae.

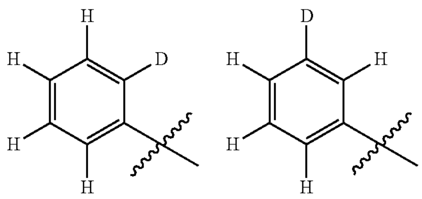

-continued

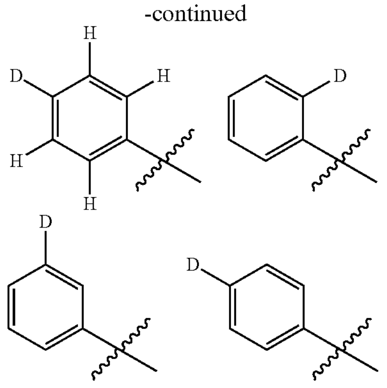

In addition, in one embodiment of the present application, "a phenyl group having a deuterium content of 0%" may mean a phenyl group that does not comprise a deuterium atom, that is, a phenyl group that has 5 hydrogen atoms.

In the present specification, a substituted or unsubstituted amine group may be represented by —NRR', and herein, the substituent may be R and R'.

In the present specification, the halogen may be fluorine, chlorine, bromine or iodine.

In the present specification, the alkyl group comprises linear or branched having 1 to 60 carbon atoms, and may be further substituted with other substituents. The number of carbon atoms of the alkyl group may be from 1 to 60, specifically from 1 to 40 and more specifically from 1 to 20. Specific examples thereof may comprise a methyl group, an ethyl group, a propyl group, an n-propyl group, an isopropyl group, a butyl group, an n-butyl group, an isobutyl group, a tert-butyl group, a sec-butyl group, a 1-methyl-butyl group, a 1-ethylbutyl group, a pentyl group, an n-pentyl group, an isopentyl group, a neopentyl group, a tert-pentyl group, a hexyl group, an n-hexyl group, a 1-methylpentyl group, a 2-methylpentyl group, a 4-methyl-2-pentyl group, a 3,3-dimethylbutyl group, a 2-ethylbutyl group, a heptyl group, an n-heptyl group, a 1-methylhexyl group, a cyclopentylmethyl group, a cyclohexylmethyl group, an octyl group, an n-octyl group, a tert-octyl group, a 1-methylheptyl group, a 2-ethylhexyl group, a 2-propylpentyl group, an n-nonyl group, a 2,2-dimethylheptyl group, a 1-ethyl-propyl group, a 1,1-dimethyl-propyl group, an isohexyl group, a 2-methylpentyl group, a 4-methylhexyl group, a 5-methylhexyl group and the like, but are not limited thereto.

In the present specification, the alkenyl group comprises linear or branched having 2 to 60 carbon atoms, and may be further substituted with other substituents. The number of carbon atoms of the alkenyl group may be from 2 to 60, specifically from 2 to 40 and more specifically from 2 to 20. Specific examples thereof may comprise a vinyl group, a 1-propenyl group, an isopropenyl group, a 1-butenyl group, a 2-butenyl group, a 3-butenyl group, a 1-pentenyl group, a 2-pentenyl group, a 3-pentenyl group, a 3-methyl-1-butenyl group, a 1,3-butadienyl group, an allyl group, a 1-phenylvinyl-1-yl group, a 2-phenylvinyl-1-yl group, a 2,2-diphenylvinyl-1-yl group, a 2-phenyl-2-(naphthyl-1-yl)vinyl-1-yl group, a 2,2-bis(diphenyl-1-yl)vinyl-1-yl group, a stilbenyl group, a styrenyl group and the like, but are not limited thereto.

In the present specification, the alkynyl group comprises linear or branched having 2 to 60 carbon atoms, and may be further substituted with other substituents. The number of carbon atoms of the alkynyl group may be from 2 to 60, specifically from 2 to 40 and more specifically from 2 to 20.

In the present specification, the alkoxy group may be linear, branched or cyclic. The number of carbon atoms of the alkoxy group is not particularly limited, but is preferably from 1 to 20. Specific examples thereof may comprise methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy and the like, but are not limited thereto.

In the present specification, the cycloalkyl group comprises monocyclic or polycyclic having 3 to 60 carbon atoms, and may be further substituted with other substituents. Herein, the polycyclic means a group in which the cycloalkyl group is directly linked to or fused with other cyclic groups. Herein, the other cyclic groups may be a cycloalkyl group, but may also be different types of cyclic groups such as a heterocycloalkyl group, an aryl group and a heteroaryl group. The number of carbon groups of the cycloalkyl group may be from 3 to 60, specifically from 3 to 40 and more specifically from 5 to 20. Specific examples thereof may comprise a cyclopropyl group, a cyclobutyl group, a cyclopentyl group, a 3-methylcyclopentyl group, a 2,3-dimethylcyclopentyl group, a cyclohexyl group, a 3-methylcyclohexyl group, a 4-methylcyclohexyl group, a 2,3-dimethylcyclohexyl group, a 3,4,5-trimethylcyclohexyl group, a 4-tert-butylcyclohexyl group, a cycloheptyl group, a cyclooctyl group and the like, but are not limited thereto.

In the present specification, the heterocycloalkyl group comprises O, S, Se, N or Si as a heteroatom, comprises monocyclic or polycyclic having 2 to 60 carbon atoms, and may be further substituted with other substituents. Herein, the polycyclic means a group in which the heterocycloalkyl group is directly linked to or fused with other cyclic groups. Herein, the other cyclic groups may be a heterocycloalkyl group, but may also be different types of cyclic groups such as a cycloalkyl group, an aryl group and a heteroaryl group. The number of carbon atoms of the heterocycloalkyl group may be from 2 to 60, specifically from 2 to 40 and more specifically from 3 to 20.

In the present specification, the aryl group comprises monocyclic or polycyclic having 6 to 60 carbon atoms, and may be further substituted with other substituents. Herein, the polycyclic means a group in which the aryl group is directly linked to or fused with other cyclic groups. Herein, the other cyclic groups may be an aryl group, but may also be different types of cyclic groups such as a cycloalkyl group, a heterocycloalkyl group and a heteroaryl group. The number of carbon atoms of the aryl group may be from 6 to 60, specifically from 6 to 40 and more specifically from 6 to 25. Specific examples of the aryl group may comprise a phenyl group, a biphenyl group, a triphenyl group, a naphthyl group, an anthryl group, a chrysenyl group, a phenanthrenyl group, a perylenyl group, a fluoranthenyl group, a triphenylenyl group, a phenalenyl group, a pyrenyl group, a tetracenyl group, a pentacenyl group, an indenyl group, an acenaphthylenyl group, a 2,3-dihydro-1H-indenyl group, a fused ring group thereof, and the like, but are not limited thereto.

In the present specification, a fluorenyl group may be substituted, and adjacent substituents may bond to each other to form a ring.

When the fluorenyl group is substituted, the following structural formulae and the like may be included, however, the structure is not limited thereto.

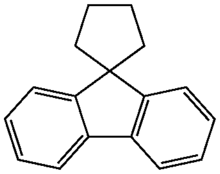,

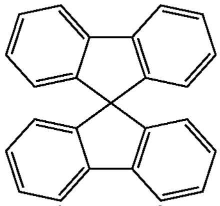,

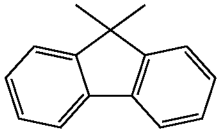,

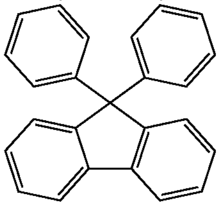,

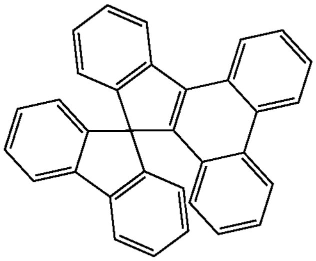,

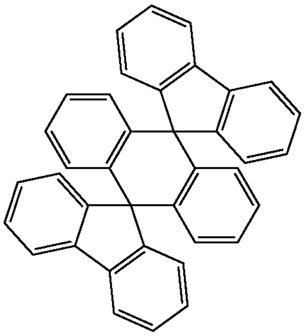

In the present specification, the heteroaryl group comprises S, O, Se, N or Si as a heteroatom, comprises monocyclic or polycyclic having 2 to 60 carbon atoms, and may be further substituted with other substituents. Herein, the polycyclic means a group in which the heteroaryl group is directly linked to or fused with other cyclic groups. Herein, the other cyclic groups may be a heteroaryl group, but may also be different types of cyclic groups such as a cycloalkyl group, a heterocycloalkyl group and an aryl group. The number of carbon atoms of the heteroaryl group may be from 2 to 60, specifically from 2 to 40 and more specifically from 3 to 25. Specific examples of the heteroaryl group may comprise a pyridyl group, a pyrrolyl group, a pyrimidyl group, a pyridazinyl group, a furanyl group, a thiophene group, an imidazolyl group, a pyrazolyl group, an oxazolyl group, an isoxazolyl group, a thiazolyl group, an isothiazolyl group, a triazolyl group, a furazanyl group, an oxadiazolyl group, a thiadiazolyl group, a dithiazolyl group, a tetrazolyl group, a pyranyl group, a thiopyranyl group, a diazinyl group, an oxazinyl group, a thiazinyl group, a dioxynyl group, a triazinyl group, a tetrazinyl group, a quinolyl group, an isoquinolyl group, a quinazolinyl group, an isoquinazolinyl group, a quinazolinyl group, a naphthyridyl group, an acridinyl group, a phenanthridinyl group, an imidazopyridinyl group, a diazanaphthalenyl group, a triazaindene group, an indolyl group, an indolizinyl group, a benzothiazolyl group, a benzoxazolyl group, a benzimidazolyl group, a benzothiophene group, a benzofuran group, a dibenzothiophene group, a dibenzofuran group, a carbazolyl group, a benzocarbazolyl group, a dibenzocarbazolyl group, a phenazinyl group, a dibenzosilole group, spirobi(dibenzosilole), a dihydrophenazinyl group, a phenoxazinyl group, a phenanthridyl group, an imidazopyridinyl group, a thienyl group, an indolo[2,3-a]carbazolyl group, an indolo[2,3-b]carbazolyl group, an indolinyl group, a 10,11-dihydrodibenzo[b,f]azepine group, a 9,10-dihydroacridinyl group, a phenanthrazinyl group, a phenothiathiazinyl group, a phthalazinyl group, a naphthylidinyl group, a phenanthrolinyl group, a benzo[c][1,2,5]thiadiazolyl group, a 5,10-dihydrobenzo[b,e][1,4]azasilinyl group, a pyrazolo[1,5-c]quinazolinyl group, a pyrido[1,2-b]indazolyl group, a pyrido[1,2-a]imidazo[1,2-e]indolinyl group, a 5,11-dihydroindeno[1,2-b]carbazolyl group and the like, but are not limited thereto.

In the present specification, the amine group may be selected from the group consisting of a monoalkylamine group; a monoarylamine group; a monoheteroarylamine group; —$NH_2$; a dialkylamine group; a diarylamine group; a diheteroarylamine group; an alkylarylamine group; an alkylheteroarylamine group; and an arylheteroarylamine group, and although not particularly limited thereto, the number of carbon atoms is preferably from 1 to 30. Specific examples of the amine group may comprise a methylamine group, a dimethylamine group, an ethylamine group, a diethylamine group, a phenylamine group, a naphthylamine group, a biphenylamine group, a dibiphenylamine group, an anthracenylamine group, a 9-methyl-anthracenylamine group, a diphenylamine group, a phenylnaphthylamine group, a ditolylamine group, a phenyltolylamine group, a triphenylamine group, a biphenylnaphthylamine group, a phenylbiphenylamine group, a biphenylfluorenylamine group, a phenyltriphenylenylamine group, a biphenyltriphenylenylamine group and the like, but are not limited thereto.

In the present specification, the arylene group means the aryl group having two bonding sites, that is, a divalent group. The descriptions on the aryl group provided above may be applied thereto except for those that are each a divalent group. In addition, the heteroarylene group means the heteroaryl group having two bonding sites, that is, a divalent group. The descriptions on the heteroaryl group provided above may be applied thereto except for those that are each a divalent group.

In the present specification, the phosphine oxide group is represented by —P(═O)R101R102, and R101 and R102 are the same as or different from each other and may be each independently a substituent formed with at least one of hydrogen; deuterium; a halogen group; an alkyl group; an alkenyl group; an alkoxy group; a cycloalkyl group; an aryl group; and a heterocyclic group. Specific examples of the phosphine oxide may comprise a diphenylphosphine oxide group, a dinaphthylphosphine oxide group and the like, but are not limited thereto.

In the present specification, the silyl group is a substituent comprising Si, having the Si atom directly linked as a radical, and is represented by —SiR104R105R106. R104 to R106 are the same as or different from each other, and may be each independently a substituent formed with at least one of hydrogen; deuterium; a halogen group; an alkyl group; an alkenyl group; an alkoxy group; a cycloalkyl group; an aryl group; and a heterocyclic group. Specific examples of the silyl group may comprise a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but are not limited thereto.

In the present specification, the "adjacent" group may mean a substituent substituting an atom directly linked to an atom substituted by the corresponding substituent, a substituent sterically most closely positioned to the corresponding substituent, or another substituent substituting an atom substituted by the corresponding substituent. For example, two substituents substituting ortho positions in a benzene ring, and two substituents substituting the same carbon in an aliphatic ring may be interpreted as groups "adjacent" to each other.

As the aliphatic or aromatic hydrocarbon ring or heteroring that adjacent groups may form, the structures illustrated as the cycloalkyl group, the cycloheteroalkyl group, the aryl group and the heteroaryl group described above may be used except for those that are not a monovalent group.

In the present specification, the term "substitution" means a hydrogen atom bonding to a carbon atom of a compound being changed to another substituent, and the position of substitution is not limited as long as it is a position at which the hydrogen atom is substituted, that is, a position at which a substituent can substitute, and when two or more substituents substitute, the two or more substituents may be the same as or different from each other.

In the present specification, "substituted or unsubstituted" means being substituted with one or more substituents selected from the group consisting of C1 to C60 linear or branched alkyl; C2 to C60 linear or branched alkenyl; C2 to C60 linear or branched alkynyl; C3 to C60 monocyclic or polycyclic cycloalkyl; C2 to C60 monocyclic or polycyclic heterocycloalkyl; C6 to C60 monocyclic or polycyclic aryl; C2 to C60 monocyclic or polycyclic heteroaryl; —SiRR'R"; —P(=O)RR'; C1 to C20 alkylamine; C6 to C60 monocyclic or polycyclic arylamine; and C2 to C60 monocyclic or polycyclic heteroarylamine, or being unsubstituted, or being substituted with a substituent linking two or more substituents selected from among the substituents illustrated above, or being unsubstituted, and R, R' and R" are the same as or different from each other, and each independently a substituted or unsubstituted C1 to C60 alkyl group; a substituted or unsubstituted C6 to C60 aryl group; or a substituted or unsubstituted C2 to C60 heteroaryl group.

One embodiment of the present application provides a compound represented by Chemical Formula 1.

In one embodiment of the present application, the heterocyclic compound represented by Chemical Formula 1 may have a deuterium content of greater than or equal to 0% and less than or equal to 100%, preferably greater than or equal to 20% and less than or equal to 100%, and more preferably greater than or equal to 40% and less than or equal to 100%.

In one embodiment of the present application, the heterocyclic compound represented by Chemical Formula 1 may have a deuterium content of 0%.

In one embodiment of the present application, the heterocyclic compound represented by Chemical Formula 1 may have a deuterium content of 20% to 60%.

In one embodiment of the present application, the heterocyclic compound represented by Chemical Formula 1 may have a deuterium content of 20% to 80%.

In one embodiment of the present application, the heterocyclic compound represented by Chemical Formula 1 may have a deuterium content of 40% to 80%.

In one embodiment of the present application, Chemical Formula 1 may be represented by the following Chemical Formula 2 or 3.

[Chemical Formula 2]

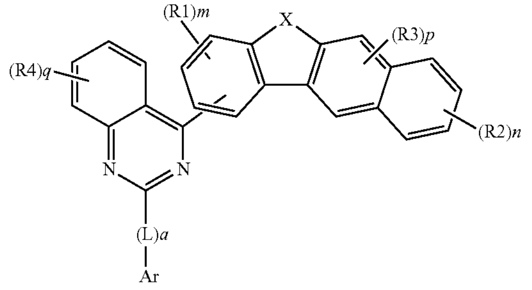

[Chemical Formula 3]

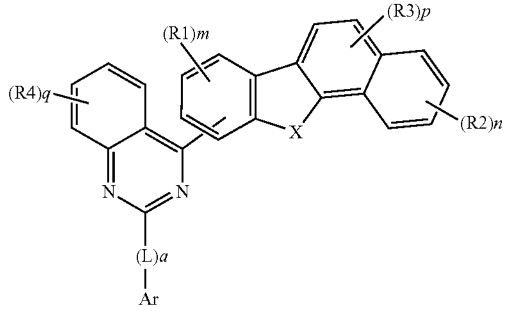

In Chemical Formulae 2 and 3,

R1 to R4, X, Ar, L, m, n, p, q and a have the same definitions as in Chemical Formula 1.

In one embodiment of the present application, Chemical Formula 1 may be represented by the following Chemical Formula 5 or Chemical Formula 6.

[Chemical Formula 5]

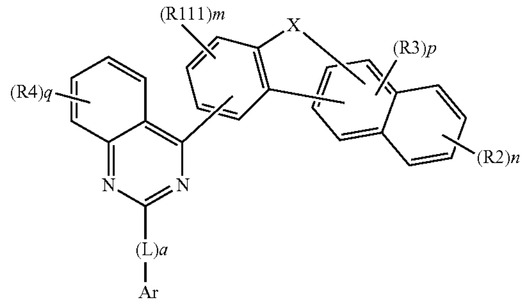

[Chemical Formula 6]

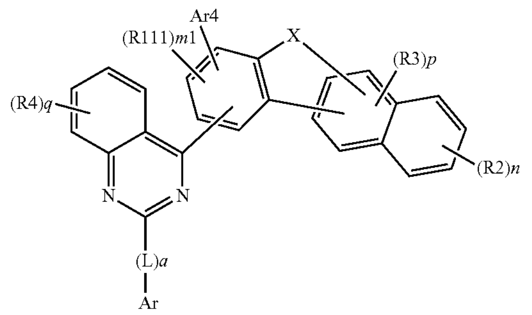

In Chemical Formulae 5 and 6,

R2 to R4, X, Ar, L, m, n, p, q and a have the same definitions as in Chemical Formula 1, R111 is hydrogen; or deuterium, Ar4 is a substituted or unsubstituted C6 to C60 aryl group, and m1 is an integer of 0 to 2, and when m1 is 2, substituents in the parentheses are the same as or different from each other.

In one embodiment of the present application, Chemical Formula 5 may be represented by any one of the following Chemical Formulae 5-1 to 5-4.

[Chemical Formula 5-1]

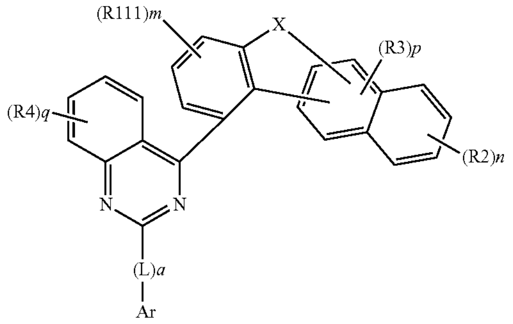

[Chemical Formula 5-2]

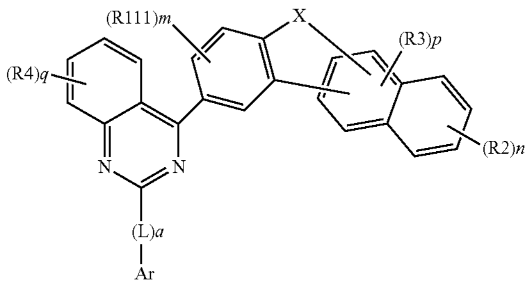

[Chemical Formula 5-3]

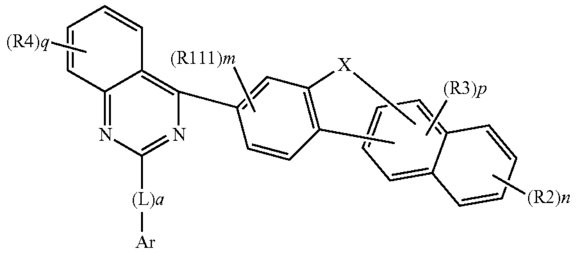

[Chemical Formula 5-4]

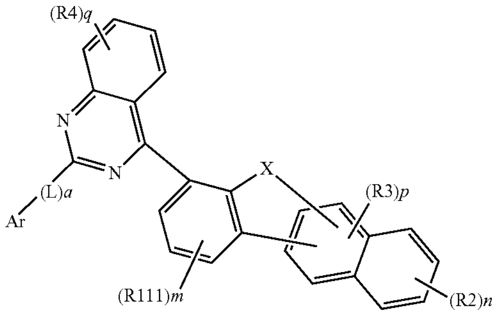

In Chemical Formulae 5-1 to 5-4,

R2 to R4, R111, X, Ar, L, m, n, p, q and a have the same definitions as in Chemical Formula 5.

In one embodiment of the present application, Chemical Formula 6 may be represented by any one of the following Chemical Formulae 6-1 to 6-5.

[Chemical Formula 6-1]

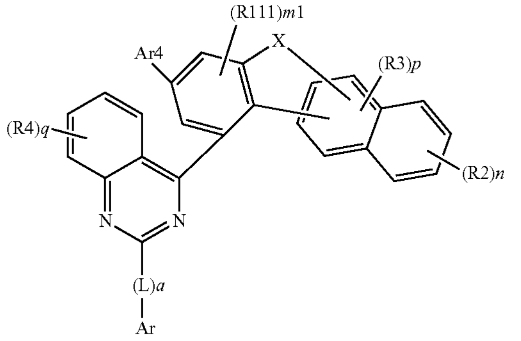

[Chemical Formula 6-2]

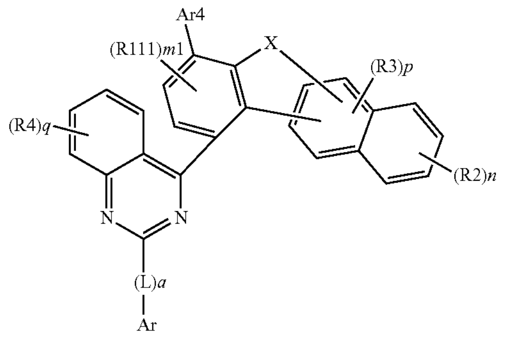

[Chemical Formula 6-3]

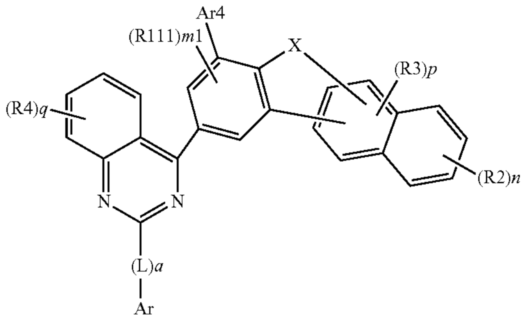

[Chemical Formula 6-4]

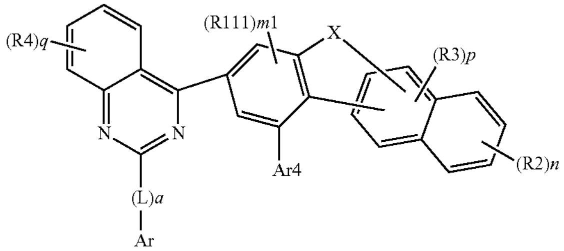

-continued

[Chemical Formula 6-5]

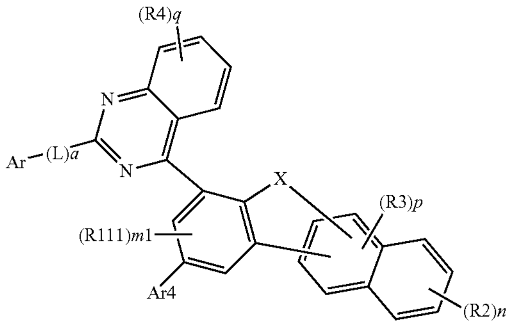

In Chemical Formulae 6-1 to 6-5,

R2 to R4, R111, X, Ar, Ar4, L, m1, n, p, q and a have the same definitions as in Chemical Formula 6.

In one embodiment of the present application, X may be O.

In one embodiment of the present application, X may be S.

In one embodiment of the present application, L may be a direct bond; a substituted or unsubstituted C6 to C60 arylene group; or a substituted or unsubstituted C2 to C60 heteroarylene group.

In another embodiment, L may be a direct bond; a substituted or unsubstituted C6 to C40 arylene group; or a substituted or unsubstituted C2 to C40 heteroarylene group.

In another embodiment, L may be a direct bond; a substituted or unsubstituted C6 to C20 arylene group; or a substituted or unsubstituted C2 to C20 heteroarylene group.

In another embodiment, L may be a direct bond; or a C6 to C20 arylene group.

In another embodiment, L may be a direct bond; or a C6 to C20 monocyclic arylene group.

In another embodiment, L may be a direct bond; or a phenylene group.

In one embodiment of the present application, R1 to R4 are the same as or different from each other, and each independently selected from the group consisting of hydrogen; deuterium; halogen; a cyano group; a substituted or unsubstituted C1 to C60 alkyl group; a substituted or unsubstituted C2 to C60 alkenyl group; a substituted or unsubstituted C2 to C60 alkynyl group; a substituted or unsubstituted C1 to C60 alkoxy group; a substituted or unsubstituted C3 to C60 cycloalkyl group; a substituted or unsubstituted C2 to C60 heterocycloalkyl group; a substituted or unsubstituted C6 to C60 aryl group; a substituted or unsubstituted C2 to C60 heteroaryl group; —P(═O)RR'; —SiRR'R" and —NRR', or two or more groups adjacent to each other may bond to each other to form a substituted or unsubstituted C6 to C60 aliphatic or aromatic hydrocarbon ring or a substituted or unsubstituted C2 to C60 aliphatic or aromatic heteroring.

In another embodiment, R1 to R4 are the same as or different from each other, and may be each independently hydrogen; a substituted or unsubstituted C6 to C60 aryl group; or a substituted or unsubstituted C2 to C60 heteroaryl group.

In another embodiment, R1 to R4 are the same as or different from each other, and may be each independently hydrogen; deuterium; a substituted or unsubstituted C6 to C40 aryl group; or a substituted or unsubstituted C2 to C40 heteroaryl group.

In another embodiment, R1 to R4 are the same as or different from each other, and may be each independently hydrogen; deuterium; a C6 to C40 aryl group; or a C2 to C40 heteroaryl group.

In another embodiment, R1 to R4 are the same as or different from each other, and may be each independently hydrogen; deuterium; or a C6 to C40 monocyclic or polycyclic aryl group.

In another embodiment, R1 to R4 are the same as or different from each other, and may be each independently hydrogen; deuterium; or a C6 to C20 monocyclic aryl group.

In another embodiment, R1 to R4 are the same as or different from each other, and may be each independently hydrogen; deuterium; or a phenyl group.

In one embodiment of the present application, R1 may be hydrogen; deuterium; or a phenyl group.

In one embodiment of the present application, R2 to R4 may be hydrogen; or deuterium.

In one embodiment of the present application, Ar may be represented by any one of the following Chemical Formula 1-1 to Chemical Formula 1-6.

[Chemical Formula 1-1]

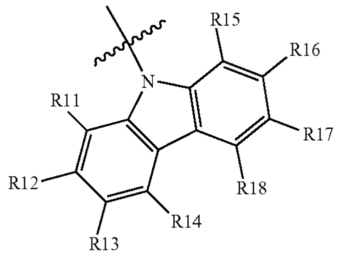

[Chemical Formula 1-2]

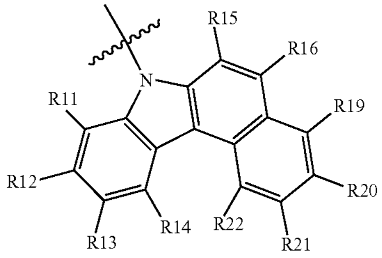

[Chemical Formula 1-3]

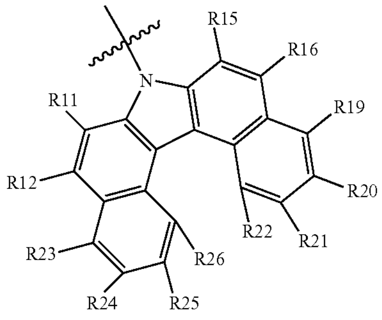

-continued

[Chemical Formula 1-4]

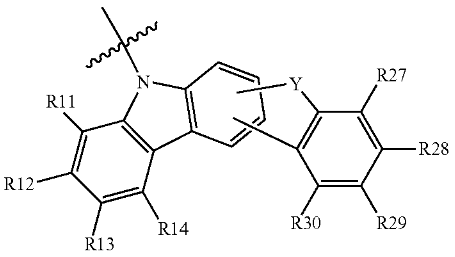

[Chemical Formula 1-5]

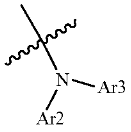

[Chemical Formula 1-6]

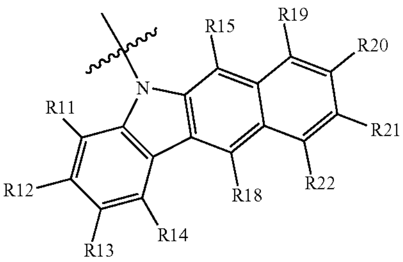

In Chemical Formulae 1-1 to 1-6,

R11 to R30 are the same as or different from each other, and each independently selected from the group consisting of hydrogen; deuterium; a substituted or unsubstituted C1 to C60 alkyl group; a substituted or unsubstituted C6 to C60 aryl group; a substituted or unsubstituted C2 to C60 heteroaryl group; —P(═O)RR'; —SiRR'R" and —NRR', Ar2 and Ar3 are the same as or different from each other, and each independently a substituted or unsubstituted C6 to C60 aryl group; or a substituted or unsubstituted C2 to C60 heteroaryl group, Y is O; S; NRa; or CRbRc, and R, R', R" and Ra to Rc are the same as or different from each other, and each independently a substituted or unsubstituted C1 to C60 alkyl group; a substituted or unsubstituted C6 to C60 aryl group; or a substituted or unsubstituted C2 to C60 heteroaryl group.

In one embodiment of the present application, R11 to R30 are the same as or different from each other, and may be each independently selected from the group consisting of hydrogen; a substituted or unsubstituted C1 to C60 alkyl group; a substituted or unsubstituted C6 to C60 aryl group; a substituted or unsubstituted C2 to C60 heteroaryl group; —P(═O)RR'; —SiRR'R" and —NRR'.

In another embodiment, R11 to R30 are the same as or different from each other, and may be each independently selected from the group consisting of hydrogen; deuterium; a substituted or unsubstituted C6 to C60 aryl group; a substituted or unsubstituted C2 to C60 heteroaryl group; and —NRR'.

In another embodiment, R11 to R30 are the same as or different from each other, and may be each independently selected from the group consisting of hydrogen; deuterium; a substituted or unsubstituted C6 to C40 aryl group; a substituted or unsubstituted C2 to C40 heteroaryl group; and —NRR'.

In another embodiment, R11 to R30 are the same as or different from each other, and may be each independently selected from the group consisting of hydrogen; deuterium; a C6 to C40 aryl group; a C2 to C40 heteroaryl group unsubstituted or substituted with a C6 to C20 aryl group; and an amine group unsubstituted or substituted with one or more substituents selected from the group consisting of a C1 to C20 alkyl group, a C6 to C20 aryl group and a C2 to C20 heteroaryl group.

In another embodiment, R11 to R30 are the same as or different from each other, and may be each independently hydrogen; deuterium; a phenyl group; a biphenyl group; a naphthyl group; a carbazole group unsubstituted or substituted with a phenyl group; a diphenylamine group; a dibenzofuran group; or a dibenzothiophene group.

In one embodiment of the present application, Y may be O.

In one embodiment of the present application, Y may be S.

In one embodiment of the present application, Y may be CRbRc.

In one embodiment of the present application, Y may be NRa.

In one embodiment of the present application, Ra to Rc are the same as or different from each other, and each independently a substituted or unsubstituted C1 to C60 alkyl group; a substituted or unsubstituted C6 to C60 aryl group; or a substituted or unsubstituted C2 to C60 heteroaryl group.

In another embodiment, Ra to Rc are the same as or different from each other, and each independently a substituted or unsubstituted C1 to C60 alkyl group; or a substituted or unsubstituted C6 to C60 aryl group.

In another embodiment, Ra to Rc are the same as or different from each other, and each independently a substituted or unsubstituted C1 to C30 alkyl group; or a substituted or unsubstituted C6 to C30 aryl group.

In another embodiment, Ra to Rc are the same as or different from each other, and each independently a C1 to C30 alkyl group; or a C6 to C30 aryl group.

In another embodiment, Ra to Rc are the same as or different from each other, and each independently a methyl group; or a phenyl group.

In one embodiment of the present application, Ar2 and Ar3 are the same as or different from each other, and may be each independently a substituted or unsubstituted C6 to C60 aryl group; or a substituted or unsubstituted C2 to C60 heteroaryl group.

In another embodiment, Ar2 and Ar3 are the same as or different from each other, and may be each independently a substituted or unsubstituted C6 to C40 aryl group; or a substituted or unsubstituted C2 to C40 heteroaryl group.

In another embodiment, Ar2 and Ar3 are the same as or different from each other, and may be each independently a C6 to C40 aryl group unsubstituted or substituted with a C1 to C20 alkyl group.

In another embodiment, Ar2 and Ar3 are the same as or different from each other, and may be each independently a C6 to C20 aryl group unsubstituted or substituted with a C1 to C20 alkyl group.

In another embodiment, Ar2 and Ar3 are the same as or different from each other, and may be each independently a monocyclic or polycyclic C6 to C20 aryl group unsubstituted or substituted with a C1 to C20 alkyl group.

In another embodiment, Ar2 and Ar3 are the same as or different from each other, and may be each independently a phenyl group; a biphenyl group; a naphthyl group; or a dimethylfluorenyl group.

In one embodiment of the present application, Ar4 has the same definition as R1 of Chemical Formula 1.

In one embodiment of the present application, R, R' and R" are the same as or different from each other, and may be each independently a substituted or unsubstituted C1 to C60 alkyl group; a substituted or unsubstituted C6 to C60 aryl group; or a substituted or unsubstituted C2 to C60 heteroaryl group.

In another embodiment, R, R' and R" are the same as or different from each other, and may be each independently a substituted or unsubstituted C6 to C60 aryl group.

In another embodiment, R, R' and R" are the same as or different from each other, and may be each independently a substituted or unsubstituted C6 to C60 monocyclic or polycyclic aryl group.

In another embodiment, R, R' and R" are the same as or different from each other, and may be each independently a substituted or unsubstituted C6 to C40 monocyclic aryl group.

In another embodiment, R, R' and R" are the same as or different from each other, and may be each independently a C6 to C20 monocyclic aryl group.

In another embodiment, R, R' and R" may be a phenyl group.

In one embodiment of the present application, Chemical Formula 1-4 may be represented by any one of the following structural formulae.

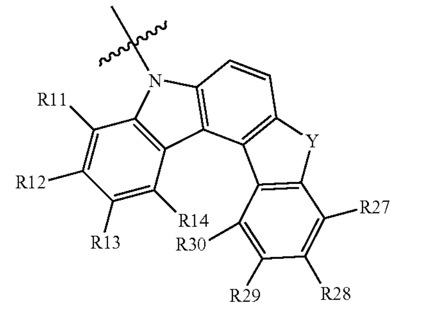

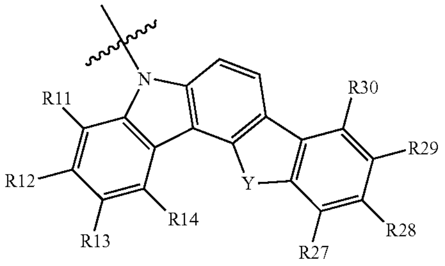

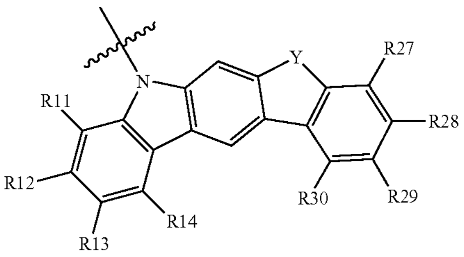

-continued

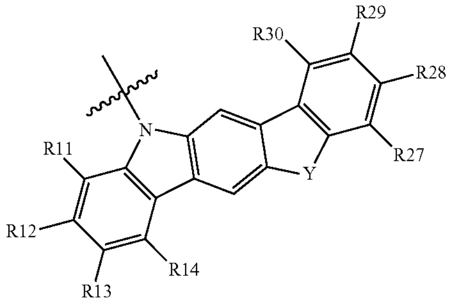

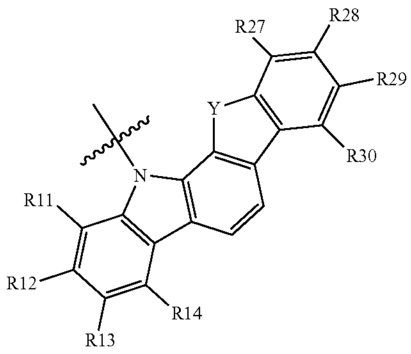

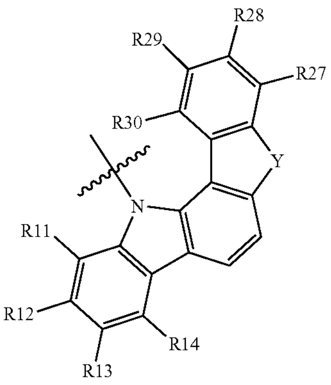

In the structural formulae, each substituent has the same definition as in Chemical Formula 1-4.

According to one embodiment of the present application, Chemical Formula 1 may be represented by any one of the following compounds, but is not limited thereto.

-continued
1
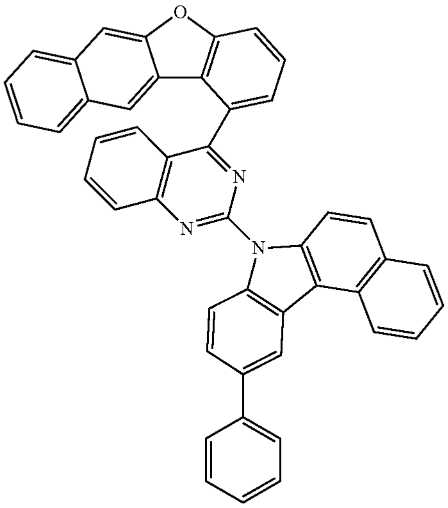
4
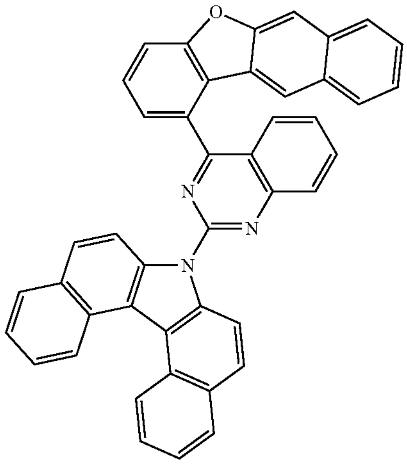
2
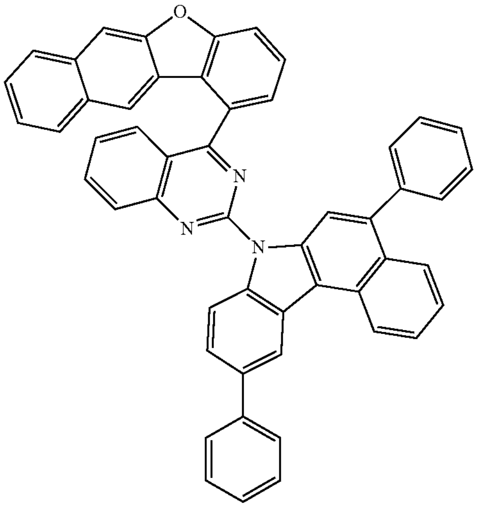
5
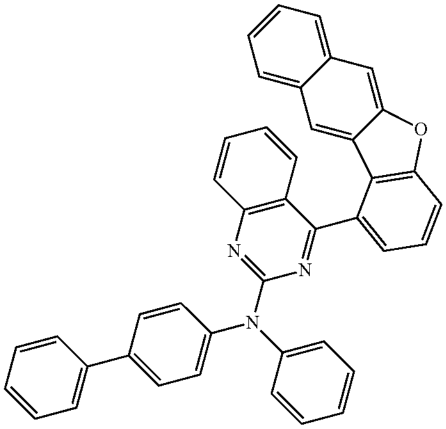
3
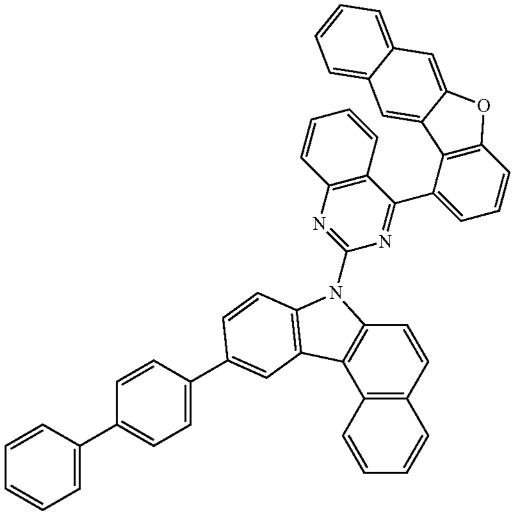
6
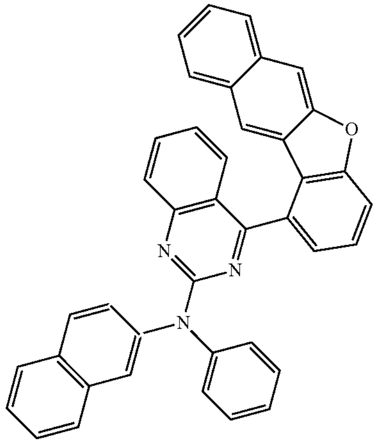

-continued
7
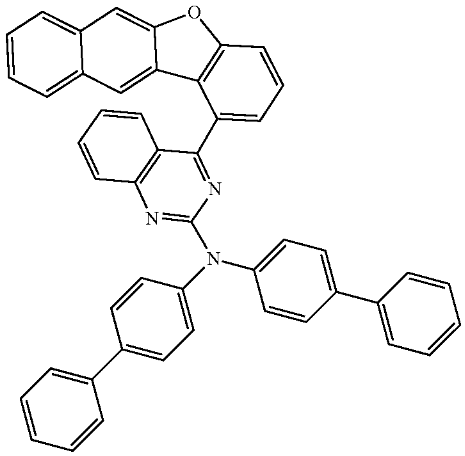
8
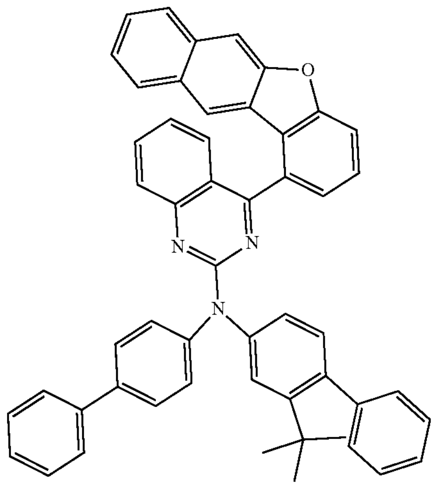
9
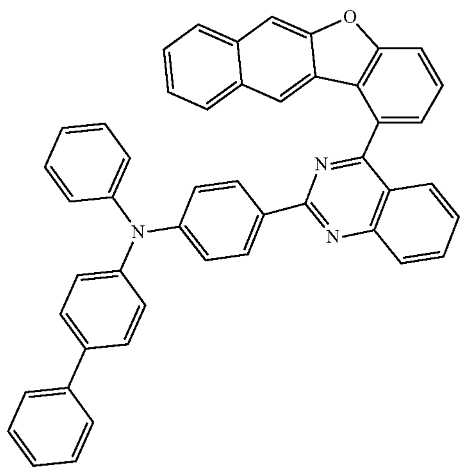
-continued
10
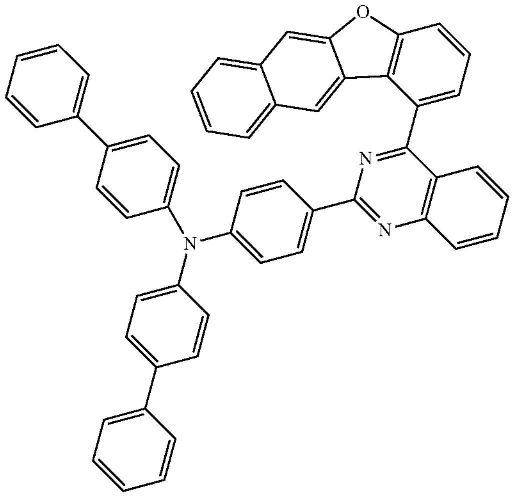
11
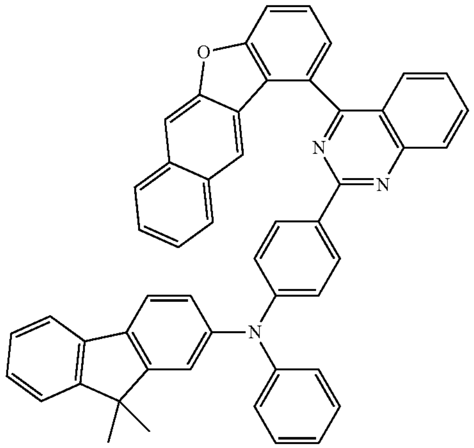
12
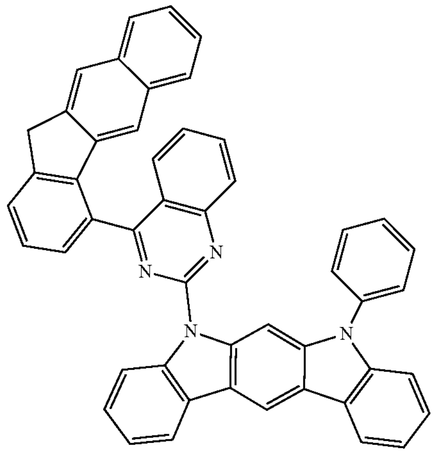

-continued
13
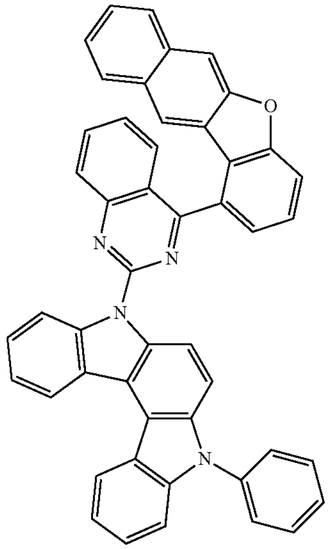
14
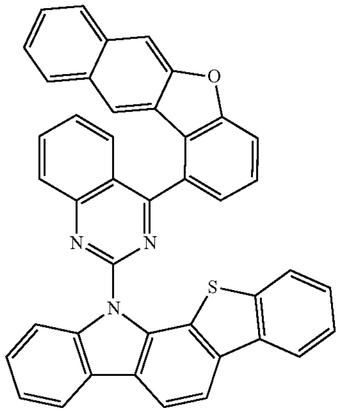
15
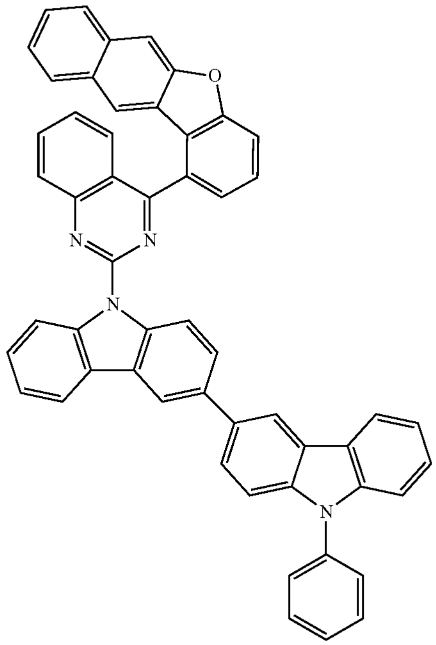
-continued
16
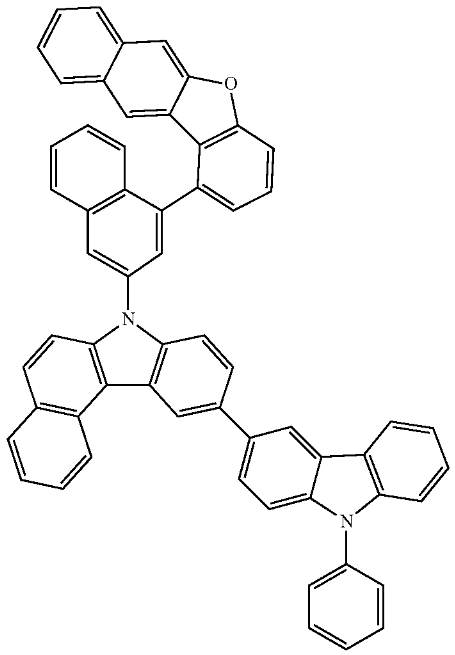
17
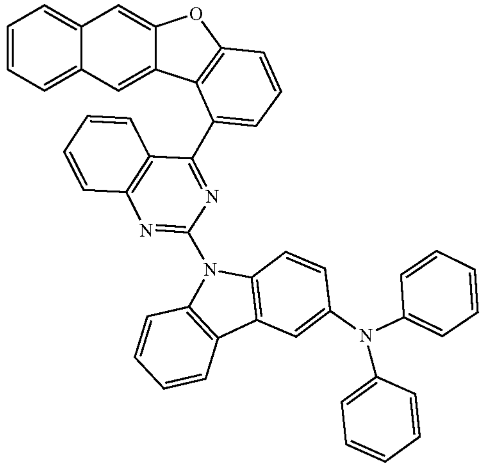
18
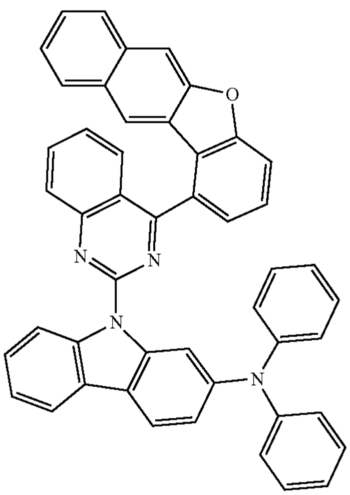

-continued
19
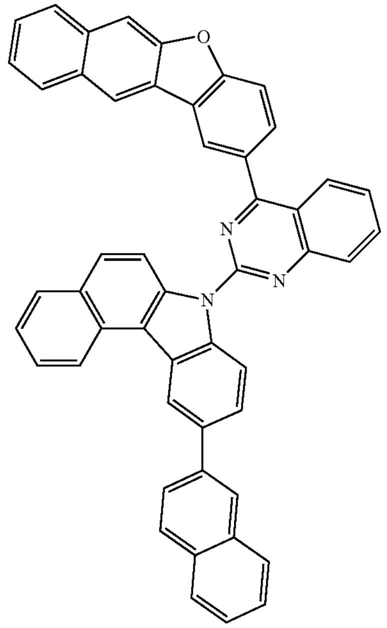
20
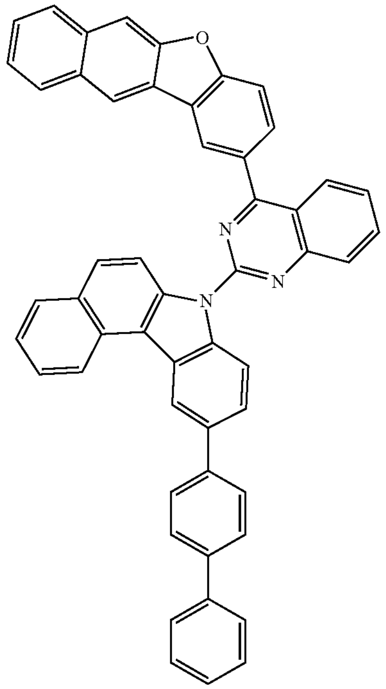
-continued
21
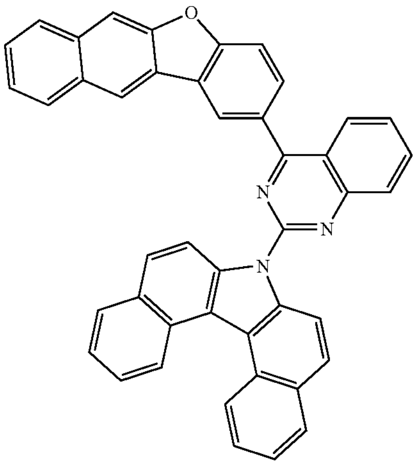
22
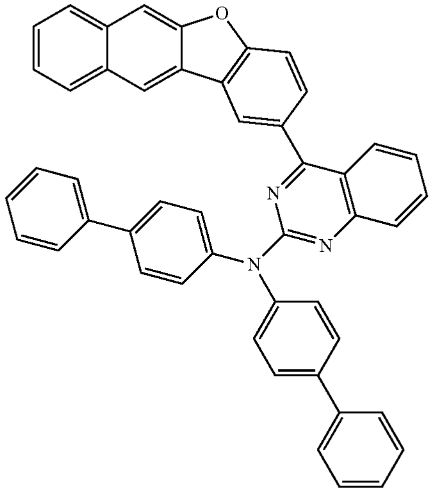
23
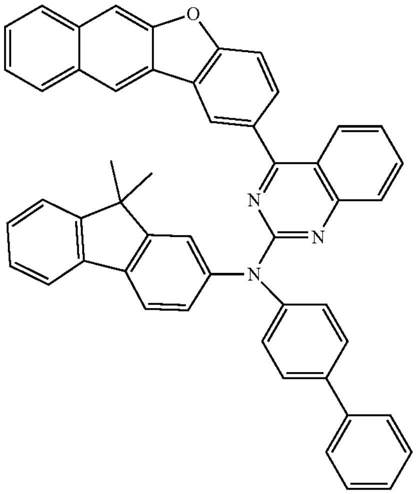

-continued
24
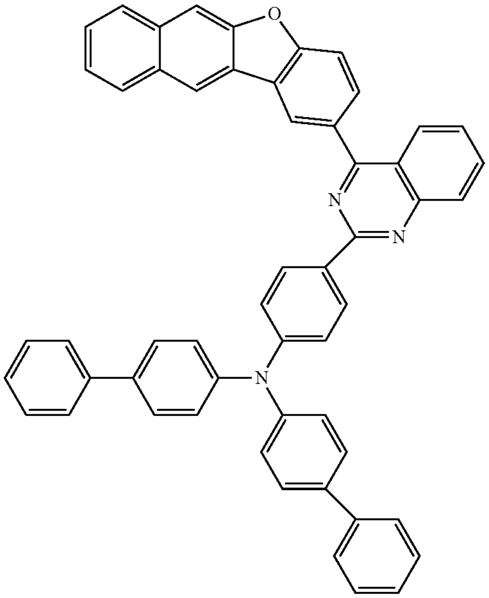
25
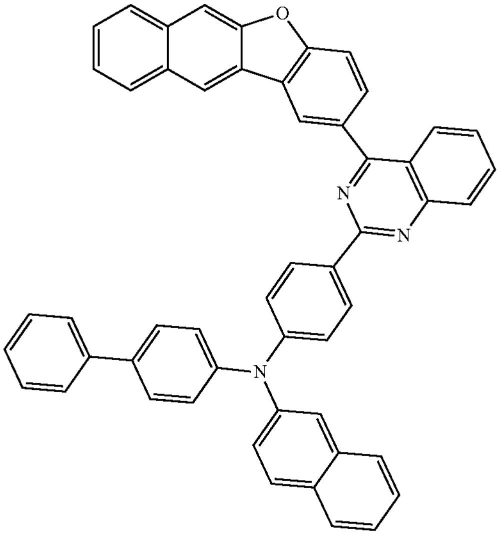
26
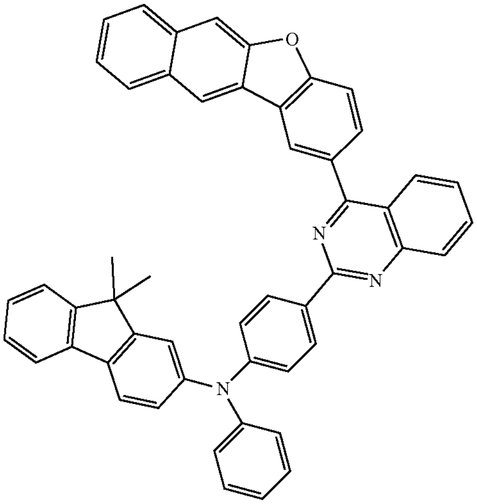
-continued
27
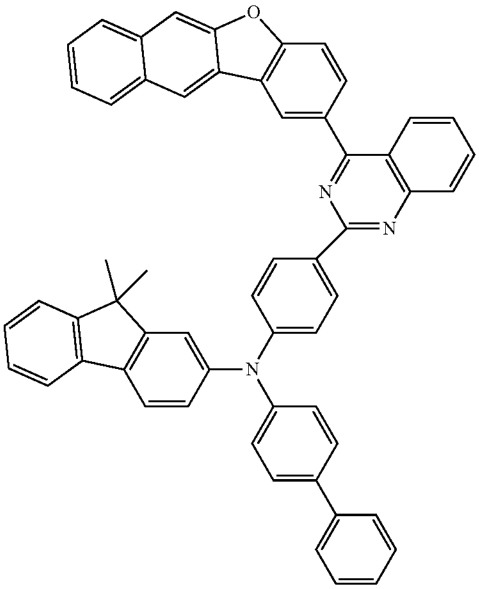
28
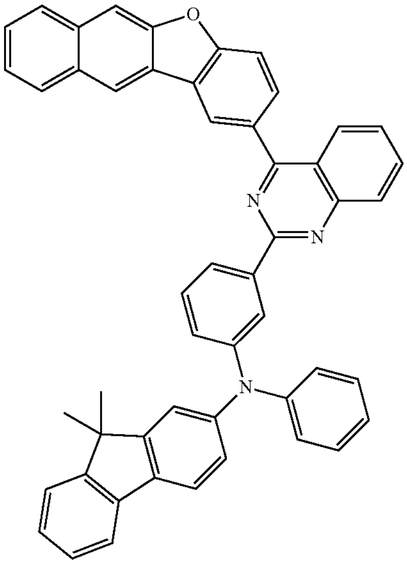

29
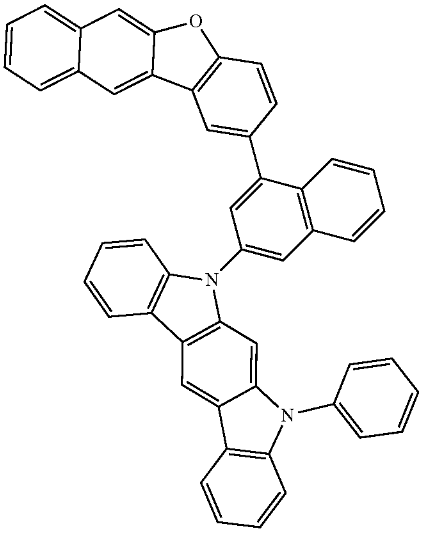
30
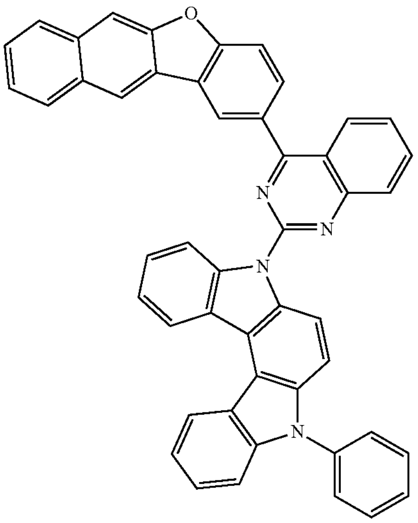
31
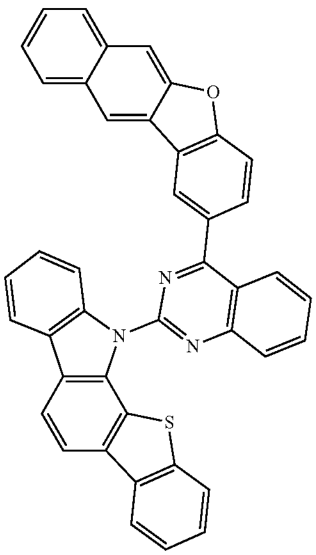
32
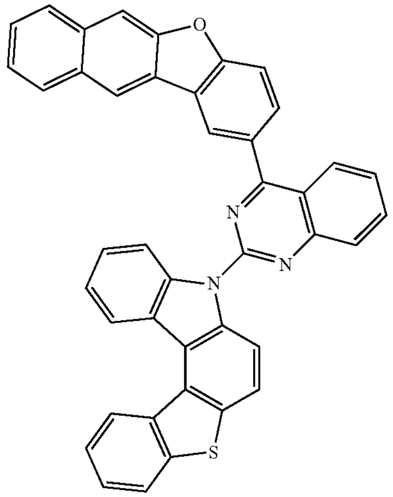
33
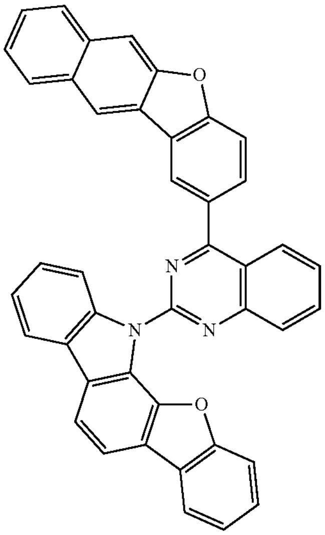
34
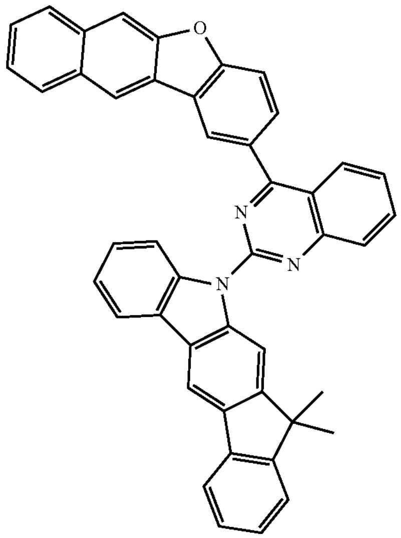

-continued
35
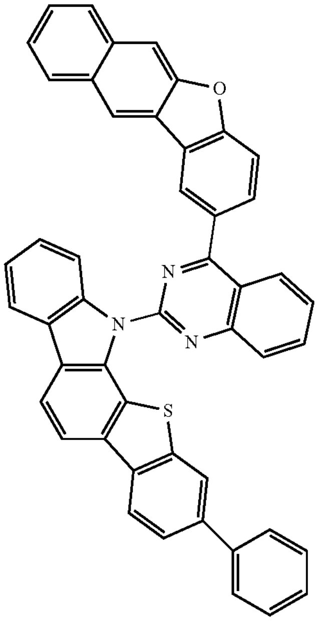
36
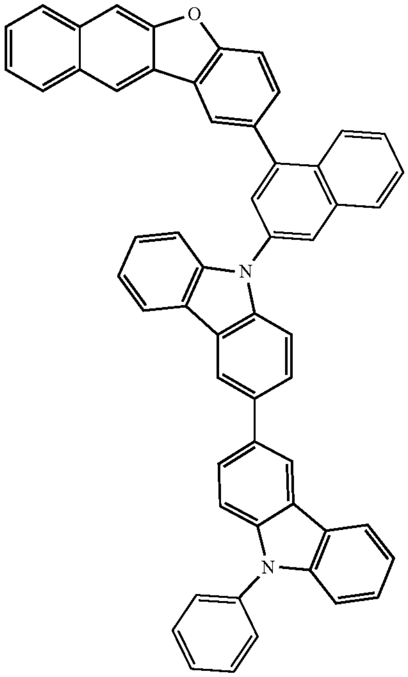
-continued
37
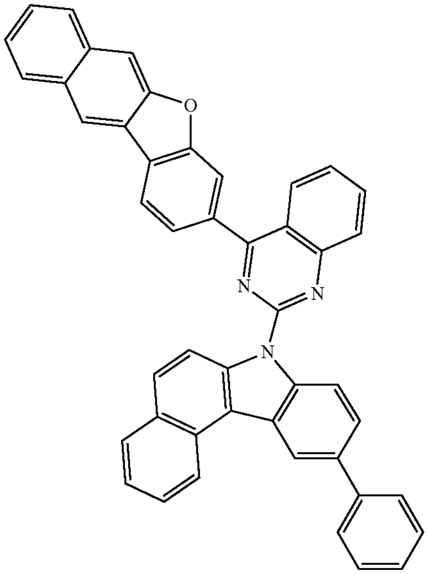
38
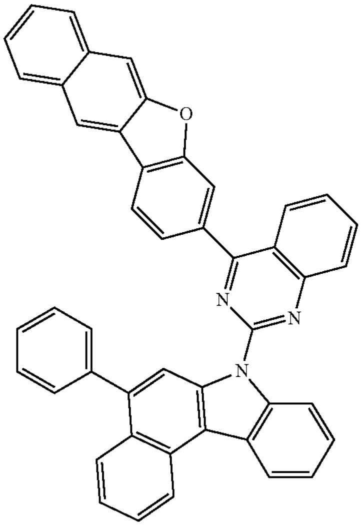

-continued
39
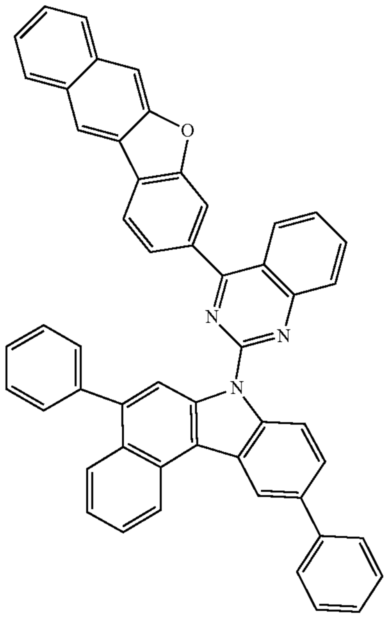
40
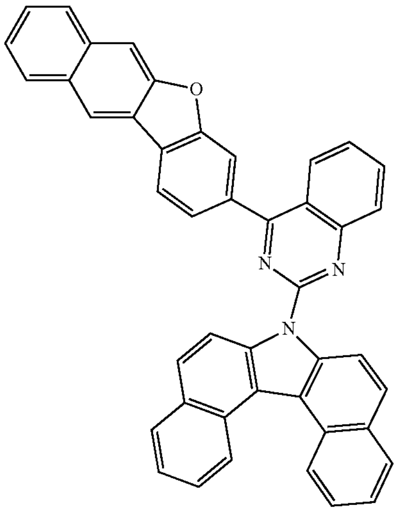
-continued
41
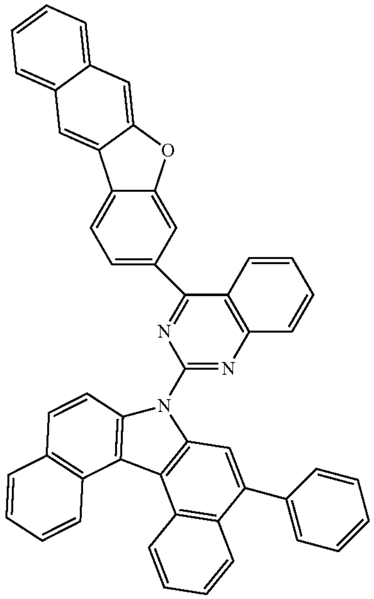
42
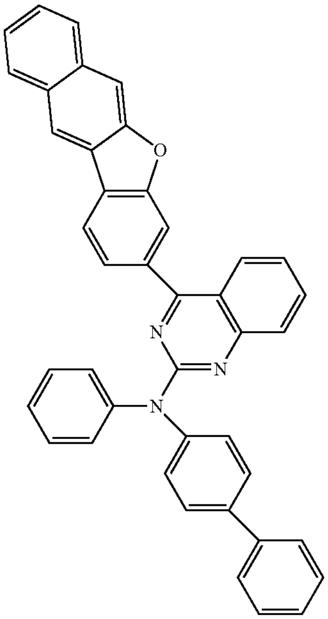

-continued
43
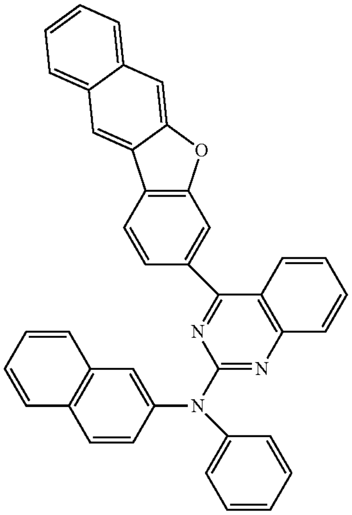
44
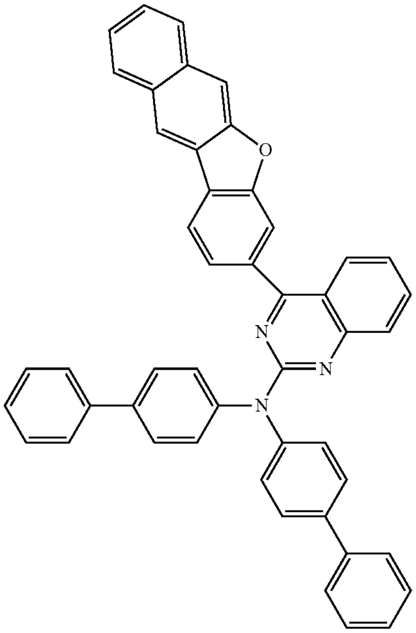
-continued
45
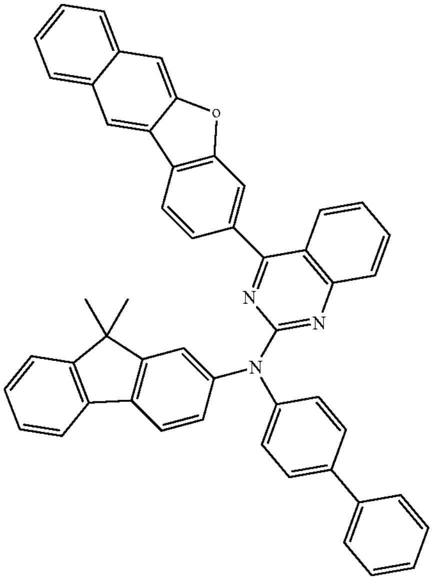
46
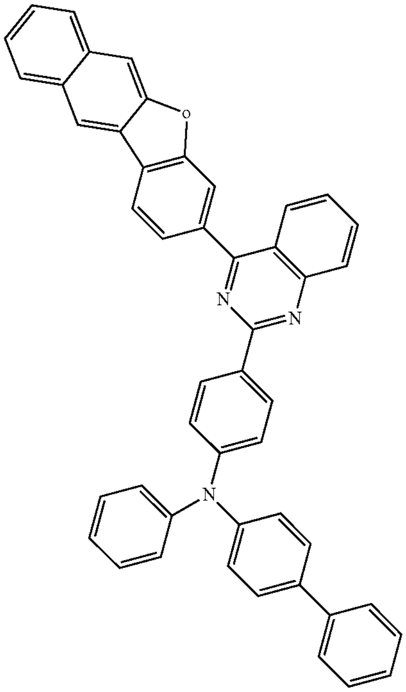

-continued
47
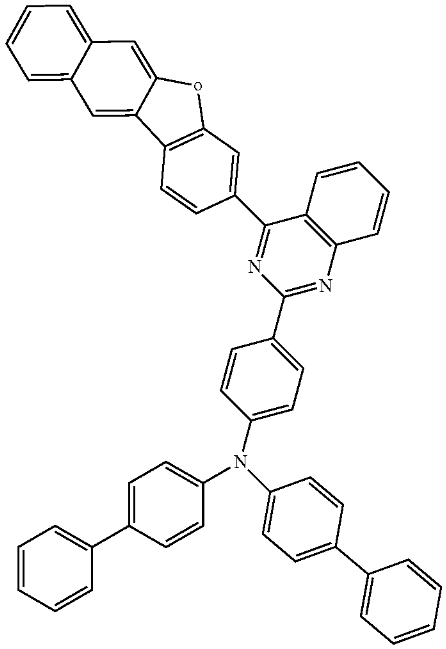
48
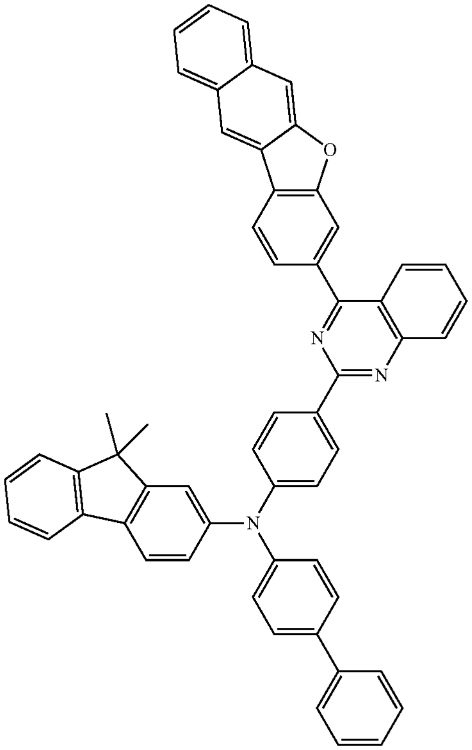
-continued
49
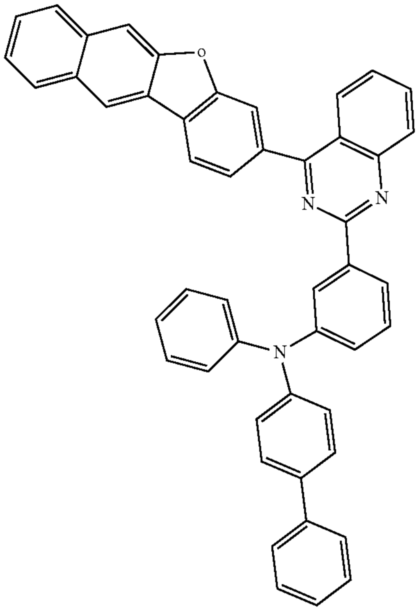
50
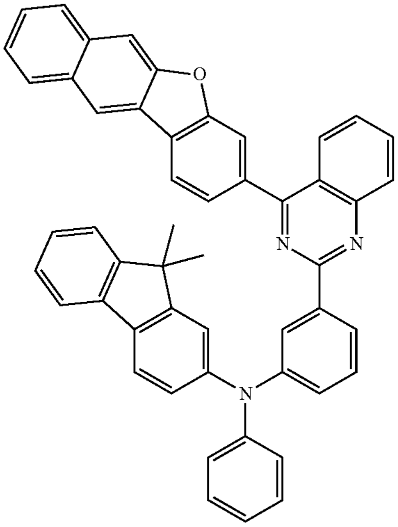

-continued
51
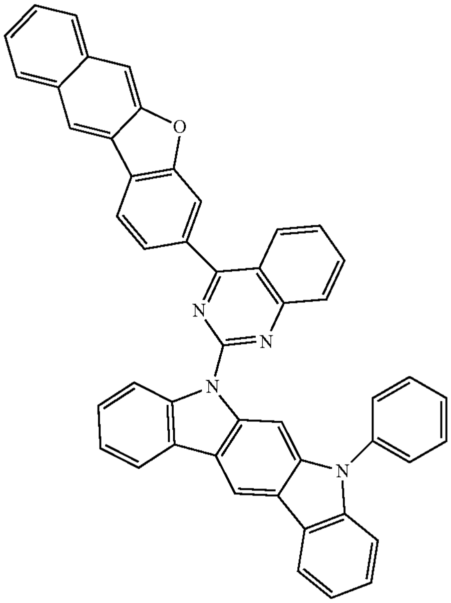
53
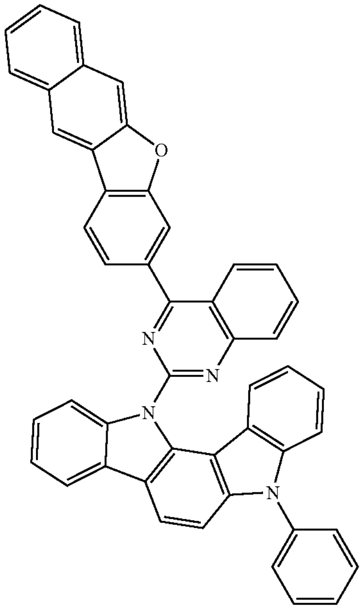
52
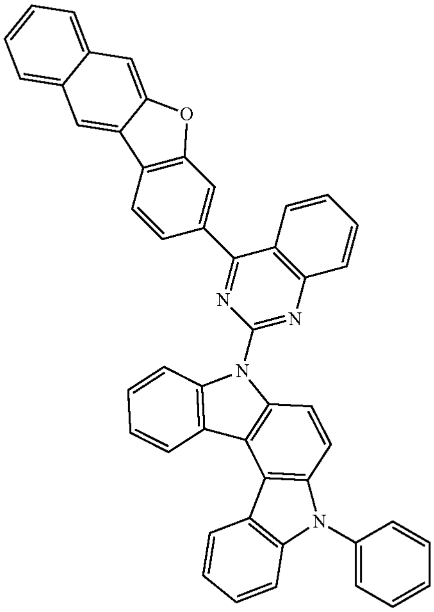
54
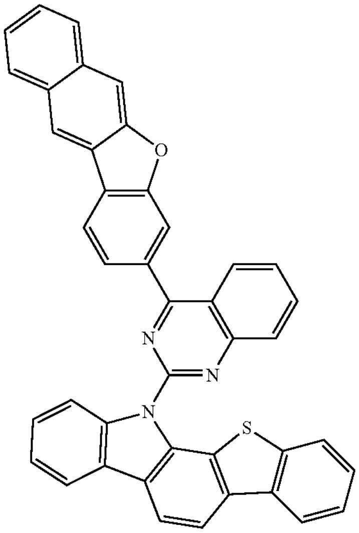

55
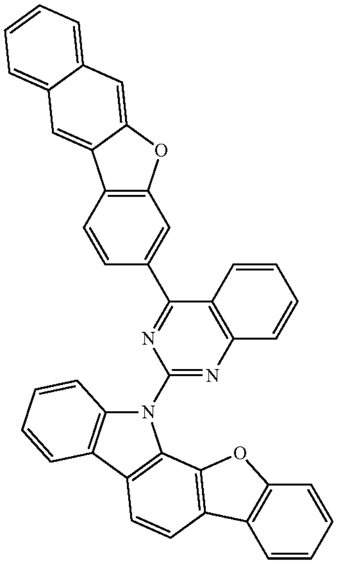
56
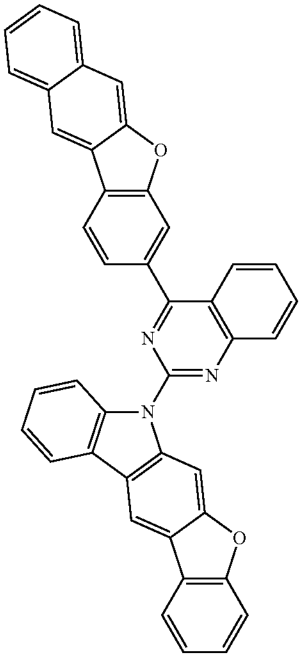
57
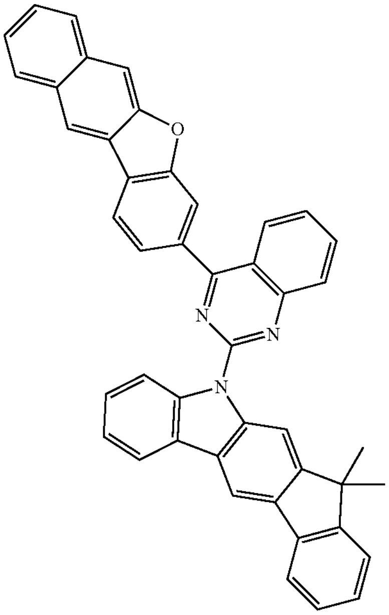
58
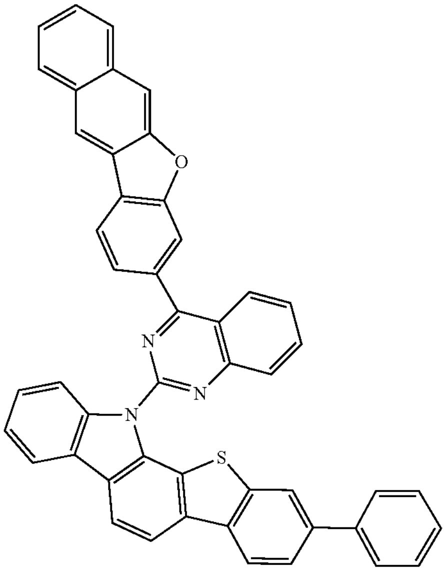

-continued
59
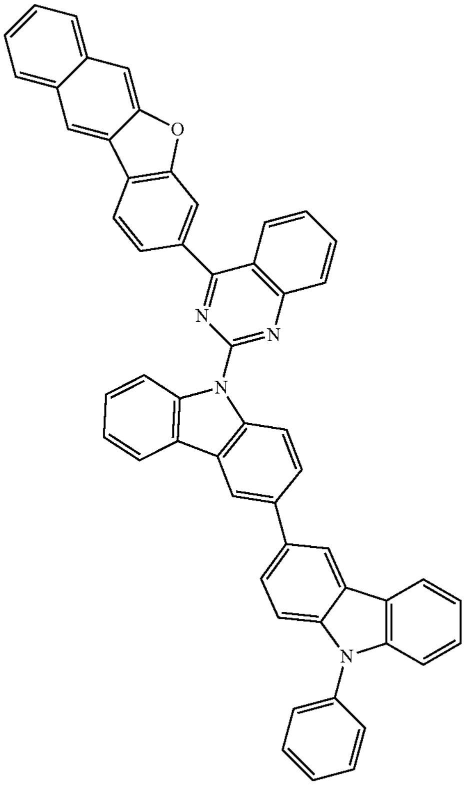
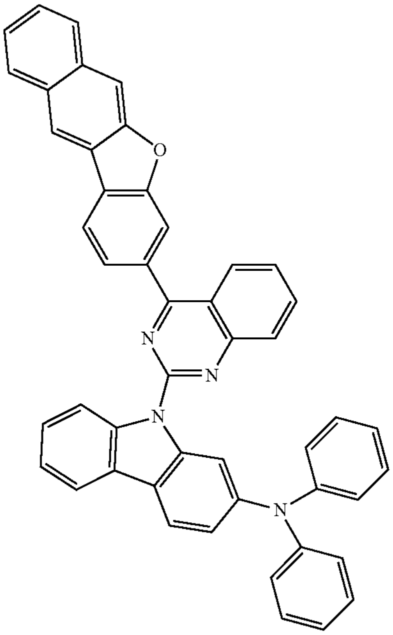
-continued
61
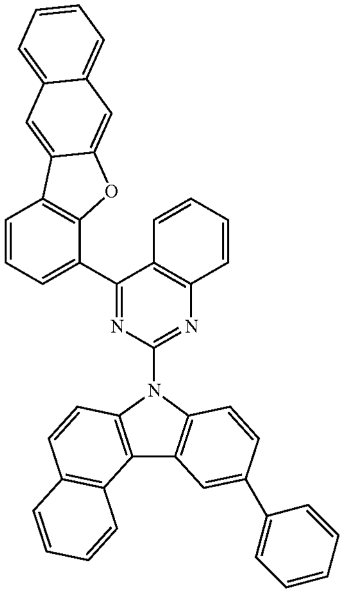
62
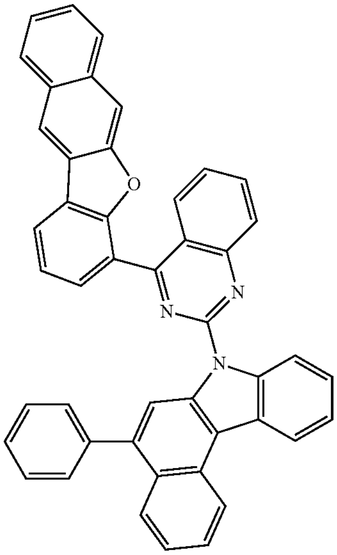

63
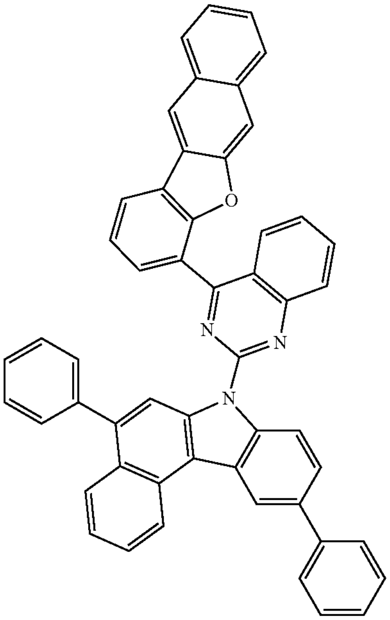
64
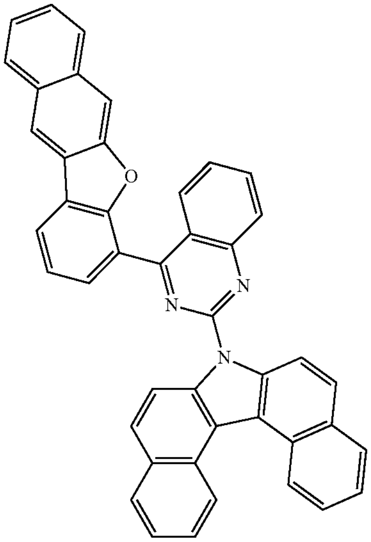
65
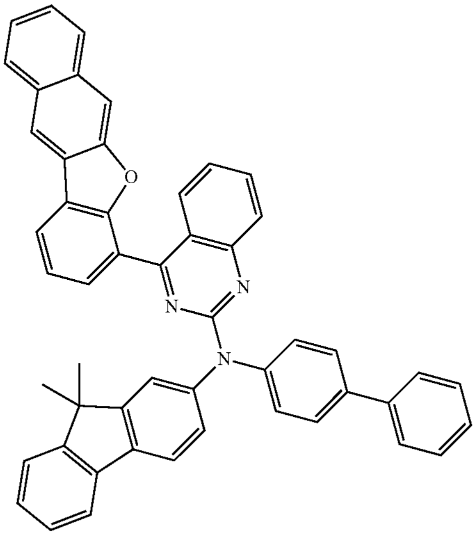
66
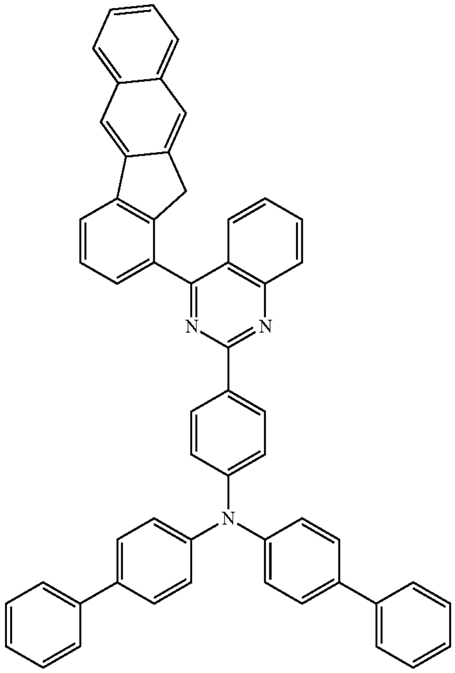

-continued
67
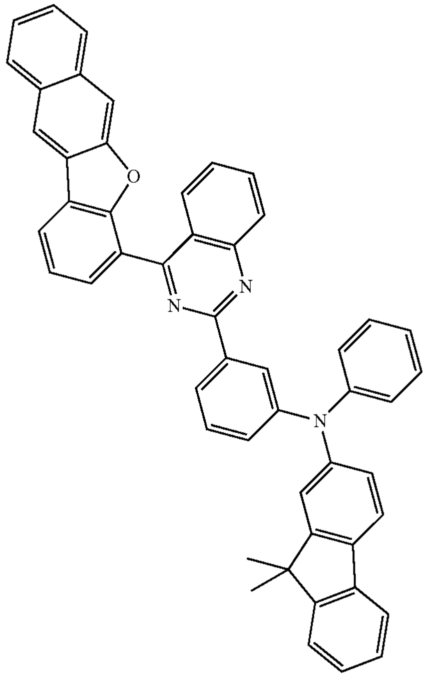
68
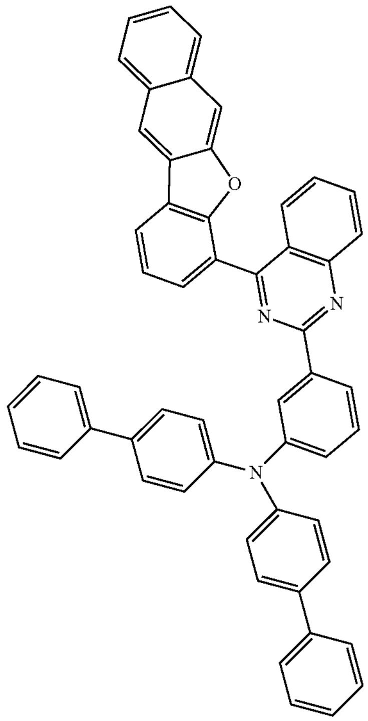
-continued
69
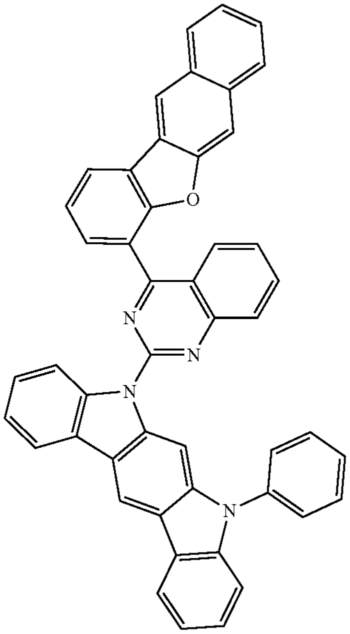
70
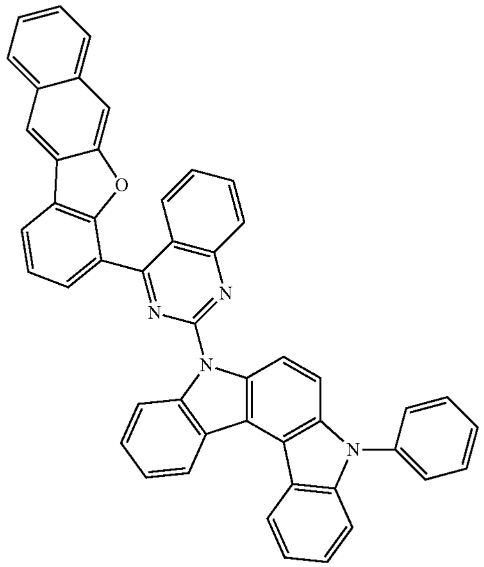

-continued
71
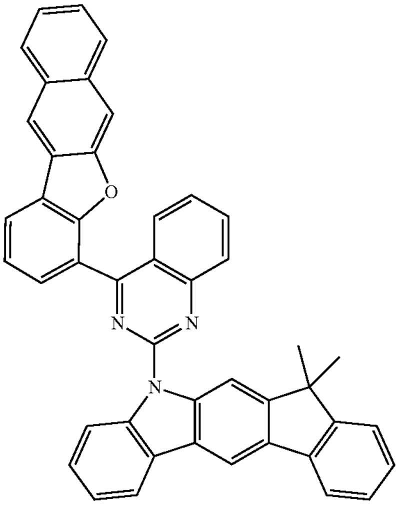
72
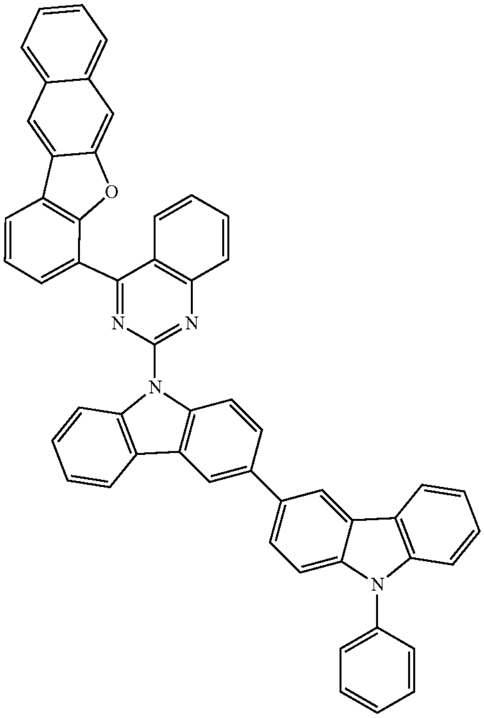
-continued
73
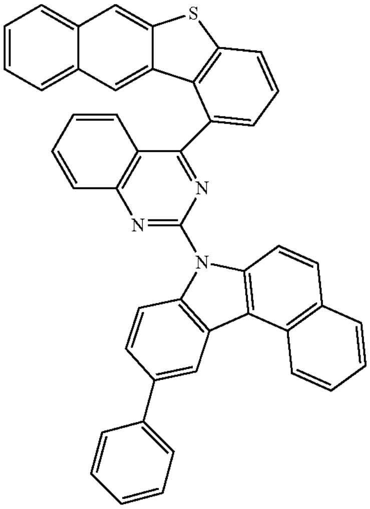
74
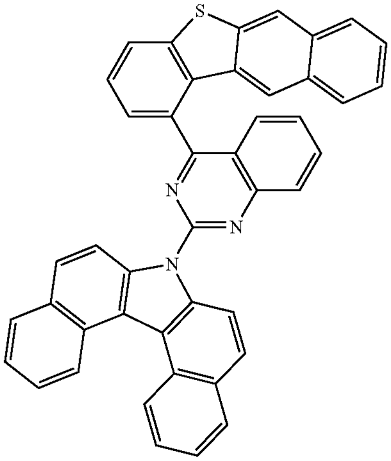
75
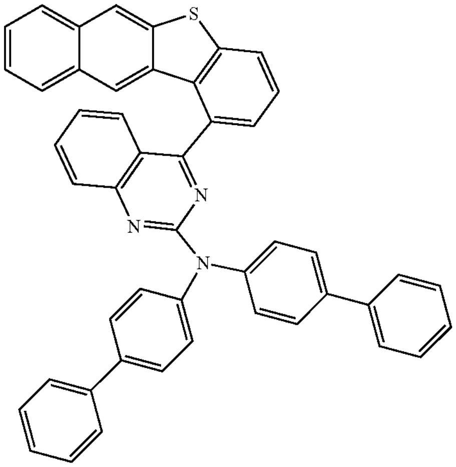

-continued
76
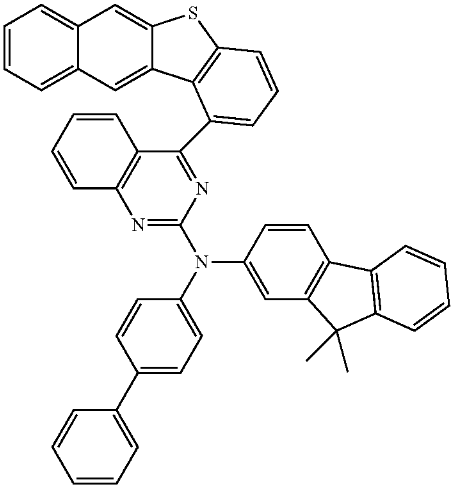
77
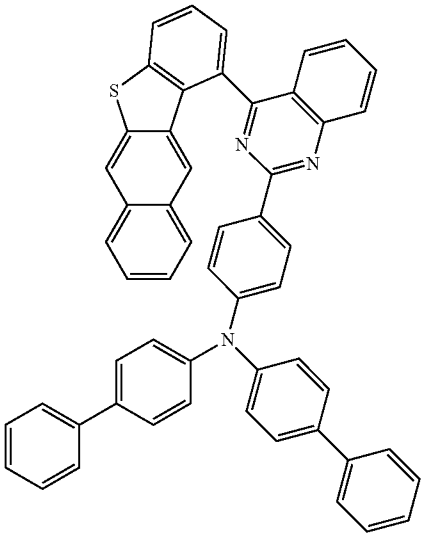
78
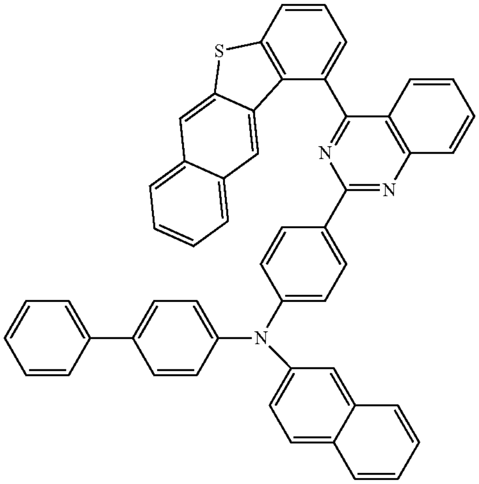
-continued
79
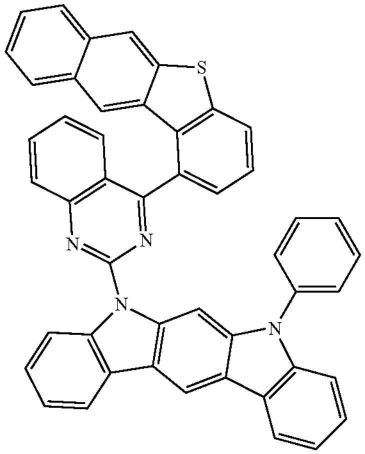
80
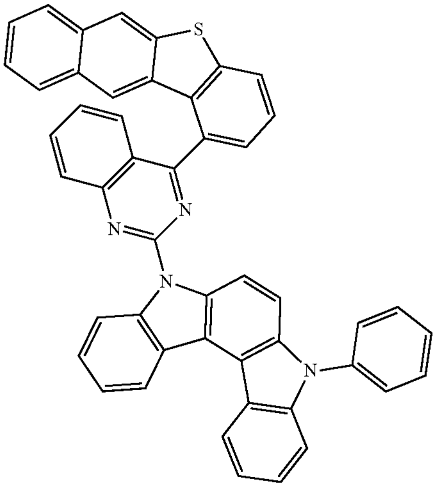
81
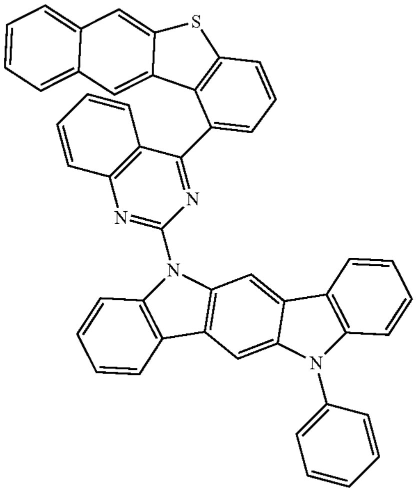

-continued
82
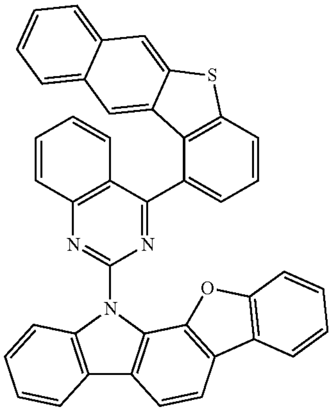
83
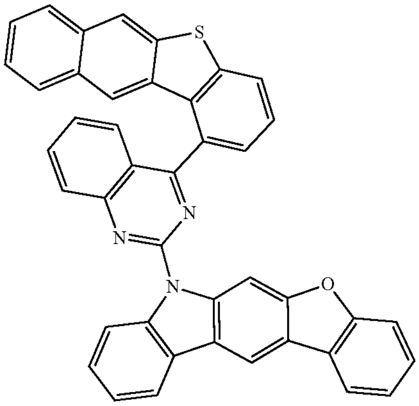
84
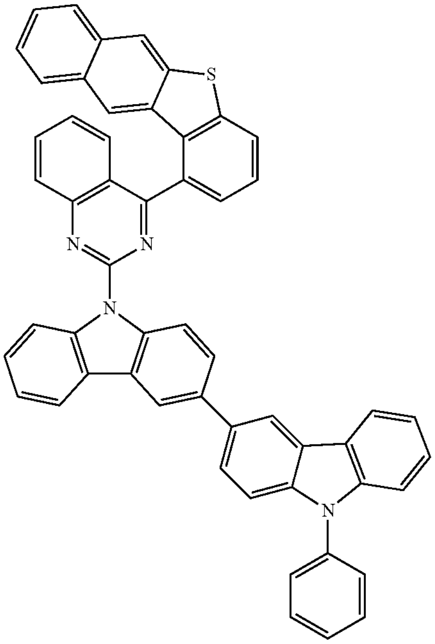
-continued
85
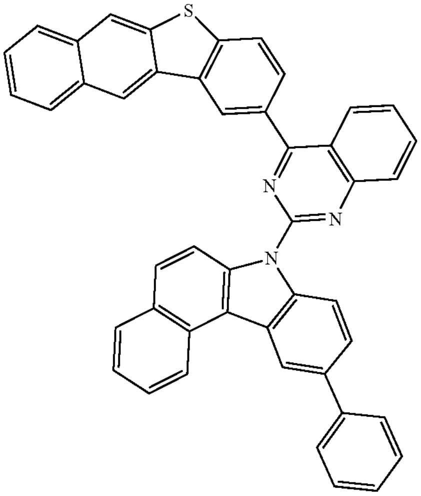
86
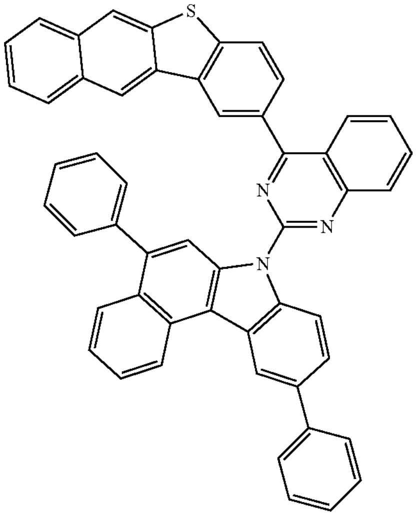
87
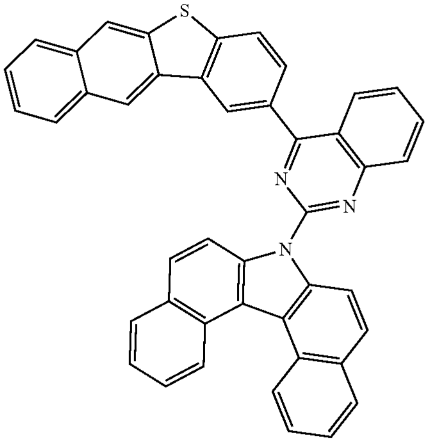

-continued
88
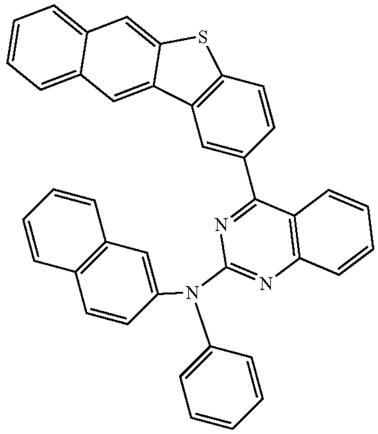
89
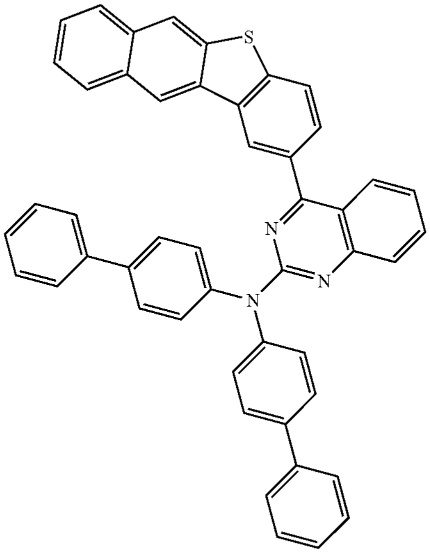
90
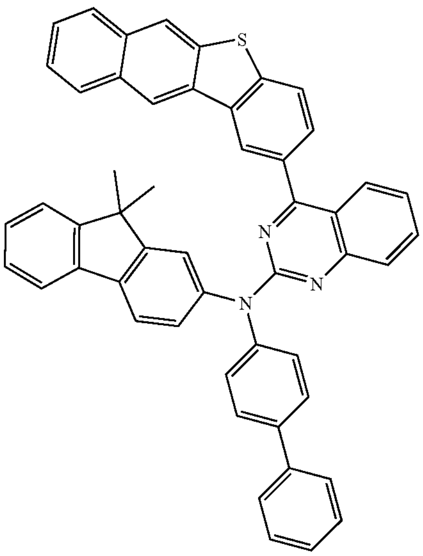
-continued
91
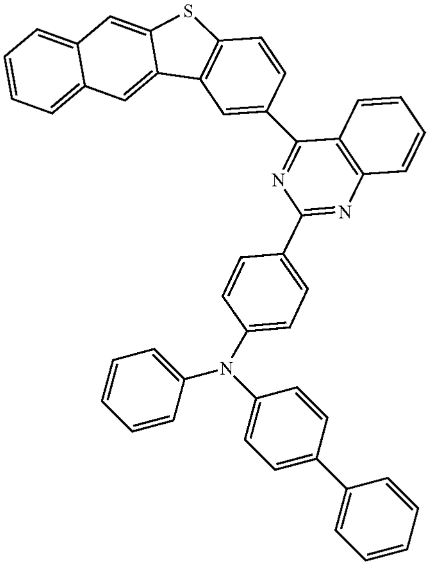
92
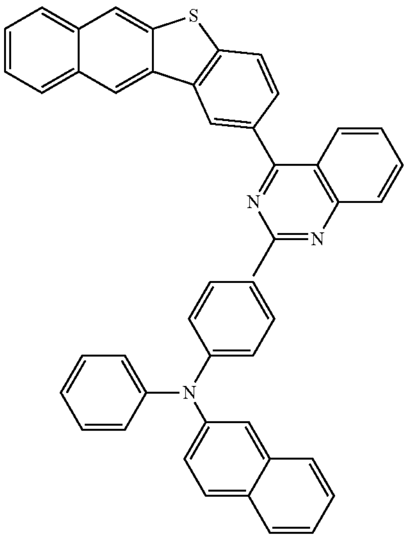
93
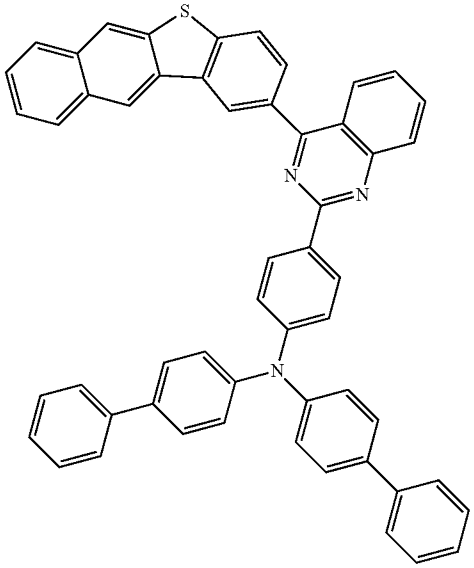

-continued
94
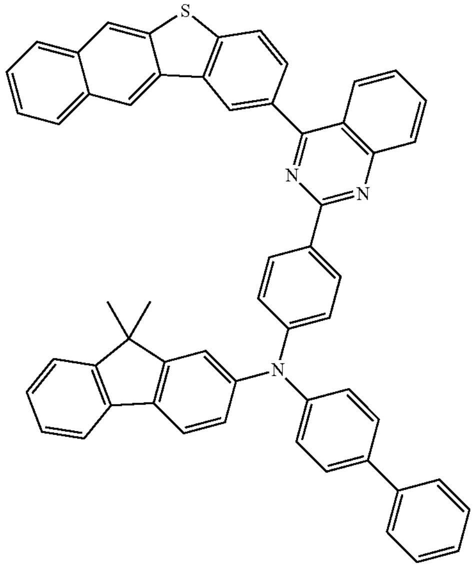
95
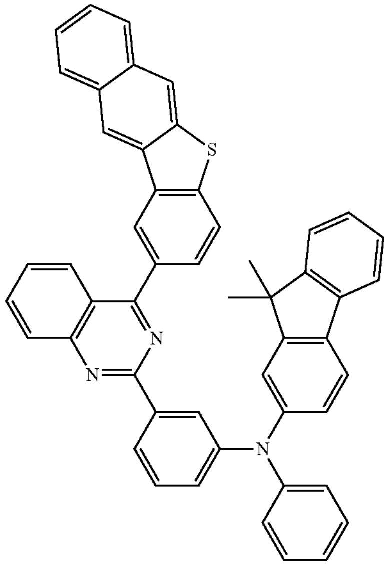
-continued
96
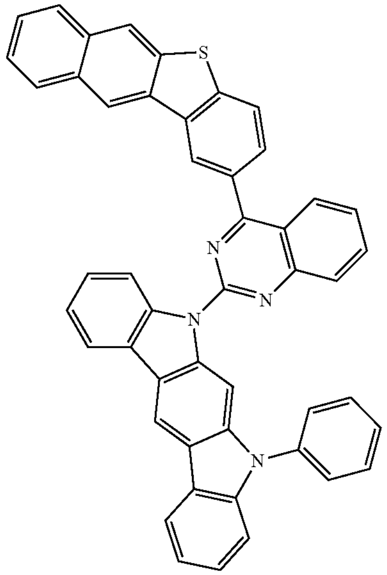
97
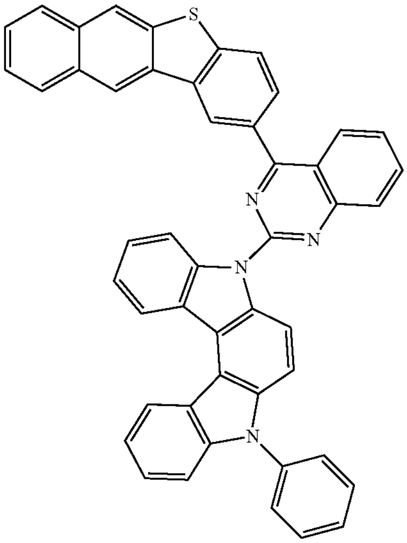
98
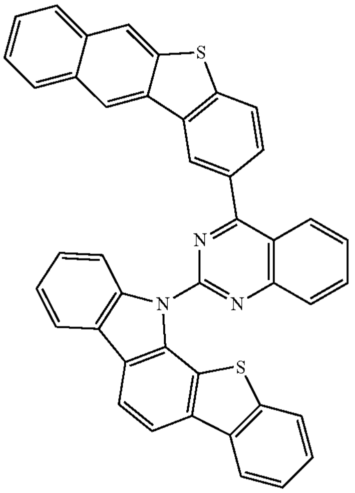

-continued
99
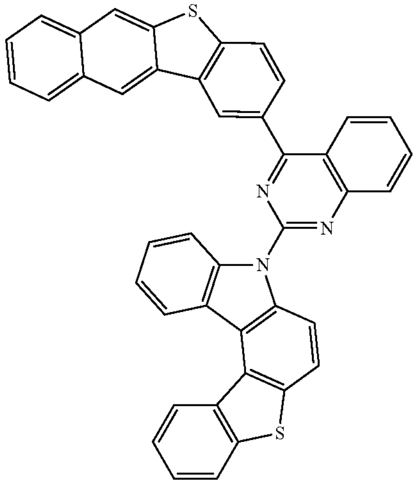
100
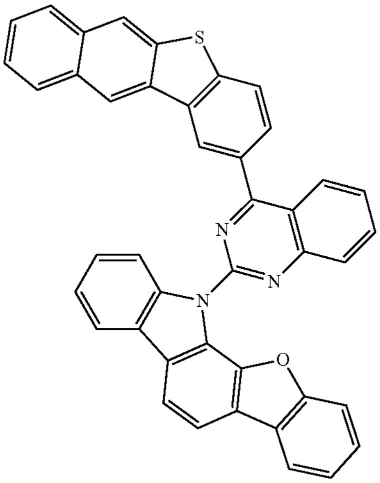
101
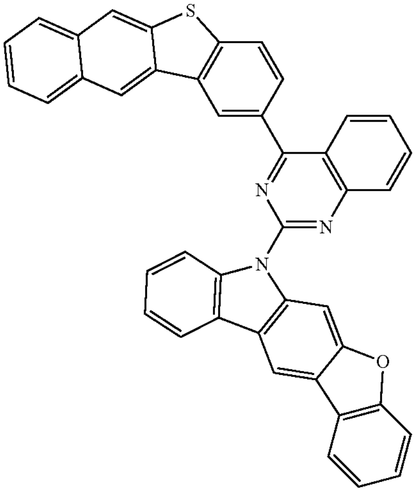
-continued
102
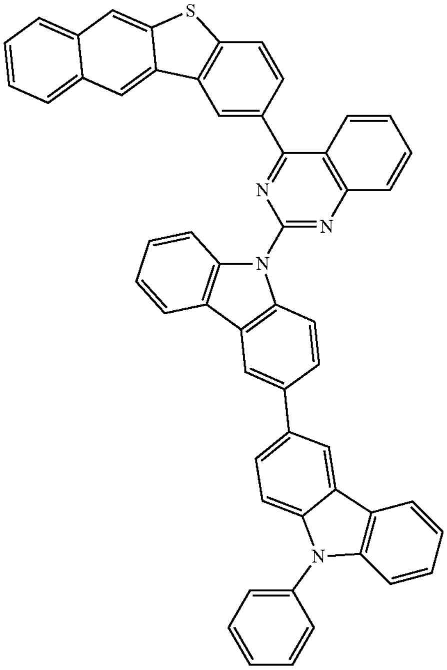
103
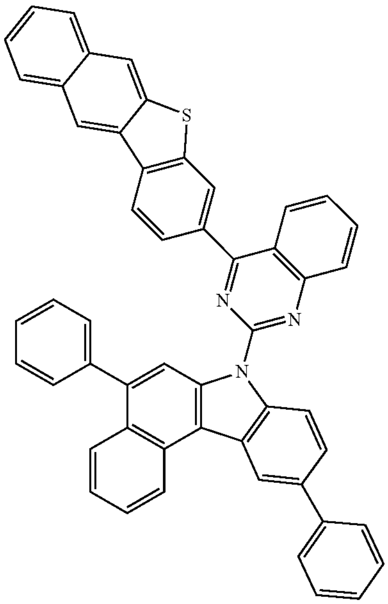

-continued
104
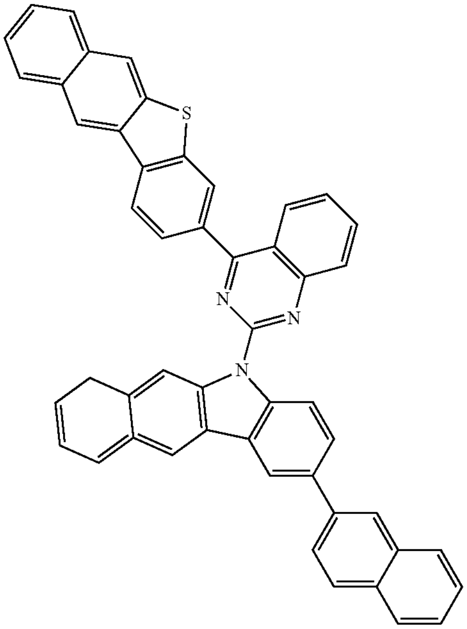
105
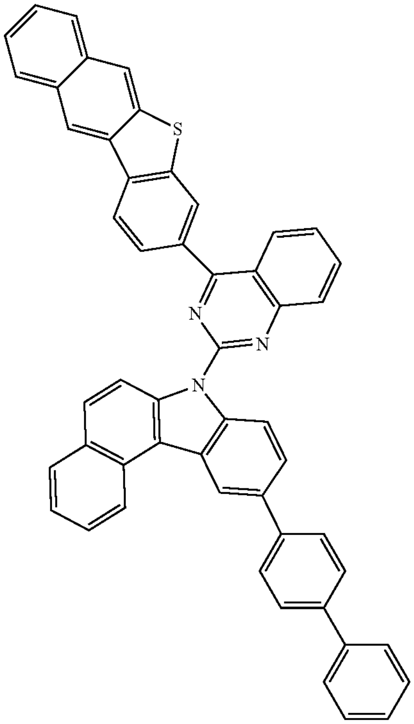
-continued
106
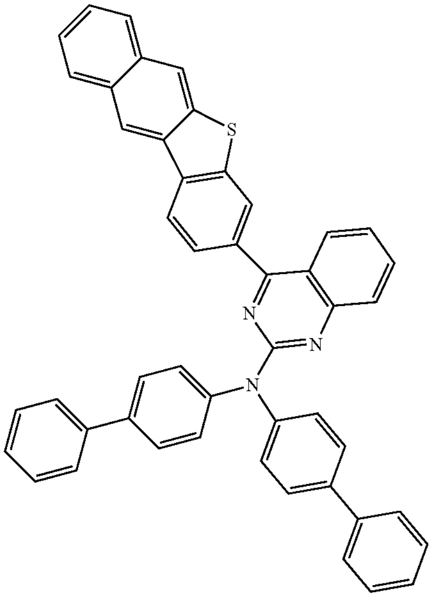
107
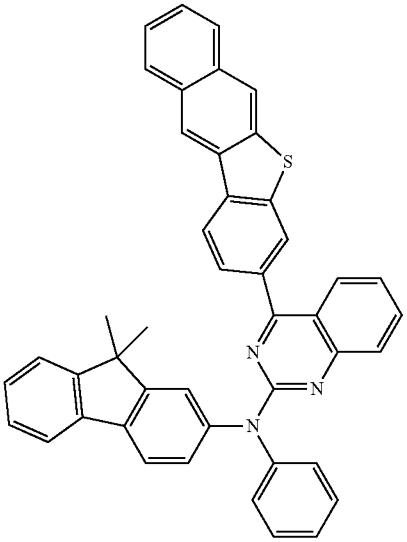

-continued
108
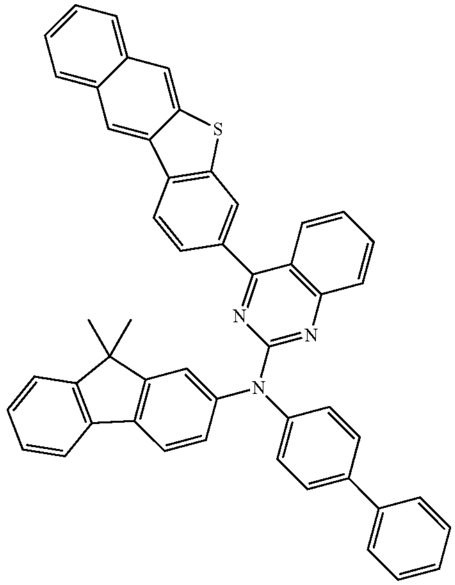
109
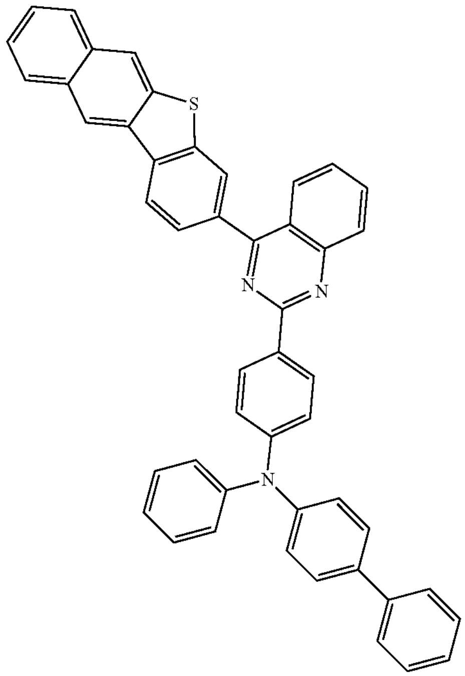
-continued
110
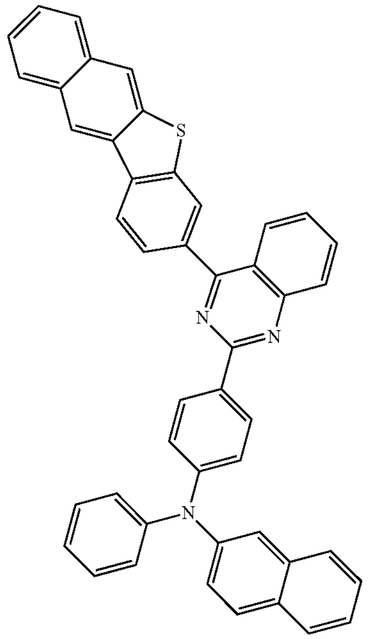
111
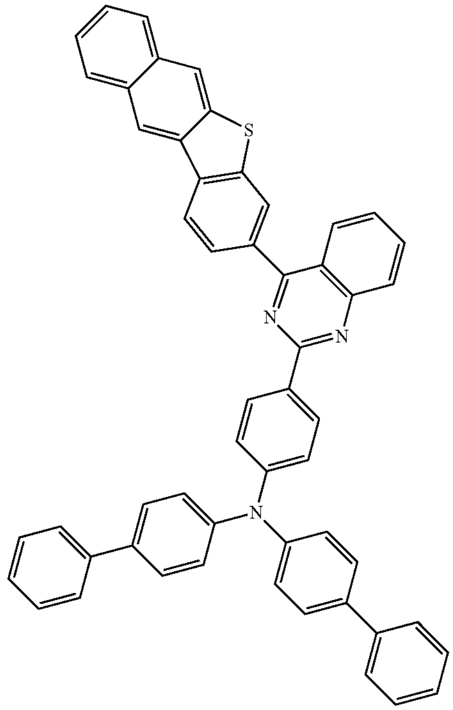

-continued
112
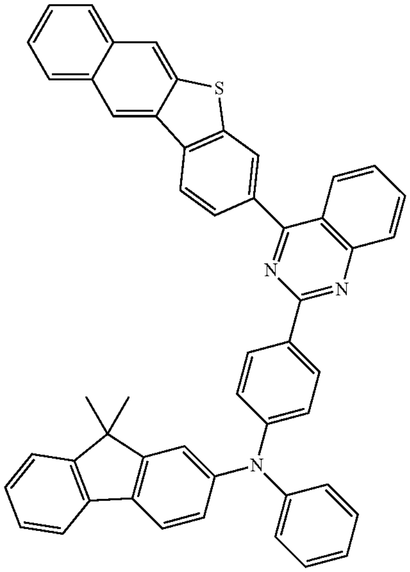
113
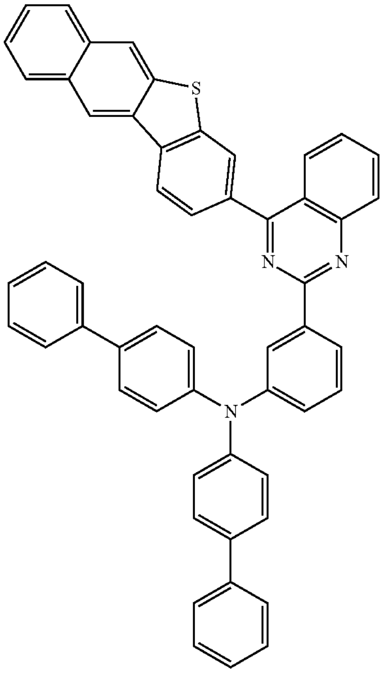
-continued
114
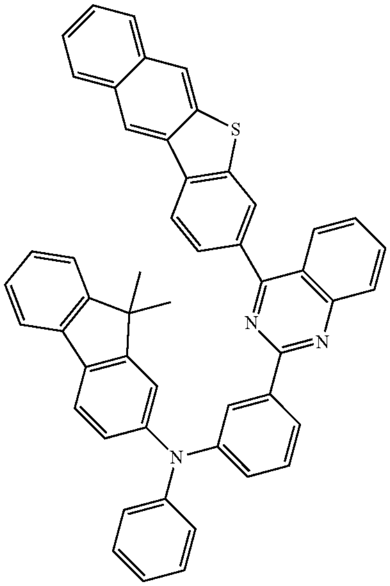
115
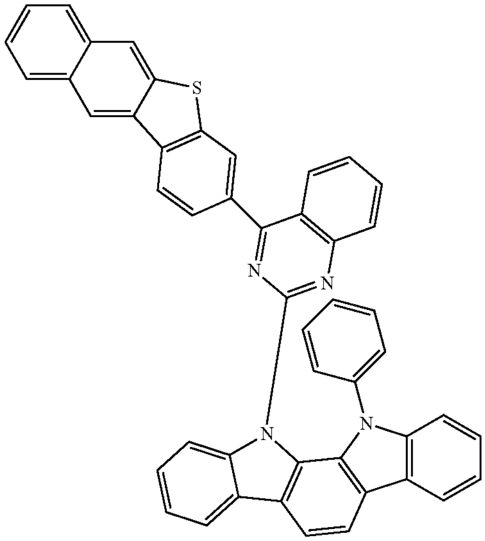

-continued
116
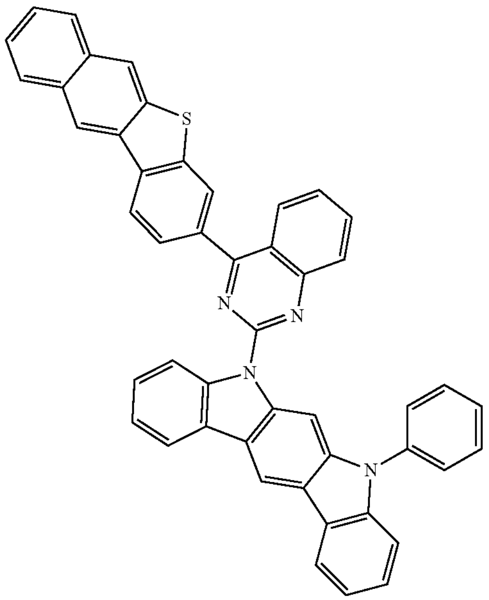
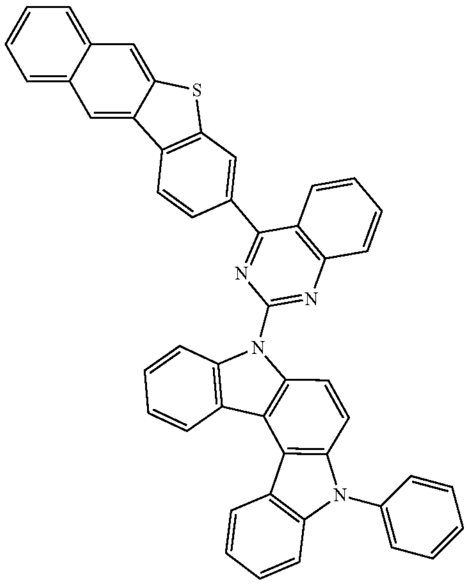
118
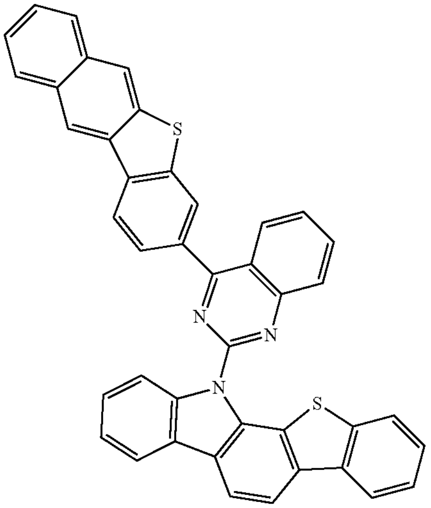
-continued
119
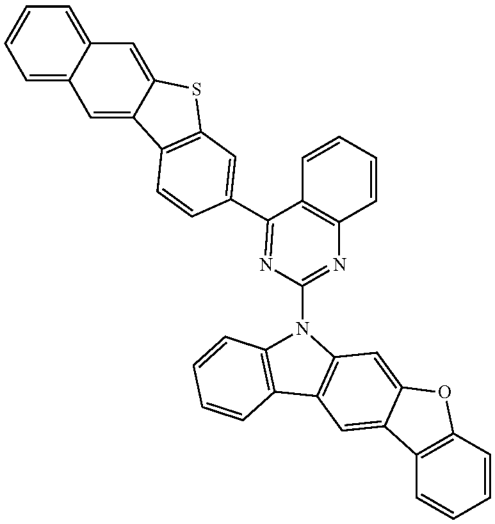
120
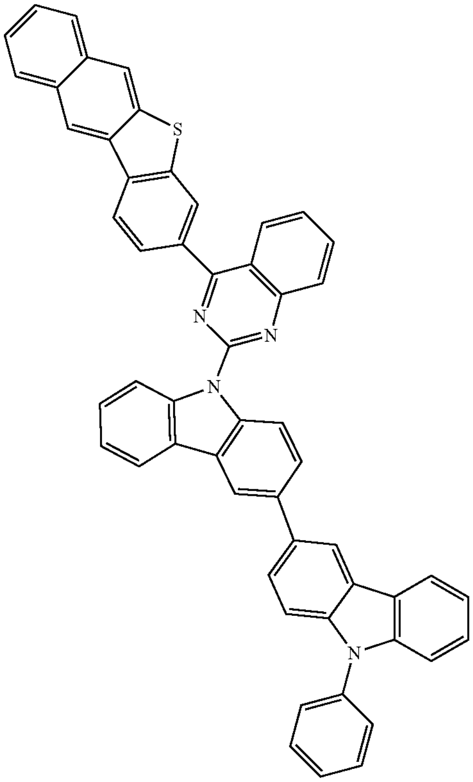

-continued
121
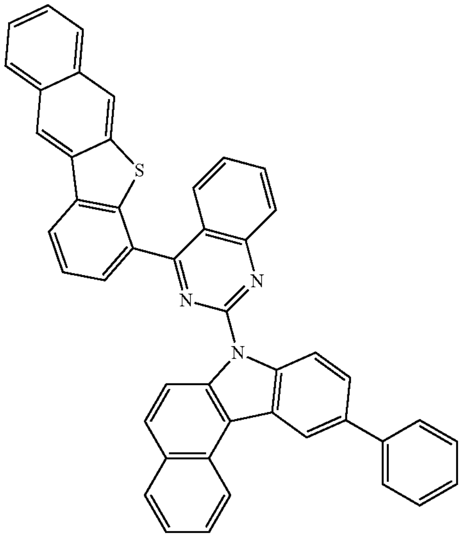
122
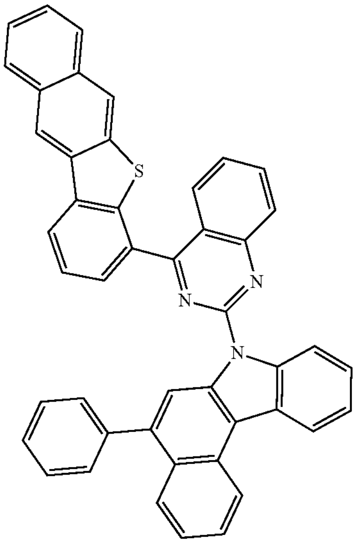
123
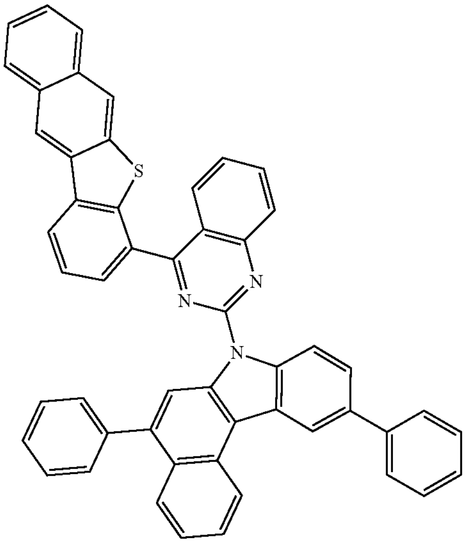
-continued
124
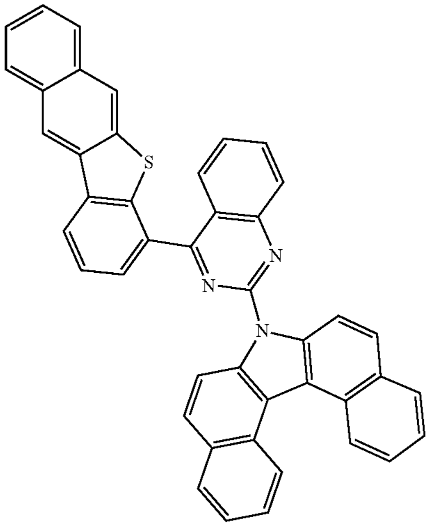
125
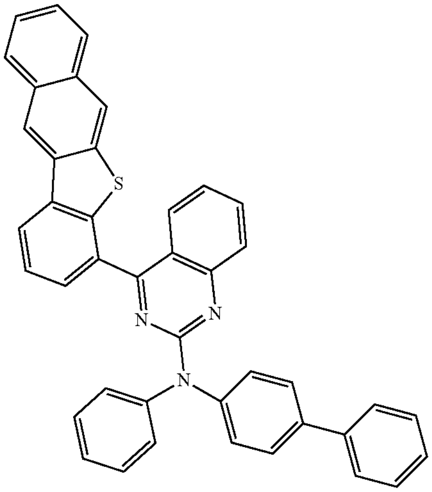
126
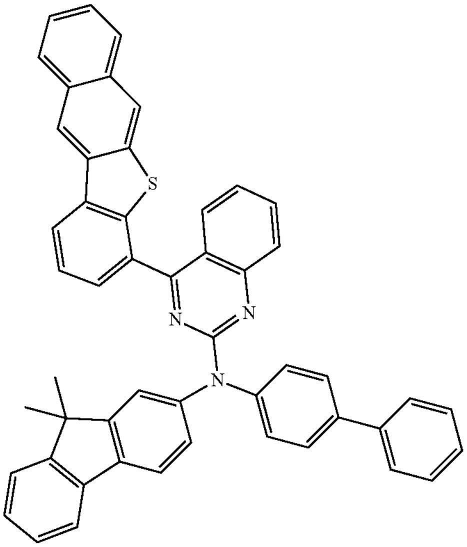

-continued
127
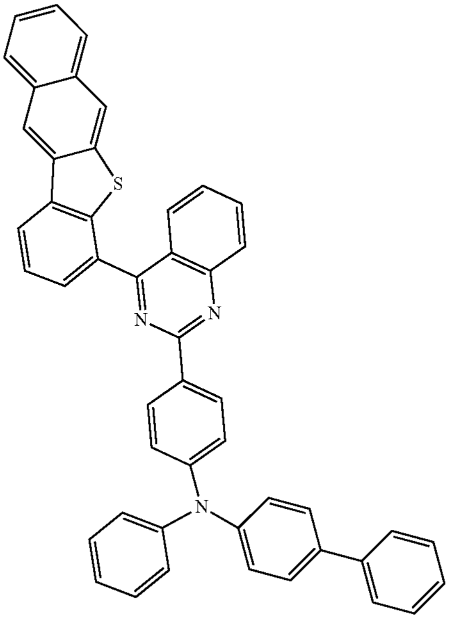
128
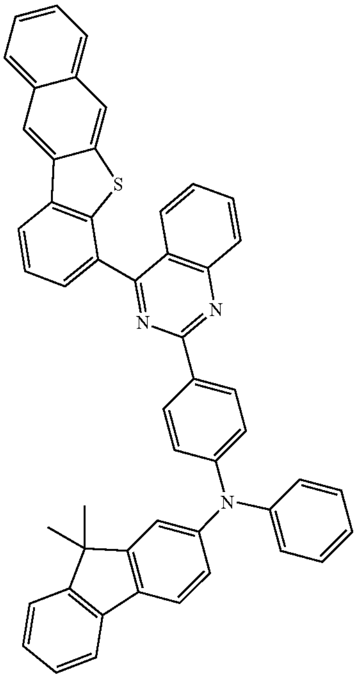
-continued
129
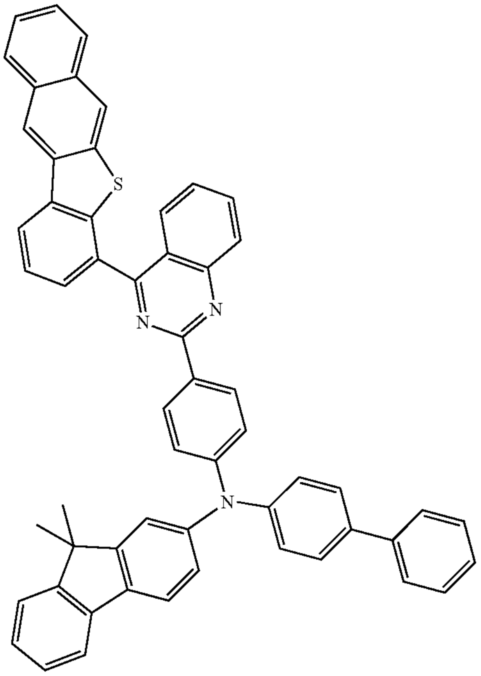
130
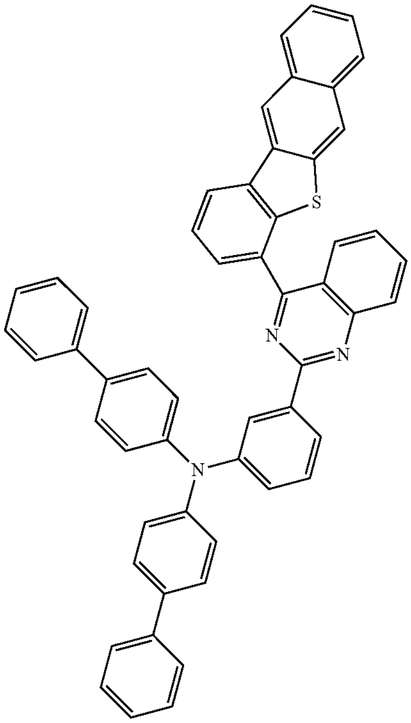

-continued
131
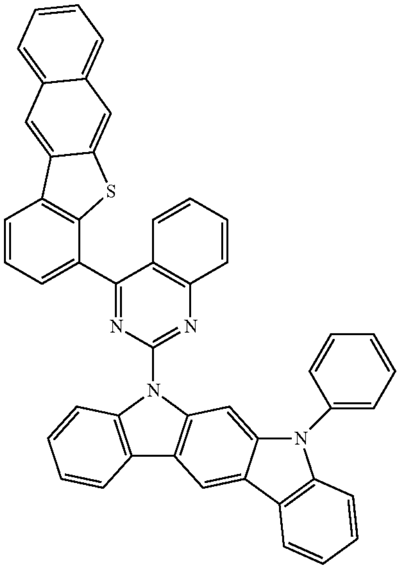
132
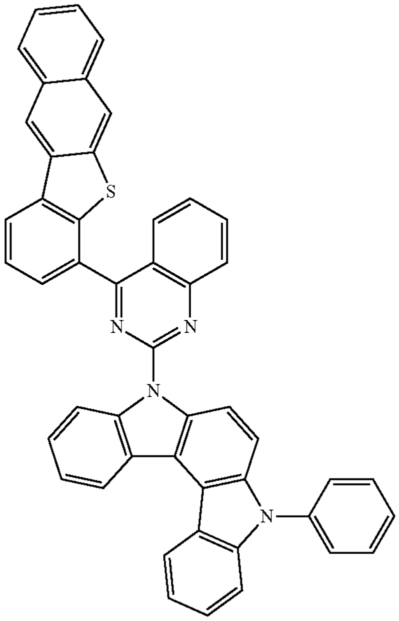
-continued
133
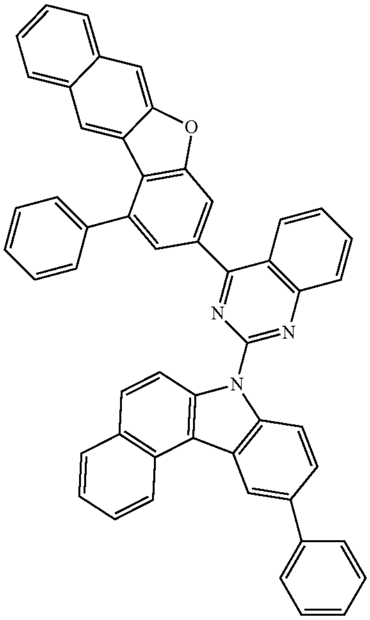
134
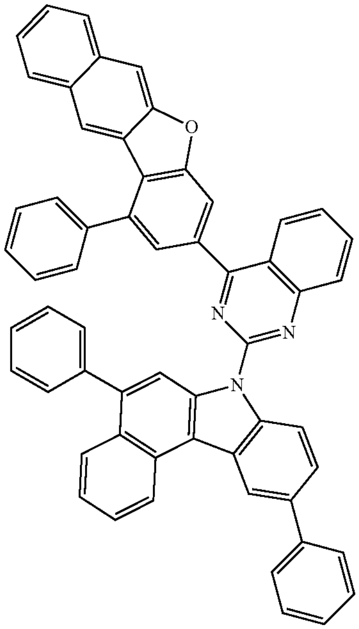

-continued
135
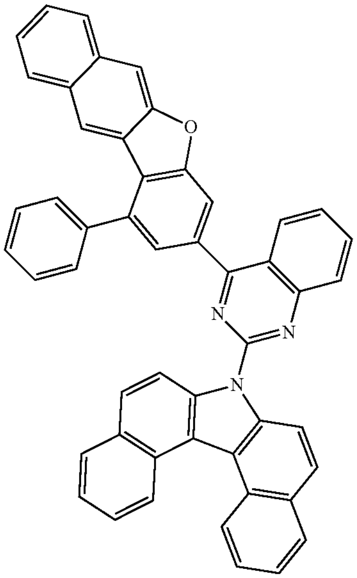
136
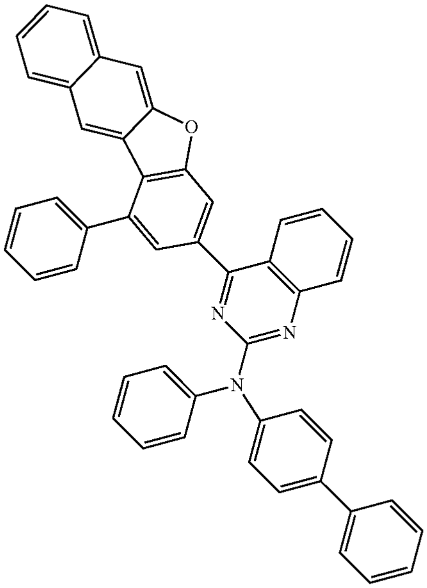
-continued
137
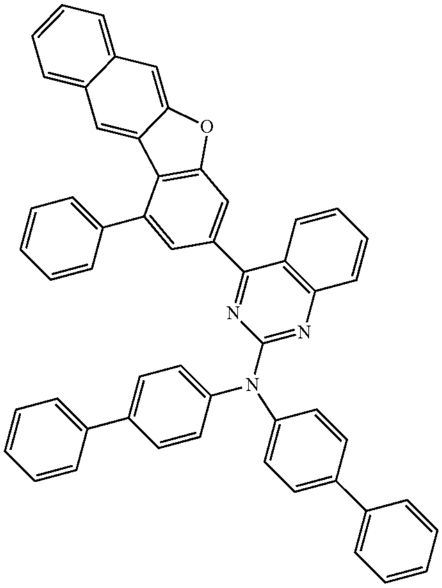
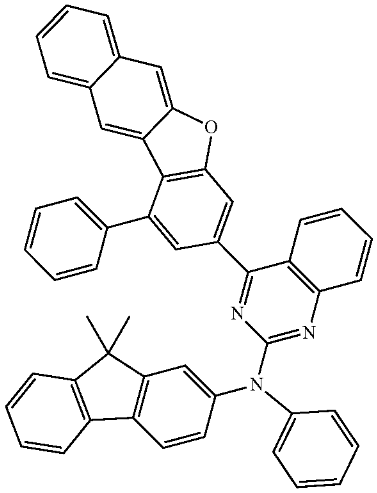
139
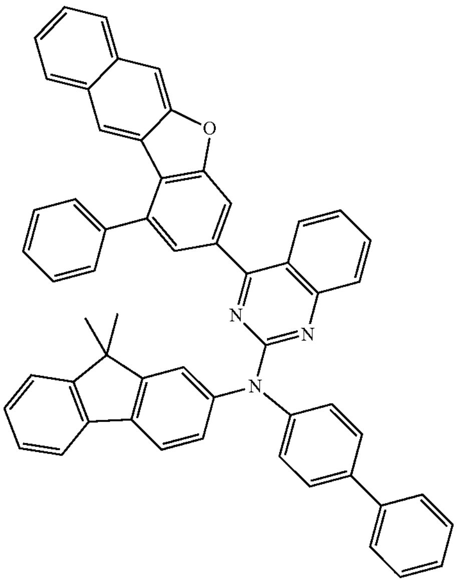

-continued
140
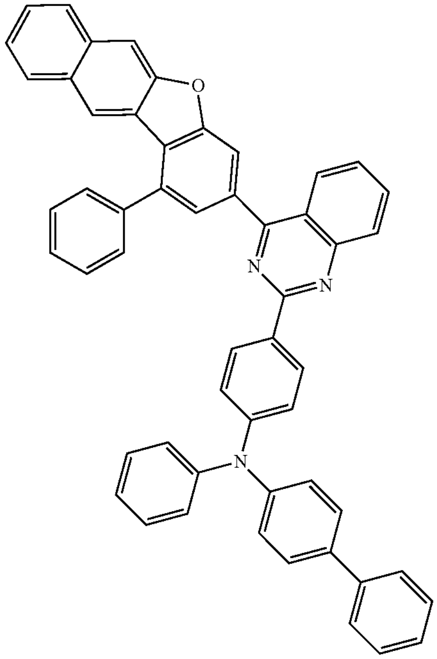
141
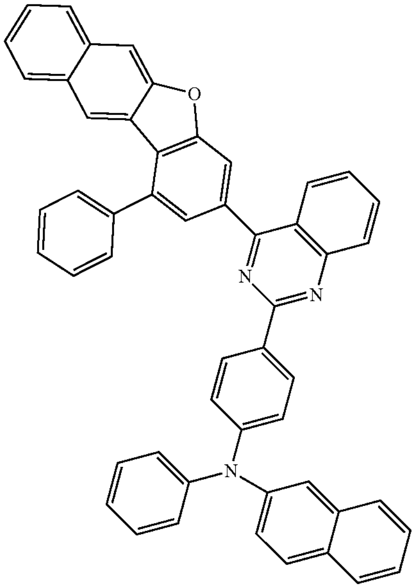
-continued
142
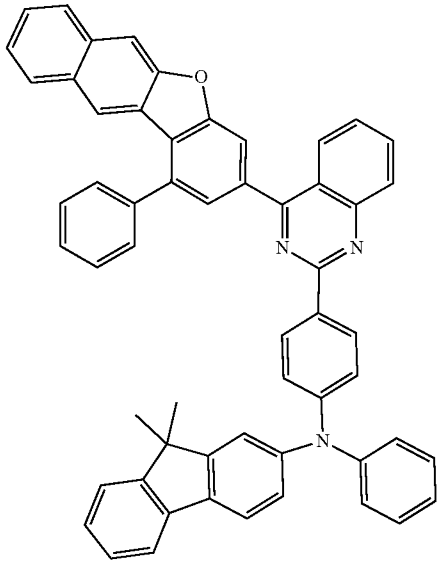
143
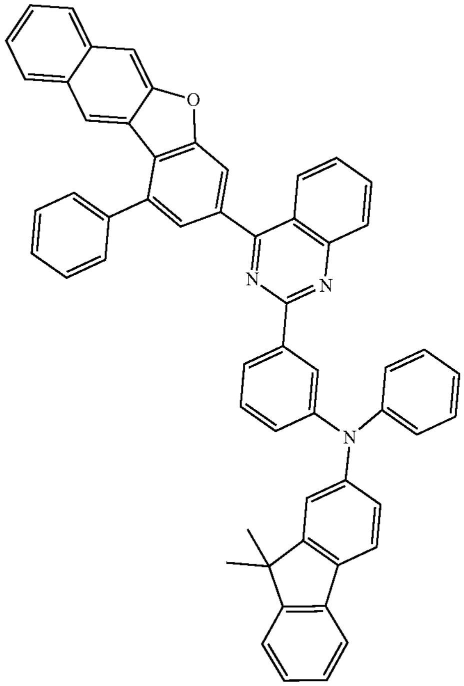

-continued
144
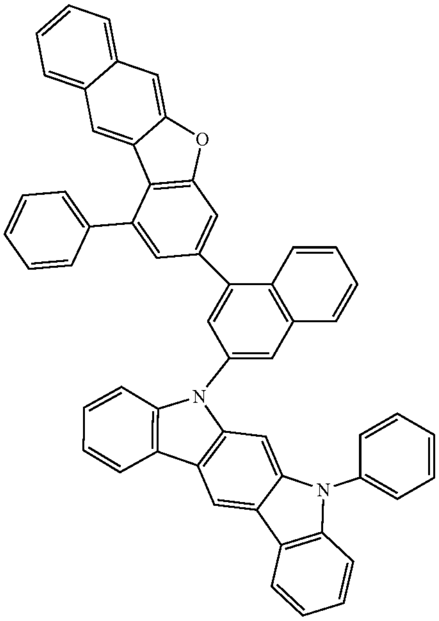
145
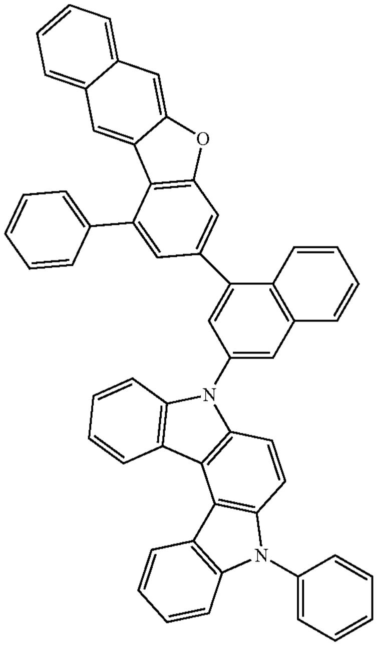
-continued
146
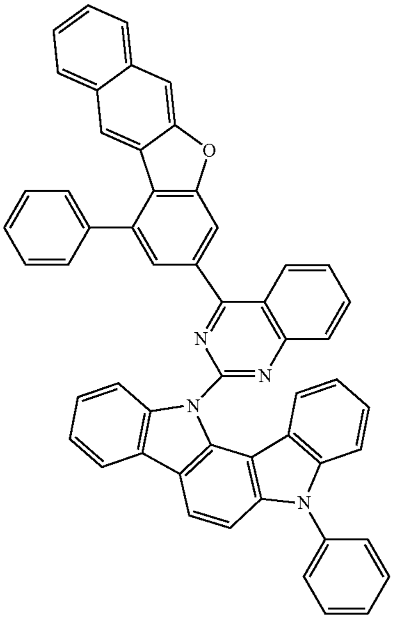
147
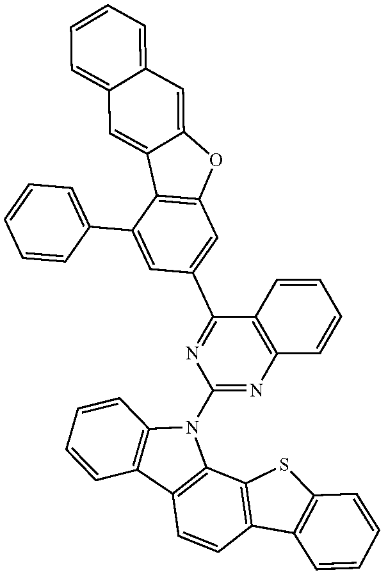

-continued
148
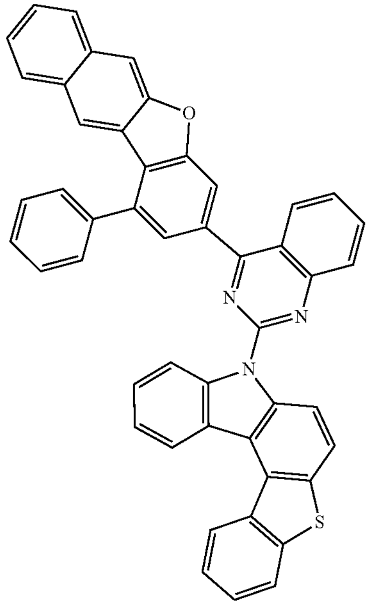
149
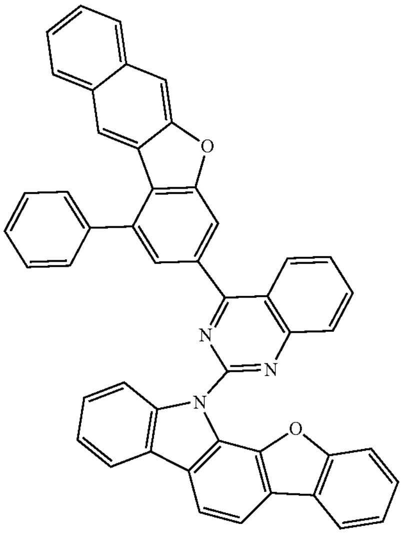
-continued
150
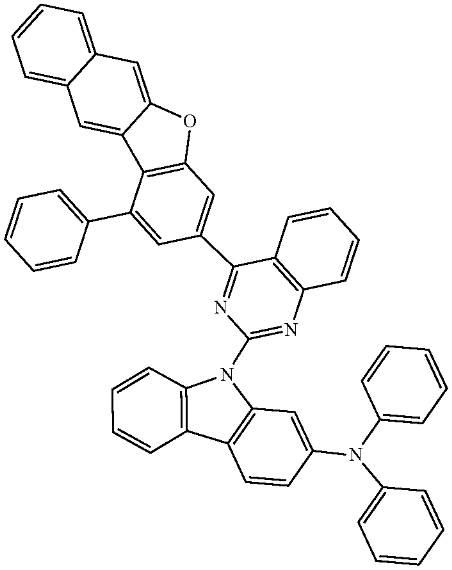
151
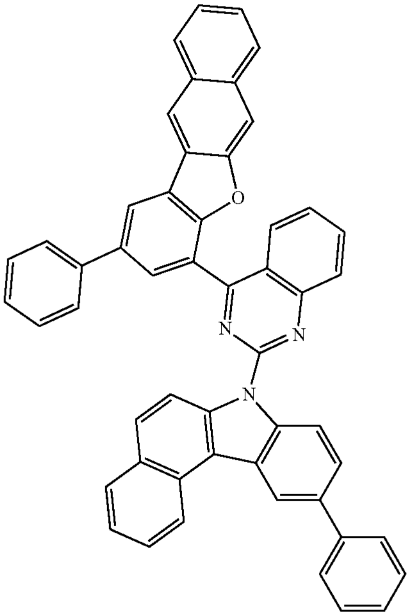

-continued
152
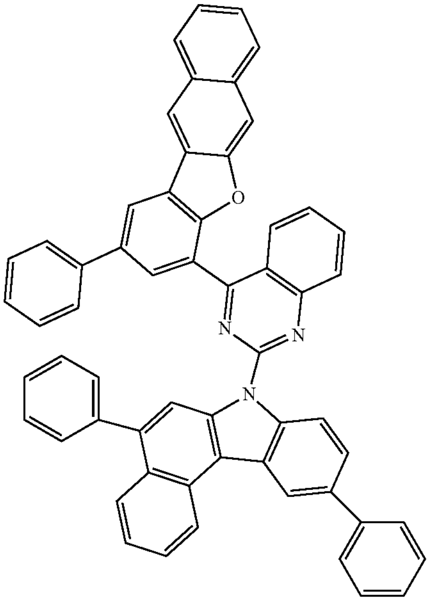
153
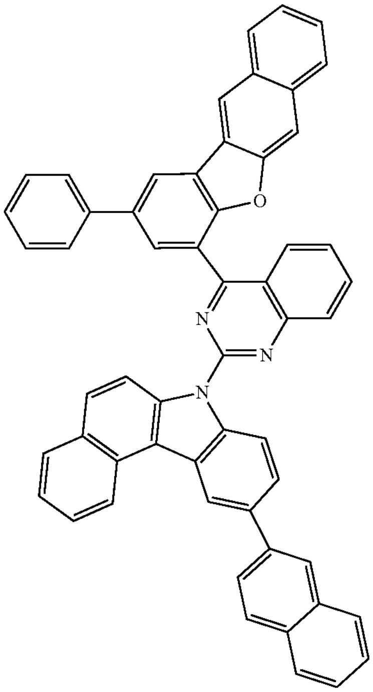
-continued
154
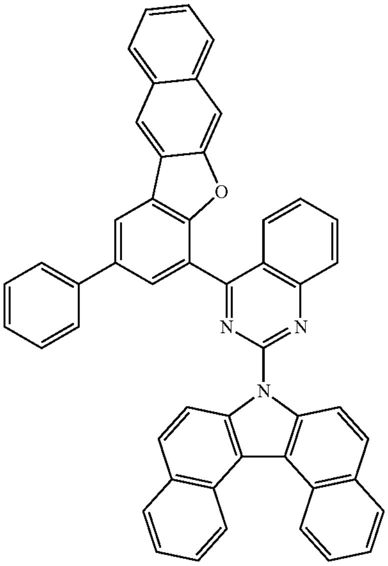
155
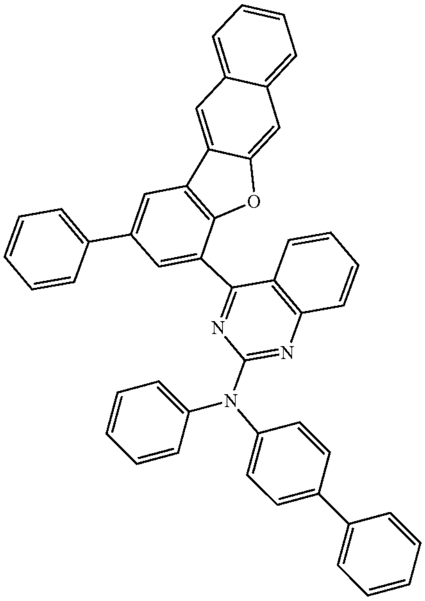
156
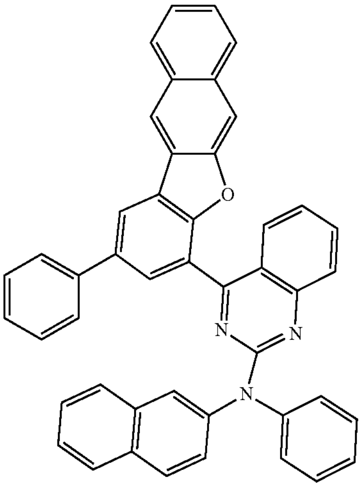

-continued
157
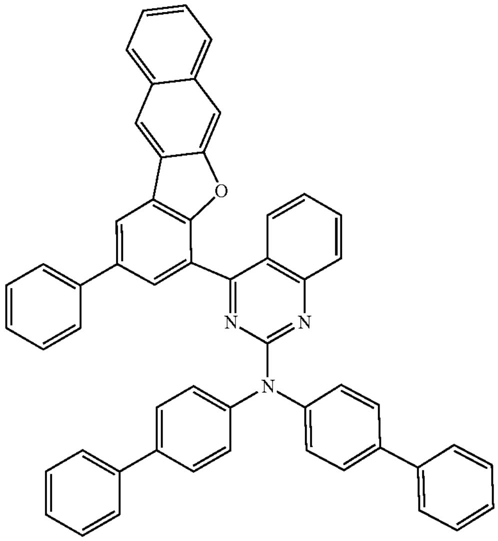
158
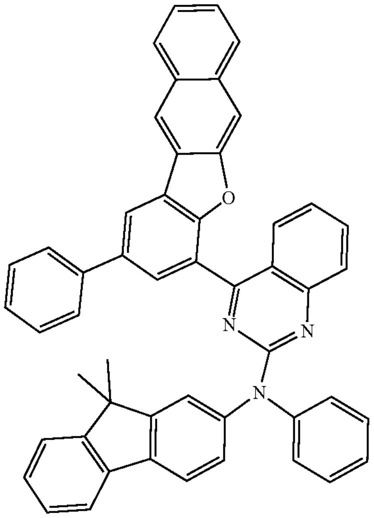
159
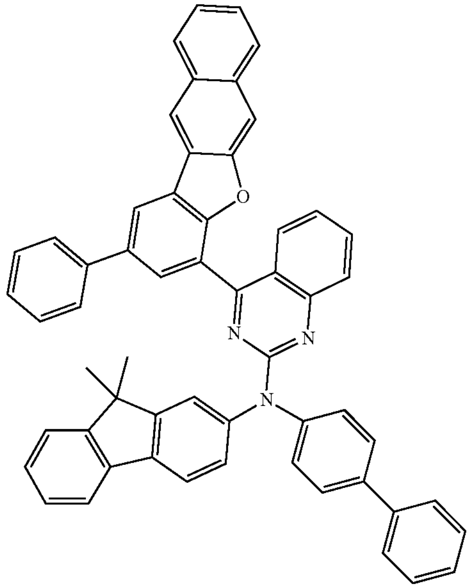
-continued
160
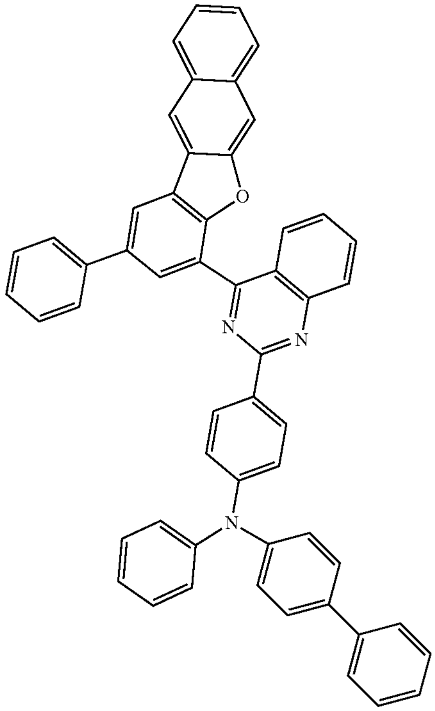
161
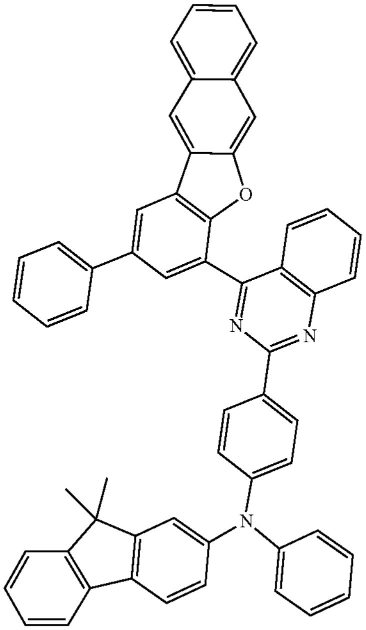

-continued
162
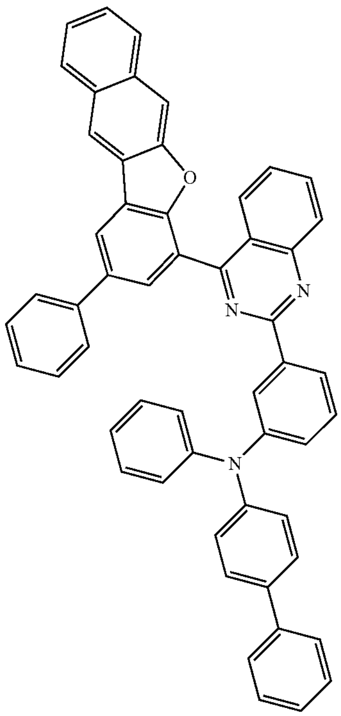
163
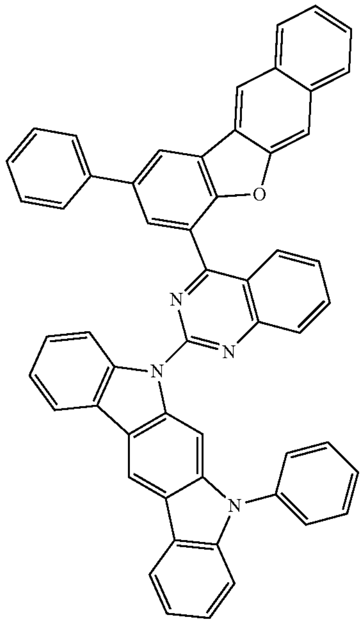
-continued
164
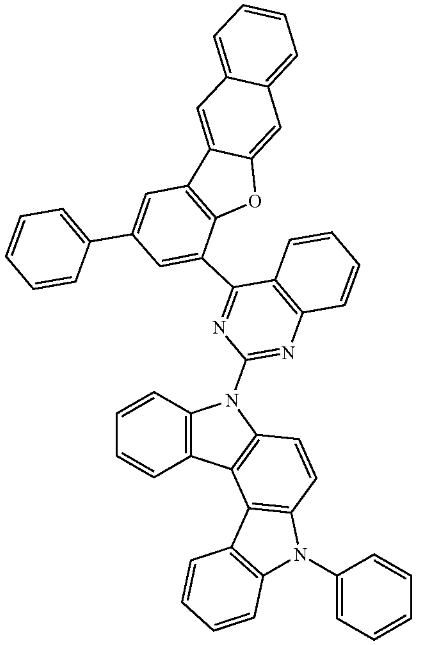
165
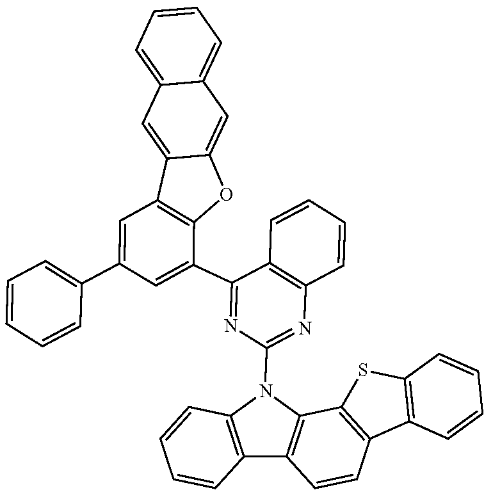

-continued
166
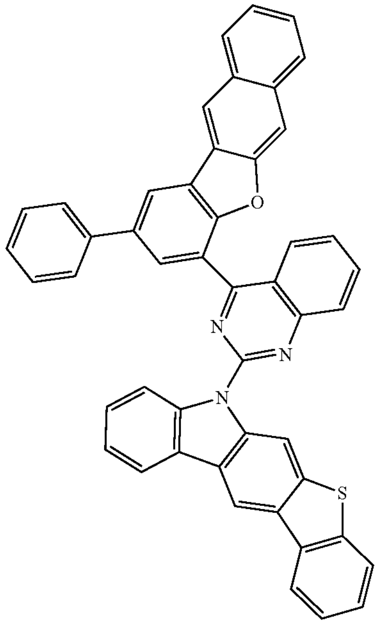
167
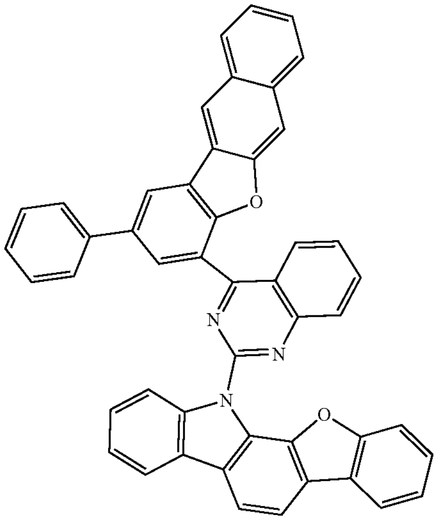
-continued
168
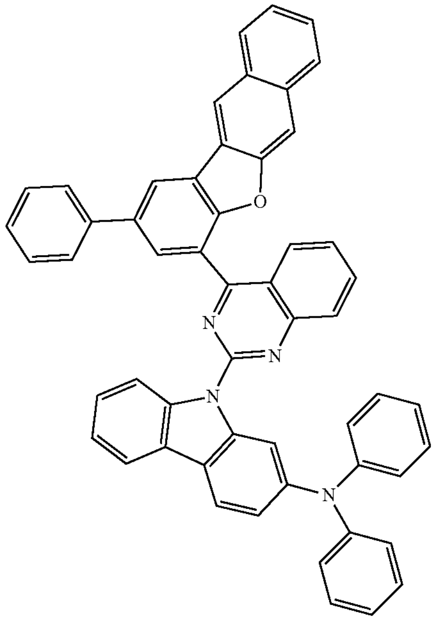
169
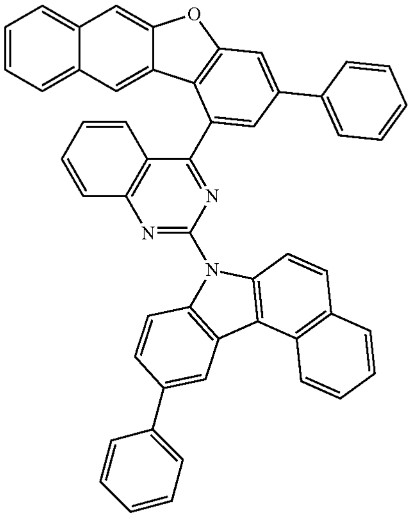
170
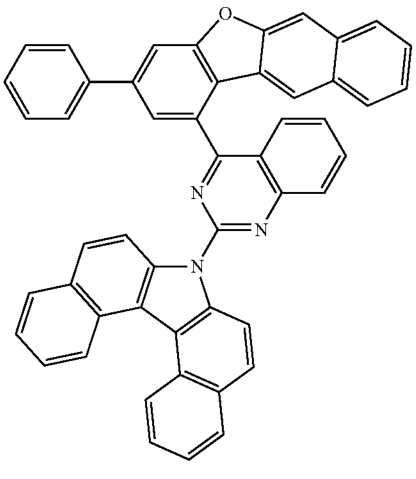

-continued
171
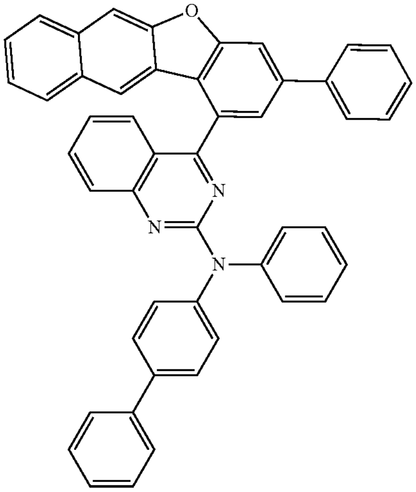
172
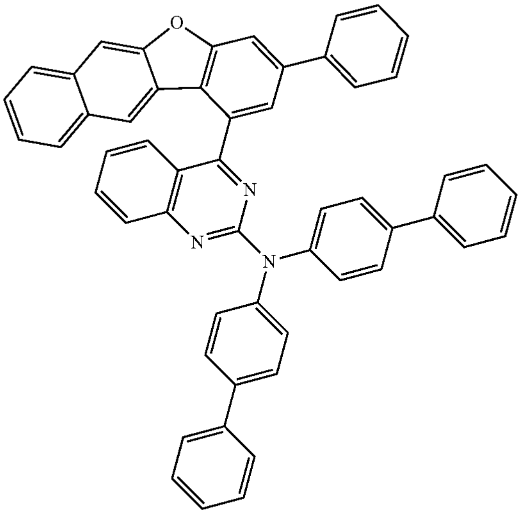
173
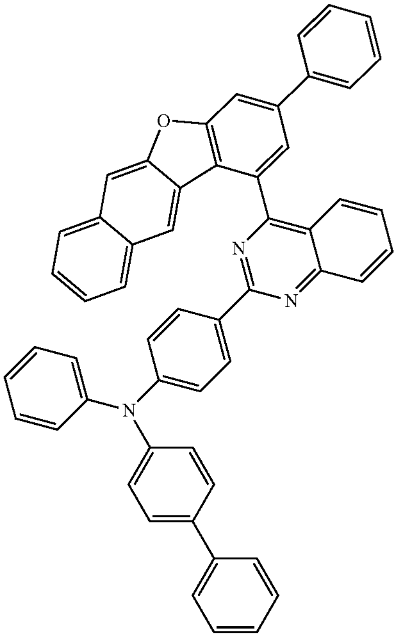
-continued
174
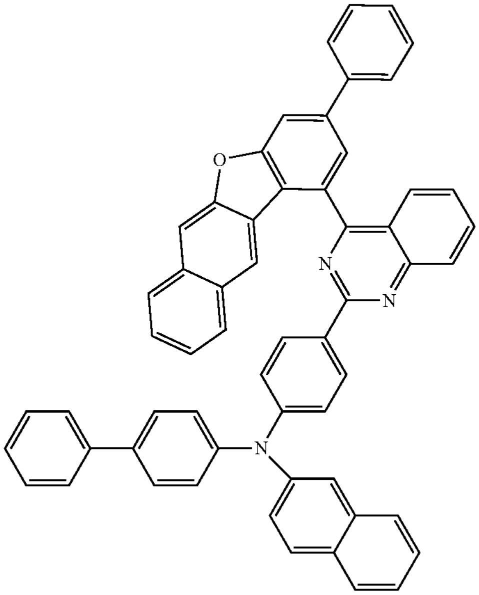
175
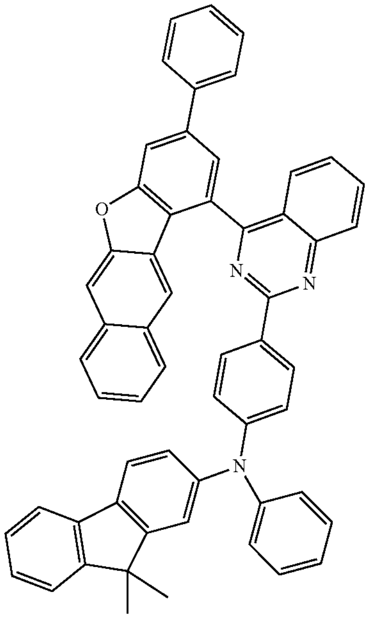

-continued
176
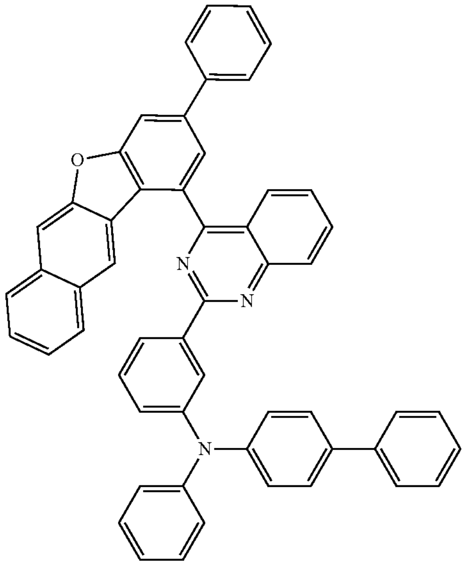
177
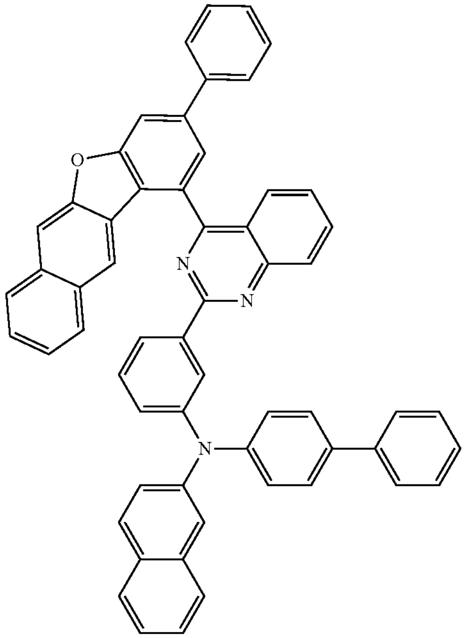
-continued
178
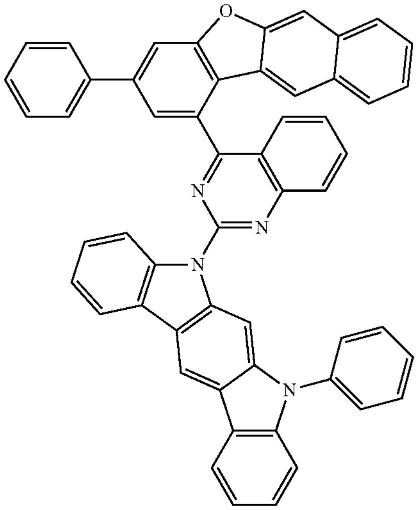
179
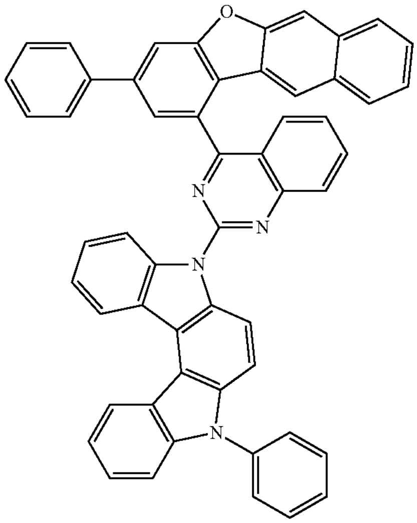
180
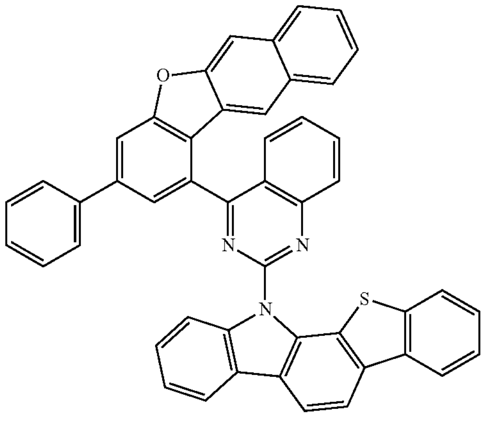

181
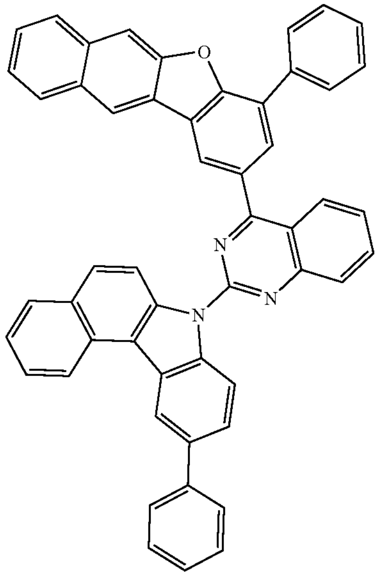
182
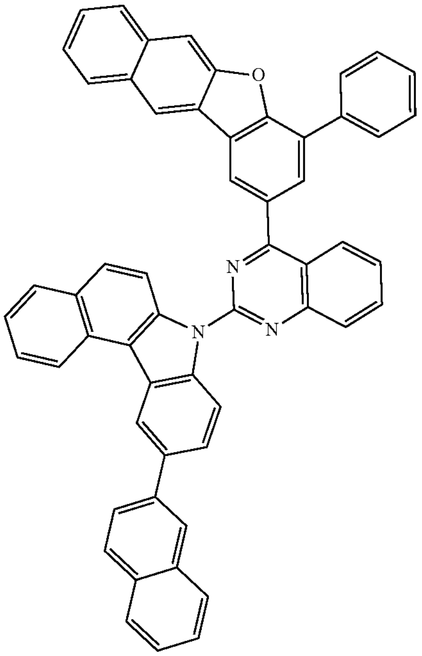
183
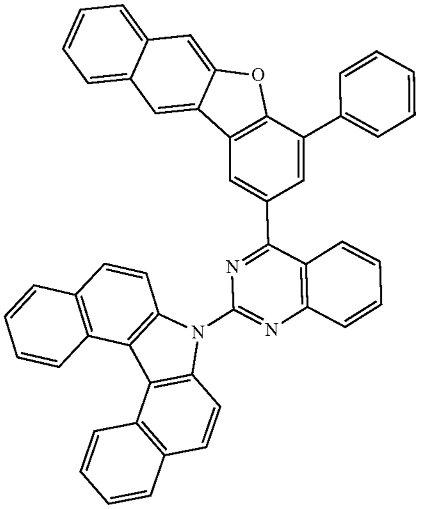
184
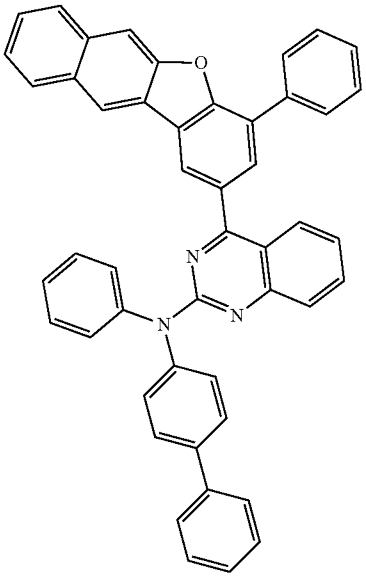
185
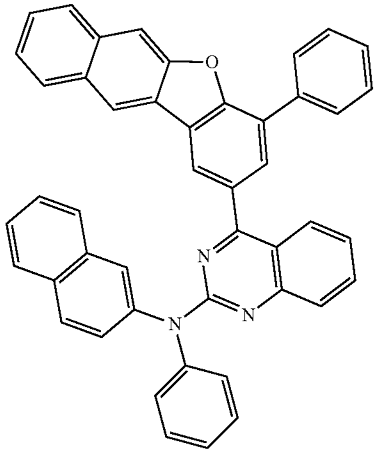

-continued
186
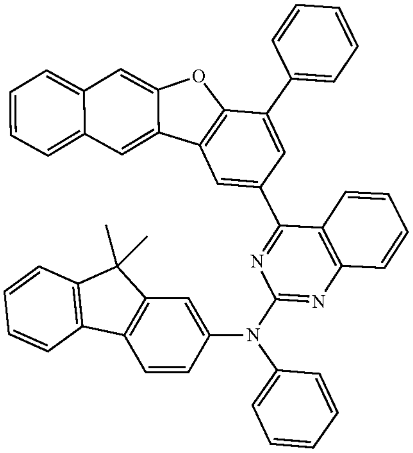
187
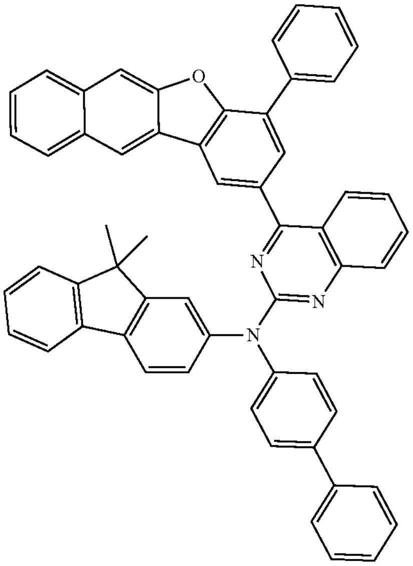
-continued
188
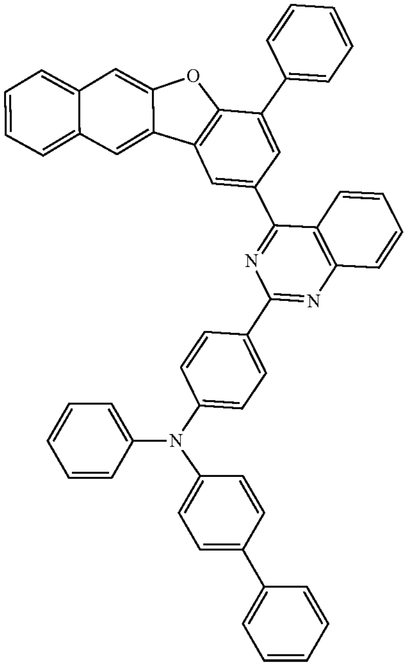
189
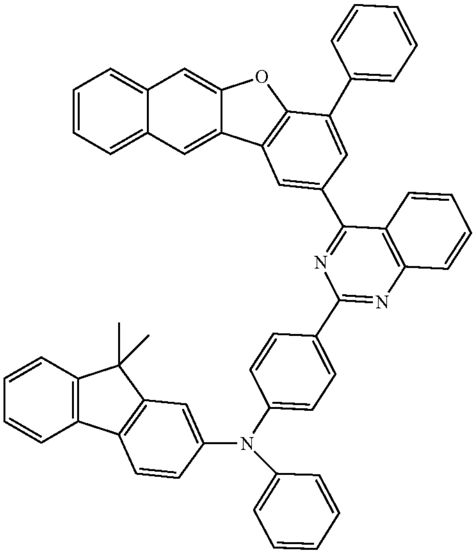

-continued
190
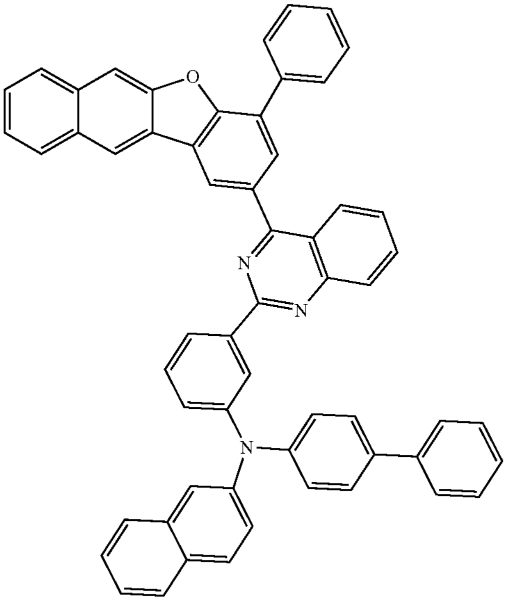
191
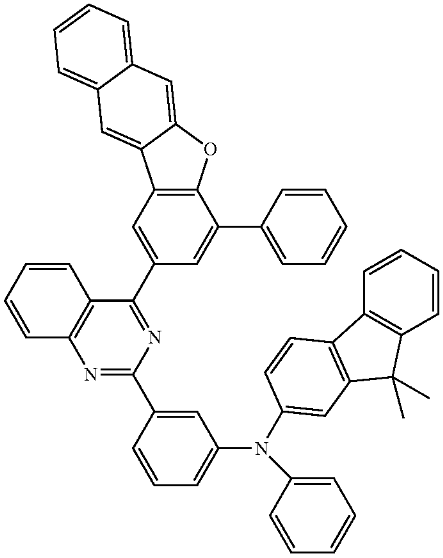
-continued
192
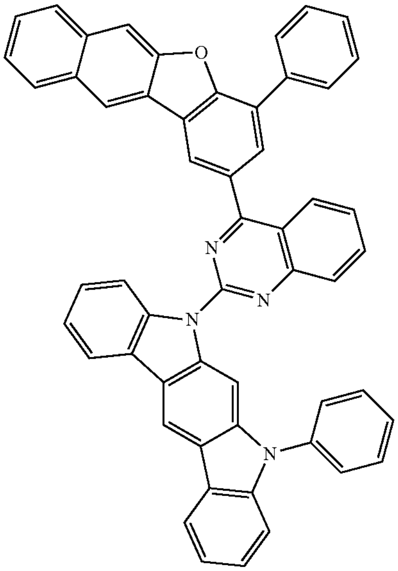
193
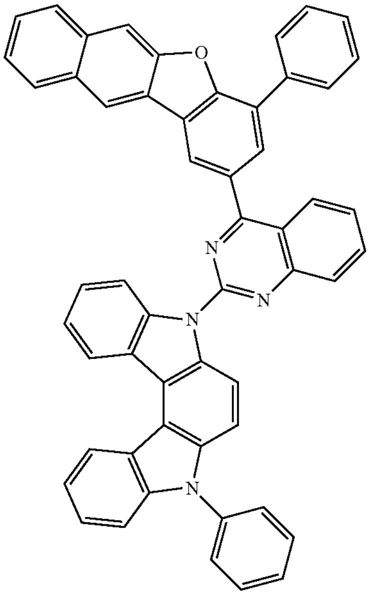
194
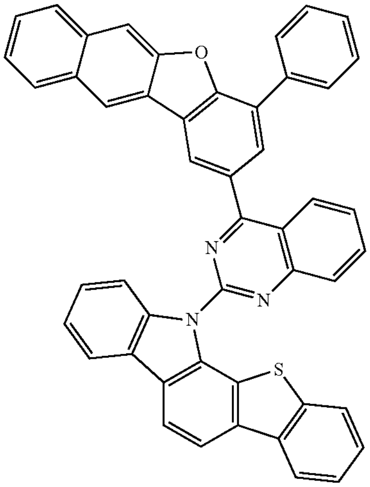

195
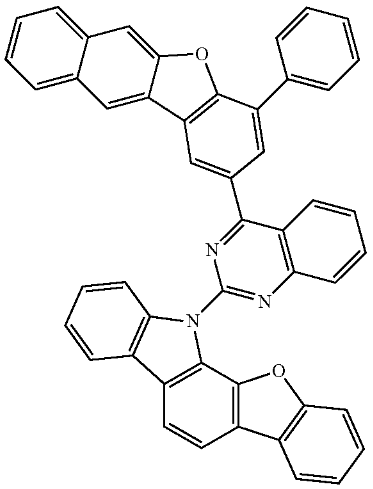
196
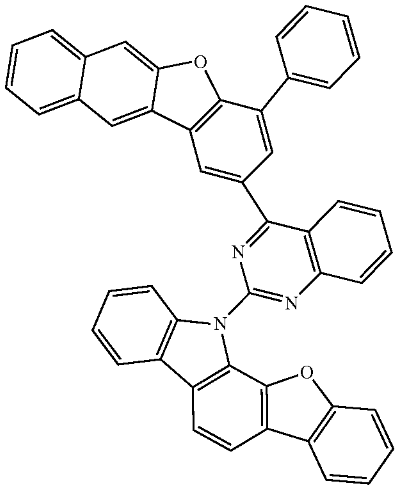
197
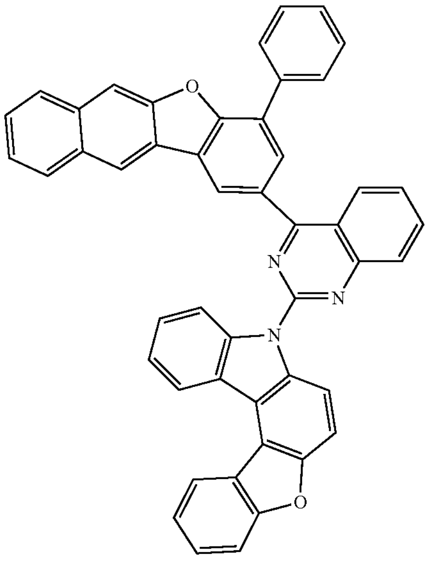
198
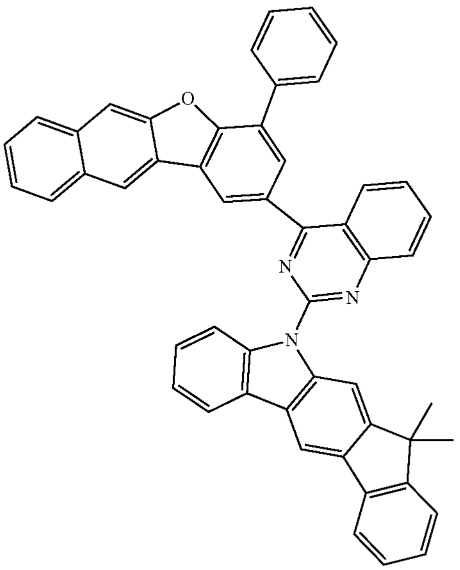
199
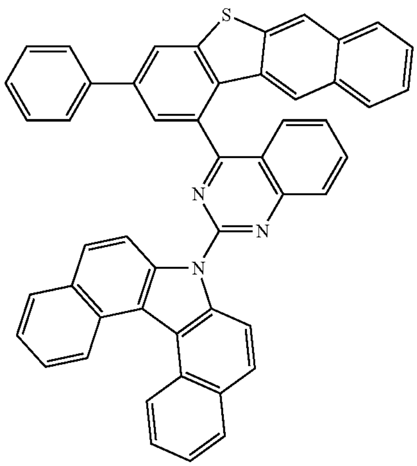

-continued
200
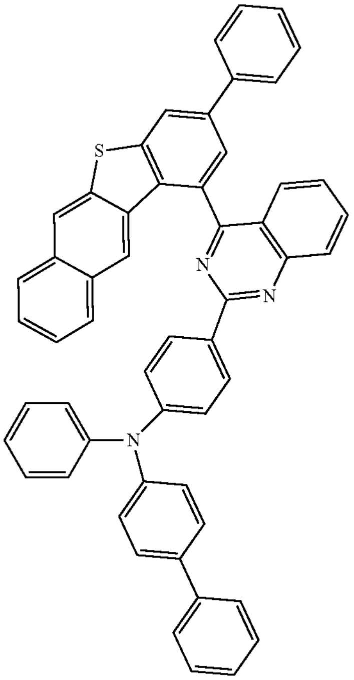
201
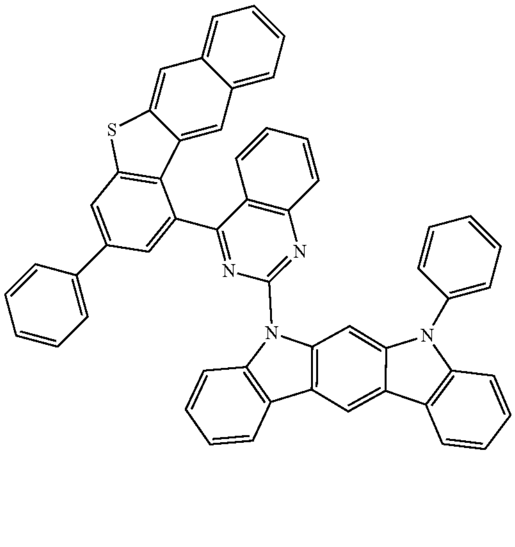
-continued
202
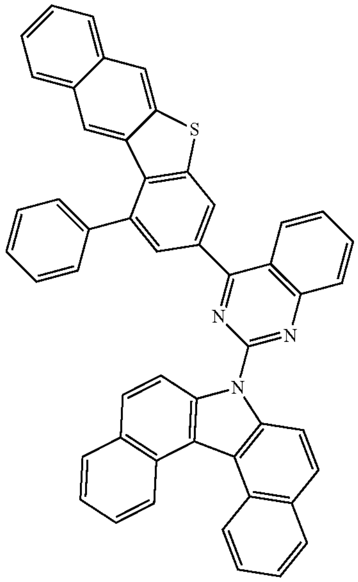
203
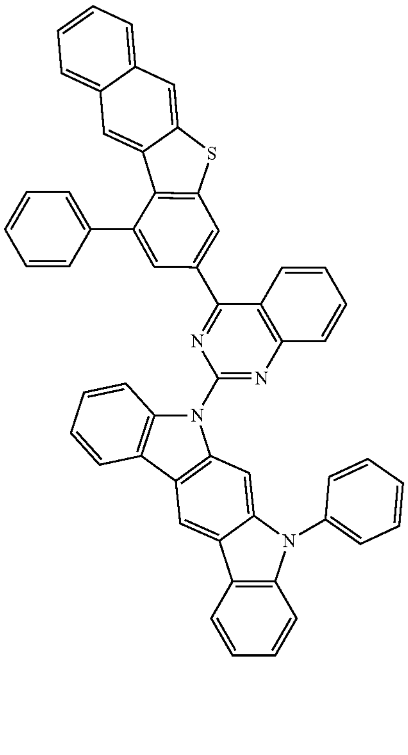

-continued
204
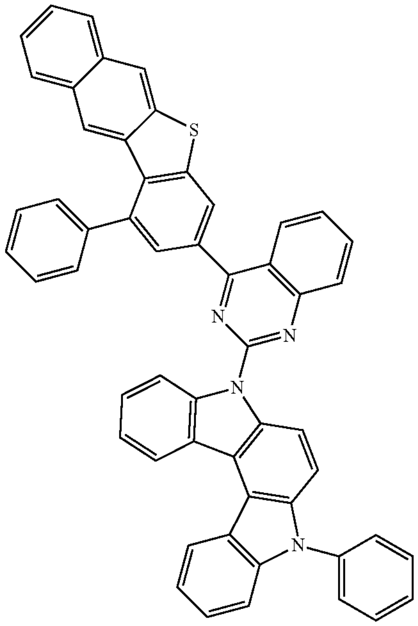
205
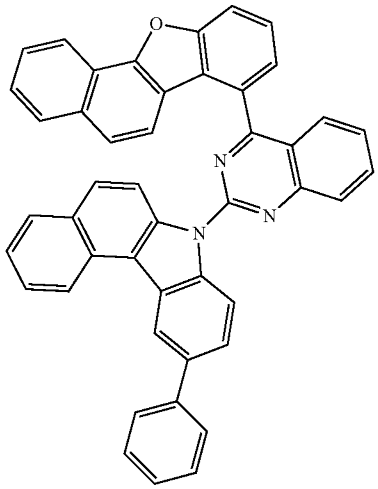
206
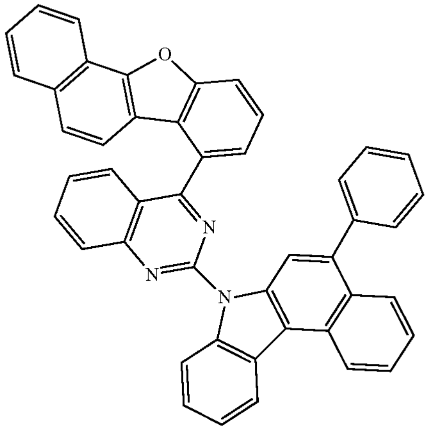
-continued
207
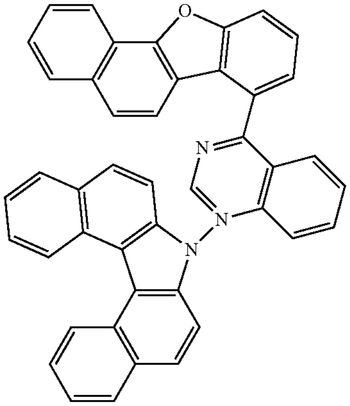
208
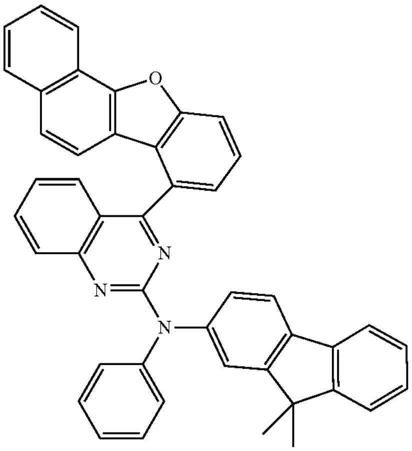
209
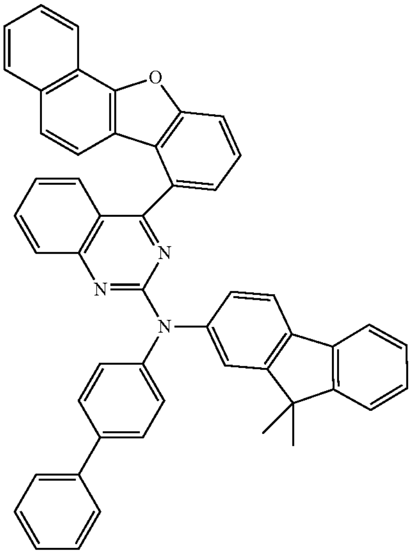

-continued
210
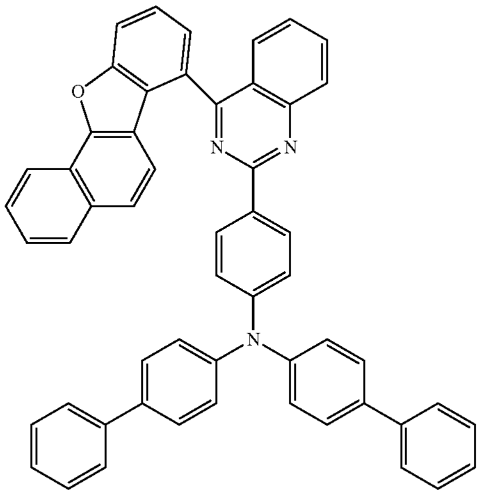
211
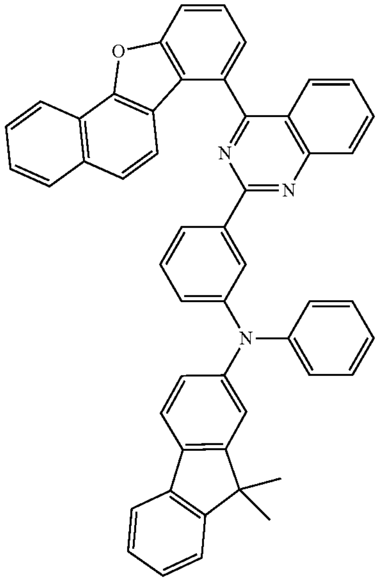
212
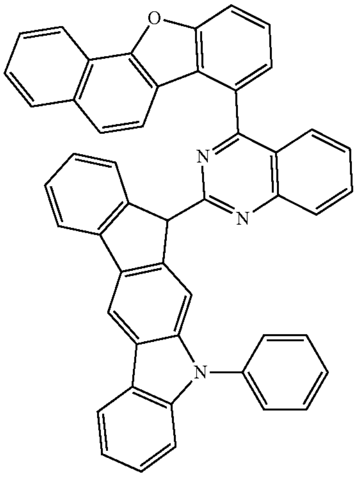
-continued
213
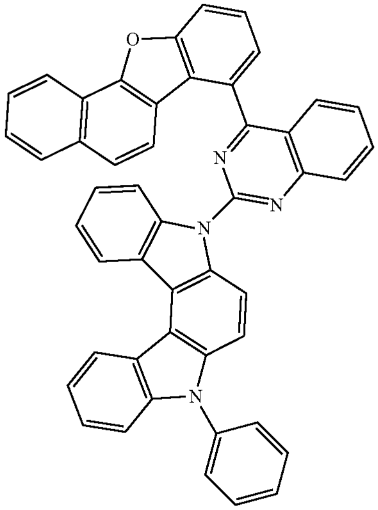
214
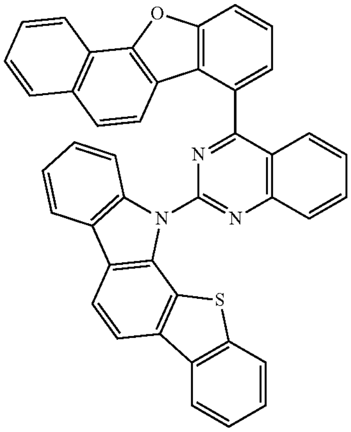
215
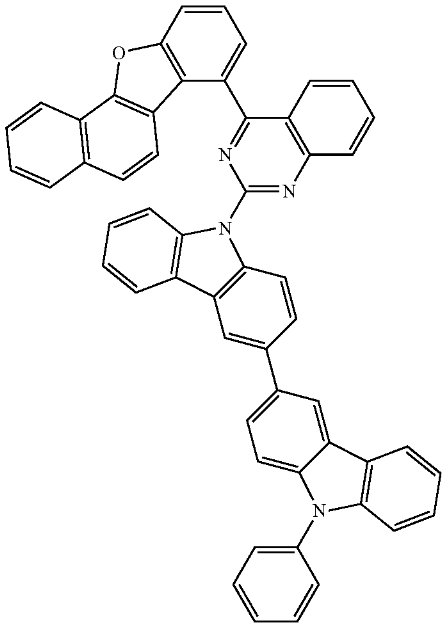

-continued
216
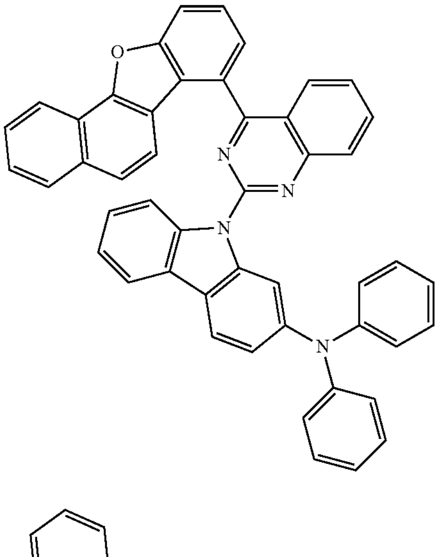
217
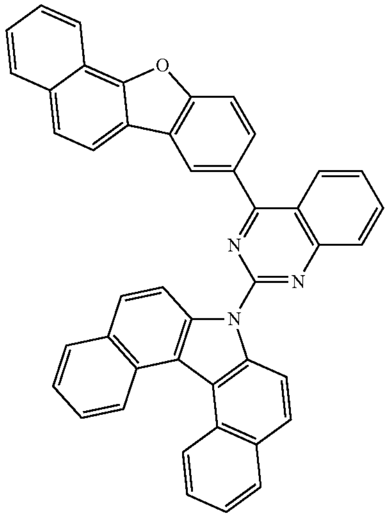
218
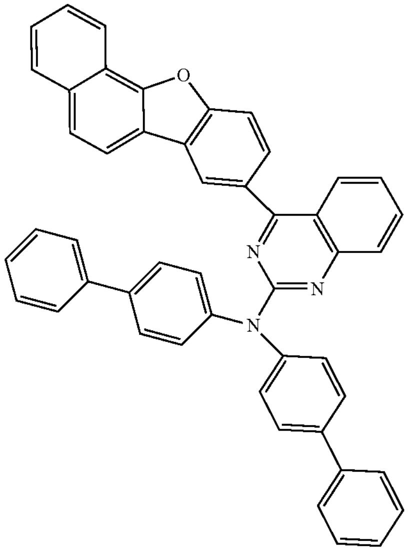
-continued
219
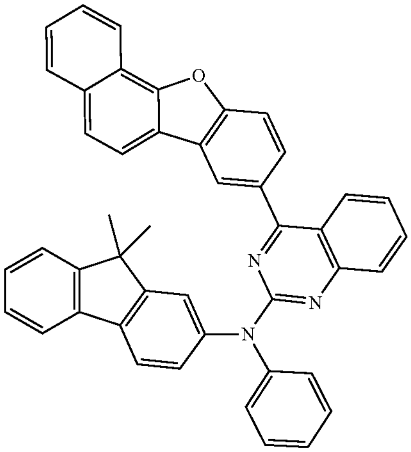
220
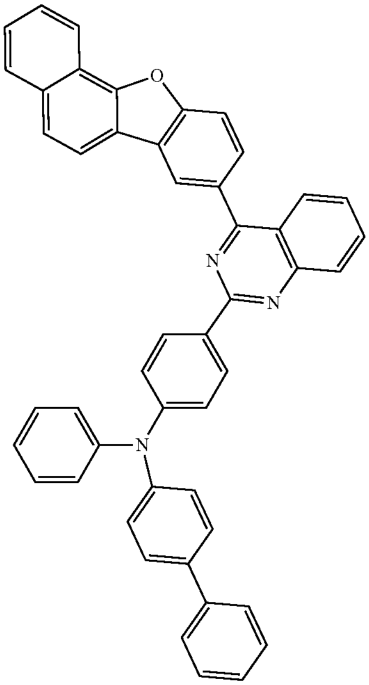

-continued
221
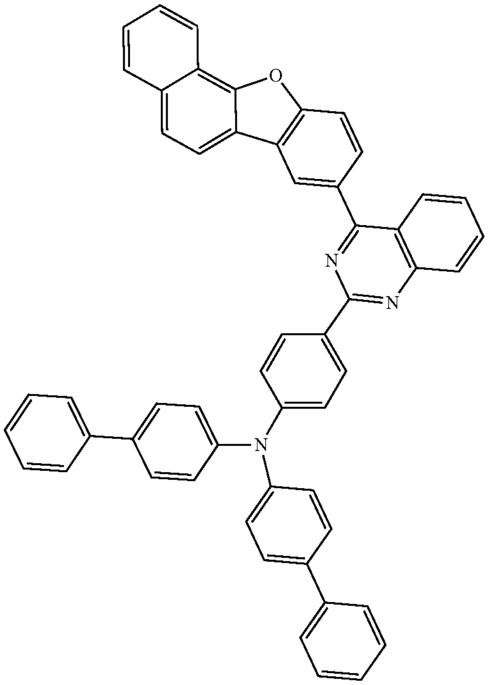
222
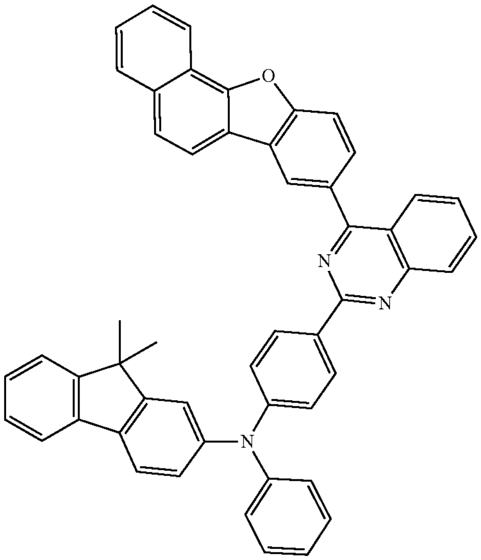
-continued
223
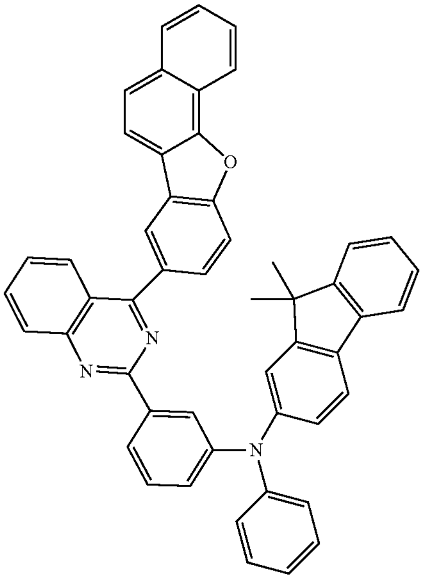
224
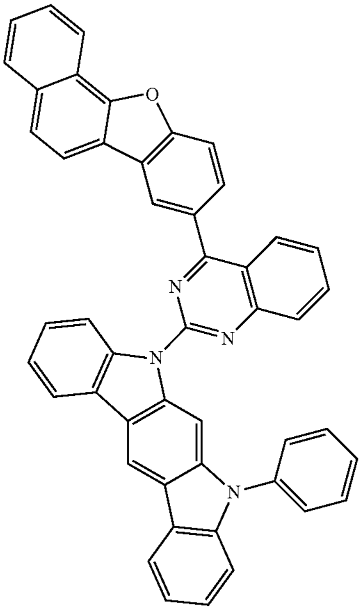

-continued
225
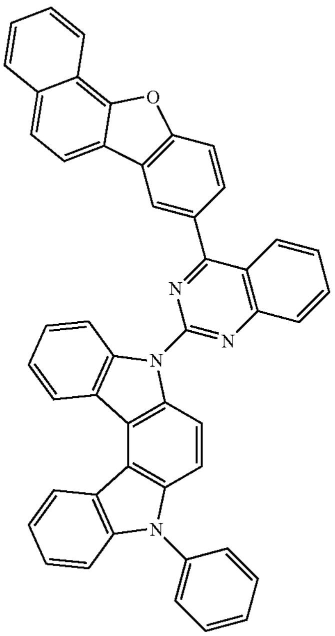
226
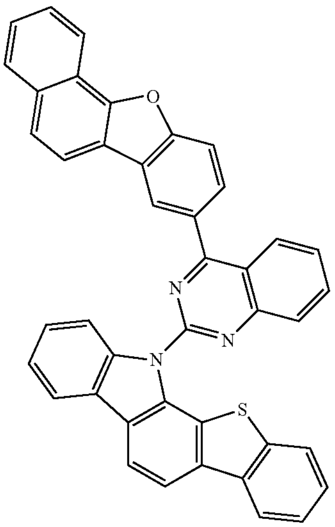
-continued
227
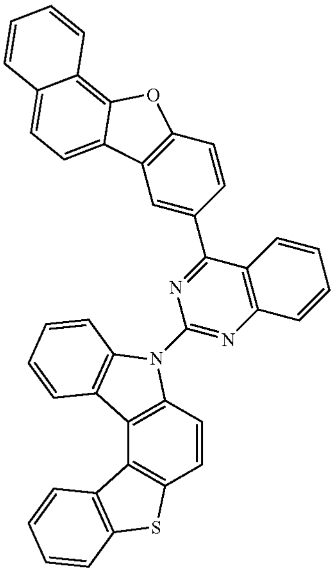
228
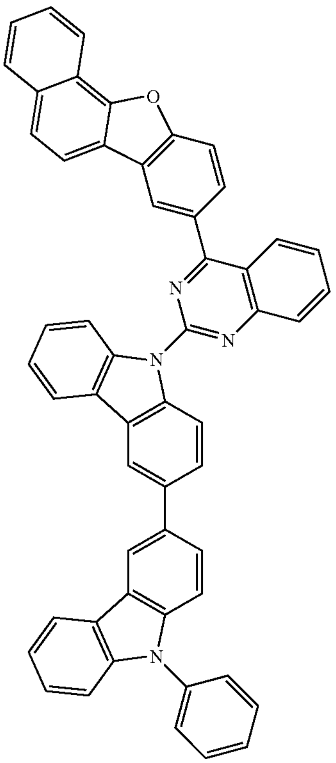

-continued
229
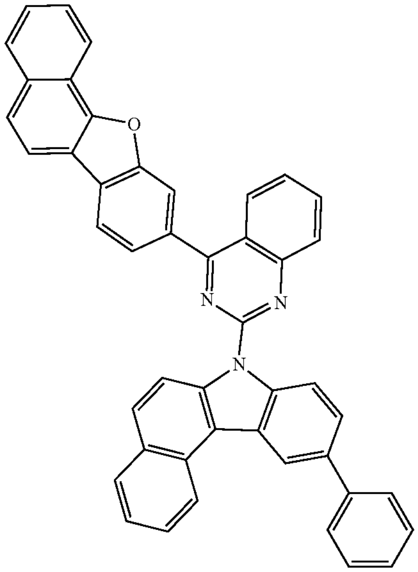
230
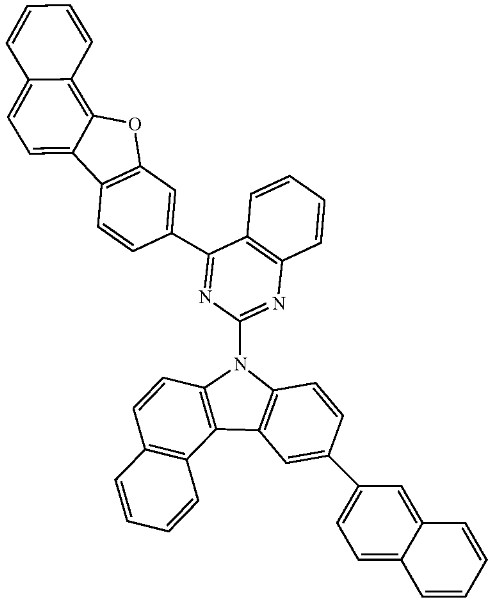
-continued
231
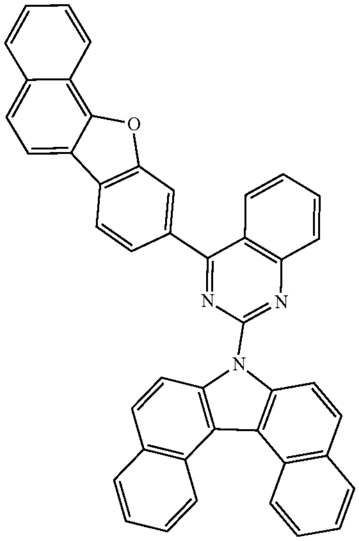
232
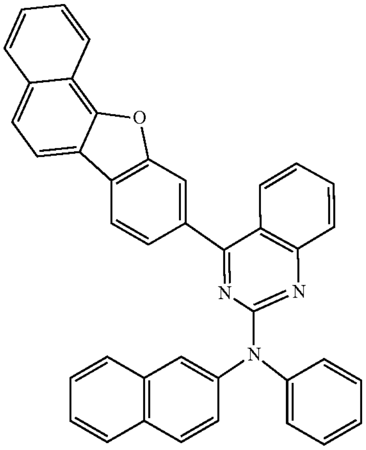
233
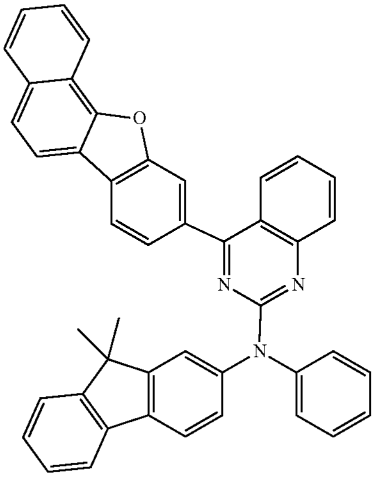

-continued
234
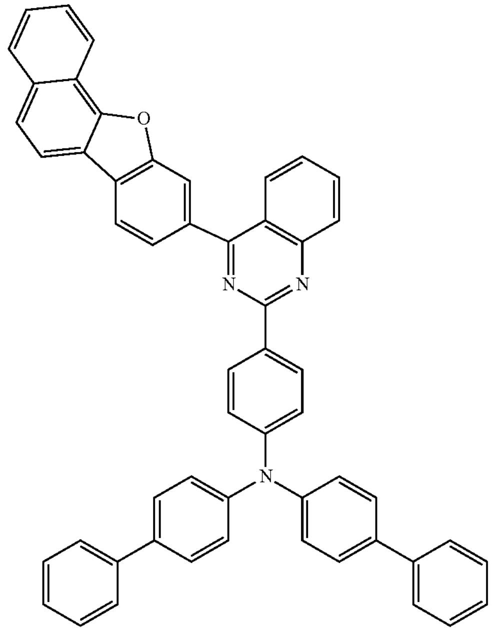
235
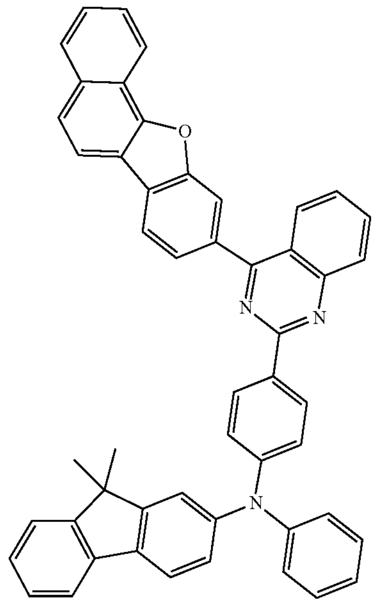
-continued
236
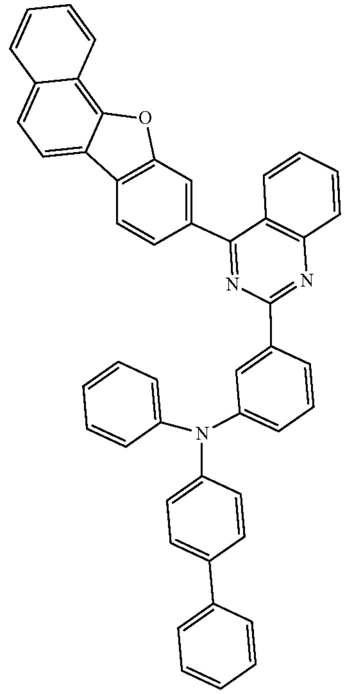
237
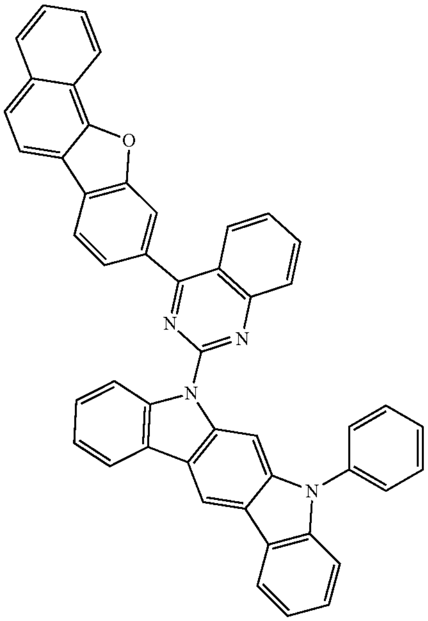

238
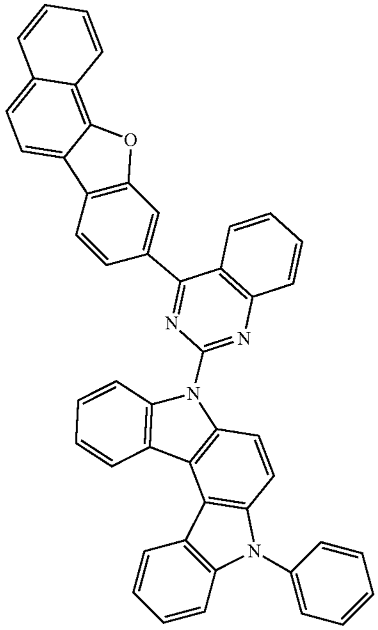
239
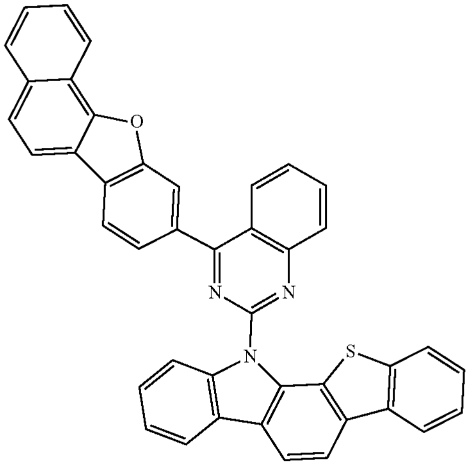
240
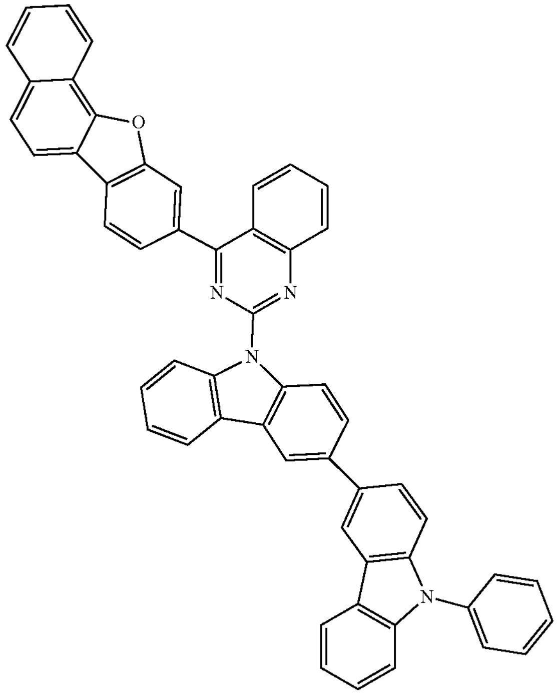
241
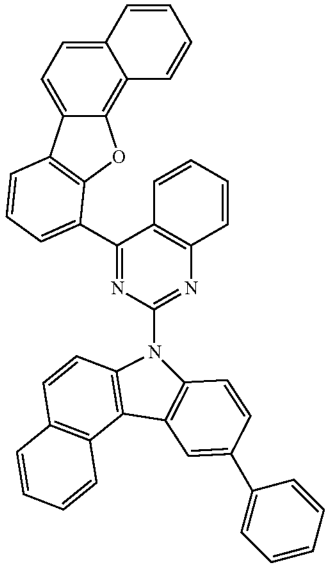

242
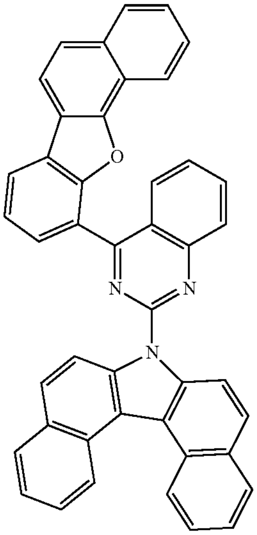
243
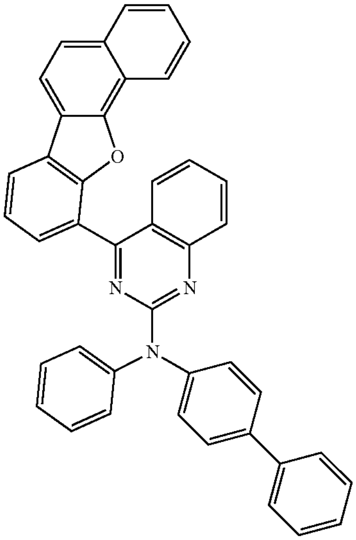
244
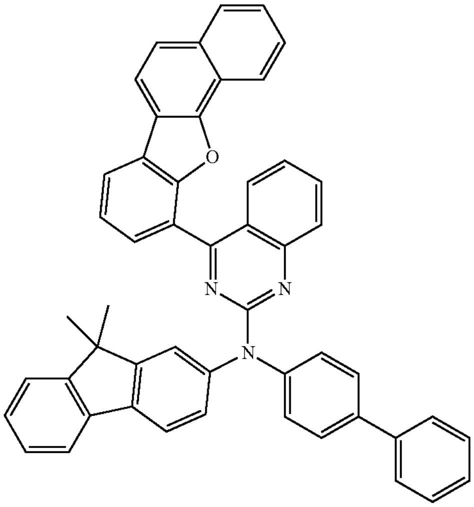
245
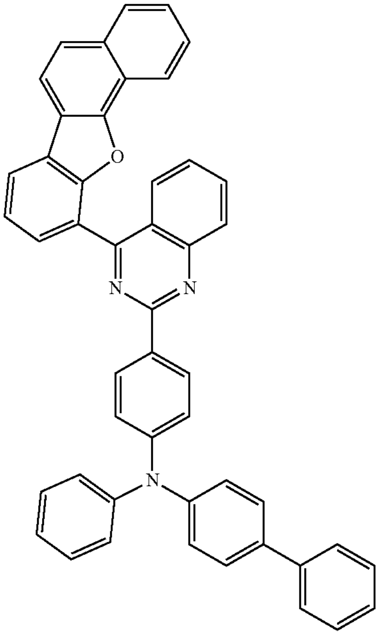
246
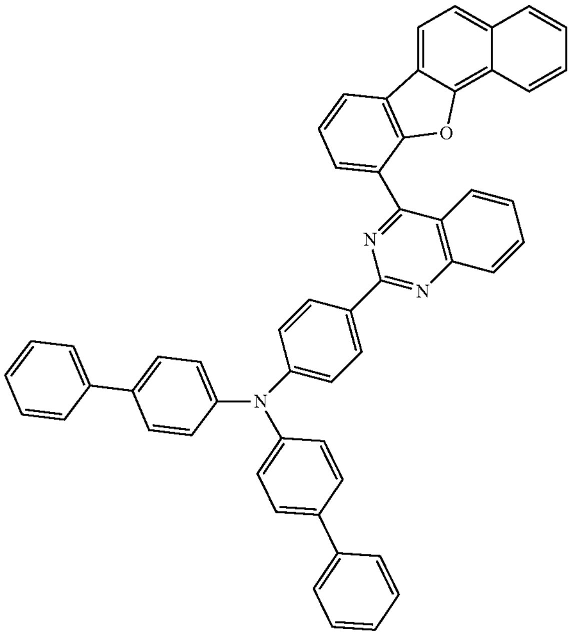

-continued
247
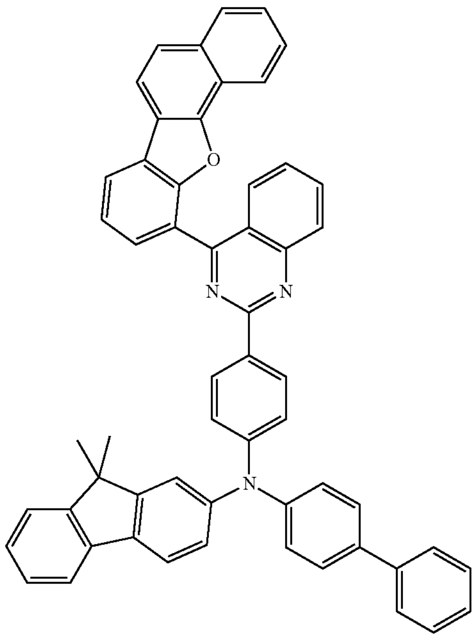
248
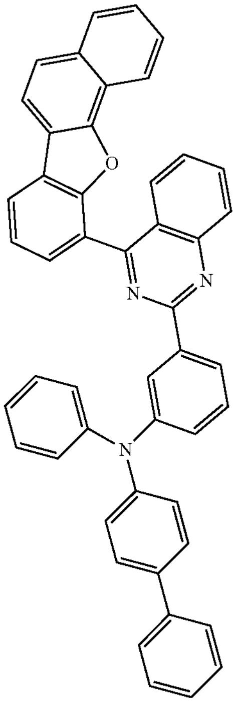
-continued
249
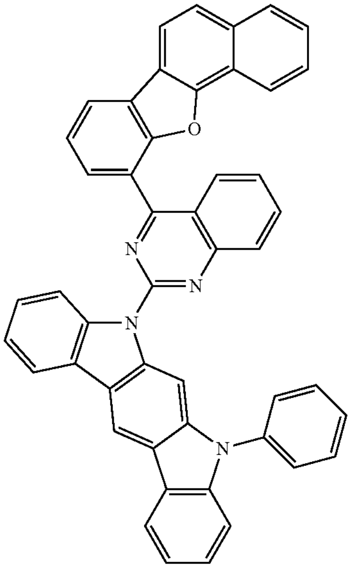
250
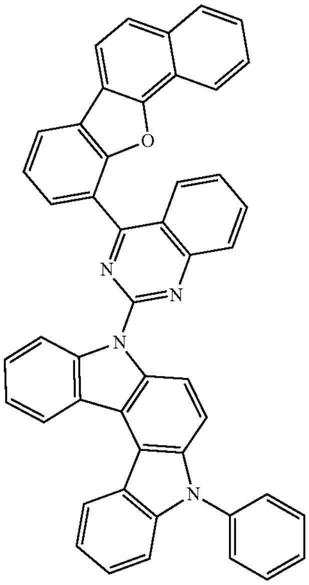
251
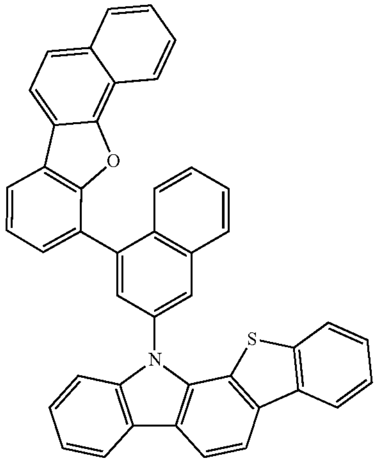

-continued
252
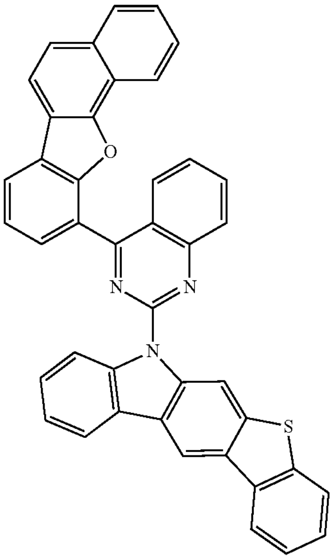
253
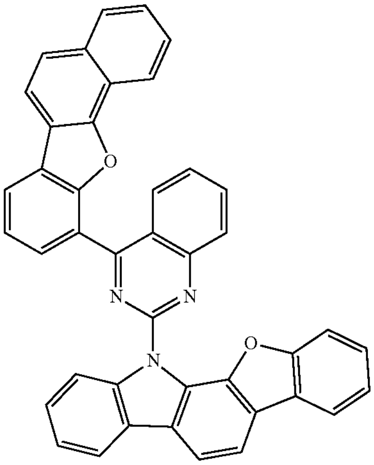
254
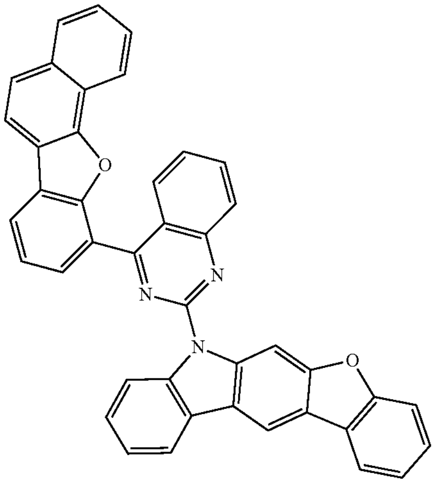
-continued
255
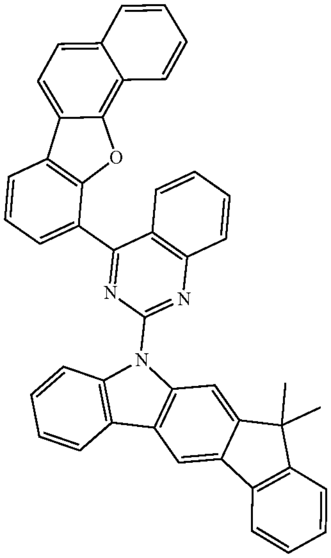
256
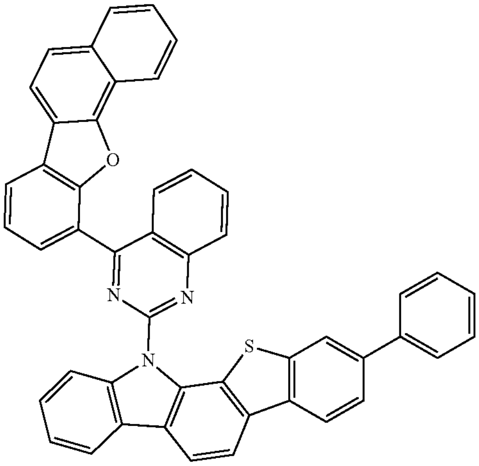

-continued
257
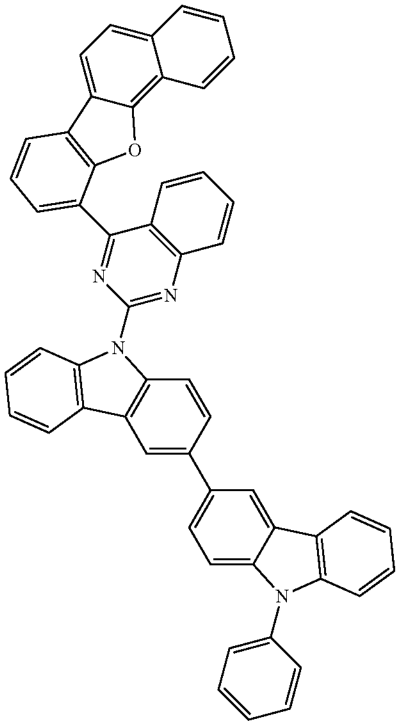
258
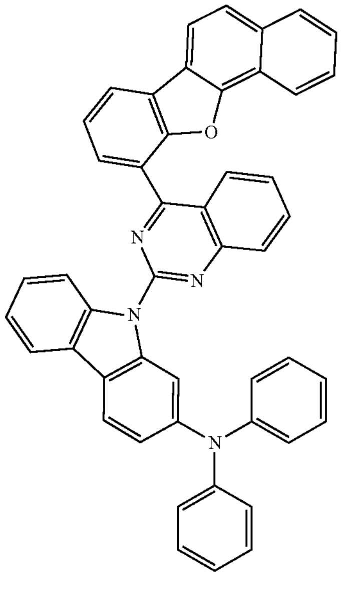
-continued
259
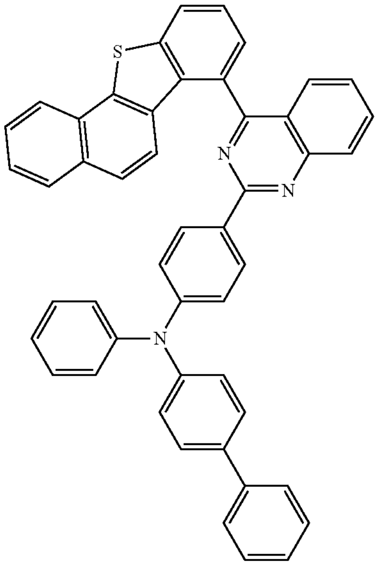
260
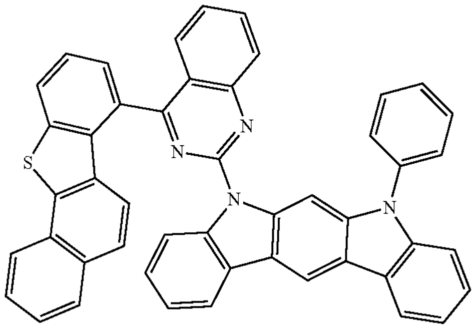
261
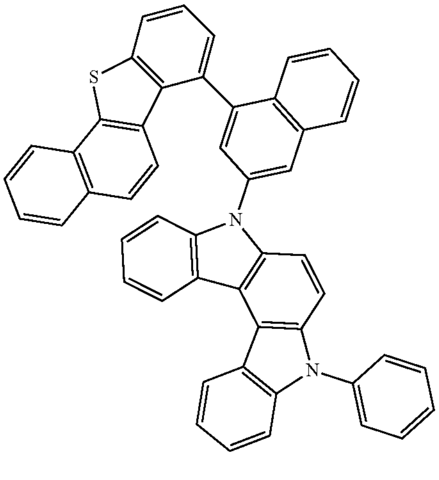

-continued
262
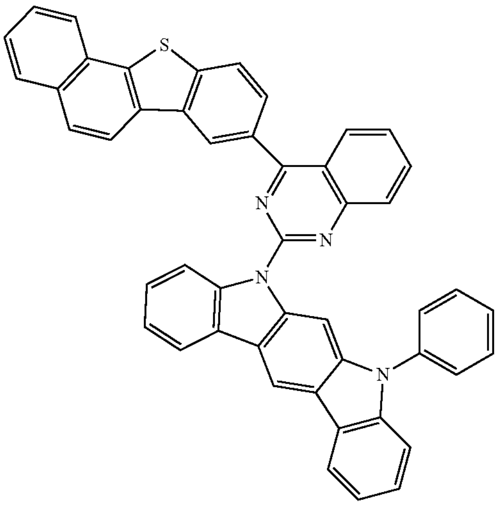
263
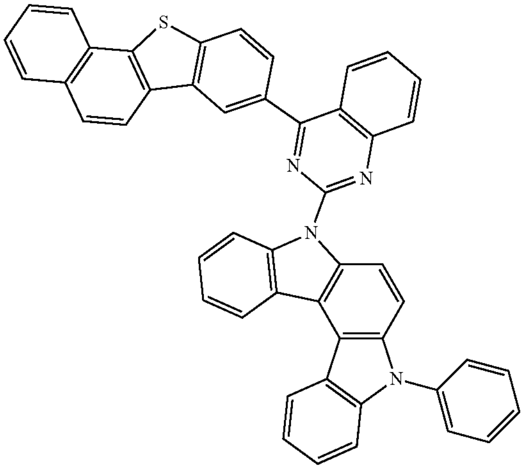
264
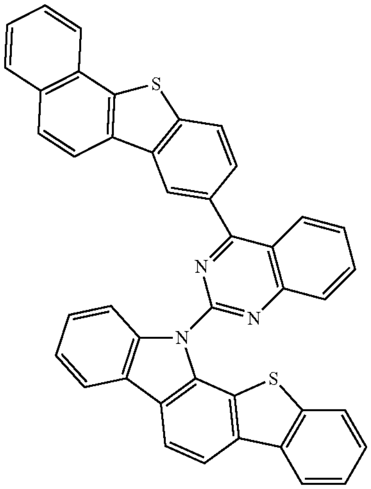
-continued
265
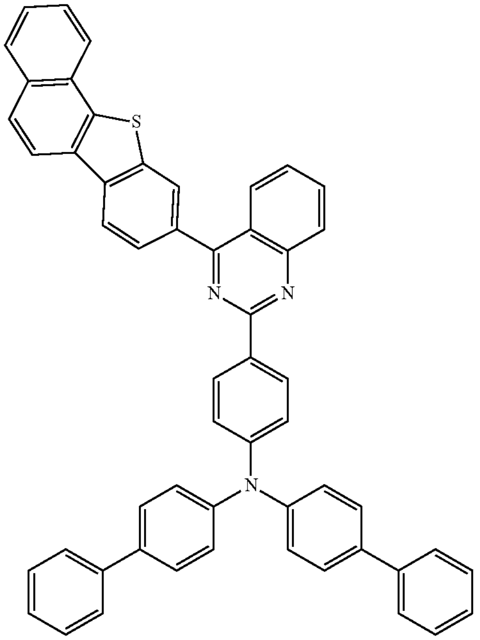
266
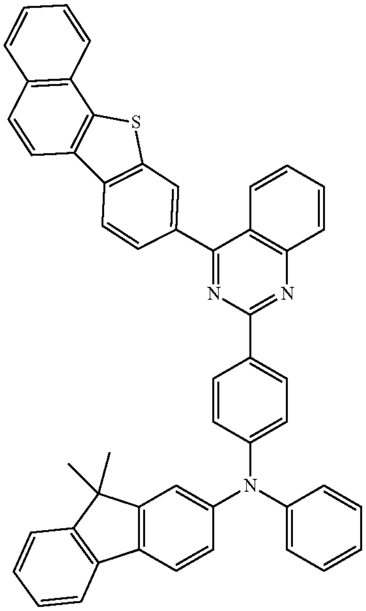

-continued
267
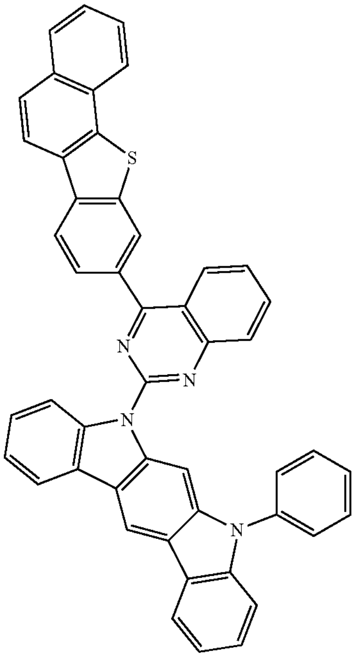
268
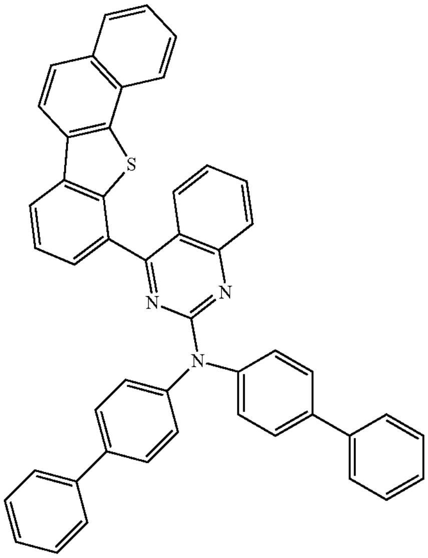
-continued
269
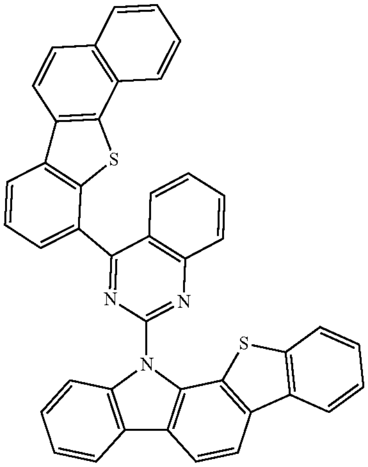
270
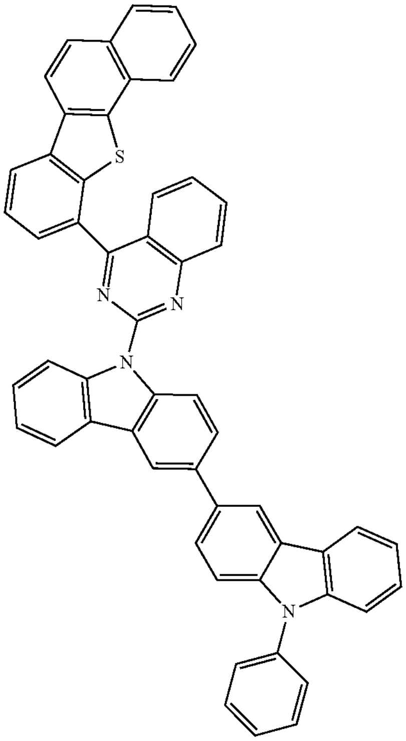

-continued
271
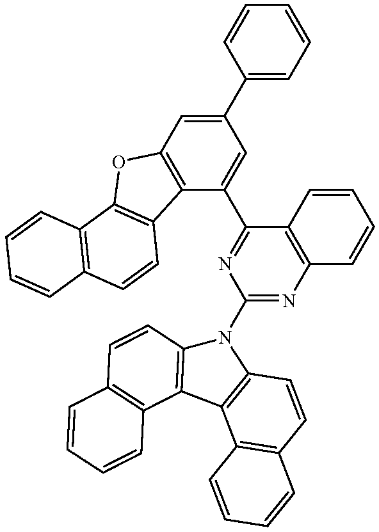
272
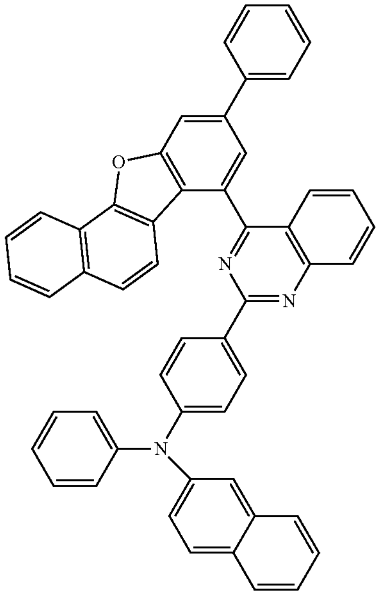
-continued
273
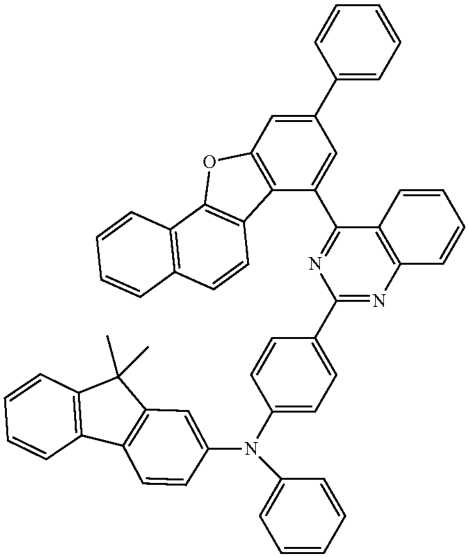
274
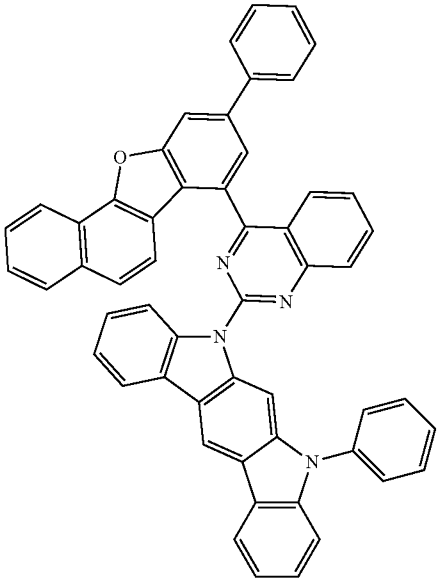

-continued
275
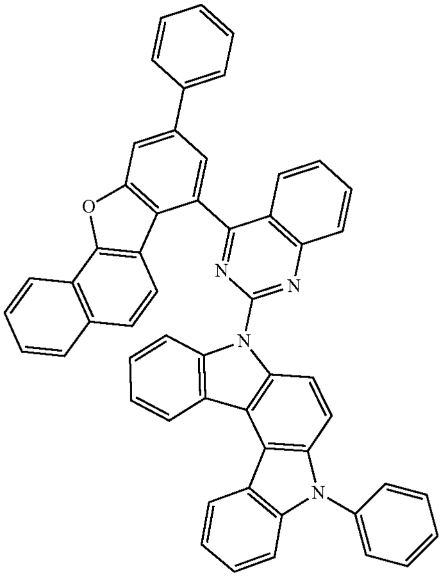
276
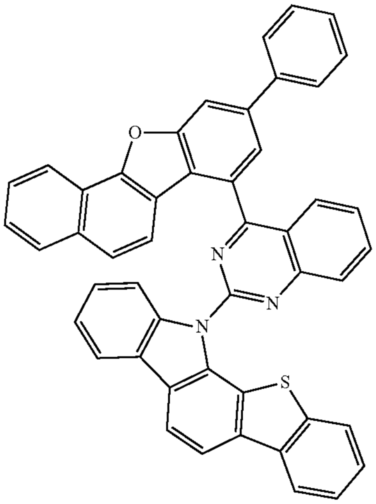
277
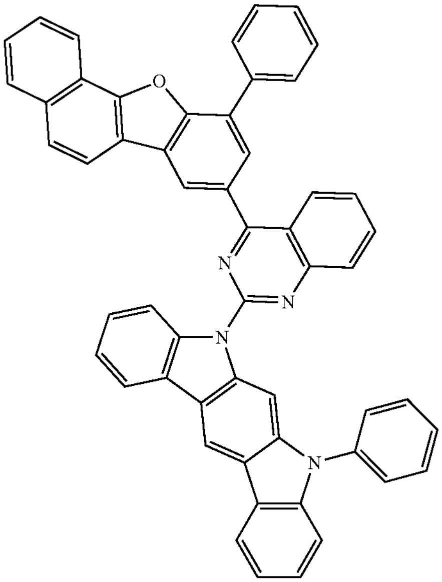
-continued
278
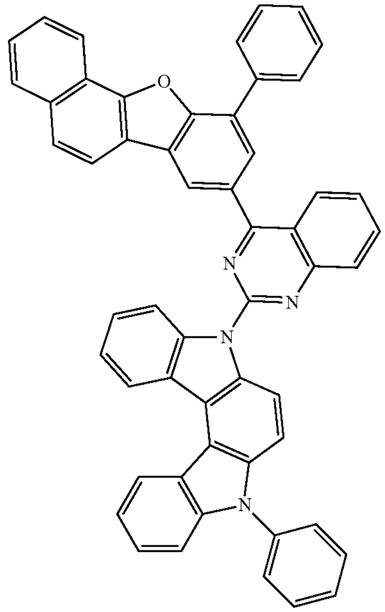
279
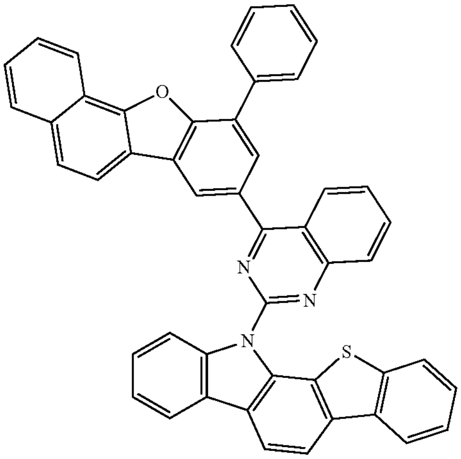

-continued
280
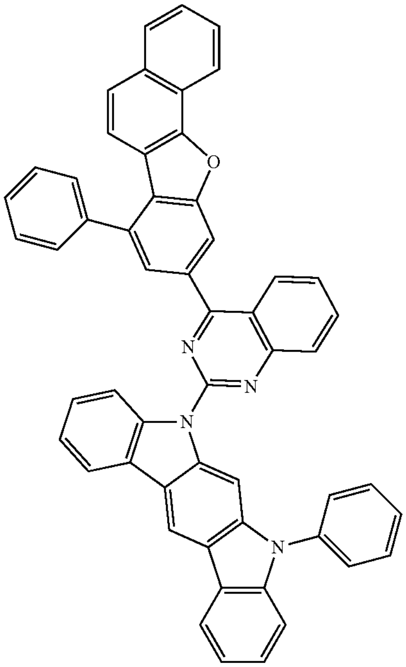
281
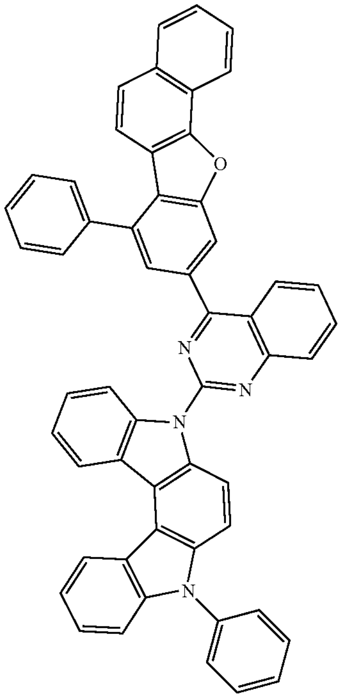
-continued
282
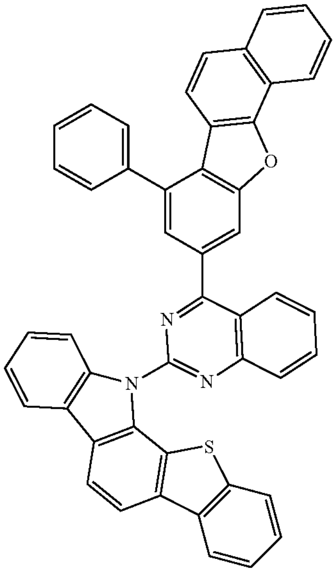
283
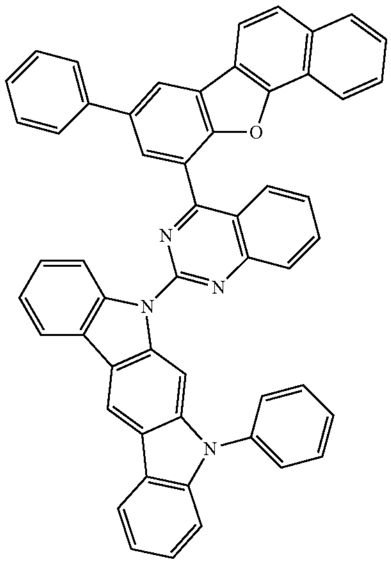

-continued
284
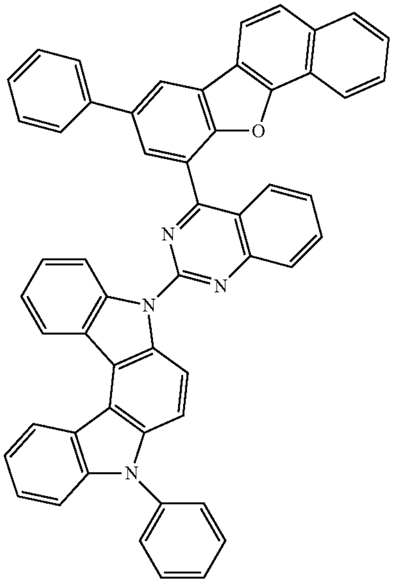
285
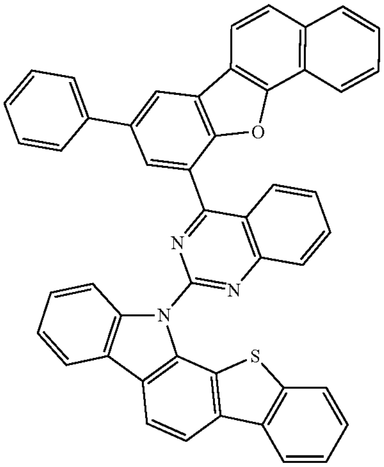
286
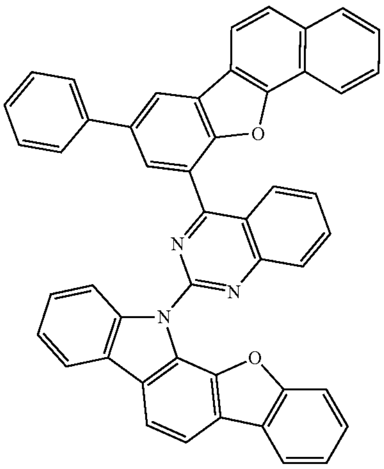
-continued
287
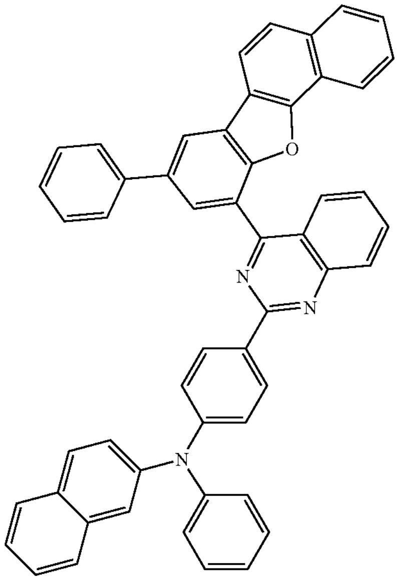
288
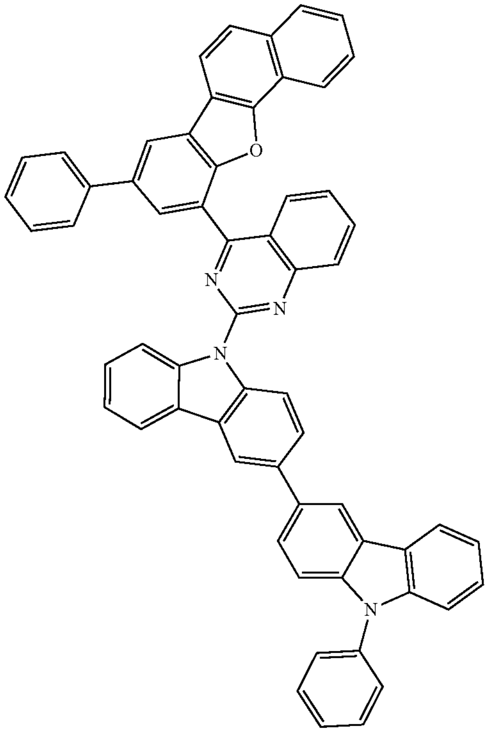

289
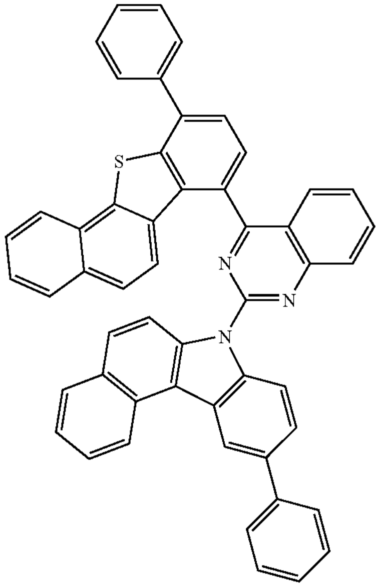
290
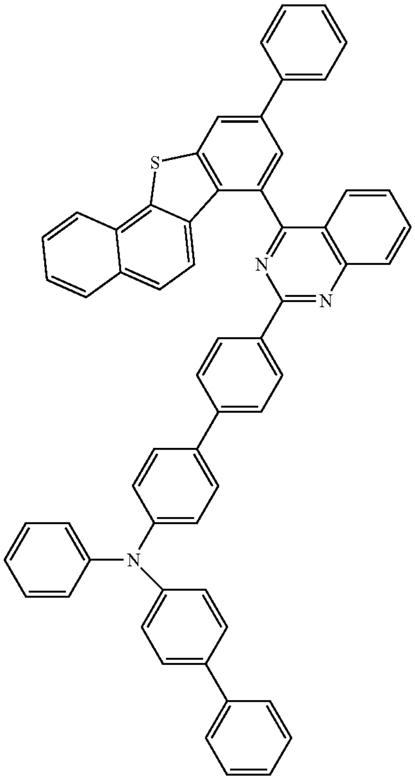
291
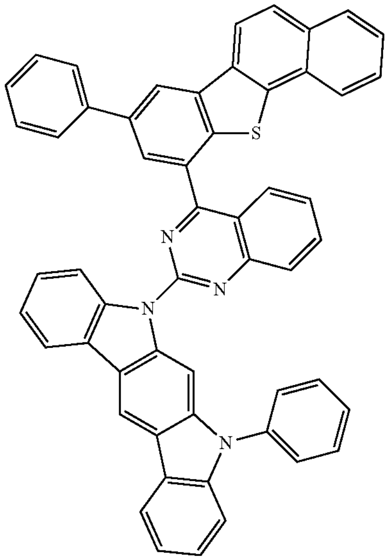
292
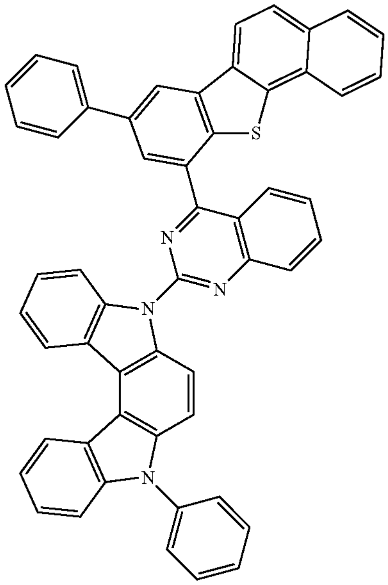
293
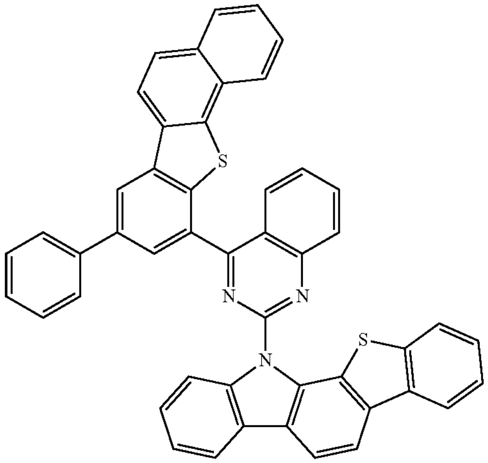

-continued
294
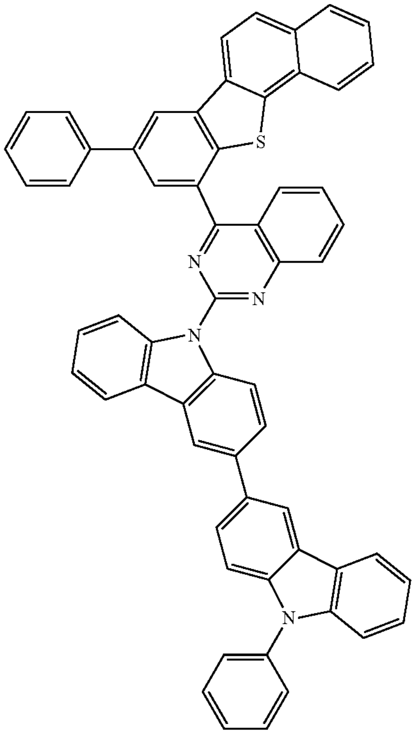
-continued
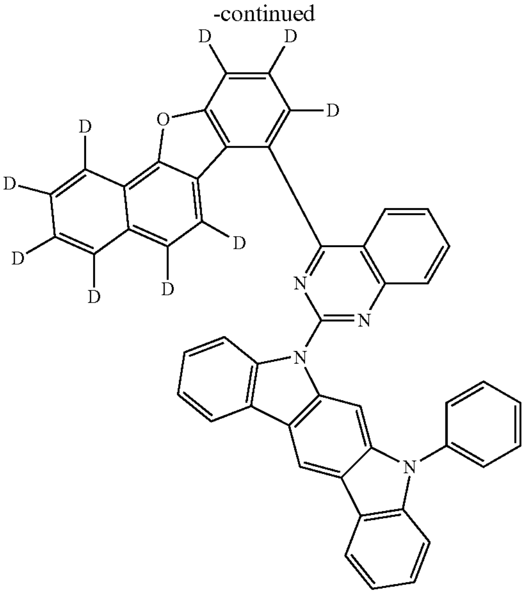
297
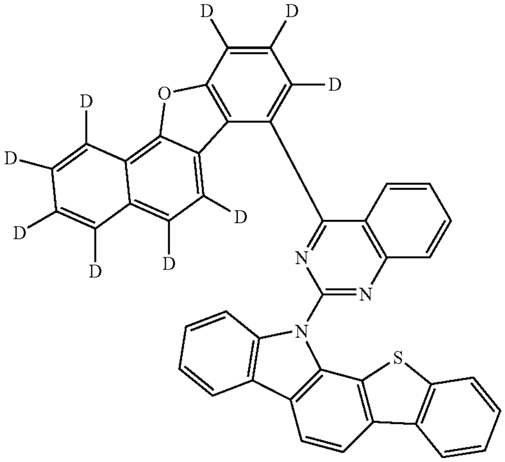
295
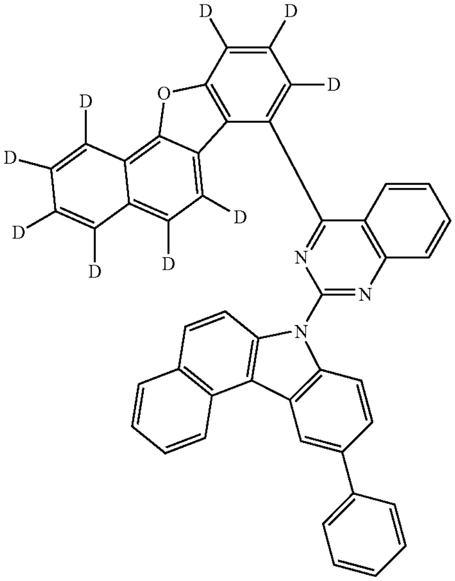
298
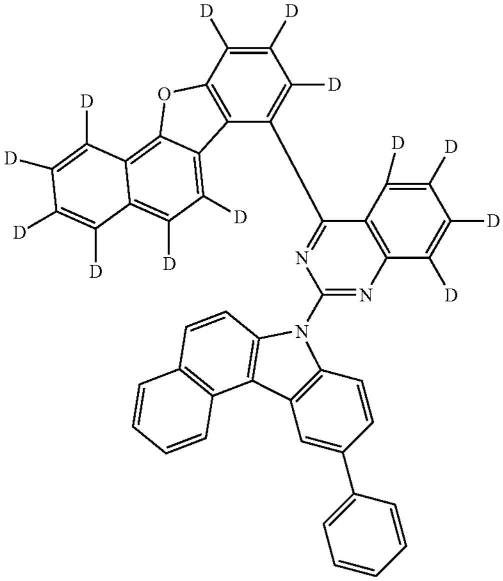

-continued
299
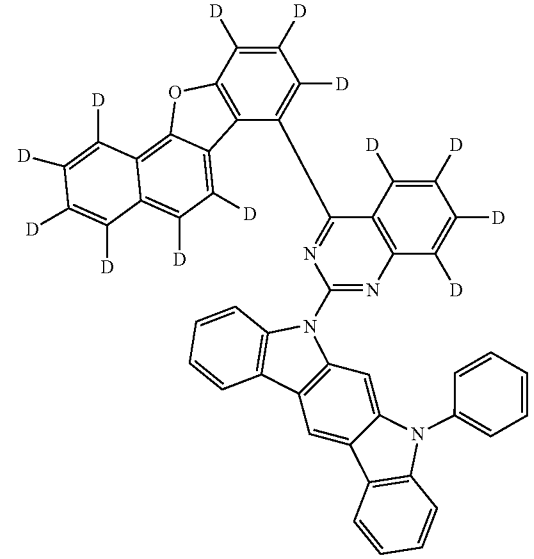
300
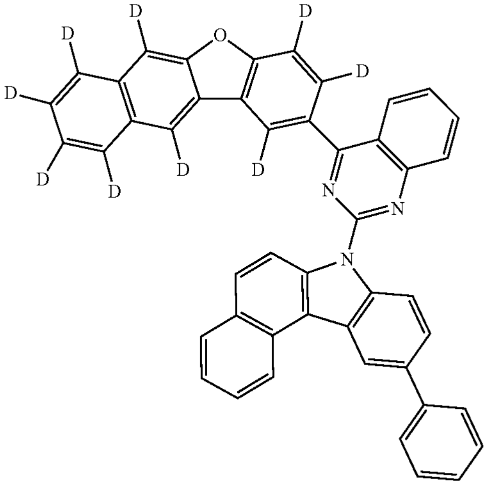
301
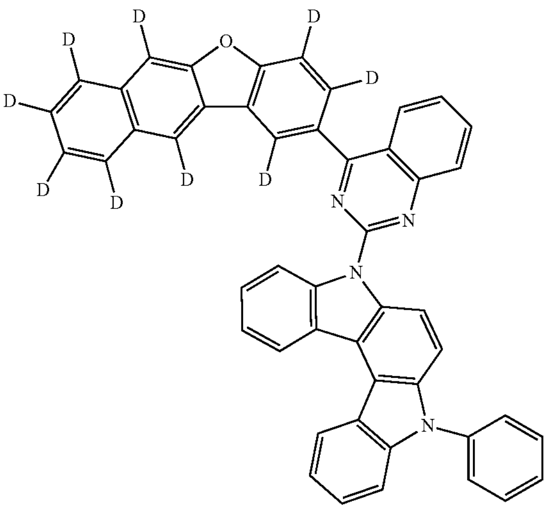
-continued
302
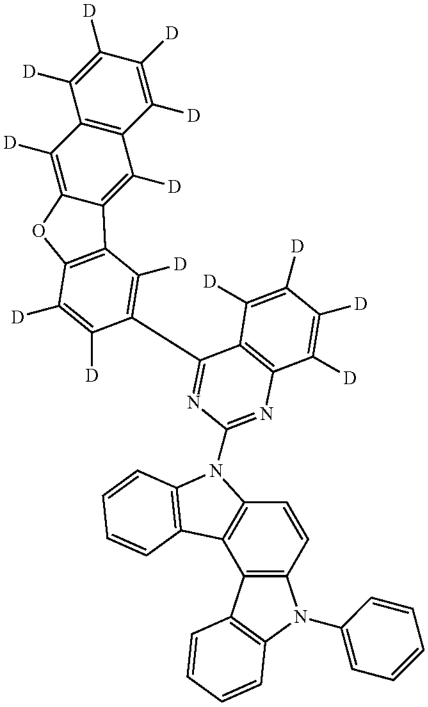
303
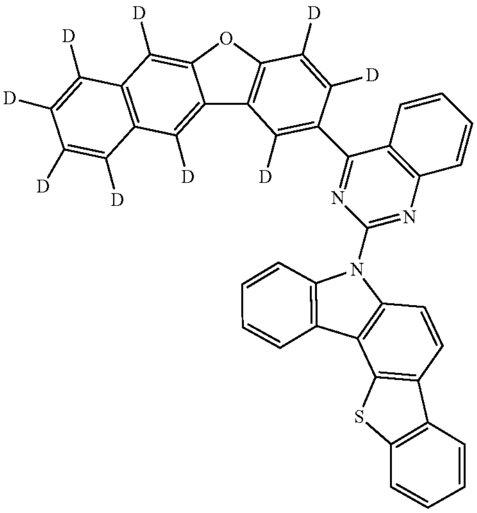

-continued
304
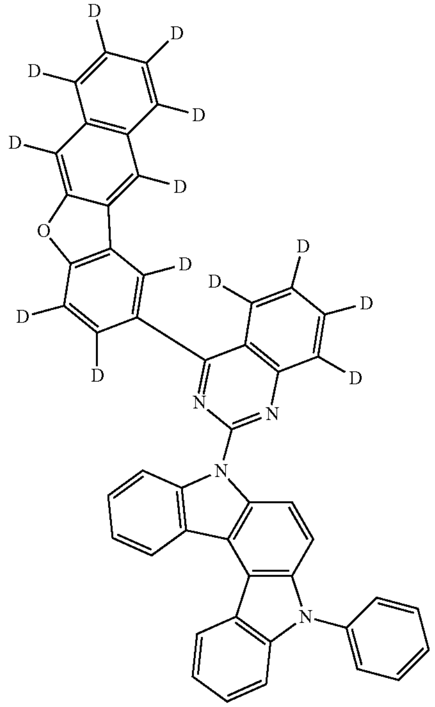
305
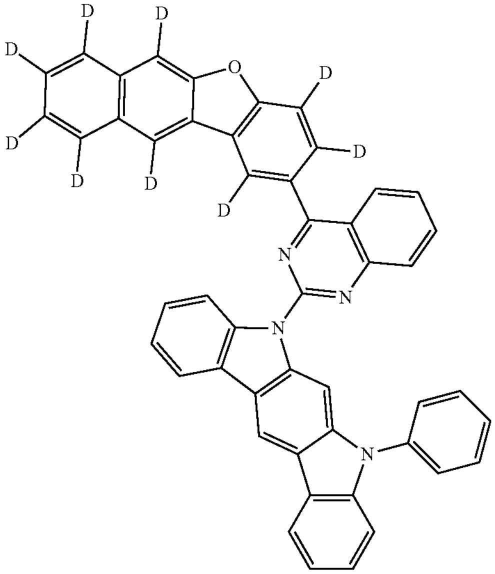
-continued
306
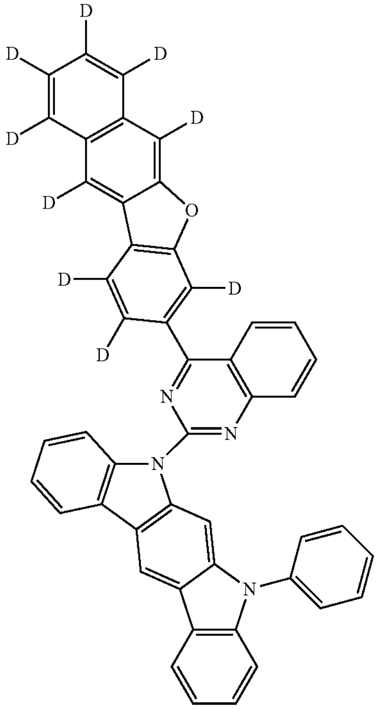
307
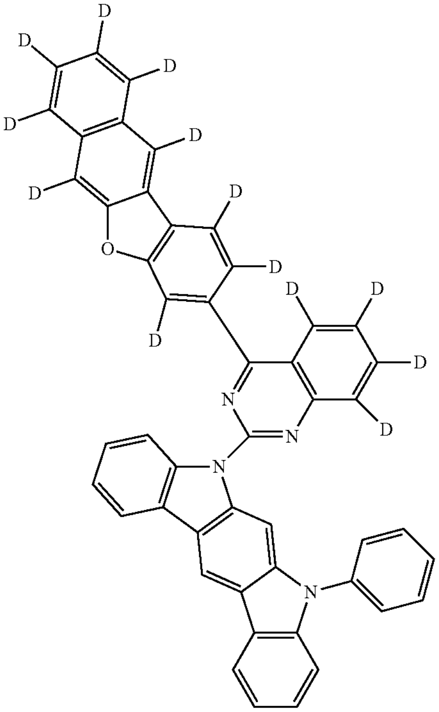

-continued
308
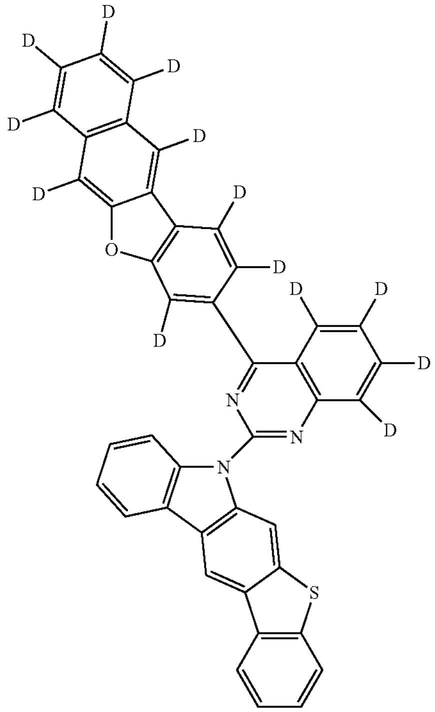
309
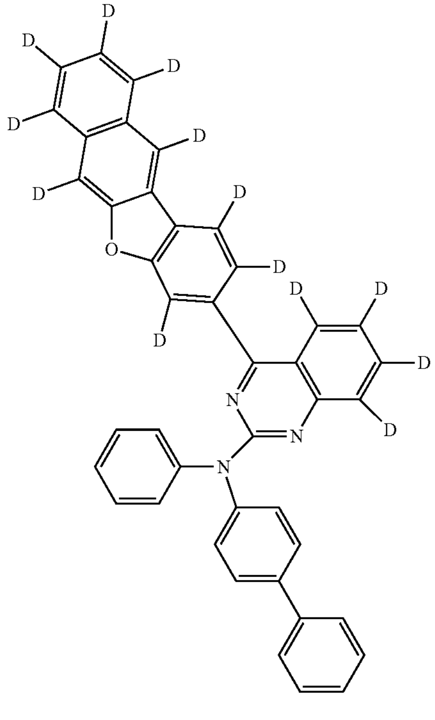
-continued
310
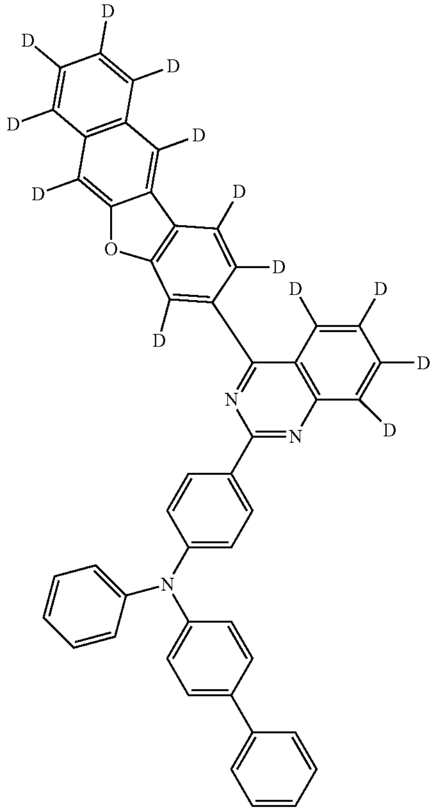
311
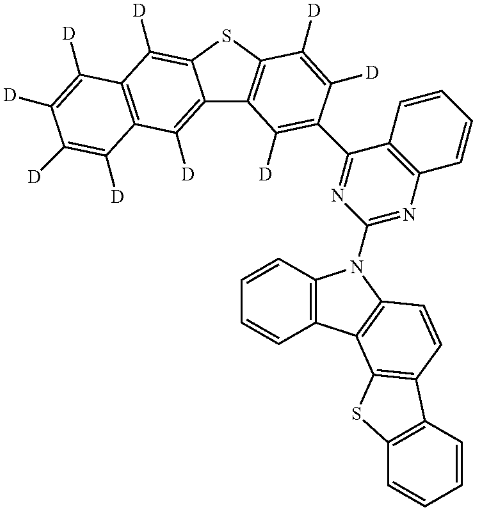

-continued
312
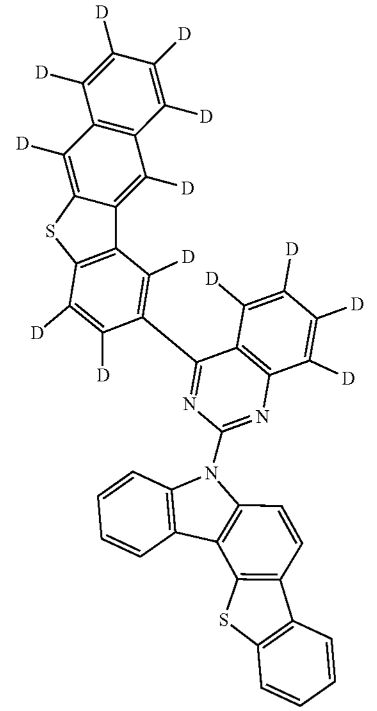
313
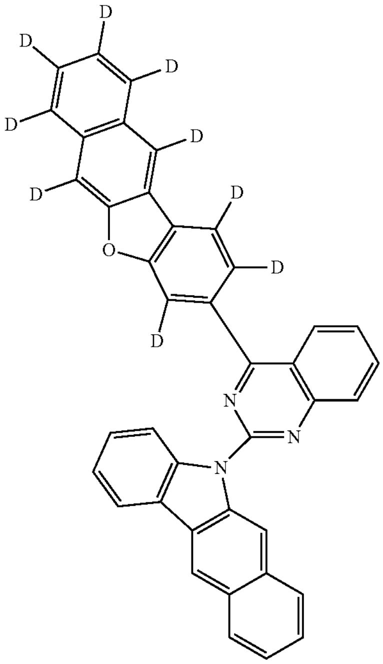
-continued
314
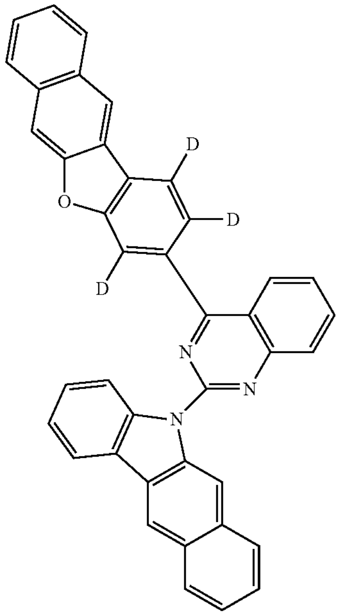
315
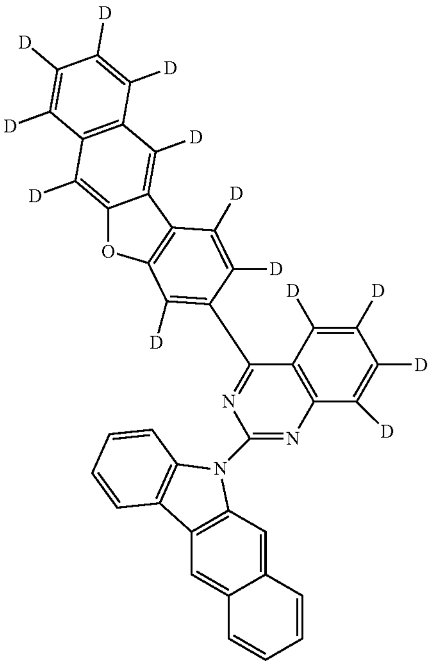

-continued

316

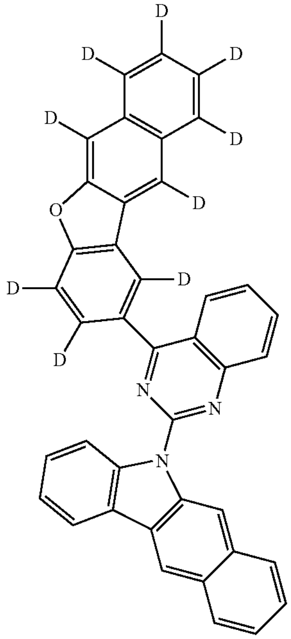

317

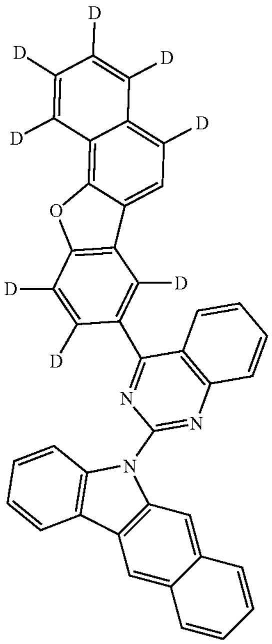

-continued

318

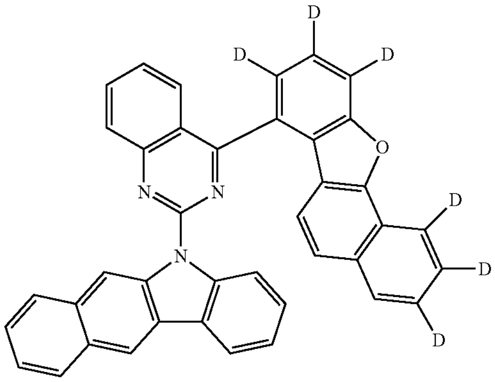

In addition, by introducing various substituents to the structure of Chemical Formula 1, compounds having unique properties of the introduced substituents may be synthesized. For example, by introducing substituents normally used as hole injection layer materials, hole transfer layer materials, light emitting layer materials, electron transfer layer materials and charge generation layer materials used for manufacturing an organic light emitting device to the core structure, materials satisfying conditions required for each organic material layer may be synthesized.

In addition, by introducing various substituents to the structure of Chemical Formula 1, the energy band gap may be finely controlled, and meanwhile, properties at interfaces between organic materials are enhanced, and material applications may become diverse.

In addition, one embodiment of the present application provides an organic light emitting device comprising a first electrode; a second electrode provided opposite to the first electrode; and one or more organic material layers provided between the first electrode and the second electrode, wherein one or more layers of the organic material layers comprise the heterocyclic compound according to Chemical Formula 1.

Another embodiment of the present application provides an organic light emitting device comprising a first electrode; a second electrode provided opposite to the first electrode; and one or more organic material layers provided between the first electrode and the second electrode, wherein one or more layers of the organic material layers comprise one heterocyclic compound according to Chemical Formula 1.

Another embodiment of the present application provides an organic light emitting device comprising a first electrode; a second electrode provided opposite to the first electrode; and one or more organic material layers provided between the first electrode and the second electrode, wherein one or more layers of the organic material layers comprise two types of the heterocyclic compound according to Chemical Formula 1.

Specific descriptions on the heterocyclic compound represented by Chemical Formula 1 are the same as the descriptions provided above.

In one embodiment of the present application, the first electrode may be an anode, and the second electrode may be a cathode.

In another embodiment, the first electrode may be a cathode, and the second electrode may be an anode.

In one embodiment of the present application, the organic light emitting device may be a blue organic light emitting device, and the heterocyclic compound according to Chemical Formula 1 may be used as a material of the blue organic light emitting device. For example, the heterocyclic compound according to Chemical Formula 1 may be included in a host material of a blue light emitting layer of the blue organic light emitting device.

In one embodiment of the present application, the organic light emitting device may be a green organic light emitting device, and the heterocyclic compound according to Chemical Formula 1 may be used as a material of the green organic light emitting device. For example, the heterocyclic compound according to Chemical Formula 1 may be included in a host material of a green light emitting layer of the green organic light emitting device.

In one embodiment of the present application, the organic light emitting device may be a red organic light emitting device, and the heterocyclic compound according to Chemical Formula 1 may be used as a material of the red organic light emitting device. For example, the heterocyclic compound according to Chemical Formula 1 may be included in a host material of a red light emitting layer of the red organic light emitting device.

The organic light emitting device of the present disclosure may be manufactured using common organic light emitting device manufacturing methods and materials except that one or more of the organic material layers are formed using the heterocyclic compound described above.

The heterocyclic compound may be formed into an organic material layer through a solution coating method as well as a vacuum deposition method when manufacturing the organic light emitting device. Herein, the solution coating method means spin coating, dip coating, inkjet printing, screen printing, a spray method, roll coating and the like, but is not limited thereto.

The organic material layer of the organic light emitting device of the present disclosure may be formed in a single layer structure, but may be formed in a multilayer structure in which two or more organic material layers are laminated. For example, the organic light emitting device of the present disclosure may have a structure comprising a hole injection layer, a hole transfer layer, a light emitting layer, an electron transfer layer, an electron injection layer and the like as the organic material layer. However, the structure of the organic light emitting device is not limited thereto, and may comprise a smaller number of organic material layers.

In addition, in the organic light emitting device provided in one embodiment of the present application, the organic material layer comprising the heterocyclic compound of Chemical Formula 1 further comprises a heterocyclic compound represented by the following Chemical Formula 7.

[Chemical Formula 7]

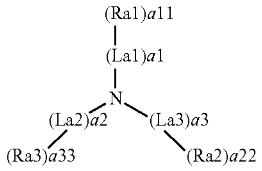

In Chemical Formula 7,

La1 to La3 are the same as or different from each other, and each independently a direct bond; a substituted or unsubstituted C6 to C60 arylene group; or a substituted or unsubstituted C2 to C60 heteroarylene group, Ra1 is a substituted or unsubstituted C6 to C60 aryl group, Ra2 and Ra3 are the same as or different from each other, and each independently selected from the group consisting of hydrogen; deuterium; halogen; a cyano group; a substituted or unsubstituted C1 to C60 alkyl group; a substituted or unsubstituted C2 to C60 alkenyl group; a substituted or unsubstituted C2 to C60 alkynyl group; a substituted or unsubstituted C1 to C60 alkoxy group; a substituted or unsubstituted C3 to C60 cycloalkyl group; a substituted or unsubstituted C2 to C60 heterocycloalkyl group; a substituted or unsubstituted C6 to C60 aryl group; a substituted or unsubstituted C2 to C60 heteroaryl group; and —NRR', or two or more groups adjacent to each other bond to each other to form a substituted or unsubstituted C6 to C60 aliphatic or aromatic hydrocarbon ring or a substituted or unsubstituted C2 to C60 aliphatic or aromatic heteroring, R and R' are the same as or different from each other, and each independently a substituted or unsubstituted C1 to C60 alkyl group; a substituted or unsubstituted C6 to C60 aryl group; or a substituted or unsubstituted C2 to C60 heteroaryl group, a1 to a3 are an integer of 0 to 4, a11, a22 and a33 are an integer of 1 to 6, and when a1 to a3, a11, a22 and a33 are 2 or greater, substituents in the parentheses are the same as or different from each other.

In one embodiment of the present application, La1 to La3 of Chemical Formula 7 are the same as or different from each other, and may be each independently a direct bond; a substituted or unsubstituted C6 to C60 arylene group; or a substituted or unsubstituted C2 to C60 heteroarylene group.

In another embodiment, La1 to La3 of Chemical Formula 7 are the same as or different from each other, and may be each independently a direct bond; a substituted or unsubstituted C6 to C40 arylene group; or a substituted or unsubstituted C2 to C40 heteroarylene group.

In another embodiment, La1 to La3 of Chemical Formula 7 are the same as or different from each other, and may be each independently a direct bond; a substituted or unsubstituted C6 to C20 arylene group; or a substituted or unsubstituted C2 to C20 heteroarylene group.

In another embodiment, La1 to La3 of Chemical Formula 7 are the same as or different from each other, and may be each independently a direct bond; a C6 to C20 arylene group; or a C2 to C20 heteroarylene group.

In another embodiment, La1 to La3 of Chemical Formula 7 are the same as or different from each other, and may be each independently a direct bond; a C6 to C20 monocyclic or polycyclic arylene group; or a C2 to C20 heteroarylene group.

In another embodiment, La1 to La3 of Chemical Formula 7 are the same as or different from each other, and may be each independently a direct bond; a phenylene group; a biphenylene group; or a divalent dibenzothiophene group.

In one embodiment of the present application, Ra1 may be a substituted or unsubstituted C6 to C60 aryl group.

In another embodiment, Ra1 may be a substituted or unsubstituted C6 to C40 aryl group.

In another embodiment, Ra1 may be a C6 to C40 aryl group.

In another embodiment, Ra1 may be a C6 to C40 monocyclic or polycyclic aryl group.

In another embodiment, Ra1 may be a C6 to C10 monocyclic aryl group; or a C10 to C40 polycyclic aryl group.

In another embodiment, Ra1 may be a phenyl group; a biphenyl group; a naphthyl group; or a terphenyl group.

In one embodiment of the present application, Ra2 and Ra3 are the same as or different from each other, and each independently selected from the group consisting of hydrogen; deuterium; halogen; a cyano group; a substituted or unsubstituted C1 to C60 alkyl group; a substituted or unsubstituted C2 to C60 alkenyl group; a substituted or unsubstituted C2 to C60 alkynyl group; a substituted or unsubstituted C1 to C60 alkoxy group; a substituted or unsubstituted C3 to C60 cycloalkyl group; a substituted or unsubstituted C2 to C60 heterocycloalkyl group; a substituted or unsubstituted C6 to C60 aryl group; a substituted or unsubstituted C2 to C60 heteroaryl group; and —NRR', or two or more groups adjacent to each other may bond to each other to form a substituted or unsubstituted C6 to C60 aliphatic or aromatic hydrocarbon ring or a substituted or unsubstituted C2 to C60 aliphatic or aromatic heteroring.

In another embodiment, Ra2 and Ra3 are the same as or different from each other, and each independently selected from the group consisting of a substituted or unsubstituted C6 to C60 aryl group; and a substituted or unsubstituted C2 to C60 heteroaryl group, or two or more groups adjacent to each other may bond to each other to form a substituted or unsubstituted C6 to C60 aliphatic or aromatic hydrocarbon ring or a substituted or unsubstituted C2 to C60 aliphatic or aromatic heteroring.

In another embodiment, Ra2 and Ra3 are the same as or different from each other, and each independently selected from the group consisting of a substituted or unsubstituted C6 to C40 aryl group; and a substituted or unsubstituted C2 to C40 heteroaryl group, or two or more groups adjacent to each other may bond to each other to form a substituted or unsubstituted C6 to C40 aliphatic or aromatic hydrocarbon ring.

In another embodiment, Ra2 and Ra3 are the same as or different from each other, and each independently selected from the group consisting of a phenyl group; a biphenyl group; a terphenyl group; and a carbazole group, or two or more groups adjacent to each other may bond to each other to form a substituted or unsubstituted fluorene ring.

The two or more groups adjacent to each other of Ra2 and Ra3 bonding to each other to form a substituted or unsubstituted fluorene ring may mean ultimately forming the following structure.

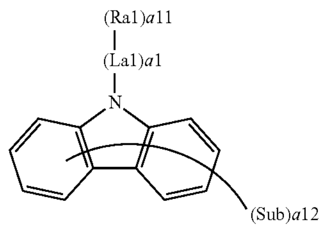

In the structure, Sub has the same definition as the substituent in "substituted" of the "substituted or unsubstituted", and a12 is an integer of 0 to 8.

In another embodiment, Ra2 and Ra3 are the same as or different from each other, and each independently selected from the group consisting of a phenyl group; a biphenyl group; a terphenyl group; and a carbazole group, or two or more groups adjacent to each other may bond to each other to form a fluorene ring unsubstituted or substituted with one or more substituents selected from the group consisting of a C6 to C20 aryl group and a C2 to C30 heteroaryl group.

In another embodiment, Ra2 and Ra3 are the same as or different from each other, and each independently selected from the group consisting of a phenyl group; a biphenyl group; a terphenyl group; and a carbazole group, or two or more groups adjacent to each other may bond to each other to form a fluorene ring unsubstituted or substituted with one or more substituents selected from the group consisting of a phenyl group, a biphenyl group, a naphthyl group, dibenzofuran and dibenzothiophene, or a substituent linking one or more substituents selected from the group consisting of a phenyl group, a biphenyl group, a naphthyl group, dibenzofuran and dibenzothiophene.

In one embodiment of the present application, the terphenyl group may be any one selected from the group consisting of an M-terphenyl group, an O-terphenyl group and a P-terphenyl group.

In one embodiment of the present application, Chemical Formula 7 may be represented by the following Chemical Formula 8 or Chemical Formula 9.

[Chemical Formula 8]

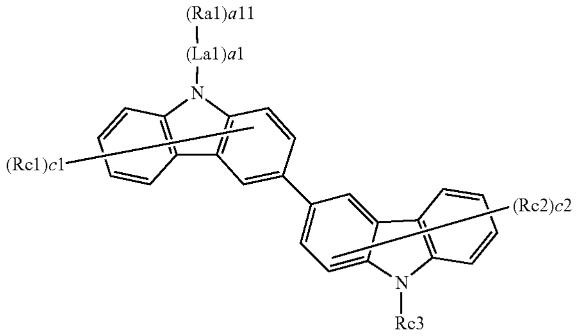

[Chemical Formula 9]

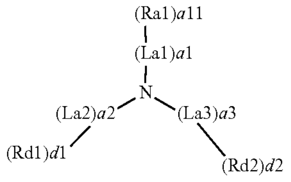

In Chemical Formulae 8 and 9,

Ra1, La1 to La3, a1 to a3 and a11 have the same definitions as in Chemical Formula 7, Rc1 and Rc2 are the same as or different from each other, and each independently selected from the group consisting of hydrogen; deuterium; halogen; a cyano group; a substituted or unsubstituted C1 to C60 alkyl group; a substituted or unsubstituted C2 to C60 alkenyl group; a substituted or unsubstituted C2 to C60 alkynyl group; a substituted or unsubstituted C1 to C60 alkoxy group; a substituted or unsubstituted C3 to C60 cycloalkyl group; a substituted or unsubstituted C2 to C60 heterocycloalkyl group; a substituted or unsubstituted C6 to C60 aryl group; a substituted or unsubstituted C2 to C60 heteroaryl group; and —NRR', or two or more groups adjacent to each other bond to each other to form a substituted or unsubstituted C6 to C60 aliphatic or aromatic hydrocarbon ring or a substituted or unsubstituted C2 to C60 aliphatic or aromatic heteroring, Rc3, Rd1 and Rd2 are the same as or different from each other, and each independently a substituted or unsubstituted C6 to C60 aryl group; or a substituted or unsubstituted C2 to C60 heteroaryl group, R and R' are the same as or different from each other, and each independently a substituted or unsubstituted C1 to C60 alkyl group; a substituted or unsubstituted C6 to C60 aryl group; or a substituted or unsubstituted C2 to C60 heteroaryl group, c1 and c2 are an integer of 0 to 7, and d1 and d2 are an integer of 1 to 4.

In one embodiment of the present application, Rc1 and Rc2 of Chemical Formula 8 are the same as or different from each other, and each independently selected from the group consisting of hydrogen; deuterium; halogen; a cyano group; a substituted or unsubstituted C1 to C60 alkyl group; a substituted or unsubstituted C2 to C60 alkenyl group; a substituted or unsubstituted C2 to C60 alkynyl group; a substituted or unsubstituted C1 to C60 alkoxy group; a substituted or unsubstituted C3 to C60 cycloalkyl group; a substituted or unsubstituted C2 to C60 heterocycloalkyl group; a substituted or unsubstituted C6 to C60 aryl group; a substituted or unsubstituted C2 to C60 heteroaryl group; and —NRR', or two or more groups adjacent to each other may bond to each other to form a substituted or unsubstituted C6 to C60 aliphatic or aromatic hydrocarbon ring or a substituted or unsubstituted C2 to C60 aliphatic or aromatic heteroring.

In another embodiment, Rc1 and Rc2 of Chemical Formula 8 may be hydrogen.

In one embodiment of the present application, Rc3, Rd1 and Rd2 are the same as or different from each other, and may be each independently a substituted or unsubstituted C6 to C60 aryl group; or a substituted or unsubstituted C2 to C60 heteroaryl group.

In another embodiment, Rc3, Rd1 and Rd2 are the same as or different from each other, and may be each independently a substituted or unsubstituted C6 to C40 aryl group; or a substituted or unsubstituted C2 to C40 heteroaryl group.

In another embodiment, Rc3, Rd1 and Rd2 are the same as or different from each other, and may be each independently a substituted or unsubstituted C6 to C20 aryl group; or a substituted or unsubstituted C2 to C20 heteroaryl group.

In another embodiment, Rc3, Rd1 and Rd2 are the same as or different from each other, and may be each independently a C6 to C20 aryl group unsubstituted or substituted with a C6 to C20 aryl group; or a C2 to C20 heteroaryl group unsubstituted or substituted with a C6 to C20 aryl group.

In another embodiment, Rc3, Rd1 and Rd2 are the same as or different from each other, and may be each independently a phenyl group; a biphenyl group; a naphthyl group unsubstituted or substituted with a phenyl group; a dibenzofuran group; or a dibenzothiophene group unsubstituted or substituted with a phenyl group.

Effects of more superior efficiency and lifetime are obtained when comprising the heterocyclic compound of Chemical Formula 1 and the heterocyclic compound of Chemical Formula 7 in the organic material layer of the organic light emitting device. Such results may lead to a forecast that an exciplex phenomenon occurs when comprising the two compounds at the same time.

The exciplex phenomenon is a phenomenon of releasing energy having sizes of a donor (p-host) HOMO level and an acceptor (n-host) LUMO level due to electron exchanges between two molecules. When the exciplex phenomenon occurs between two molecules, reverse intersystem crossing (RISC) occurs, and as a result, internal quantum efficiency of fluorescence may increase up to 100%. When a donor (p-host) having a favorable hole transfer ability and an acceptor (n-host) having a favorable electron transfer ability are used as a host of a light emitting layer, holes are injected to the p-host and electrons are injected to the n-host, and therefore, a driving voltage may be lowered, which resultantly helps with enhancement in the lifetime.

In one embodiment of the present application, Chemical Formula 7 may be any one of the following compounds.

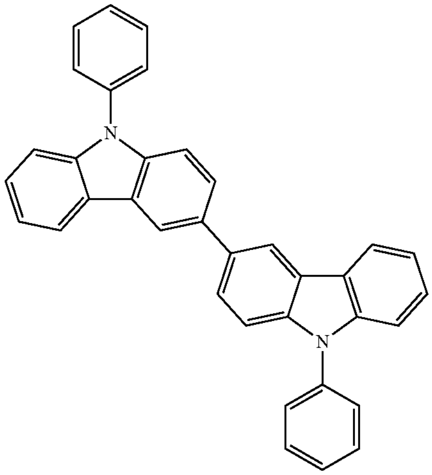

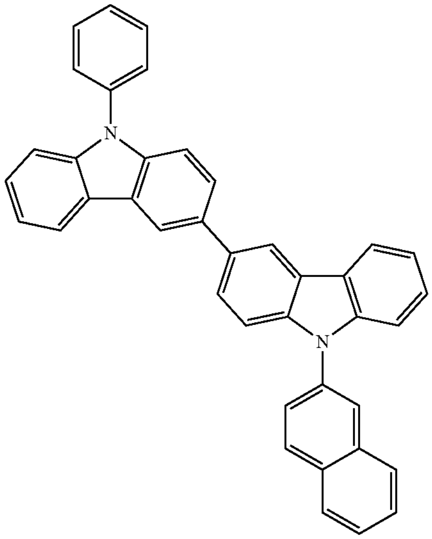

-continued
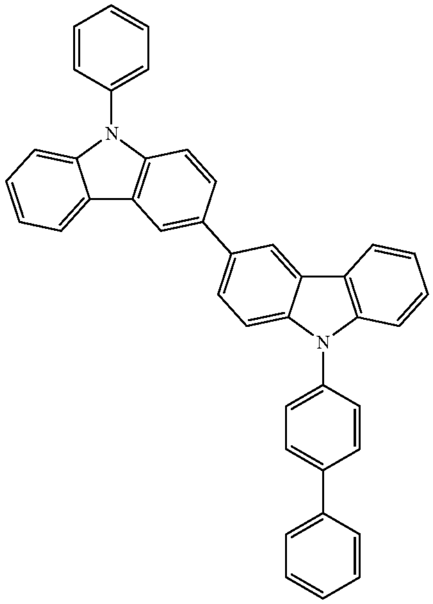
-continued
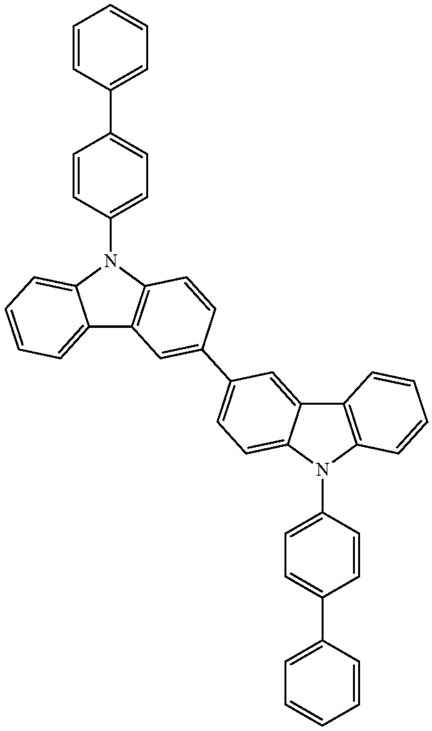
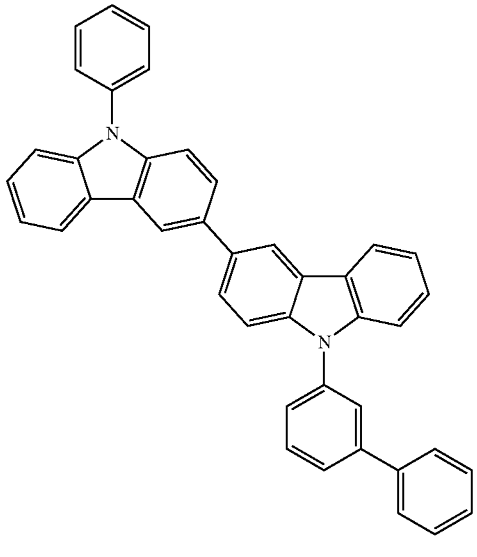
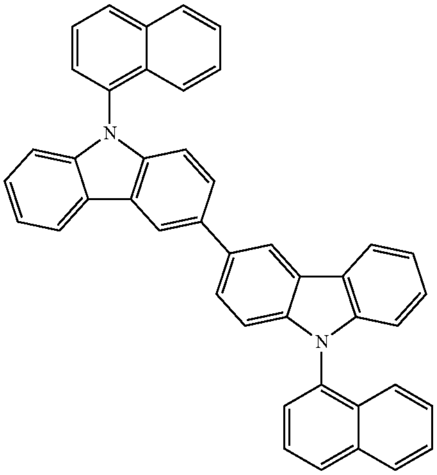

-continued
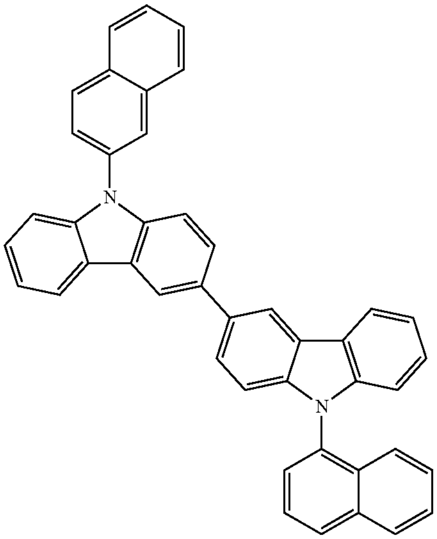
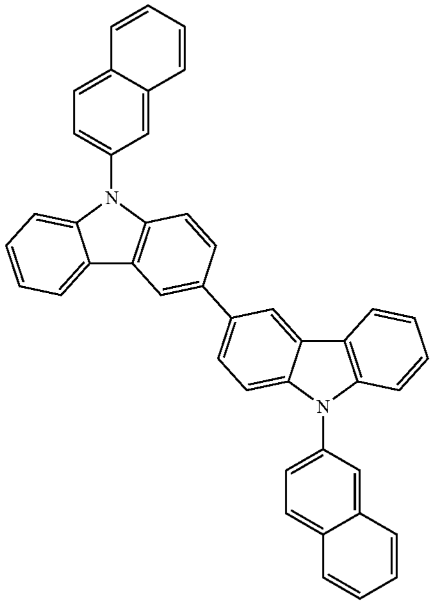
-continued
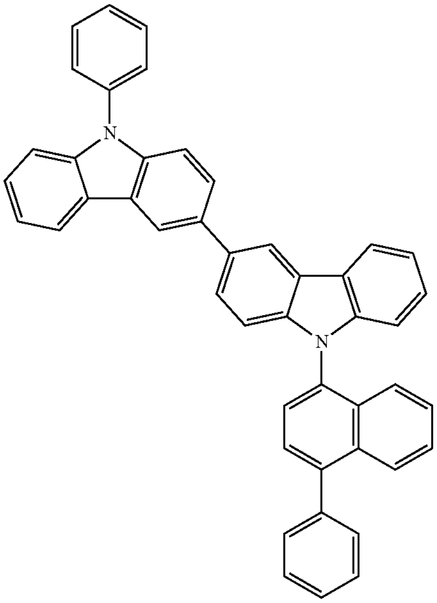
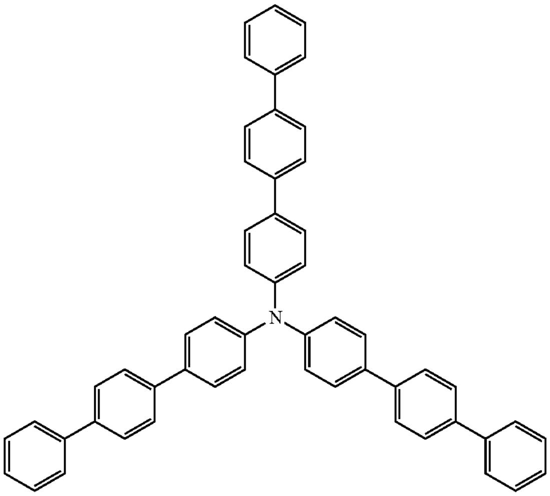
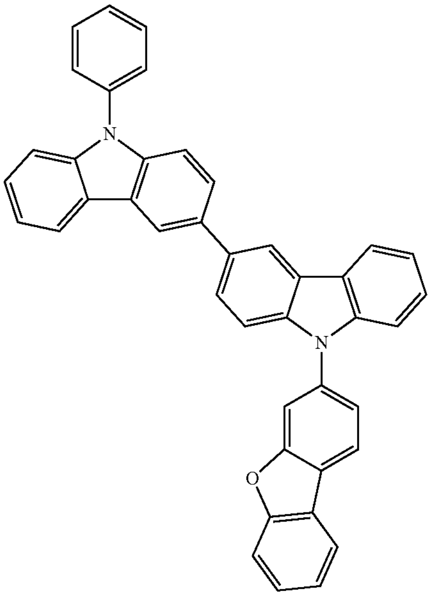

-continued

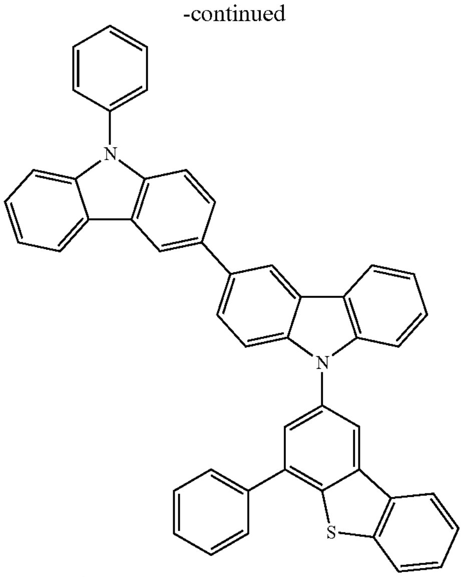

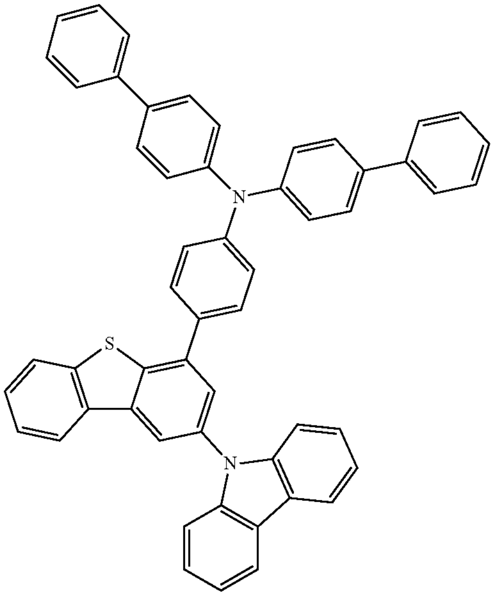

Another embodiment of the present application provides a composition for an organic material layer of an organic light emitting device, the composition comprising the heterocyclic compound represented by Chemical Formula 1, and the heterocyclic compound represented by Chemical Formula 7.

Specific descriptions on the heterocyclic compound represented by Chemical Formula 1 and the heterocyclic compound represented by Chemical Formula 7 are the same as the descriptions provided above.

In the composition, the heterocyclic compound represented by Chemical Formula 1: the heterocyclic compound represented by Chemical Formula 7 may have a weight ratio of 1:10 to 10:1, 1:8 to 8:1, 1:5 to 5:1, 1:2 to 2:1 or 1:1 to 1:1, however, the weight ratio is not limited thereto.

The composition may be used when forming an organic material of an organic light emitting device, and may be more preferably used when forming a host of a light emitting layer.

In one embodiment of the present application, the organic material layer comprises the heterocyclic compound represented by Chemical Formula 1 and the heterocyclic compound represented by Chemical Formula 7, and a phosphorescent dopant may be used therewith.

In one embodiment of the present application, the organic material layer comprises the heterocyclic compound represented by Chemical Formula 1 and the heterocyclic compound represented by Chemical Formula 7, and an iridium-based dopant may be used therewith.

As a material of the phosphorescent dopant, those known in the art may be used.

For example, phosphorescent dopant materials represented by LL'MX', LL'L"M, LMX'X", L2MX' and L3M may be used, however, the scope of the present disclosure is not limited to these examples.

Herein, L, L', L", X' and X" are a bidentate ligand different from each other, and M is a metal forming an octahedral complex.

M may comprise iridium, platinum, osmium and the like.

L is an anionic bidentate ligand coordinated to M as the iridium-based dopant by sp2 carbon and heteroatom, and X may function to trap electrons or holes. Nonlimiting examples of L may comprise 2-(1-naphthyl)benzoxazole, (2-phenylbenzoxazole), (2-phenylbenzothiazole), (2-phenylbenzothiazole), (7,8-benzoquinoline), (thiophene group pyrizine), phenylpyridine, benzothiophene group pyrizine, 3-methoxy-2-phenylpyridine, thiophene group pyrizine, tolylpyridine and the like. Nonlimiting examples of X' and X" may comprise acetylacetonate (acac), hexafluoroacetylacetonate, salicylidene, picolinate, 8-hydroxyquinolinate and the like.

More specific examples of the phosphorescent dopant are described below, however, the phosphorescent dopant is not limited to these examples.

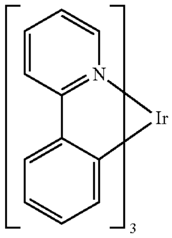
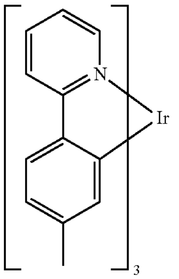
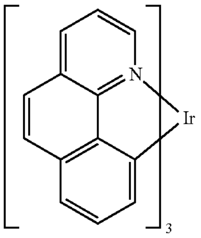

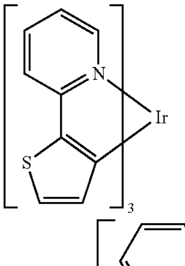
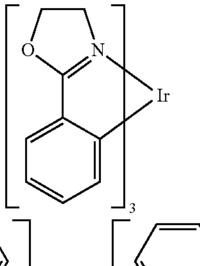
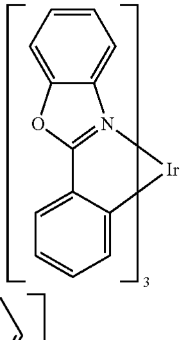

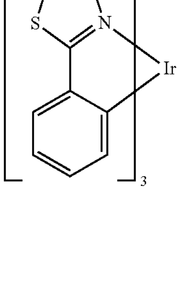
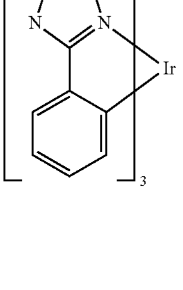

-continued

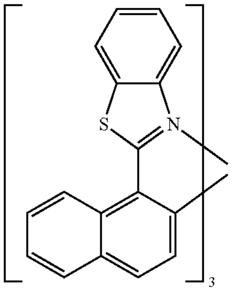

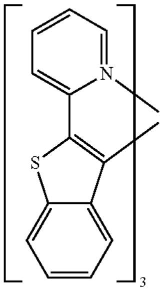

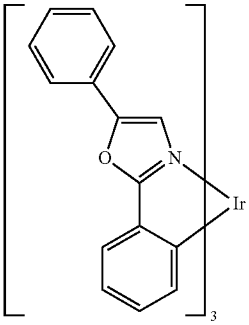

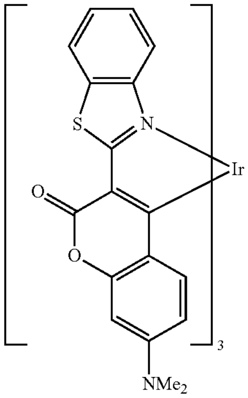

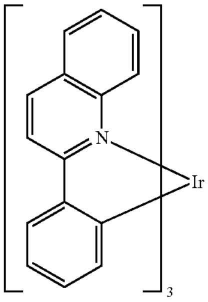

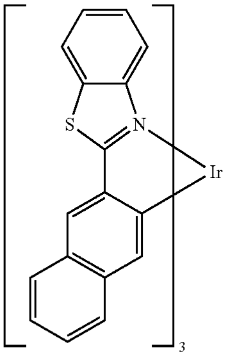

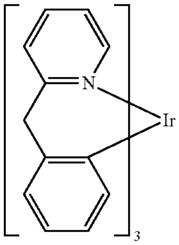

In another organic light emitting device, the organic material layer comprises a light emitting layer, the light emitting layer comprises a host material, and the host material may comprise the heterocyclic compound.

In the organic light emitting device of the present disclosure, the organic material layer comprises an electron injection layer or an electron transfer layer, and the electron injection layer or the electron transfer layer may comprise the heterocyclic compound.

In another organic light emitting device, the organic material layer comprises an electron blocking layer or a hole blocking layer, and the electron blocking layer or the hole blocking layer may comprise the heterocyclic compound.

In another organic light emitting device, the organic material layer comprises an electron transfer layer, a light emitting layer or a hole blocking layer, and the electron transfer layer, the light emitting layer or the hole blocking layer may comprise the heterocyclic compound.

The organic light emitting device of the present disclosure may further comprise one, two or more layers selected from the group consisting of a light emitting layer, a hole injection layer, a hole transfer layer, an electron injection layer, an electron transfer layer, an electron blocking layer and a hole blocking layer.

FIG. 1 to FIG. 3 illustrate a lamination order of electrodes and organic material layers of an organic light emitting device according to one embodiment of the present application. However, the scope of the present application is not limited to these diagrams, and structures of organic light emitting devices known in the art may also be used in the present application.

FIG. 1 illustrates an organic light emitting device in which an anode (200), an organic material layer (300) and a cathode (400) are consecutively laminated on a substrate (100). However, the structure is not limited to such a structure, and as illustrated in FIG. 2, an organic light emitting device in which a cathode, an organic material layer and an anode are consecutively laminated on a substrate may also be obtained.

FIG. 3 illustrates a case of the organic material layer being a multilayer. The organic light emitting device according to FIG. 3 comprises a hole injection layer (301), a hole transfer layer (302), a light emitting layer (303), a hole blocking layer (304), an electron transfer layer (305) and an electron injection layer (306). However, the scope of the present application is not limited to such a lamination structure, and as necessary, layers other than the light emitting layer may not be included, and other necessary functional layers may be further added.

One embodiment of the present application provides a method for manufacturing an organic light emitting device, the method comprising preparing a substrate; forming a first electrode on the substrate; forming one or more organic material layers on the first electrode; and forming a second electrode on the organic material layer, wherein the forming of organic material layers comprises forming one or more organic material layers using the composition for an organic material layer according to one embodiment of the present application.

In the method for manufacturing an organic light emitting device provided in one embodiment of the present application, the forming of organic material layers is forming the heterocyclic compound of Chemical Formula 1 and the heterocyclic compound of Chemical Formula 7 using a thermal vacuum deposition method after pre-mixing.

The pre-mixing means first mixing the heterocyclic compound of Chemical Formula 1 and the heterocyclic compound of Chemical Formula 7 in one source of supply before depositing on the organic material layer.

The premixed material may be referred to as the composition for an organic material layer according to one embodiment of the present application.

The organic material layer comprising Chemical Formula 1 may further comprise other materials as necessary.

The organic material layer comprising both Chemical Formula 1 and Chemical Formula 7 may further comprise other materials as necessary.

In the organic light emitting device according to one embodiment of the present application, materials other than the compound of Chemical Formula 1 or Chemical Formula 7 are illustrated below, however, these are for illustrative purposes only and not for limiting the scope of the present application, and may be replaced by materials known in the art.

As the anode material, materials having relatively large work function may be used, and transparent conductive oxides, metals, conductive polymers or the like may be used. Specific examples of the anode material comprise metals such as vanadium, chromium, copper, zinc and gold, or alloys thereof; metal oxides such as zinc oxide, indium oxide, indium tin oxide (ITO) and indium zinc oxide (IZO); combinations of metals and oxides such as ZnO:Al or $SnO_2$:Sb; conductive polymers such as poly(3-methylthiophene), poly[3,4-(ethylene-1,2-dioxy)thiophene] (PEDOT), polypyrrole and polyaniline, and the like, but are not limited thereto.

As the cathode material, materials having relatively small work function may be used, and metals, metal oxides, conductive polymers or the like may be used. Specific examples of the cathode material comprise metals such as magnesium, calcium, sodium, potassium, titanium, indium, yttrium, lithium, gadolinium, aluminum, silver, tin and lead, or alloys thereof; multilayer structure materials such as LiF/Al or $LiO_2$/Al, and the like, but are not limited thereto.

As the hole injection material, known hole injection materials may be used, and for example, phthalocyanine compounds such as copper phthalocyanine disclosed in U.S. Pat. No. 4,356,429, or starburst-type amine derivatives such as tris(4-carbazoyl-9-ylphenyl)amine (TCTA), 4,4',4"-tri[phenyl(m-tolyl)amino]triphenylamine (m-MTDATA) or 1,3,5-tris[4-(3-methylphenylphenylamino)phenyl]benzene (m-MTDAPB) described in the literature [Advanced Material, 6, p. 677 (1994)], polyaniline/dodecylbenzene sulfonic acid, poly(3,4-ethylenedioxythiophene)/poly(4-styrene-sulfonate), polyaniline/camphor sulfonic acid or polyaniline/poly(4-styrene-sulfonate) that are conductive polymers having solubility, and the like, may be used.

As the hole transfer material, pyrazoline derivatives, arylamine-based derivatives, stilbene derivatives, triphenyldiamine derivatives and the like may be used, and low molecular or high molecular materials may also be used.

As the electron transfer material, metal complexes of oxadiazole derivatives, anthraquinodimethane and derivatives thereof, benzoquinone and derivatives thereof, naphthoquinone and derivatives thereof, anthraquinone and derivatives thereof, tetracyanoanthraquinodimethane and derivatives thereof, fluorenone derivatives, diphenyldicyanoethylene and derivatives thereof, diphenoquinone derivatives, 8-hydroxyquinoline and derivatives thereof, and the like, may be used, and high molecular materials may also be used as well as low molecular materials.

As examples of the electron injection material, LiF is typically used in the art, however, the present application is not limited thereto.

As the light emitting material, red, green or blue light emitting materials may be used, and as necessary, two or more light emitting materials may be mixed and used. Herein, two or more light emitting materials may be used by being deposited as individual sources of supply or by being premixed and deposited as one source of supply. In addition, fluorescent materials may also be used as the light emitting material, however, phosphorescent materials may also be used. As the light emitting material, materials emitting light by bonding electrons and holes injected from an anode and a cathode, respectively, may be used alone, however, materials having a host material and a dopant material involving in light emission together may also be used.

When mixing light emitting material hosts, same series hosts may be mixed, or different series hosts may be mixed. For example, any two or more types of materials among n-type host materials or p-type host materials may be selected and used as a host material of a light emitting layer.

The organic light emitting device according to one embodiment of the present application may be a top-emission type, a bottom-emission type or a dual-emission type depending on the materials used.

The heterocyclic compound according to one embodiment of the present application may also be used in an organic electronic device comprising an organic solar cell, an organic photo conductor, an organic transistor and the like under a similar principle used in the organic light emitting device.

Hereinafter, the present specification will be described in more detail with reference to examples, however, these are for illustrative purposes only, and the scope of the present application is not limited thereto.

<Preparation Example 1> Preparation of Compound A13

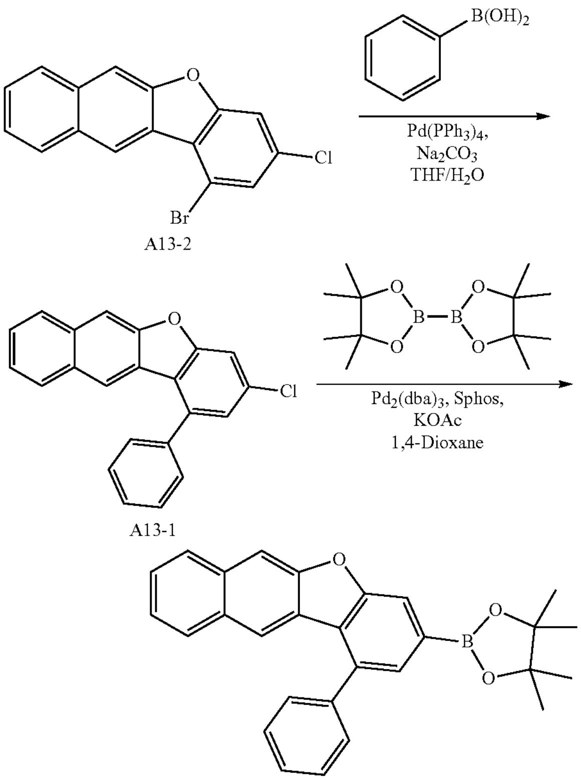

A13-2
A13-1
A13

Preparation of Compound A13-1

A13-2 (20 g, 60.3 mmol), phenylboronic acid (7.4 g, 60.3 mmol), $Pd(PPh_3)_4$ (3.5 g, 3.0 mmol) and $Na_2CO_3$ (12.8 g, 120.6 mmol) were introduced to a 500 ml round bottom flask, and after introducing $THF/H_2O$ (250 ml/50 ml) thereto, the mixture was stirred at 65° C. After the reaction was completed, the temperature was lowered to room temperature, and the result was extracted and then concentrated. The result was purified by a MC:hexane=1:3 (v/v) column to synthesize Compound A13-1 (16.0 g, 48.7 mmol, yield: 80.8%).

Preparation of Compound A13

A13-1 (16.0 g, 48.7 mmol), SM2 (18.6 g, 73.1 mmol), $Pd_2dba_3$ (2.2 g, 2.4 mmol), Sphos (4.0 g, 9.7 mmol) and KOAc (9.6 g, 97.4 mmol) were introduced to a 500 ml round bottom flask, and after introducing 1,4-dioxane (200 ml) thereto, the mixture was stirred at 110° C. After the reaction was completed, the temperature was lowered to room temperature, and the result was filtered under vacuum and then concentrated. The result was purified by a MC:hexane=1:4 (v/v) column to synthesize Compound A13 (16.4 g, 39.0 mmol, yield: 80.1%).

<Preparation Example 2> Preparation of Compound A14

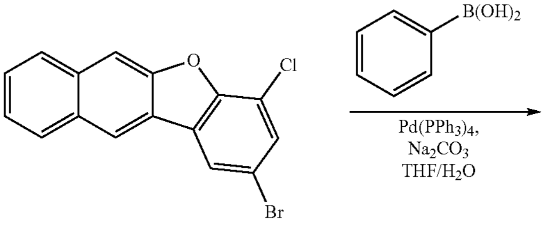

A14-2

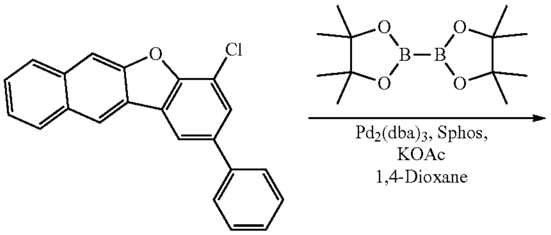

A14-1

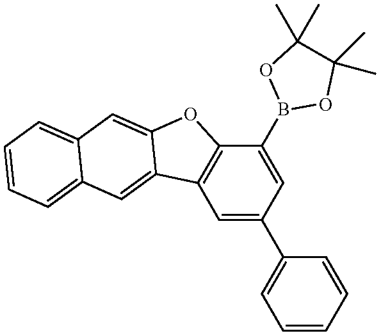

A14

Compound A14 was synthesized in the same manner as in Preparation Example 1 except that Compound A14-2 was used instead of Compound A13-2.

<Preparation Example 3> Preparation of Compound C

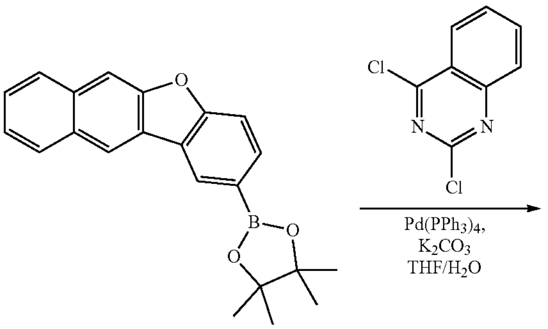

A2

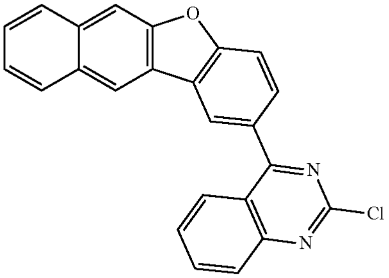

C2

A2 (30.0 g, 87.2 mmol), B1 (26.0 g, 130.7 mmol), $Pd(PPh_3)_4$ (5.0 g, 4.35 mmol) and $K_2CO_3$ (36.1 g, 261 mmol) were introduced to a 500 mL round bottom flask, and after introducing $THF/H_2O$ (250 ml/50 ml) thereto, the mixture was stirred at 65° C. After the reaction was completed, the temperature was lowered to room temperature, acetone was introduced thereto, and the result was stirred. The result was filtered, then slurried with acetone and water, and recrystallized with toluene to obtain Compound C2 (27.0 g, 70.9 mmol, yield: 81.5%).

Compounds were synthesized in the same manner as in Preparation Example 3 except that compounds A1 to A14 of the following Table 1 were used instead of Compound A2.

TABLE 1

| A | B | C | C Yield |
|---|---|---|---|
| 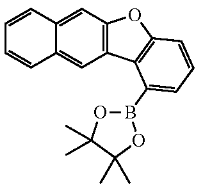 A1 | 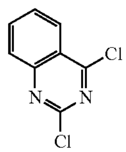 B1 | 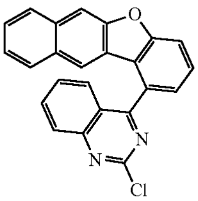 C1 | 80.3% |

TABLE 1-continued
| A | B | C | C Yield |
|---|---|---|---|
| 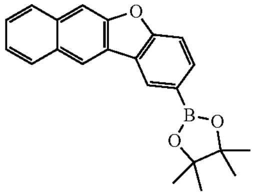 A2 | 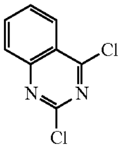 B1 | 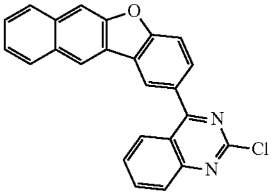 C2 | 81.5% |
| 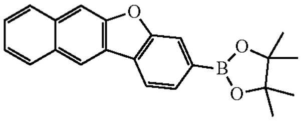 A3 | 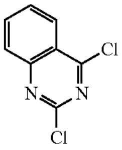 B1 | 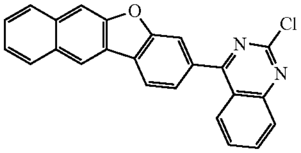 C3 | 81.3% |
| 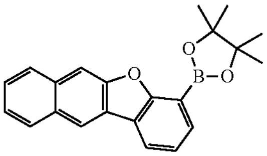 A4 | 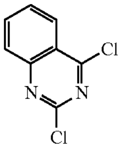 B1 | 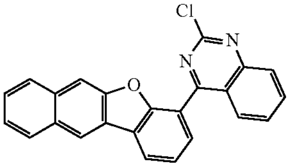 C4 | 79.9% |
| 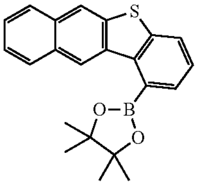 A5 | 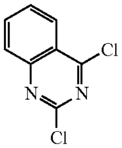 B1 | 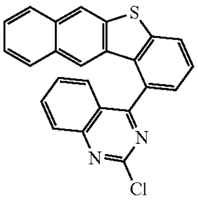 C5 | 60.8% |
| 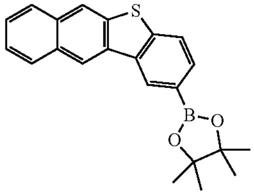 A6 | 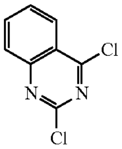 B1 | 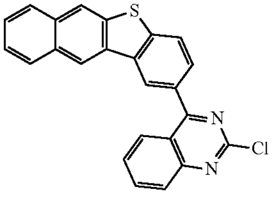 C6 | 57.3% |
| 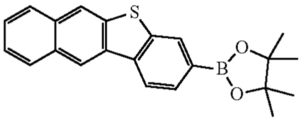 A7 | 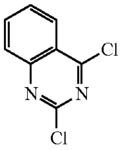 B1 | 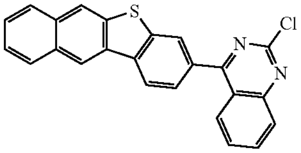 C7 | 65.3% |
| 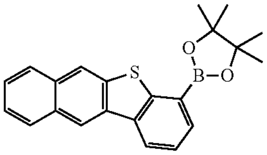 A8 | 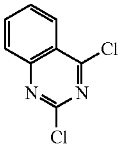 B1 | 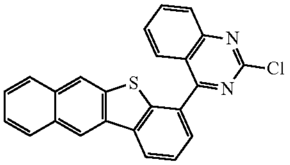 C8 | 61.3% |

TABLE 1-continued
| A | B | C | C Yield |
|---|---|---|---|
| 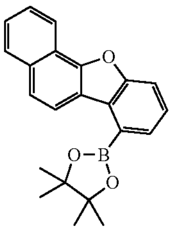<br>A9 | 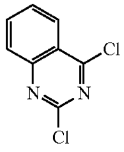<br>B1 | 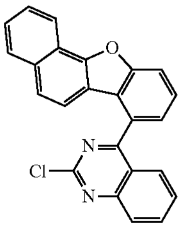<br>C9 | 79.3% |
| 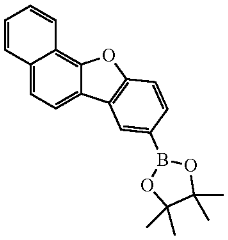<br>A10 | 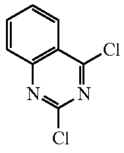<br>B1 | 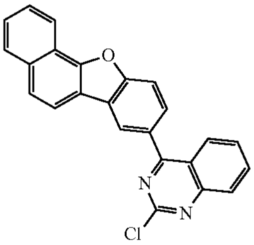<br>C10 | 75.5% |
| 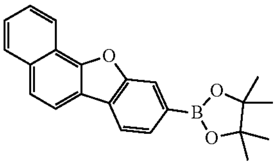<br>A11 | 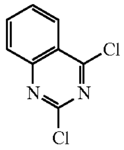<br>B1 | 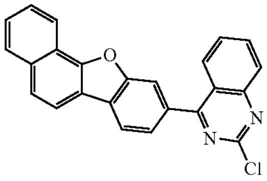<br>C11 | 74.9% |
| 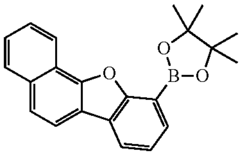<br>A12 | 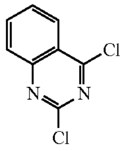<br>B1 | 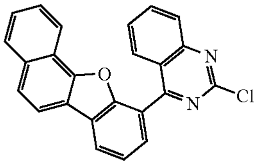<br>C12 | 75.0% |
| 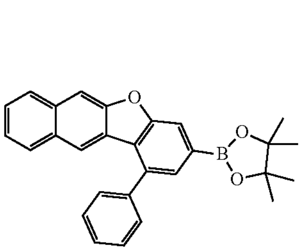<br>A13 | 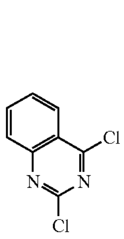<br>B1 | 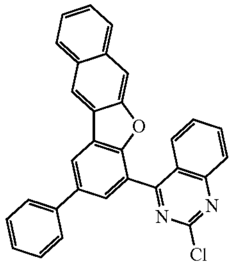<br>C13 | 70.0% |

TABLE 1-continued

| A | B | C | C Yield |
|---|---|---|---|
| 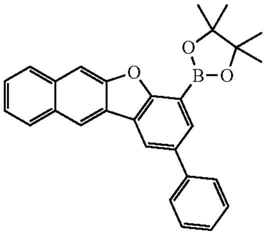 A14 | 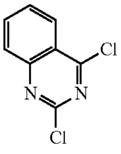 B1 | 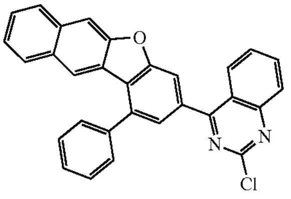 C14 | 69.8% |

<Preparation Example 4> Preparation of Compound I12

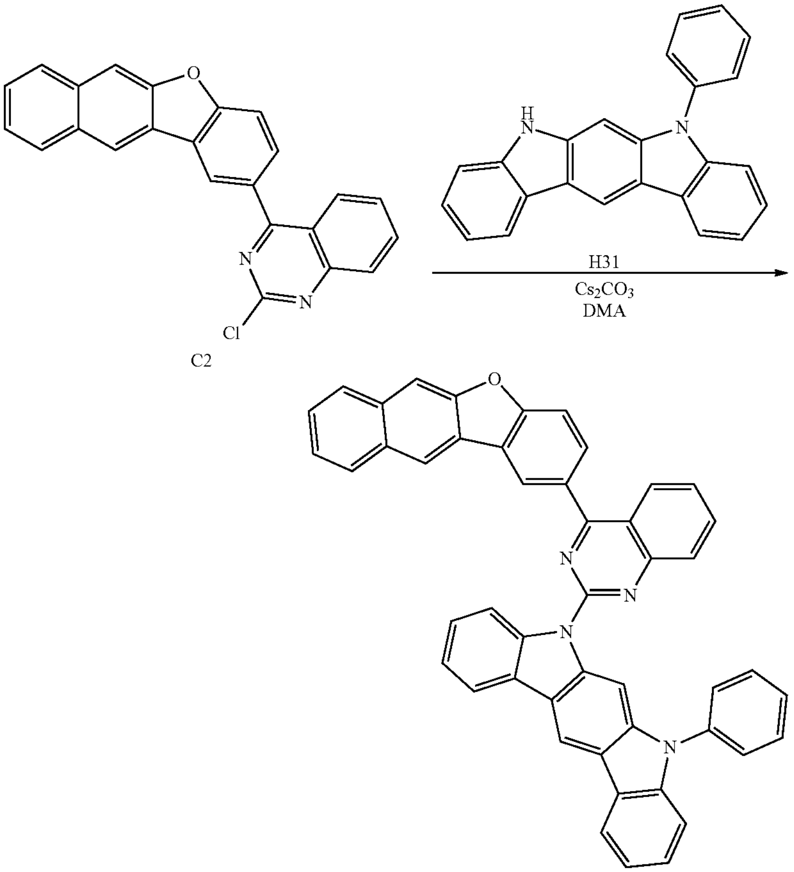

C2

I12

C2 (7.0 g, 18.3 mmol), H31 (6.7 g, 20.1 mmol) and $Cs_2CO_3$ (11.9 g, 36.6 mmol) were introduced to a 500 mL round bottom flask, and after introducing DMA (70 mL) thereto, the mixture was stirred at 150° C. After the reaction was completed, the temperature was lowered to room temperature, and precipitated solids were filtered. After that, the result was slurried with $H_2O$ for 30 minutes, then filtered, and recrystallized with DCB to obtain Compound I12 (9.5 g, 14.0 mmol, yield: 76.5%).

Target compounds were synthesized in the same manner as in Preparation Example 4 except that compounds described in C of the following Table 2 were used instead of Compound C2, and compounds described in H of the following Table 2 were used instead of Compound H31.

TABLE 2

| C | H | I | I Yield |
|---|---|---|---|
| C1 | H1 | I1 | 80.3% |
| C1 | H3 | I2 | 79.5% |
| C1 | H5 | I3 | 81.0% |

TABLE 2-continued
| C | H | I | I Yield |
|---|---|---|---|
| C1 | H8 | I4 | 81.3% |
| C2 | H4 | I5 | 85.1% |
| C2 | H8 | I6 | 80.3% |
| C2 | H31 | I12 | 76.5% |
| C2 | H32 | I13 | 79.5% |
| C2 | H35 | I14 | 82.0% |
| C2 | H41 | I15 | 82.3% |
| C2 | H47 | I16 | 77.5% |
| C2 | H49 | I17 | 70.3% |
| C3 | H1 | I18 | 90.1% |
| C3 | H2 | I19 | 91.1% |
| C3 | H3 | I20 | 90.5% |
| C3 | H8 | I21 | 89.7% |
| C3 | H9 | I22 | 85.1% |
| C3 | H31 | I30 | 85.5% |
| C3 | H32 | I31 | 80.7% |
| C3 | H35 | I32 | 81.9% |
| C3 | H41 | I33 | 82.0% |
| C3 | H42 | I34 | 81.7% |
| C3 | H48 | I35 | 80.0% |
| C3 | H49 | I36 | 80.9% |
| C3 | H52 | I37 | 82.8% |
| C4 | H32 | I38 | 75.1% |
| C14 | H8 | I39 | 80.3% |
| C14 | H31 | I42 | 81.5% |
| C14 | H32 | I43 | 81.1% |
| C14 | H35 | I44 | 80.1% |
| C14 | H41 | I45 | 79.9% |
| C13 | H8 | I46 | 75.7% |
| C13 | H31 | I49 | 71.7% |
| C13 | H32 | I50 | 71.9% |
| C13 | H35 | I51 | 70.0% |
| C9 | H8 | I52 | 85.3% |
| C9 | H31 | I54 | 84.9% |
| C9 | H32 | I55 | 83.1% |
| C9 | H35 | I56 | 85.1% |
| C9 | H49 | I57 | 85.9% |
| C10 | H8 | I58 | 90.1% |
| C10 | H31 | I60 | 89.9% |
| C10 | H37 | I61 | 88.7% |
| C10 | H49 | I62 | 87.9% |
| C11 | H4 | I63 | 90.1% |
| C11 | H35 | I65 | 90.5% |
| C12 | H1 | I66 | 75.1% |
| C12 | H31 | I69 | 74.9% |
| C12 | H35 | I70 | 76.5% |
| C6 | H31 | I71 | 70.5% |
| C6 | H32 | I72 | 73.5% |
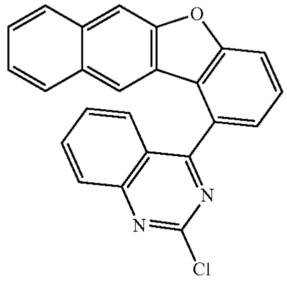
C1
-continued
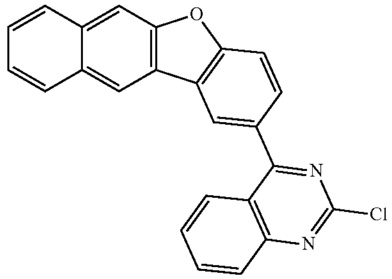
C2
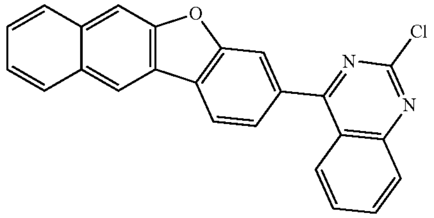
C3
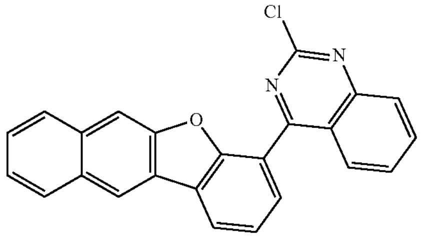
C4
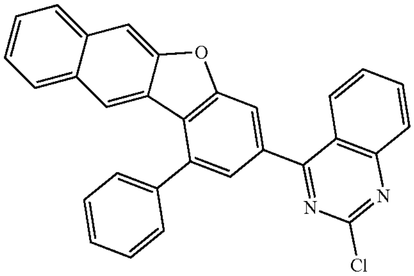
C14
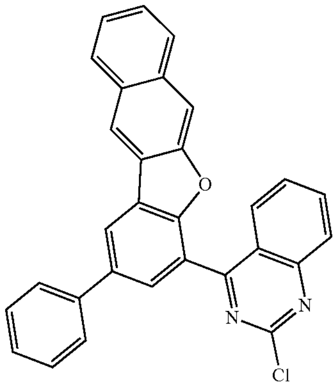
C13

-continued
C9
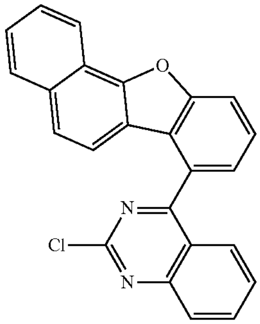
C10
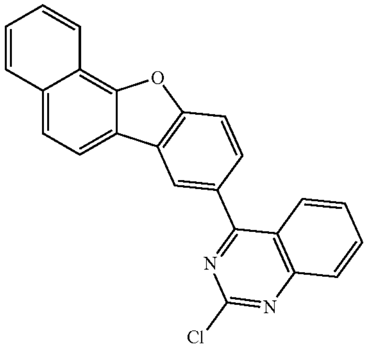
C11
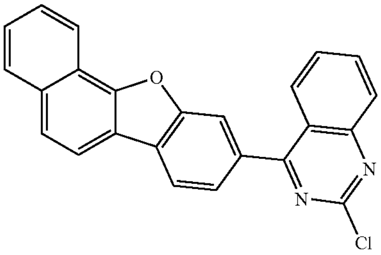
C12
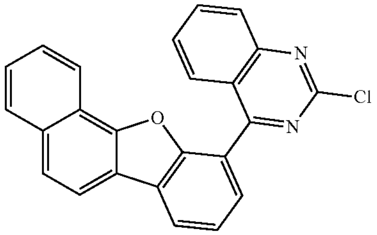
C6
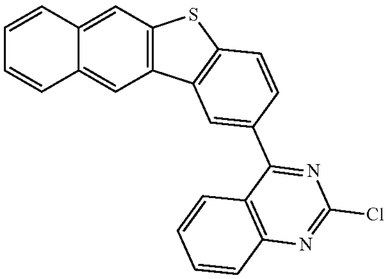
-continued
H1
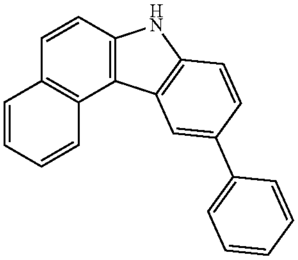
H3
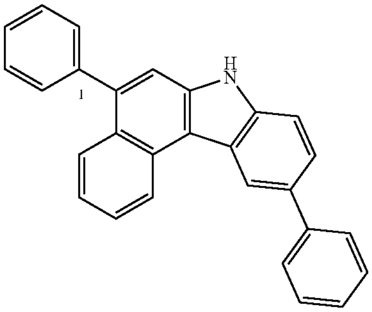
H5
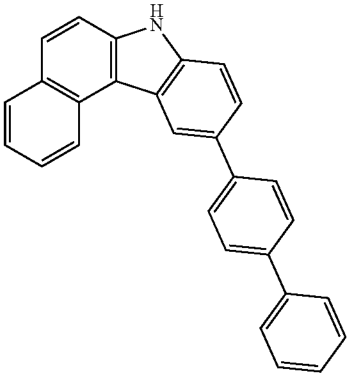
H8
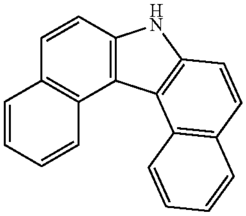
H4
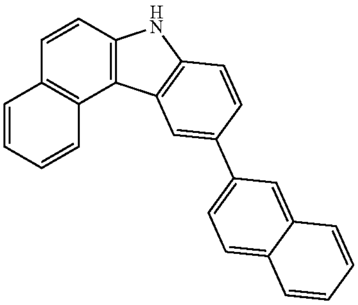

-continued
H31
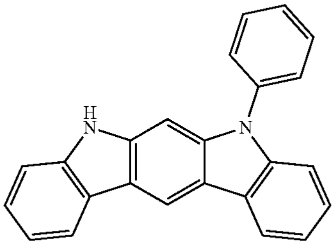
H32
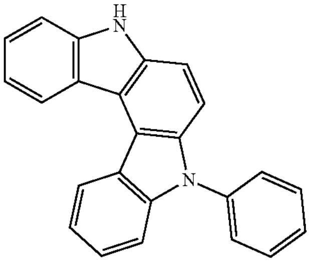
H35
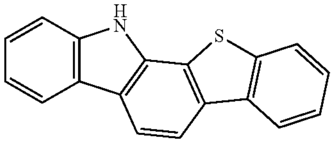
H41
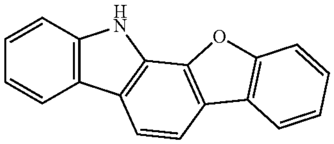
H47
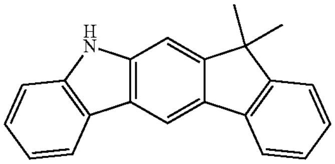
H49
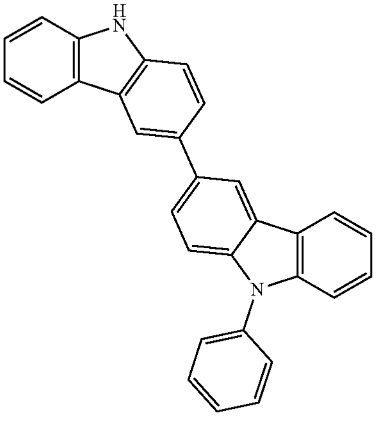
-continued
H2
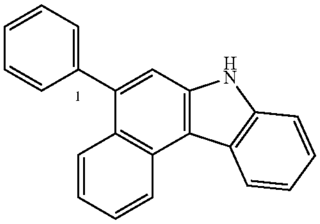
H9
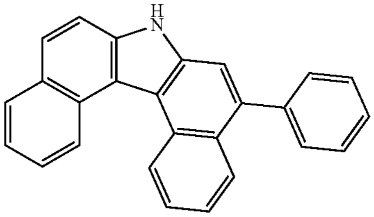
H42
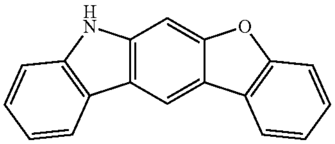
H48
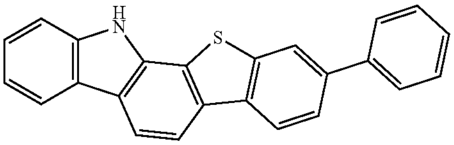
H52
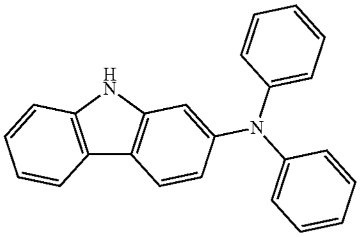
H37
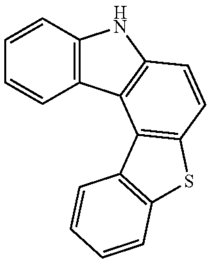

<Preparation Example 5> Preparation of Compound I23

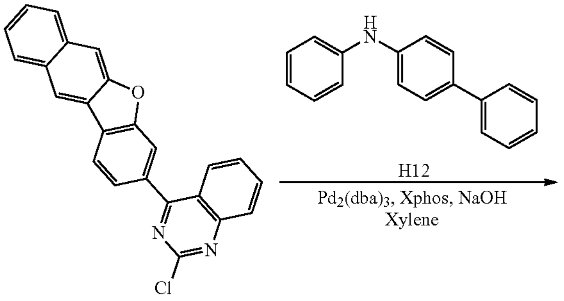

C3

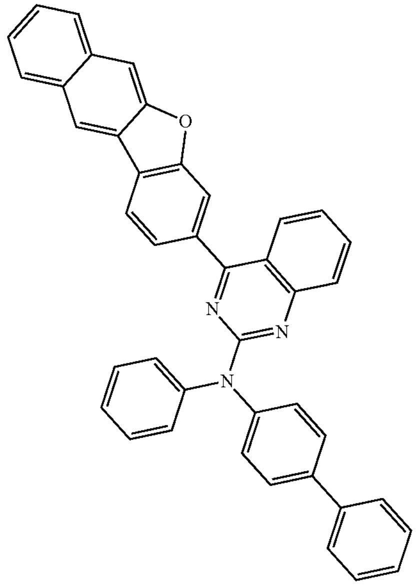

I23

C3 (10.0 g, 26.3 mmol), H12 (7.1 g, 28.9 mmol), $Pd_2dba_3$ (1.2 g, 1.3 mmol), Xphos (2.5 g, 5.3 mmol) and NaOH (2.1 g, 52.6 mmol) were introduced to a 500 mL round bottom flask, and after introducing xylene (100 mL) thereto, the mixture was stirred at 150° C. After the reaction was completed, the temperature was lowered to room temperature, and precipitated solids were filtered. After that, the result was slurried with $H_2O$ for 30 minutes, then filtered, and recrystallized with DCB to obtain Compound I23 (13.0 g, 22.0 mmol, yield: 83.7%).

Target compounds were synthesized in the same manner as in Preparation Example 5 except that compounds described in C of the following Table 3 were used instead of Compound C3, and compounds described in H of the following Table 3 were used instead of Compound H12.

TABLE 3

| C | H | I | I Yield |
|---|---|---|---|
| C2 | H17 | I7 | 80.4% |
| C3 | H12 | I23 | 83.7% |

TABLE 3-continued

| C | H | I | I Yield |
|---|---|---|---|
| C3 | H13 | I24 | 85.1% |
| C3 | H17 | I25 | 84.9% |
| C14 | H16 | I40 | 80.7% |
| C13 | H14 | I47 | 83.1% |
| C12 | H17 | I67 | 83.9% |

H17

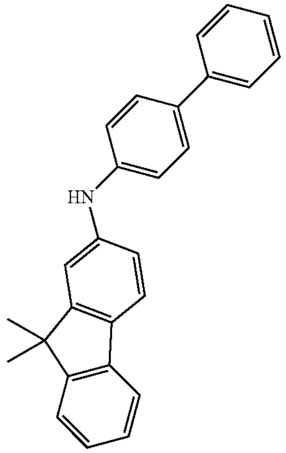

H12

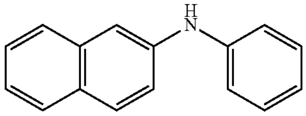

H16

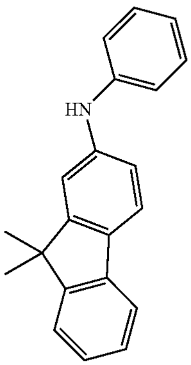

H14

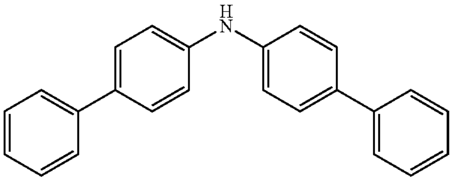

<Preparation Example 6> Preparation of Compound I26

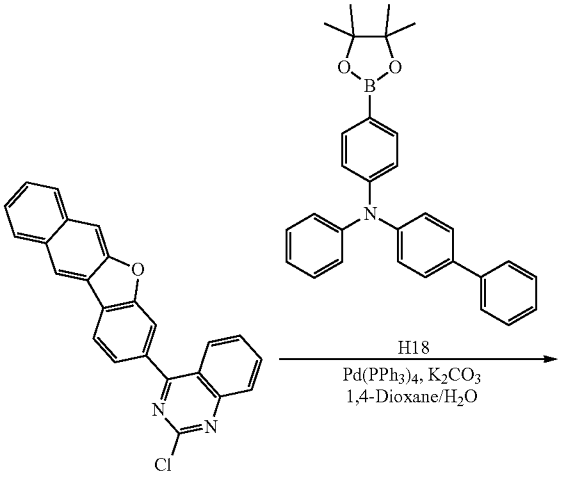

C3

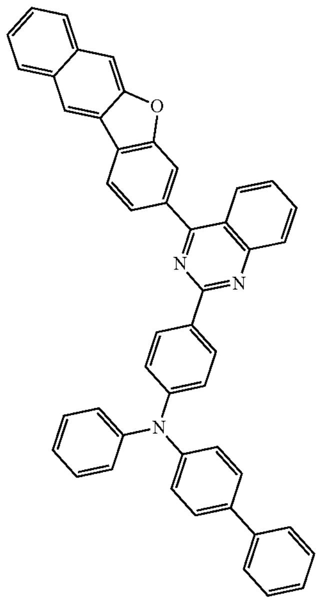

I26

Preparation of Compound C

C3 (10.0 g, 26.3 mmol), H18 (12.9 g, 28.9 mmol), $Pd(PPh_3)_4$ (1.5 g, 1.3 mmol) and $K_2CO_3$ (9.1 g, 65.8 mmol) were introduced to a 500 mL round bottom flask, and after introducing 1,4-dioxane/$H_2O$ (100 ml/20 ml) thereto, the mixture was stirred at 130° C. After the reaction was completed, the temperature was lowered to room temperature, and precipitated solids were filtered. After that, the result was slurried with $H_2O$ for 30 minutes, then filtered, and recrystallized with DCB to obtain Compound I26 (12.3 g, 18.5 mmol, yield: 70.3%).

Target compounds were synthesized in the same manner as in Preparation Example 6 except that compounds described in C of the following Table 4 were used instead of Compound C3, and compounds described in H of the following Table 4 were used instead of Compound H18.

TABLE 4

| C | H | I | I Yield |
|---|---|---|---|
| C2 | H20 | I8 | 90.1% |
| C2 | H21 | I9 | 92.3% |
| C2 | H22 | I10 | 89.3% |
| C2 | H28 | I11 | 85.7% |
| C3 | H18 | I26 | 70.3% |
| C3 | H20 | I27 | 72.0% |
| C3 | H23 | I28 | 72.1% |
| C3 | H28 | I29 | 73.5% |
| C14 | H18 | I41 | 80.1% |
| C9 | H20 | I53 | 82.3% |
| C10 | H18 | I59 | 83.1% |
| C11 | H22 | I64 | 79.9% |
| C12 | H24 | I68 | 80.0% |

H20

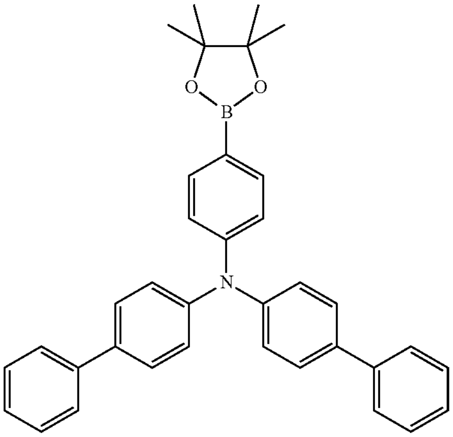

H21

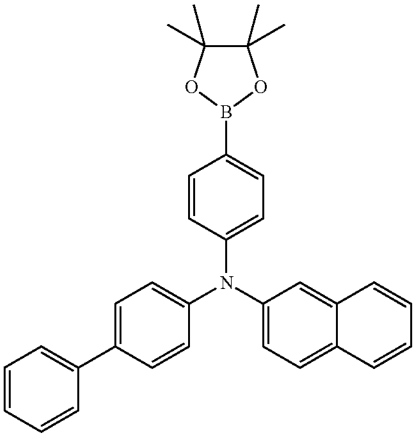

-continued
H22
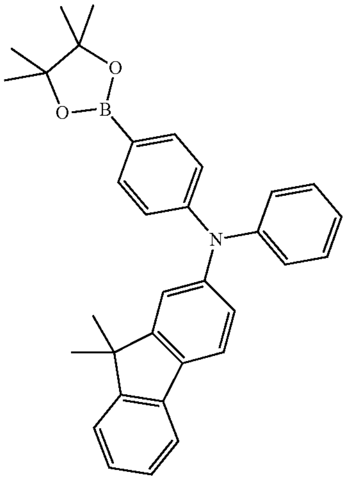
H28
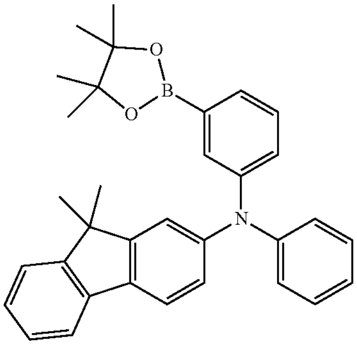
H18
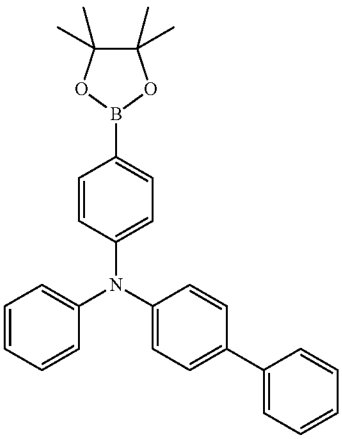
-continued
H23
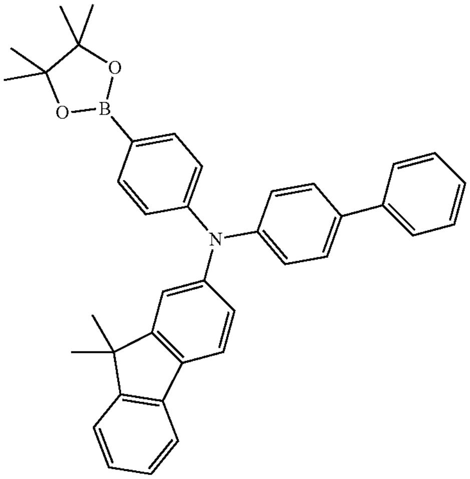
H24
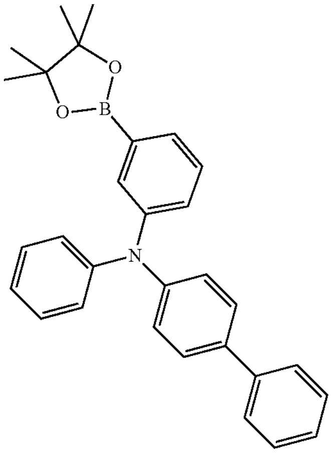
Heterocyclic compounds corresponding to Chemical Formula 1 other than the compounds described in Preparation Examples 1 to 6 and Tables 1 to 4 were also prepared in the same manner as in the preparation examples described above.
Preparation Example 7) Preparation of Compound I
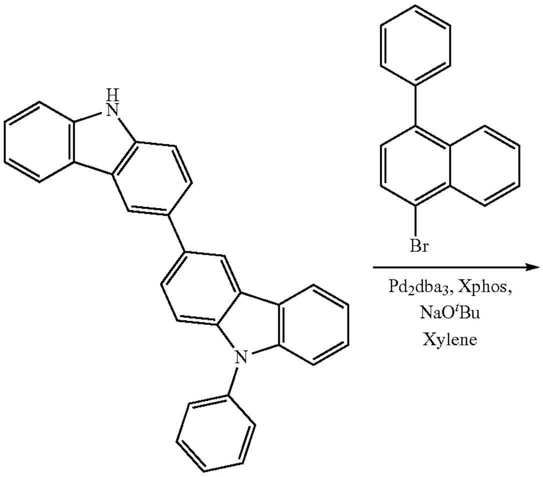

-continued

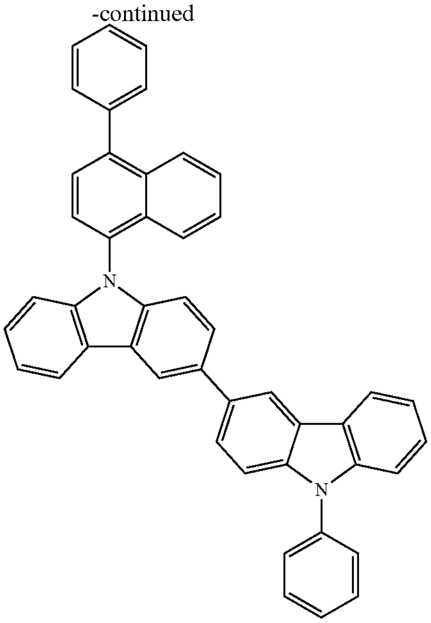

9-Phenyl-9H, 9'H-3,3'-bicarbazole (10.0 g, 24.5 mmol), 1-bromo-4-phenylnaphthalene (7.6 g, 27.0 mmol), $Pd_2dba_3$ (1.1 g, 1.2 mmol), Xphos (1.2 g, 2.5 mmol) and NaOtBu (7.1 g, 73.5 mmol) were introduced to a 500 mL round bottom flask, and after introducing xylene (100 mL) thereto, the mixture was stirred at 150° C. After the reaction was completed, the temperature was lowered to room temperature, and the result was celite filtered. After that, the result was purified by a MC:HX=1:2 column to obtain Compound I (12.7 g, 20.8 mmol, yield: 84.9%).

Preparation Example 8) Preparation of Compound J

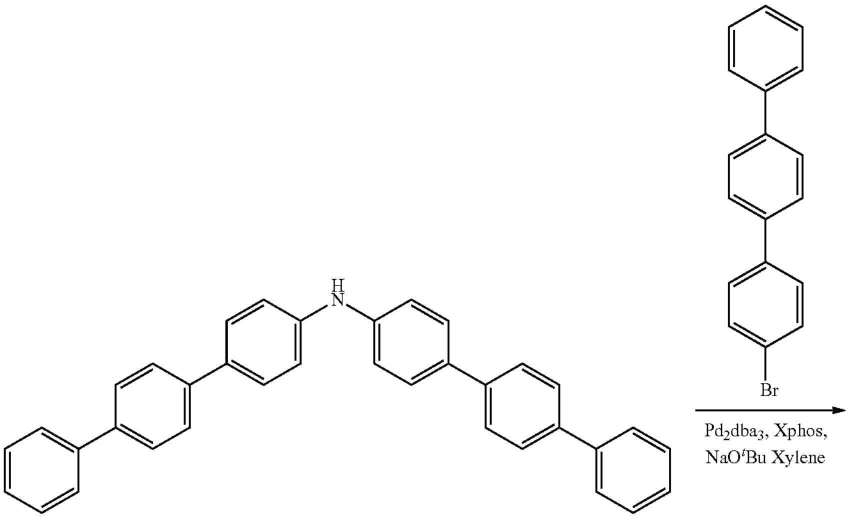

-continued

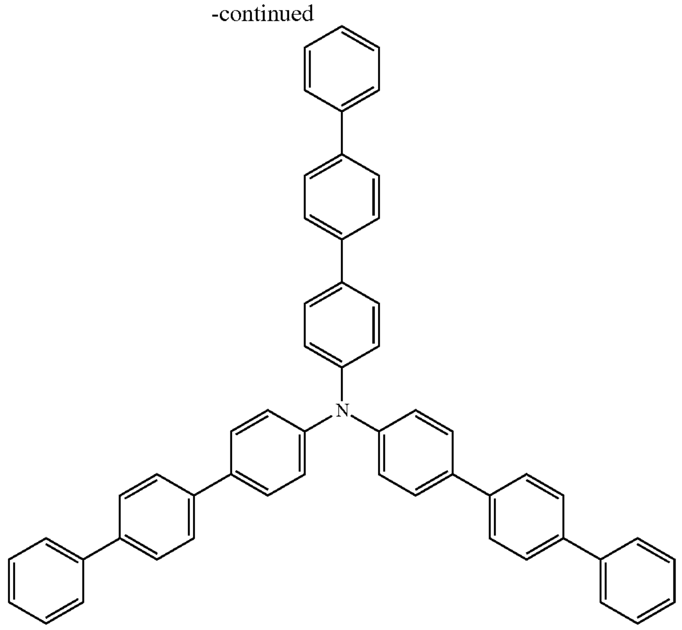

Di([1,1':4',1"-terphenyl]-4-yl)amine (10.0 g, 21.1 mmol), 4-bromo-1,1':4',1"-terphenyl (7.2 g, 23.2 mmol), $Pd_2dba_3$ (1.0 g, 1.1 mmol), Xphos (1.0 g, 2.1 mmol) and NaOtBu (6.1 g, 63.3 mmol) were introduced to a 500 mL round bottom flask, and after introducing xylene (100 mL) thereto, the mixture was stirred at 150° C. After the reaction was completed, the temperature was lowered to room temperature, and the result was filtered. After that, the result was recrystallized with DCB to obtain Compound J (12.1 g, 17.2 mmol, yield: 81.5%).

Preparation Example 9) Preparation of Compound K

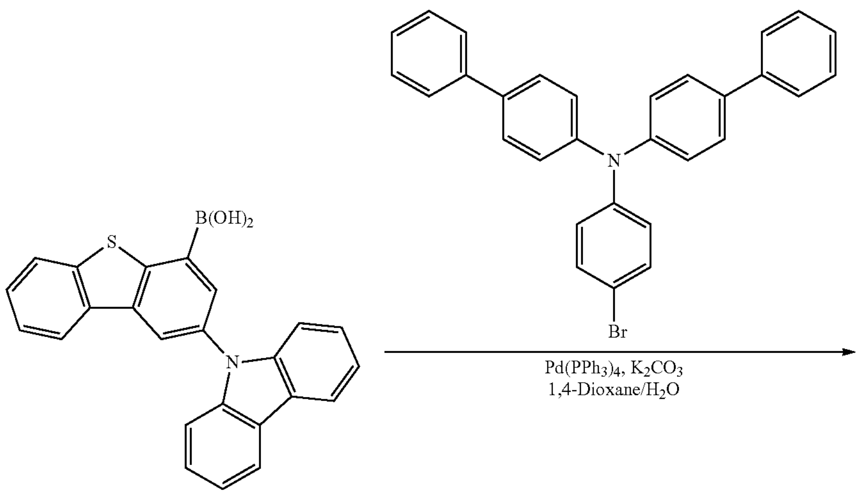

-continued

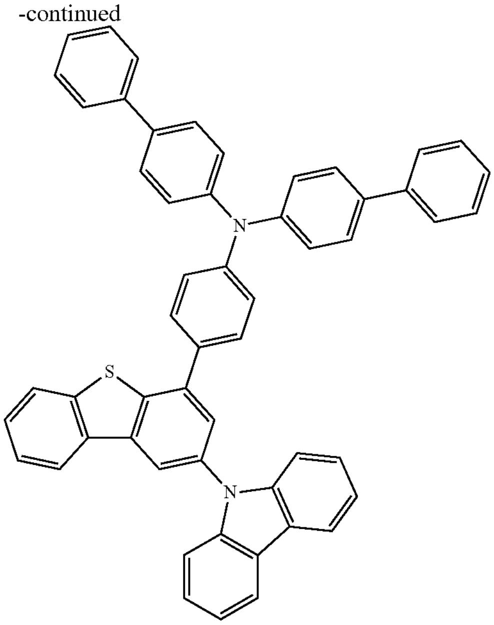

(2-(9H-carbazol-9-yl)dibenzo[b,d]thiophen-4-yl)boronic acid (15 g, 38.1 mmol), N-([1,1'-biphenyl]-4-yl)-N-(4-bromophenyl)-[1,1'-biphenyl]-4-amine (18.1 g, 38.1 mmol), $Pd(PPh_3)_4$ (2.2 g, 1.9 mmol) and $K_2CO_3$ (13.1 g, 95.3 mmol) were introduced to a 500 ml round bottom flask, and after introducing 1,4-dioxane/$H_2O$ (200 ml/40 ml) thereto, the mixture was stirred at 160° C. After the reaction was completed, the temperature was lowered to room temperature, and the result was extracted with MC/$H_2O$ and then concentrated. The result was purified by a MC:hexane=1:1 (v/v) column to obtain Compound K (26.3 g, 35.3 mmol, yield: 92.7%).

Synthesis identification data of the compounds prepared above are as described in the following [Table 5] and [Table 6].

TABLE 5

| Compound | FD-Mass |
|---|---|
| 1 | m/z = 637.7420 (C46H27N3O, 637.2154) |
| 2 | m/z = 713.8400 (C52H31N3O, 713.2467) |
| 3 | m/z = 713.8400 (C52H31N3O, 713.2467) |
| 4 | m/z = 611.7040 (C44H25N3O, 611.1998) |
| 5 | m/z = 589.6980 (C42H27N3O, 589.2154) |
| 6 | m/z = 563.6600 (C40H25N3O, 563.1998) |
| 7 | m/z = 665.7960 (C48H31N3O, 665.2467) |
| 8 | m/z = 705.8610 (C51H35N3O, 705.2780) |
| 9 | m/z = 665.7960 (C48H31N3O, 665.2467) |
| 10 | m/z = 741.8940 (C54H35N3O, 741.2780) |
| 11 | m/z = 705.8610 (C51H35N3O, 705.2780) |
| 12 | m/z = 676.7790 (C48H28N4O, 676.2263) |
| 13 | m/z = 676.7790 (C48H28N4O, 676.2263) |
| 14 | m/z = 617.7260 (C42H23N3OS, 617.1562) |
| 15 | m/z = 752.8770 (C54H32N4O, 752.2576) |
| 16 | m/z = 802.9370 (C58H34N4O, 802.2733) |
| 17 | m/z = 678.7950 (C48H30N4O, 678.2420) |
| 18 | m/z = 678.7950 (C48H30N4O, 678.2420) |
| 19 | m/z = 687.8020 (C50H29N3O, 687.2311) |
| 20 | m/z = 713.8400 (C52H31N3O, 713.2467) |
| 21 | m/z = 611.7040 (C44H25N3O, 611.1998) |
| 22 | m/z = 665.7960 (C48H31N3O, 665.2467) |
| 23 | m/z = 705.8610 (C51H35N3O, 705.2780) |
| 24 | m/z = 741.8940 (C54H35N3O, 741.2780) |
| 25 | m/z = 715.8560 (C52H33N3O, 715.2624) |

TABLE 5-continued

| Compound | FD-Mass |
|---|---|
| 26 | m/z = 705.8610 (C51H35N3O, 705.2780) |
| 27 | m/z = 781.9590 (C57H39N3O, 781.3093) |
| 28 | m/z = 705.8610 (C51H35N3O, 705.2780) |
| 29 | m/z = 676.7790 (C48H28N4O, 676.2263) |
| 30 | m/z = 676.7790 (C48H28N4O, 676.2263) |
| 31 | m/z = 617.7260 (C42H23N3OS, 617.1562) |
| 32 | m/z = 617.7260 (C42H23N3OS, 617.1562) |
| 33 | m/z = 601.6650 (C42H23N3O2, 601.1790) |
| 34 | m/z = 627.7470 (C45H29N3O, 627.2311) |
| 35 | m/z = 693.8240 (C48H27N3OS, 693.1875) |
| 36 | m/z = 752.8770 (C54H32N4O, 752.2576) |
| 37 | m/z = 637.7420 (C46H27N3O, 637.2154) |
| 38 | m/z = 637.7420 (C46H27N3O, 637.2154) |
| 39 | m/z = 713.8400 (C52H31N3O, 713.2467) |
| 40 | m/z = 611.7040 (C44H25N3O, 611.1998) |
| 41 | m/z = 687.8020 (C50H29N3O, 687.2311) |
| 42 | m/z = 589.6980 (C42H27N3O, 589.2154) |
| 43 | m/z = 563.6600 (C40H25N3O, 563.1998) |
| 44 | m/z = 665.7960 (C48H31N3O, 665.2467) |
| 45 | m/z = 705.8610 (C51H35N3O, 705.2780) |
| 46 | m/z = 665.7960 (C48H31N3O, 665.2467) |
| 47 | m/z = 741.8940 (C54H35N3O, 741.2780) |
| 48 | m/z = 781.9590 (C57H39N3O, 781.3093) |
| 49 | m/z = 665.7960 (C48H31N3O, 665.2467) |
| 50 | m/z = 705.8610 (C51H35N3O, 705.2780) |
| 51 | m/z = 676.7790 (C48H28N4O, 676.2263) |
| 52 | m/z = 676.7790 (C48H28N4O, 676.2263) |
| 53 | m/z = 676.7790 (C48H28N4O, 676.2263) |
| 54 | m/z = 617.7260 (C42H23N3OS, 617.1562) |
| 55 | m/z = 601.6650 (C42H23N3O2, 601.1790) |
| 56 | m/z = 601.6650 (C42H23N3O2, 601.1790) |
| 57 | m/z = 627.7470 (C45H29N3O, 627.2311) |
| 58 | m/z = 693.8240 (C48H27N3OS, 693.1875) |
| 59 | m/z = 752.8770 (C54H32N4O, 752.2576) |
| 60 | m/z = 678.7950 (C48H30N4O, 678.2420) |
| 61 | m/z = 637.7420 (C46H27N3O, 637.2154) |
| 62 | m/z = 637.7420 (C46H27N3O, 637.2154) |
| 63 | m/z = 713.8400 (C52H31N3O, 713.2467) |
| 64 | m/z = 611.7040 (C44H25N3O, 611.1998) |
| 65 | m/z = 705.8610 (C51H35N3O, 705.2780) |
| 66 | m/z = 741.8940 (C54H35N3O, 741.2780) |
| 67 | m/z = 705.8610 (C51H35N3O, 705.2780) |
| 68 | m/z = 741.8940 (C54H35N3O, 741.2780) |
| 69 | m/z = 676.7790 (C48H28N4O, 676.2263) |
| 70 | m/z = 676.7790 (C48H28N4O, 676.2263) |

TABLE 5-continued

| Compound | FD-Mass |
|---|---|
| 71 | m/z = 627.7470 (C45H29N3O, 627.2311) |
| 72 | m/z = 752.8770 (C54H32N4O, 752.2576) |
| 73 | m/z = 653.8030 (C46H27N3S, 653.1926) |
| 74 | m/z = 627.7650 (C44H25N3S, 627.1769) |
| 75 | m/z = 681.8570 (C48H31N3S, 681.2239) |
| 76 | m/z = 721.9220 (C51H35N3S, 721.2552) |
| 77 | m/z = 757.9550 (C54H35N3S, 757.2552) |
| 78 | m/z = 731.9170 (C52H33N3S, 731.2395) |
| 79 | m/z = 692.8400 (C48H28N4S, 692.2035) |
| 80 | m/z = 692.8400 (C48H28N4S, 692.2035) |
| 81 | m/z = 692.8400 (C48H28N4S, 692.2035) |
| 82 | m/z = 617.7260 (C42H23N3OS, 617.1562) |
| 83 | m/z = 617.7260 (C42H23N3OS, 617.1562) |
| 84 | m/z = 768.9380 (C54H32N4S, 768.2348) |
| 85 | m/z = 653.8030 (C46H27N3S, 653.1926) |
| 86 | m/z = 729.9010 (C52H31N3S, 729.2239) |
| 87 | m/z = 627.7650 (C44H25N3S, 627.1769) |
| 88 | m/z = 579.7210 (C40H25N3S, 579.1769) |
| 89 | m/z = 681.8570 (C48H31N3S, 681.2239) |
| 90 | m/z = 721.9220 (C51H35N3S, 721.2552) |
| 91 | m/z = 681.8570 (C48H31N3S, 681.2239) |
| 92 | m/z = 655.8190 (C46H29N3S, 655.2082) |
| 93 | m/z = 757.9550 (C54H35N3S, 757.2552) |
| 94 | m/z = 798.0200 (C57H39N3S, 797.2865) |
| 95 | m/z = 721.9220 (C51H35N3S, 721.2552) |
| 96 | m/z = 692.8400 (C48H28N4S, 692.2035) |
| 97 | m/z = 692.8400 (C48H28N4S, 692.2035) |
| 98 | m/z = 633.7870 (C42H23N3S2, 633.1333) |
| 99 | m/z = 633.7870 (C42H23N3S2, 633.1333) |
| 100 | m/z = 617.7260 (C42H23N3OS, 617.1562) |
| 101 | m/z = 617.7260 (C42H23N3OS, 617.1562) |
| 102 | m/z = 768.9380 (C54H32N4S, 768.2348) |
| 103 | m/z = 729.9010 (C52H31N3S, 729.2239) |
| 104 | m/z = 703.8630 (C50H29N3S, 703.2082) |
| 105 | m/z = 729.9010 (C52H31N3S, 729.2239) |
| 106 | m/z = 681.8570 (C48H31N3S, 681.2239) |
| 107 | m/z = 645.8240 (C45H31N3S, 645.2239) |
| 108 | m/z = 721.9220 (C51H35N3S, 721.2552) |
| 109 | m/z = 681.8570 (C48H31N3S, 681.2239) |
| 110 | m/z = 655.8190 (C46H29N3S, 655.2082) |
| 111 | m/z = 757.9550 (C54H35N3S, 757.2552) |
| 112 | m/z = 721.9220 (C51H35N3S, 721.2552) |
| 113 | m/z = 757.9550 (C54H35N3S, 757.2552) |
| 114 | m/z = 721.9220 (C51H35N3S, 721.2552) |
| 115 | m/z = 692.8400 (C48H28N4S, 692.2035) |
| 116 | m/z = 692.8400 (C48H28N4S, 692.2035) |
| 117 | m/z = 692.8400 (C48H28N4S, 692.2035) |
| 118 | m/z = 633.7870 (C42H23N3S2, 633.1333) |
| 119 | m/z = 617.7260 (C42H23N3OS, 617.1562) |
| 120 | m/z = 768.9380 (C54H32N4S, 768.2348) |
| 121 | m/z = 653.8030 (C46H27N3S, 653.1926) |
| 122 | m/z = 653.8030 (C46H27N3S, 653.1926) |
| 123 | m/z = 729.9010 (C52H31N3S, 729.2239) |
| 124 | m/z = 627.7650 (C44H25N3S, 627.1769) |
| 125 | m/z = 605.7590 (C42H27N3S, 605.1926) |
| 126 | m/z = 721.9220 (C51H35N3S, 721.2552) |
| 127 | m/z = 681.8570 (C48H31N3S, 681.2239) |
| 128 | m/z = 721.9220 (C51H35N3S, 721.2552) |
| 129 | m/z = 798.0200 (C57H39N3S, 797.2865) |
| 130 | m/z = 757.9550 (C54H35N3S, 757.2552) |
| 131 | m/z = 692.8400 (C48H28N4S, 692.2035) |
| 132 | m/z = 692.8400 (C48H28N4S, 692.2035) |
| 133 | m/z = 713.8400 (C52H31N3O, 713.2467) |
| 134 | m/z = 789.9380 (C58H35N3O, 789.2780) |
| 135 | m/z = 687.8020 (C50H29N3O, 687.2311) |
| 136 | m/z = 665.7960 (C48H31N3O, 665.2467) |
| 137 | m/z = 741.8940 (C54H35N3O, 741.2780) |
| 138 | m/z = 705.8610 (C51H35N3O, 705.2780) |
| 139 | m/z = 781.9590 (C57H39N3O, 781.3093) |
| 140 | m/z = 741.8940 (C54H35N3O, 741.2780) |
| 141 | m/z = 715.8560 (C52H33N3O, 715.2624) |
| 142 | m/z = 781.9590 (C57H39N3O, 781.3093) |
| 143 | m/z = 781.9590 (C57H39N3O, 781.3093) |
| 144 | m/z = 752.8770 (C54H32N4O, 752.2576) |
| 145 | m/z = 752.8770 (C54H32N4O, 752.2576) |
| 146 | m/z = 752.8770 (C54H32N4O, 752.2576) |
| 147 | m/z = 693.8240 (C48H27N3OS, 693.1875) |
| 148 | m/z = 693.8240 (C48H27N3OS, 693.1875) |

TABLE 5-continued

| Compound | FD-Mass |
|---|---|
| 149 | m/z = 677.7630 (C48H27N3O2, 677.2103) |
| 150 | m/z = 754.8930 (C54H34N4O, 754.2733) |
| 151 | m/z = 713.8400 (C52H31N3O, 713.2467) |
| 152 | m/z = 789.9380 (C58H35N3O, 789.2780) |
| 153 | m/z = 763.9000 (C56H33N3O, 763.2624) |
| 154 | m/z = 687.8020 (C50H29N3O, 687.2311) |
| 155 | m/z = 665.7960 (C48H31N3O, 665.2467) |
| 156 | m/z = 639.7580 (C46H29N3O, 639.2311) |
| 157 | m/z = 741.8940 (C54H35N3O, 741.2780) |
| 158 | m/z = 705.8610 (C51H35N3O, 705.2780) |
| 159 | m/z = 781.9590 (C57H39N3O, 781.3093) |
| 160 | m/z = 741.8940 (C54H35N3O, 741.2780) |
| 161 | m/z = 781.9590 (C57H39N3O, 781.3093) |
| 162 | m/z = 741.8940 (C54H35N3O, 741.2780) |
| 163 | m/z = 752.8770 (C54H32N4O, 752.2576) |
| 164 | m/z = 752.8770 (C54H32N4O, 752.2576) |
| 165 | m/z = 693.8240 (C48H27N3OS, 693.1875) |
| 166 | m/z = 693.8240 (C48H27N3OS, 693.1875) |
| 167 | m/z = 677.7630 (C48H27N3O2, 677.2103) |
| 168 | m/z = 754.8930 (C54H34N4O, 754.2733) |
| 169 | m/z = 713.8400 (C52H31N3O, 713.2467) |
| 170 | m/z = 687.8020 (C50H29N3O, 687.2311) |
| 171 | m/z = 665.7960 (C48H31N3O, 665.2467) |
| 172 | m/z = 741.8940 (C54H35N3O, 741.2780) |
| 173 | m/z = 741.8940 (C54H35N3O, 741.2780) |
| 174 | m/z = 791.9540 (C58H37N3O, 791.2937) |
| 175 | m/z = 781.9590 (C57H39N3O, 781.3093) |
| 176 | m/z = 741.8940 (C54H35N3O, 741.2780) |
| 177 | m/z = 791.9540 (C58H37N3O, 791.2937) |
| 178 | m/z = 752.8770 (C54H32N4O, 752.2576) |
| 179 | m/z = 752.8770 (C54H32N4O, 752.2576) |
| 180 | m/z = 693.8240 (C48H27N3OS, 693.1875) |
| 181 | m/z = 713.8400 (C52H31N3O, 713.2467) |
| 182 | m/z = 763.9000 (C56H33N3O, 763.2624) |
| 183 | m/z = 687.8020 (C50H29N3O, 687.2311) |
| 184 | m/z = 665.7960 (C48H31N3O, 665.2467) |
| 185 | m/z = 639.7580 (C46H29N3O, 639.2311) |
| 186 | m/z = 705.8610 (C51H35N3O, 705.2780) |
| 187 | m/z = 781.9590 (C57H39N3O, 781.3093) |
| 188 | m/z = 741.8940 (C54H35N3O, 741.2780) |
| 189 | m/z = 781.9590 (C57H39N3O, 781.3093) |
| 190 | m/z = 791.9540 (C58H37N3O, 791.2937) |
| 191 | m/z = 781.9590 (C57H39N3O, 781.3093) |
| 192 | m/z = 752.8770 (C54H32N4O, 752.2576) |
| 193 | m/z = 752.8770 (C54H32N4O, 752.2576) |
| 194 | m/z = 693.8240 (C48H27N3OS, 693.1875) |
| 195 | m/z = 677.7630 (C48H27N3O2, 677.2103) |
| 196 | m/z = 677.7630 (C48H27N3O2, 677.2103) |
| 197 | m/z = 677.7630 (C48H27N3O2, 677.2103) |
| 198 | m/z = 703.8450 (C51H33N3O, 703.2624) |
| 199 | m/z = 703.8630 (C50H29N3S, 703.2082) |
| 200 | m/z = 757.9550 (C54H35N3S, 757.2552) |
| 201 | m/z = 768.9380 (C54H32N4S, 768.2348) |
| 202 | m/z = 703.8630 (C50H29N3S, 703.2082) |
| 203 | m/z = 768.9380 (C54H32N4S, 768.2348) |
| 204 | m/z = 768.9380 (C54H32N4S, 768.2348) |
| 205 | m/z = 737.7420 (C46H27N3O, 737.2154) |
| 206 | m/z = 737.7420 (C46H27N3O, 737.2154) |
| 207 | m/z = 611.7040 (C44H25N3O, 611.1998) |
| 208 | m/z = 629.7630 (C45H31N3O, 629.2467) |
| 209 | m/z = 705.8610 (C51H35N3O, 705.2780) |
| 210 | m/z = 741.8940 (C54H35N3O, 741.2780) |
| 211 | m/z = 705.8610 (C51H35N3O, 705.2780) |
| 212 | m/z = 676.7790 (C48H28N4O, 676.2263) |
| 213 | m/z = 676.7790 (C48H28N4O, 676.2263) |
| 214 | m/z = 617.7260 (C42H23N3OS, 617.1562) |
| 215 | m/z = 752.8770 (C54H32N4O, 752.2576) |
| 216 | m/z = 678.7950 (C48H30N4O, 678.2420) |
| 217 | m/z = 611.7040 (C44H25N3O, 611.1998) |
| 218 | m/z = 665.7960 (C48H31N3O, 665.2467) |
| 219 | m/z = 629.7630 (C45H31N3O, 629.2467) |
| 220 | m/z = 665.7960 (C48H31N3O, 665.2467) |
| 221 | m/z = 741.8940 (C54H35N3O, 741.2780) |
| 222 | m/z = 705.8610 (C51H35N3O, 705.2780) |
| 223 | m/z = 705.8610 (C51H35N3O, 705.2780) |
| 224 | m/z = 676.7790 (C48H28N4O, 676.2263) |
| 225 | m/z = 676.7790 (C48H28N4O, 676.2263) |
| 226 | m/z = 617.7260 (C42H23N3OS, 617.1562) |

TABLE 5-continued

| Compound | FD-Mass |
|---|---|
| 227 | m/z = 617.7260 (C42H23N3OS, 617.1562) |
| 228 | m/z = 752.8770 (C54H32N4O, 752.2576) |
| 229 | m/z = 637.7420 (C46H27N3O, 637.2154) |
| 230 | m/z = 687.8020 (C50H29N3O, 687.2311) |
| 231 | m/z = 611.7040 (C44H25N3O, 611.1998) |
| 232 | m/z = 563.6600 (C40H25N3O, 563.1998) |
| 233 | m/z = 629.7630 (C45H31N3O, 629.2467) |
| 234 | m/z = 741.8940 (C54H35N3O, 741.2780) |
| 235 | m/z = 705.8610 (C51H35N3O, 705.2780) |
| 236 | m/z = 665.7960 (C48H31N3O, 665.2467) |
| 237 | m/z = 676.7790 (C48H28N4O, 676.2263) |
| 238 | m/z = 676.7790 (C48H28N4O, 676.2263) |
| 239 | m/z = 617.7260 (C42H23N3OS, 617.1562) |
| 240 | m/z = 752.8770 (C54H32N4O, 752.2576) |
| 241 | m/z = 637.7420 (C46H27N3O, 637.2154) |
| 242 | m/z = 611.7040 (C44H25N3O, 611.1998) |
| 243 | m/z = 589.6980 (C42H27N3O, 589.2154) |
| 244 | m/z = 705.8610 (C51H35N3O, 705.2780) |
| 245 | m/z = 665.7960 (C48H31N3O, 665.2467) |
| 246 | m/z = 741.8940 (C54H35N3O, 741.2780) |
| 247 | m/z = 781.9590 (C57H39N3O, 781.3093) |
| 248 | m/z = 665.7960 (C48H31N3O, 665.2467) |
| 249 | m/z = 676.7790 (C48H28N4O, 676.2263) |
| 250 | m/z = 676.7790 (C48H28N4O, 676.2263) |
| 251 | m/z = 617.7260 (C42H23N3OS, 617.1562) |
| 252 | m/z = 617.7260 (C42H23N3OS, 617.1562) |
| 253 | m/z = 601.6650 (C42H23N3O2, 601.1790) |
| 254 | m/z = 601.6650 (C42H23N3O2, 601.1790) |
| 255 | m/z = 627.7470 (C45H29N3O, 627.2311) |
| 256 | m/z = 693.8240 (C48H27N3OS, 693.1875) |
| 257 | m/z = 752.8770 (C54H32N4O, 752.2576) |
| 258 | m/z = 678.7950 (C48H30N4O, 678.2420) |
| 259 | m/z = 681.8570 (C48H31N3S, 681.2239) |
| 260 | m/z = 692.8400 (C48H28N4S, 692.2035) |
| 261 | m/z = 692.8400 (C48H28N4S, 692.2035) |
| 262 | m/z = 692.8400 (C48H28N4O, 692.2035) |
| 263 | m/z = 692.8400 (C48H28N4O, 692.2035) |
| 264 | m/z = 633.7870 (C42H23N3S2, 633.1333) |
| 265 | m/z = 757.9550 (C54H35N3S, 757.2552) |
| 266 | m/z = 721.9220 (C51H35N3S, 721.2552) |
| 267 | m/z = 692.8400 (C48H28N4O, 692.2035) |
| 268 | m/z = 681.8570 (C48H31N3S, 681.2239) |
| 269 | m/z = 633.7870 (C42H23N3S2, 633.1333) |
| 270 | m/z = 768.9380 (C54H32N4S, 768.2348) |
| 271 | m/z = 687.8020 (C50H29N3O, 687.2311) |
| 272 | m/z = 715.8560 (C52H33N3O, 715.2624) |
| 273 | m/z = 781.9590 (C57H39N3O, 781.3093) |

TABLE 5-continued

| Compound | FD-Mass |
|---|---|
| 274 | m/z = 752.8770 (C54H32N4O, 752.2576) |
| 275 | m/z = 752.8770 (C54H32N4O, 752.2576) |
| 276 | m/z = 693.8240 (C48H27N3OS, 693.1875) |
| 277 | m/z = 752.8770 (C54H32N4O, 752.2576) |
| 278 | m/z = 752.8770 (C54H32N4O, 752.2576) |
| 279 | m/z = 693.8240 (C48H27N3OS, 693.1875) |
| 280 | m/z = 752.8770 (C54H32N4O, 752.2576) |
| 281 | m/z = 752.8770 (C54H32N4O, 752.2576) |
| 282 | m/z = 693.8240 (C48H27N3OS, 693.1875) |
| 283 | m/z = 752.8770 (C54H32N4O, 752.2576) |
| 284 | m/z = 752.8770 (C54H32N4O, 752.2576) |
| 285 | m/z = 693.8240 (C48H27N3OS, 693.1875) |
| 286 | m/z = 677.7630 (C48H27N3O2, 677.2103) |
| 287 | m/z = 715.8560 (C52H33N3O, 715.2624) |
| 288 | m/z = 828.9750 (C60H36N4O, 828.2889) |
| 289 | m/z = 729.9010 (C52H31N3S, 729.2239) |
| 290 | m/z = 757.9550 (C54H35N3S, 757.2552) |
| 291 | m/z = 768.9380 (C54H32N4S, 768.2348) |
| 292 | m/z = 768.9380 (C54H32N4S, 768.2348) |
| 293 | m/z = 709.8850 (C48H27N3S2, 709.1646) |
| 294 | m/z = 845.0360 (C60H36N4S, 844.2661) |
| 295 | m/z = 646.7969 (C46H18D9N3O, 646.2719) |
| 296 | m/z = 685.8339 (C48H19D9N4O, 685.2828) |
| 297 | m/z = 626.7809 (C42H14D9N3OS, 626.2127) |
| 298 | m/z = 650.8213 (C46H14D13N3O, 650.2970) |
| 299 | m/z = 689.8583 (C48H15D13N4O, 689.3079) |
| 300 | m/z = 646.7969 (C46H18D9N3O, 646.2719) |
| 301 | m/z = 685.8339 (C48H19D9N4O, 685.2828) |
| 302 | m/z = 689.8583 (C48H15D13N4O, 689.3079) |
| 303 | m/z = 626.7809 (C42H14D9N3OS, 626.2127) |
| 304 | m/z = 689.8583 (C48H15D13N4O, 689.3079) |
| 305 | m/z = 685.8339 (C48H19D9N4O, 685.2828) |
| 306 | m/z = 685.8339 (C48H19D9N4O, 685.2828) |
| 307 | m/z = 689.8583 (C48H15D13N4O, 689.3079) |
| 308 | m/z = 630.8053(C42H10D13N3OS, 630.2378) |
| 309 | m/z = 602.7773 (C42H14D13N3O, 602.2970) |
| 310 | m/z = 678.8753 (C48H18D13N3O, 678.3283) |
| 311 | m/z = 642.8419 (C42H14D9N3S2, 642.1898) |
| 312 | m/z = 646.8663(C42H10D13N3S2, 646.2149) |
| 313 | m/z = 570.6989 (C40H14D9N3O, 642.1898) |
| 314 | m/z = 564.6623 (C40H20DDN3O, 564.6623) |
| 315 | m/z = 574.7233 (C40H10D13N3O, 574.2657) |
| 316 | m/z = 570.6989 (C40H14D9N3O, 642.1898) |
| 317 | m/z = 570.6989 (C40H14D9N3O, 642.1898) |
| 318 | m/z = 570.6989 (C40H14D9N3O, 642.1898) |

TABLE 6

| | |
|---|---|
| I1 | δ = 9.12(s, 1H), 9.06~9.04(d, 1H), 8.79(s, 1H), 8.54(s, 1H), 8.43(s, 1H), 8.28~8.22(m, 3H), 8.08~8.02(m, 3H), 7.99~7.91(m, 2H), 7.71~7.69(d, 1H), 7.60~7.49(m, 6H), 7.46~7.42(t, 1H), 7.38~7.26(m, 3H), 7.19~7.15(t, 2H), 7.12~7.08(t, 1H) |
| I2 | δ = 9.12-9.10(d, 2H), 9.10~9.08(d, 2H), 8.50~8.48(d, 3H), 8.43(s, 1H), 8.35(s, 1H), 8.26~8.21(m, 3H), 8.08~8.01(m, 3H), 7.98~7.91(m, 2H), 7.71~7.69(d, 1H), 7.60~7.49(m, 6H), 7.46~7.42(t, 1H), 7.38~7.26(m, 3H), 7.19~7.15(t, 2H), 7.12~7.08(t, 1H) |
| I3 | δ = 9.10-9.08(d, 2H), 8.90~8.85(d, 2H), 8.50~8.48(d, 3H), 8.43(s, 1H), 8.35(s, 1H), 8.26~8.21(m, 3H), 8.08~7.91(m, 5H), 7.81~7.79(d, 1H), 7.60~7.49(m, 6H), 7.46~7.42(t, 1H), 7.38~7.26(m, 3H), 7.19~7.15(t, 2H), 7.12~7.08(t, 1H) |
| I4 | δ = 9.11-9.10(d, 2H), 9.07~9.05(d, 2H), 8.50~8.47(d, 3H), 8.44(s, 1H), 8.41(s, 1H), 8.26~8.21(m, 3H), 8.08~8.01(m, 3H), 7.98~7.91(m, 2H), 7.69~7.49(m, 3H), 7.46~7.42(t, 1H), 7.38~7.26(m, 3H), 7.12~7.08(t, 1H) |
| I5 | δ = 9.12-9.10(d, 2H), 9.10~9.08(d, 2H), 8.50~8.47(d, 3H), 8.44(s, 1H), 8.41(s, 1H), 8.26~8.21(m, 3H), 8.08~8.01(m, 2H), 7.98~7.79(m, 4H), 7.60~7.49(m, 4H), 7.46~7.42(t, 1H), 7.38~7.26(m, 3H), 7.19~7.15(t, 2H), 7.12~7.08(t, 1H) |
| I6 | δ = 9.11-9.10(d, 2H), 9.07(s, 2H), 8.50~8.47(d, 3H), 8.44(s, 1H), 8.41(s, 1H), 8.26~8.21(m, 3H), 8.08~8.01(m, 3H), 7.98~7.91(m, 2H), 7.69~7.49(m, 3H), 7.46~7.42(t, 1H), 7.38~7.26(m, 3H), 7.12~7.08(t, 1H) |
| I7 | δ = 9.11-9.09(d, 1H), 8.98~8.94(m, 2H), 8.47~8.41(m, 4H), 8.43(s, 1H), 8.25~8.20(m, 3H), 8.08~8.01(m, 3H), 7.98~7.91(m, 4H), 7.69~7.49(m, 6H), 7.46~7.42(t, 1H), 7.38~7.26(m, 4H), 1.60(s, 6H) |
| I8 | δ = 9.12-9.10(d, 2H), 9.10~9.08(d, 2H), 8.50~8.44(m, 4H), 8.38(s, 1H), 8.26~8.21(m, 3H), 8.08~8.01(m, 3H), 7.98~7.79(m, 3H), 7.60~7.49(m, 10H), 7.46~7.42(t, 1H), 7.38~7.26(m, 3H), 7.19~7.15(t, 2H), 7.12~7.08(t, 1H) |

TABLE 6-continued

| | |
|---|---|
| I9 | δ = 9.12-9.10(d, 2H), 9.10~9.08(d, 2H), 8.50~8.44(m, 4H), 8.38(s, 1H), 8.26~8.21(m, 3H), 8.08~8.01(m, 3H), 7.98~7.79(m, 3H), 7.60~7.49(m, 8H), 7.46~7.42(t, 1H), 7.38~7.26(m, 3H), 7.19~7.15(t, 2H), 7.12~7.08(t, 1H) |
| I10 | δ = 9.10-9.09(d, 1H), 8.97~8.94(m, 2H), 8.46~8.41(m, 4H), 8.42(s, 1H), 8.25~8.20(m, 3H), 8.08~8.01(m, 3H), 7.98~7.91(m, 4H), 7.69~7.49(m, 6H), 7.46~7.42(t, 1H), 7.38~7.26(m, 4H), 1.60(s, 6H) |
| I11 | δ = 9.10-9.09(d, 1H), 8.97~8.94(m, 2H), 8.46~8.41(m, 4H), 8.42(s, 1H)8.25~8.20(m, 3H), 8.08~8.01(m, 3H), 7.98~7.91(m, 4H), 7.69~7.49(m, 6H), 7.46~7.42(t, 1H), 7.38~7.26(m, 4H), 1.60(s, 6H) |
| I12 | δ = 9.21(s, 1H), 9.16~9.14(d, 1H), 8.79(s, 1H), 8.54(s, 1H), 8.43(s, 1H), 8.28~8.22(m, 3H), 8.08~8.02(m, 4H), 7.99~7.91(m, 2H), 7.71~7.69(d, 1H), 7.60~7.49(m, 6H), 7.46~7.42(t, 1H), 7.38~7.26(m, 3H), 7.19~7.15(t, 2H), 7.12~7.08(t, 1H) |
| I13 | δ = 9.15~9.12(d, 1H), 9.11~9.10(d, 1H), 9.02~8.98(t, 2H), 8.66(s, 1H), 8.50(s, 1H), 8.29~8.27(d, 1H), 8.21~8.19(d, 1H), 8.16~8.13(d, 1H), 8.04~7.95(m, 4H), 7.83~7.81(d, 1H), 7.63~7.55(m, 9H), 7.52~7.45(m, 5H) |
| I14 | δ = 9.19~9.17(d, 1H), 9.00~8.99(d, 1H), 8.50~8.49(d, 1H), 8.13~8.05(m, 3H), 7.98~7.86(m, 4H), 7.80~7.65(m, 6H), 7.60~7.45(m, 6H), 7.20~7.18(t, 1H) |
| I15 | δ = 9.18~9.17(d, 1H), 9.00~8.98(d, 1H), 8.50~8.49(d, 1H), 8.13~8.05(m, 3H), 7.98~7.86(m, 4H), 7.80~7.65(m, 6H), 7.60~7.45(m, 6H), 7.20~7.18(t, 1H) |
| I16 | δ = 9.21(s, 1H), 9.16~9.14(d, 1H), 8.79(s, 1H), 8.54(s, 1H), 8.43(s, 1H), 8.28~8.22(m, 3H), 8.08~8.02(m, 4H), 7.99~7.91(m, 2H), 7.71~7.69(d, 1H), 7.60~7.49(m, 4H), 7.46~7.42(t, 1H), 7.19~7.15(t, 2H), 7.12~7.08(t, 1H), 1.62(s, 6H) |
| I17 | δ = 9.20~9.17(d, 1H), 9.16~9.14(d, 1H), 8.69(s, 1H), 8.53~8.51(d, 2H), 8.43(s, 1H), 8.28~8.21(m, 4H), 8.18~8.15(m, 2H), 8.07~7.81(m, 7H), 7.66~7.41(m, 13H), 7.34~7.30(t, 1H) |
| I18 | δ = 9.12(s, 1H), 9.06~9.04(d, 1H), 8.79(s, 1H), 8.54(s, 1H), 8.43(s, 1H), 8.28~8.22(m, 3H), 8.08~8.02(m, 3H), 7.99~7.91(m, 2H), 7.71~7.69(d, 1H), 7.60~7.49(m, 6H), 7.46~7.42(t, 1H), 7.38~7.26(m, 3H), 7.19~7.15(t, 2H), 7.12~7.08(t, 1H) |
| I19 | δ = 9.12-9.10(d, 2H), 9.10~9.08(d, 2H), 8.50~8.48(d, 3H), 8.43(s, 1H), 8.35(s, 1H), 8.26~8.21(m, 3H), 8.08~8.01(m, 3H), 7.98~7.91(m, 2H), 7.71~7.69(d, 1H), 7.60~7.49(m, 6H), 7.46~7.42(t, 1H), 7.12~7.08(t, 1H) |
| I20 | δ = 9.12-9.10(d, 2H), 9.10~9.08(d, 2H), 8.50~8.48(d, 3H), 8.43(s, 1H), 8.35(s, 1H), 8.26~8.21(m, 3H), 8.08~8.01(m, 3H), 7.96~7.90(m, 2H), 7.70~7.68(d, 1H), 7.55~7.49(m, 6H), 7.46~7.42(t, 1H), 7.38~7.26(m, 3H), 7.19~7.15(t, 2H), 7.12~7.08(t, 1H) |
| I21 | δ = 9.11-9.10(d, 2H), 9.07(s, 2H), 8.50~8.47(d, 3H), 8.44(s, 1H), 8.41(s, 1H), 8.26~8.21(m, 3H), 8.08~8.01(m, 3H), 7.98~7.91(m, 2H), 7.69~7.49(m, 3H), 7.46~7.42(t, 1H), 7.38~7.26(m, 3H), 7.12~7.08(t, 1H) |
| I22 | δ = 9.10-9.09(d, 2H), 9.07(s, 2H), 8.50~8.47(d, 3H), 8.43(s, 1H), 8.40(s, 1H), 8.26~8.21(m, 3H), 8.08~8.01(m, 3H), 7.98~7.91(m, 4H), 7.69~7.49(m, 5H), 7.46~7.42(t, 1H), 7.38~7.26(m, 3H), 7.12~7.08(t, 1H) |
| I23 | δ = 9.13-9.12d, 1H), 9.02~8.94(m, 2H), 8.47~8.41(m, 4H), 8.40(s, 1H), 8.25~8.20(m, 3H), 8.08~8.01(m, 3H), 7.98~7.91(m, 6H), 7.69~7.49(m, 6H), 7.46~7.42(t, 1H) |
| I24 | δ = 9.12-9.10d, 1H), 9.07(s, 1H), 9.02~8.94(m, 2H), 8.45~8.41(m, 4H), 8.40(s, 1H), 8.25~8.20(m, 3H), 8.08~8.01(m, 3H), 7.98~7.91(m, 6H), 7.69~7.49(m, 3H), 7.46~7.42(t, 1H) |
| I25 | δ = 9.11-9.09(d, 1H), 8.98~8.95(m, 2H), 8.46~8.41(m, 4H), 8.39(s, 1H), 8.25~8.20(m, 3H), 8.07~8.01(m, 3H), 7.96~7.91(m, 4H), 7.69~7.49(m, 6H), 7.46~7.42(t, 1H), 7.38~7.26(m, 4H), 1.60(s, 6H) |
| I26 | δ = 9.13~9.11(d, 1H), 9.10~9.08(d, 2H), 8.50~8.44(m, 4H), 8.38(s, 1H), 8.26~8.21(m, 3H), 8.08~8.01(m, 3H), 7.98~7.79(m, 3H), 7.60~7.49(m, 8H), 7.38~7.26(m, 3H), 7.19~7.15(t, 2H), 7.12~7.08(t, 1H) |
| I27 | δ = 9.13~9.11(d, 1H), 9.10~9.08(d, 2H), 8.50~8.44(m, 4H), 8.38(s, 1H), 8.26~8.21(m, 3H), 8.08~8.01(m, 3H), 7.98~7.79(m, 3H), 7.60~7.49(m, 12H), 7.38~7.26(m, 3H), 7.19~7.15(t, 2H), 7.12~7.08(t, 1H) |
| I28 | δ = 9.13~9.11(d, 1H), 8.97~8.94(m, 2H), 8.46~8.41(m, 4H), 8.42(s, 1H), 8.25~8.20(m, 3H), 8.08~91(m, 8H), 7.69~7.49(m, 8H), 7.46~7.42(t, 1H), 7.39~7.26(m, 5H), 1.60(s, 6H) |
| I29 | δ = 9.13~9.11(d, 1H), 8.97~8.94(m, 2H), 8.45~8.41(m, 4H), 8.42(s, 1H), 8.23~8.20(m, 3H), 8.07~8.01(m, 3H), 7.98~7.91(m, 4H), 7.69~7.49(m, 6H), 7.46~7.42(t, 1H), 7.38~7.26(m, 4H), 1.60(s, 6H) |
| I30 | δ = 9.20(s, 1H), 9.13~9.11(d, 1H), 8.78(s, 1H), 8.60(s, 1H), 8.28~8.14(m, 5H), 8.07~8.04(m, 4H), 7.94~7.90(t, 1H), 7.84~7.82(d, 1H), 7.64~7.50(m, 6H), 7.45~7.32(m, 6H), 7.08~7.05(t, 1H) |
| I31 | δ = 9.16~9.14(d, 1H), 9.13~9.11(d, 1H), 9.02~8.98(t, 2H), 8.54(s, 1H), 8.31~8.26(m, 2H), 8.20~8.18(d, 2H), 8.10~8.08(d, 1H), 8.03~7.94(m, 4H), 7.64~7.45(m, 14H) |
| I32 | δ = 9.19~9.17(d, 1H), 9.13~9.11(d, 1H), 8.99~8.98(d, 1H), 8.50~8.49(d, 1H), 8.12~8.05(m, 3H), 7.98~7.65(m, 9H), 7.60~7.45(m, 6H), 7.20~7.18(t, 1H) |
| I33 | δ = 9.20~9.18(d, 1H), 9.14~9.13(d, 1H), 9.00~8.99(d, 1H), 8.49~8.48(d, 1H), 8.12~8.05(m, 3H), 7.98~7.65(m, 9H), 7.60~7.45(m, 6H), 7.23~7.20(t, 1H) |
| I34 | δ = 9.20(s, 1H), 9.13~9.11(d, 1H), 8.78(s, 1H), 8.60(s, 1H), 8.28~8.14(m, 3H), 8.07~8.04(m, 4H) . 7.94~7.82(m, 3H), 7.64~7.50(m, 4H), 7.45~7.32(m, 4H), 7.23~7.20(t, 1H) |
| I35 | δ = 9.19~9.17(d, 1H), 9.13~9.11(d, 1H), 8.99~8.98(d, 1H), 8.50~8.49(d, 1H), 8.12~8.05(m, 4H), 7.98~7.65(m, 9H), 7.60~7.45(m, 9H), 7.20~7.18(t, 1H) |
| I36 | δ = 9.20~9.17(d, 1H), 9.16~9.14(d, 1H), 8.69(s, 1H), 8.53~8.51(d, 2H), 8.43(s, 1H), 8.28~8.21(m, 4H), 8.18~8.15(m, 2H), 8.07~7.81(m, 7H), 7.66~7.41(m, 13H), 7.34~7.30(t, 1H) |
| I37 | δ = 9.20(s, 1H), 9.13~9.11(d, 1H), 8.78(s, 1H), 8.60(s, 1H), 8.28~8.14(m, 5H), 8.07~8.04(m, 4H) . 7.93~7.82(m, 6H), 7.65~7.50(m, 6H), 7.45~7.32(m, 4H), 7.20~7.17(t, 1H) |
| I38 | δ = 9.17~9.16(d, 1H), 9.14~9.12(d, 1H), 9.02~8.98(t, 2H), 8.57(s, 1H), 8.31~8.26(m, 1H), 8.20~8.08(m, 4H), 8.03~7.94(m, 4H), 7.61~7.40(m, 14H) |
| I39 | δ = 9.11-9.10(d, 2H), 8.50~8.47(d, 2H), 8.13~8.11(m, 2H), 7.98~7.81(m, 8H), 7.75~7.69(m, 3H), 7.51~7.42(m, 8H), 7.38~7.26(m, 3H), 7.12~7.08(t, 1H) |

TABLE 6-continued

| | |
|---|---|
| I40 | δ = 8.99~8.98(d, 1H), 8.50~8.49(m, 2H), 7.90~7.75(m, 10H), 7.55~7.41(m, 7H), 7.33~7.28(m, 8H), 7.04~7.01(t, 1H), 1.69(s, 6H) |
| I41 | δ = 9.13~9.12(d, 1H), 9.10~9.09(d, 2H), 8.50~8.44(m, 4H), 8.38(s, 1H), 8.26~8.21(m, 3H), 8.08~8.01(m, 3H), 7.98~7.79(m, 3H), 7.60~7.49(m, 8H), 7.38~7.26(m, 7H), 7.19~7.15(t, 2H), 7.12~7.08(t, 1H) |
| I42 | δ = 9.20(s, 1H), 9.13~9.11(d, 1H), 8.78(s, 1H), 8.60(s, 1H), 8.28~8.14(m, 5H), 8.07~8.04(m, 4H), 7.94~7.75(m, 5H), 7.63~7.49(m, 7H), 7.44~7.30(m, 6H), 7.08~7.05(t, 1H) |
| I43 | δ = 9.16~9.14(d, 1H), 9.13~9.11(d, 1H), 9.02~8.98(t, 2H), 8.54(s, 1H), 8.29~8.17(m, 5H), 8.09~8.08(d, 1H), 7.99~7.75(m, 6H), 7.63~7.39(m, 15H) |
| I44 | δ = 9.19~9.17(d, 1H), 9.13~9.11(d, 1H), 8.98~8.97(d, 1H), 8.49~8.47(d, 1H), 8.12~8.05(m, 3H), 7.97~7.64(m, 10H), 7.59~7.45(m, 9H), 7.20~7.18(t, 1H) |
| I45 | δ = 9.20~9.18(d, 1H), 9.14~9.13(d, 1H), 8.99~8.98(d, 1H), 8.48~8.47(d, 1H), 8.11~8.03(m, 3H), 7.97~7.60(m, 11H), 7.50~7.43(m, 8H), 7.23~7.20(t, 1H) |
| I46 | δ = 9.11-9.10(d, 2H), 8.50~8.47(d, 2H), 8.13~8.11(m, 2H), 7.98~7.81(m, 8H), 7.75~7.69(m, 3H), 7.51~7.42(m, 8H), 7.38~7.26(m, 3H), 7.12~7.08(t, 1H) |
| I47 | δ = 9.13~9.12(d, 1H), 9.10~9.09(d, 2H), 8.39(s, 1H), 8.25~8.20(m, 3H), 8.09~8.03(m, 3H), 7.97~7.80(m, 3H), 7.60~7.49(m, 10H), 7.38~7.26(m, 9H), 7.19~7.15(t, 2H), 7.12~7.08(t, 1H) |
| I48 | δ = 9.13~9.12(d, 1H), 9.10~9.09(d, 2H), 8.50~8.44(m, 4H), 8.38(s, 1H), 8.26~8.21(m, 3H), 8.08~8.01(m, 3H), 7.98~7.79(m, 3H), 7.60~7.49(m, 8H), 7.38~7.26(m, 7H), 7.19~7.15(t, 2H), 7.12~7.08(t, 1H) |
| I49 | δ = 9.21(s, 1H), 9.12~9.11(d, 1H), 8.69(s, 1H), 8.59(s, 1H), 8.30~8.14(m, 5H), 8.07~8.04(m, 4H) . 7.94~7.75(m, 5H), 7.63~7.49(m, 7H), 7.44~7.30(m, 6H), 7.11~7.09(t, 1H) |
| I50 | δ = 9.18~9.16(d, 1H), 9.14~9.13(d, 1H), 9.00~8.98(t, 2H), 8.53(s, 1H), 8.29~8.17(m, 5H), 8.09~8.08(d, 1H), 7.99~7.75(m, 6H), 7.63~7.39(m, 15H) |
| I51 | δ = 9.20~9.18(d, 1H), 9.15~9.14(d, 1H), 9.00~8.98(d, 1H), 8.49~8.47(d, 1H), 8.12~8.05(m, 3H), 7.96~7.64(m, 10H), 7.60~7.50(m, 9H), 7.20~7.18(t, 1H) |
| I52 | δ = 9.15-9.14(d, 2H), 9.10~9.09(d, 2H), 8.50~8.47(d, 4H), 8.05~7.91(m, 5H), 7.70~7.49(m, 7H), 7.45~7.26(m, 4H), 7.12~7.08(t, 1H) |
| I53 | δ = 9.12-9.10(d, 2H), 9.09~9.08(d, 2H), 8.50~8.44(m, 4H), 8.00~8.01(m, 3H), 7.80~7.75(m, 5H), 7.60~7.49(m, 12H), 7.46~7.42(t, 1H), 7.38~7.26(m, 3H), 7.19~7.15(t, 2H), 7.12~7.08(t, 1H) |
| I54 | δ = 9.21(s, 1H), 9.16~9.14(d, 1H), 9.09~9.08(d, 2H), 8.79(s, 1H), 8.28~8.22(m, 3H), 8.08~8.02(m, 4H), 7.99~7.91(m, 2H), 7.71~7.69(d, 1H), 7.60~7.49(m, 1H), 7.38~7.26(m, 3H), 7.19~7.15(t, 2H), 7.12~7.08(t, 1H)6H), 7.46~7.42(t, |
| I55 | δ = 9.20~9.19(d, 1H), 9.17~9.15(d, 1H), 9.05~9.02(t, 2H), 8.59(s, 1H), 8.33~8.29(m, 1H), 8.20~8.08(m, 4H), 8.03~7.94(m, 4H), 7.49~7.39(m, 14H) |
| I56 | δ = 9.18~9.17(d, 1H), 9.12~9.10(d, 1H), 8.98~8.97(d, 1H), 8.50~8.49(d, 1H), 8.12~8.05(m, 3H), 7.98~7.65(m, 9H), 7.60~7.45(m, 6H), 7.19~7.16(t, 1H) |
| I57 | δ = 9.21~9.18(d, 1H), 9.15~9.13(d, 1H), 8.70(s, 1H), 8.50~8.49(d, 2H), 8.43~8.26(m, 4H), 8.10~7.89(m, 9H), 7.66~7.41(m, 13H), 7.34~7.30(t, 1H) |
| I58 | δ = 9.19-9.18(d, 2H), 9.07~9.06(d, 2H), 8.50~8.48(d, 3H), 8.44(s, 1H)8.26~8.21(m, 3H), 8.08~8.01(m, 4H), 7.98~7.91(m, 2H), 7.69~7.49(m, 3H), 7.46~7.42(t, 1H), 7.38~7.26(m, 3H), 7.12~7.08(t, 1H) |
| I59 | δ = 9.17-9.16(d, 2H), 9.05~9.03(d, 2H), 8.49~8.44(m, 4H), 8.38(s, 1H), 8.26~8.21(m, 3H), 8.08~7.79(m, 6H), 7.60~7.49(m, 6H), 7.46~7.42(t, 1H), 7.38~7.26(m, 3H), 7.19~7.15(t, 2H), 7.12~7.08(t, 1H) |
| I60 | δ = 9.20(s, 1H), 9.15~9.14(d, 1H), 8.78(s, 1H), 8.28~8.18(m, 5H), 8.05~8.00(m, 4H), 7.99~7.91(m, 2H), 7.71~7.69(d, 1H), 7.60~7.49(m, 6H), 7.46~7.42(t, 1H), 7.38~7.26(m, 3H), 7.19~7.15(t, 2H), 7.12~7.08(t, 1H) |
| I61 | δ = 9.17~9.16(d, 1H), 9.08~9.07(d, 1H), 8.89~8.88(d, 1H), 8.38(s, 1H), 8.12~8.05(m, 3H), 7.97~7.67(m, 9H), 7.59~7.45(m, 6H), 7.19~7.16(t, 1H) |
| I62 | δ = 9.20~9.17(d, 1H), 9.16~9.14(d, 1H), 8.69(s, 1H), 8.53~8.51(d, 2H), 8.43~8.26(m, 4H), 8.18~8.15(m, 2H), 8.07~7.81(m, 7H), 7.66~7.41(m, 13H), 7.34~7.30(t, 1H) |
| I63 | δ = 9.18~9.16(d, 1H), 9.10~9.09(d, 1H), 8.55(s, 1H), 8.39~8.38(d, 2H), 7.99~7.69(m, 11H), 7.59~7.45(m, 9H), 7.35~7.30(m, 3H), 7.19~7.16(t, 1H) |
| I64 | δ = 9.16~9.15(d, 1H), 9.05~9.04(d, 1H), 8.39(s, 1H), 8.29~8.27(d, 2H), 7.99~7.75(m, 9H), 7.69~7.49(m, 11H), 7.46~7.42(t, 1H), 7.39~7.26(m, 3H), 1.60(s, 6H) |
| I65 | 5=9.19~9.18(d, 1H), 9.14~9.13(d, 1H), 8.55(s, 1H), 8.40~8.49(d, 2H), 8.12~8.05(m, 3H), 7.98~7.65(m, 9H), 7.60~7.45(m, 5H), 7.20~7.18(t, 1H) |
| I66 | δ = 9.19~9.18(d, 1H), 9.14~9.13(d, 1H), 8.28~8.22(m, 3H), 8.08~7.91(m, 5H), 7.71~7.55(m, 10H), 7.46~7.26(m, 6H), 7.12~7.08(t, 1H) |
| I67 | δ = 9.17~9.15(d, 1H), 9.05~9.04(d, 1H), 8.40(s, 1H), 8.30~8.28(d, 2H), 7.99~7.75(m, 9H), 7.69~7.49(m, 11H), 7.46~7.42(t, 1H), 7.38~7.29(m, 3H), 1.59(s, 6H) |
| I68 | δ = 9.16-9.15(d, 1H), 9.04~9.03(d, 1H), 8.49~8.44(m, 4H), 8.26~8.21(m, 3H), 8.08~7.79(m, 8H), 7.60~7.49(m, 7H), 7.46~7.26(m, 6H), 7.12~7.08(t, 1H) |
| I69 | δ = 9.21(s, 1H), 9.12~9.11(d, 1H), 8.69(s, 1H), 8.59(s, 1H), 8.30~8.14(m, 5H), 8.03~7.94(m, 5H), 7.61~7.40(m, 14H) |
| I70 | δ = 9.20(s, 1H), 9.13~9.11(d, 1H), 8.78(s, 1H), 8.28~8.14(m, 4H), 8.07~8.04(m, 4H), 7.94~7.82(m, 3H), 7.64~7.50(m, 4H), 7.45~7.32(m, 4H), 7.23~7.20(t, 1H) |
| I71 | δ = 9.20(s, 1H), 9.16~9.15(d, 1H), 8.77(s, 1H), 8.52(s, 1H), 8.41(s, 1H), 8.28~8.22(m, 3H), 8.08~8.02(m, 4H), 7.99~7.91(m, 2H), 7.71~7.69(d, 1H), 7.60~7.49(m, 6H), 7.46~7.42(t, 1H), 7.38~7.26(m, 3H), 7.19~7.15(t, 2H), 7.11~7.08(t, 1H) |
| I72 | δ = 9.14~9.12(d, 1H), 9.10~9.08(d, 1H), 9.01~8.98(t, 2H), 8.65(s, 1H), 8.50(s, 1H), 8.29~8.27(d, 1H), 8.21~8.19(d, 1H), 8.16~8.13(d, 1H), 8.04~7.95(m, 4H), 7.83~7.81(d, 1H), 7.63~7.55(m, 9H), 7.50~7.45(m, 5H) |

<Experimental Example 1>—Manufacture of Organic Light Emitting Device

1) Manufacture of Organic Light Emitting Device (Red Single Host)

A glass substrate on which indium tin oxide (ITO) was coated as a thin film to a thickness of 1,500 Å was cleaned with distilled water ultrasonic waves. After the cleaning with distilled water was finished, the substrate was ultrasonic cleaned with solvents such as acetone, methanol and isopropyl alcohol, then dried, and ultraviolet ozone (UVO) treatment was conducted for 5 minutes using UV in an ultraviolet (UV) cleaner. After that, the substrate was transferred to a plasma cleaner (PT), and after conducting plasma treatment under vacuum for ITO work function and residual film removal, the substrate was transferred to a thermal deposition apparatus for organic deposition.

On the transparent ITO electrode (anode), a hole injection layer 2-TNATA (4,4',4"-tris[2-naphthyl(phenyl)amino]triphenylamine) and a hole transfer layer NPB (N,N'-di(1-naphthyl)-N,N'-diphenyl-(1,1'-biphenyl)-4,4'-diamine), which are common layers, were formed.

A light emitting layer was thermal vacuum deposited thereon as follows. The light emitting layer was deposited to 500 Å using a compound described in the following Table 7 as a red host and $(piq)_2(Ir)$ (acac) as a red phosphorescent dopant by doping the $(piq)_2(Ir)$ (acac) to the host by 3%. After that, BCP was deposited to 60 Å as a hole blocking layer, and Alq3 was deposited to 200 Å thereon as an electron transfer layer. Lastly, an electron injection layer was formed on the electron transfer layer by depositing lithium fluoride (LiF) to a thickness of 10 Å, and then a cathode was formed on the electron injection layer by depositing an aluminum (Al) cathode to a thickness of 1,200 Å, and as a result, an organic electroluminescent device was manufactured.

Meanwhile, a11 the organic compounds required to manufacture the OLED were vacuum sublimation purified under $10^{-8}$ torr to $10^{-6}$ torr for each material to be used in the OLED manufacture.

For each of the organic electroluminescent devices manufactured as above, electroluminescent (EL) properties were measured using M7000 manufactured by McScience Inc., and with the measurement results, $T_{90}$ was measured when standard luminance was 6,000 cd/$m^2$ through a lifetime measurement system (M6000) manufactured by McScience Inc. Properties of the organic electroluminescent devices of the present disclosure are as shown in the following Table 7.

TABLE 7

| | Compound | Driving Voltage (V) | Efficiency (cd/A) | Color Coordinate (x, y) | Lifetime ($T_{90}$) |
|---|---|---|---|---|---|
| Comparative Example 1 | A | 5.51 | 10.8 | (0.661, 0.352) | 43 |
| Comparative Example 2 | B | 5.50 | 10.9 | (0.662, 0.353) | 49 |
| Comparative Example 3 | C | 5.30 | 12.2 | (0.661, 0.352) | 60 |
| Comparative Example 4 | D | 5.00 | 15.7 | (0.661, 0.352) | 69 |
| Comparative Example 5 | E | 4.83 | 16.3 | (0.661, 0.353) | 75 |
| Comparative Example 6 | F | 4.88 | 16.0 | (0.661, 0.352) | 75 |
| Example 1 | 1 | 4.53 | 15.7 | (0.657, 0.353) | 91 |
| Example 2 | 2 | 4.55 | 15.8 | (0.658, 0.352) | 92 |
| Example 3 | 3 | 4.54 | 14.9 | (0.660, 0.351) | 90 |

TABLE 7-continued

| | Compound | Driving Voltage (V) | Efficiency (cd/A) | Color Coordinate (x, y) | Lifetime ($T_{90}$) |
|---|---|---|---|---|---|
| Example 4 | 4 | 4.49 | 19. . 0 | (0.661, 0.351) | 98 |
| Example 5 | 19 | 4.55 | 15.0 | (0.662, 0.352) | 91 |
| Example 6 | 21 | 4.31 | 19.9 | (0.663, 0.351) | 100 |
| Example 7 | 23 | 4.25 | 19.5 | (0.662, 0.349) | 68 |
| Example 8 | 24 | 4.24 | 24.0 | (0.663, 0.352) | 70 |
| Example 9 | 25 | 4.26 | 25.1 | (0.662, 0.351) | 80 |
| Example 10 | 26 | 4.20 | 24.9 | (0.663, 0.352) | 75 |
| Example 11 | 28 | 4.22 | 25.1 | (0.661, 0.351) | 79 |
| Example 12 | 29 | 3.89 | 26.5 | (0.663, 0.351) | 150 |
| Example 13 | 30 | 3.88 | 27.0 | (0.662, 0.353) | 160 |
| Example 14 | 31 | 4.10 | 25.5 | (0.658, 0.352) | 120 |
| Example 15 | 33 | 4.05 | 25.0 | (0.661, 0.353) | 121 |
| Example 16 | 34 | 4.15 | 25.1 | (0.661, 0.352) | 115 |
| Example 17 | 36 | 4.00 | 25.0 | (0.661, 0.352) | 78 |
| Example 18 | 37 | 4.45 | 15.8 | (0.660, 0.352) | 90 |
| Example 19 | 38 | 4.44 | 16.0 | (0.660, 0.351) | 91 |
| Example 20 | 39 | 4.55 | 16.1 | (0.661, 0.351) | 93 |
| Example 21 | 40 | 4.35 | 19.5 | (0.660, 0.352) | 97 |
| Example 22 | 41 | 4.40 | 19.2 | (0.658, 0.353) | 95 |
| Example 23 | 42 | 4.30 | 19.0 | (0.660, 0.352) | 67 |
| Example 24 | 43 | 4.35 | 19.2 | (0.660, 0.353) | 70 |
| Example 25 | 45 | 4.20 | 19.5 | (0.660, 0.353) | 70 |
| Example 26 | 46 | 4.20 | 24.2 | (0.660, 0.352) | 75 |
| Example 27 | 47 | 4.22 | 24.0 | (0.660, 0.348) | 77 |
| Example 28 | 48 | 4.19 | 24.5 | (0.661, 0.350) | 75 |
| Example 29 | 50 | 4.25 | 25.0 | (0.661, 0.351) | 70 |
| Example 30 | 51 | 3.90 | 27.0 | (0.660, 0.352) | 155 |
| Example 31 | 52 | 3.86 | 28.0 | (0.661, 0.351) | 170 |
| Example 32 | 54 | 4.00 | 25.0 | (0.661, 0.352) | 119 |
| Example 33 | 55 | 4.00 | 25.1 | (0.661, 0.353) | 121 |
| Example 34 | 56 | 4.01 | 25.0 | (0.660, 0.352) | 122 |
| Example 35 | 58 | 4.10 | 24.9 | (0.662, 0.350) | 110 |
| Example 36 | 59 | 3.88 | 25.1 | (0.661, 0.350) | 79 |
| Example 37 | 60 | 4.21 | 19.0 | (0.661, 0.350) | 65 |
| Example 38 | 70 | 4.00 | 26.1 | (0.660, 0.350) | 145 |
| Example 39 | 135 | 4.35 | 19.7 | (0.660, 0.350) | 97 |
| Example 40 | 138 | 4.30 | 19.6 | (0.660, 0.351) | 71 |
| Example 41 | 140 | 4.28 | 24.3 | (0.659, 0.352) | 75 |
| Example 42 | 144 | 4.11 | 27.1 | (0.660, 0.350) | 152 |
| Example 43 | 145 | 4.05 | 27.9 | (0.660, 0.351) | 168 |
| Example 44 | 147 | 4.11 | 24.9 | (0.662, 0.352) | 120 |
| Example 45 | 149 | 4.05 | 25.1 | (0.662, 0.352) | 123 |
| Example 46 | 154 | 4.40 | 19.6 | (0.661, 0.352) | 95 |
| Example 47 | 157 | 4.30 | 19.9 | (0.661, 0.352) | 73 |
| Example 48 | 160 | 4.28 | 25.0 | (0.662, 0.352) | 75 |
| Example 49 | 163 | 4.15 | 25.7 | (0.661, 0.351) | 133 |
| Example 50 | 164 | 4.12 | 26.2 | (0.661, 0.351) | 141 |
| Example 51 | 165 | 4.20 | 24.5 | (0.661, 0.353) | 118 |
| Example 52 | 207 | 4.40 | 19.0 | (0.662, 0.352) | 91 |
| Example 53 | 210 | 4.30 | 23.7 | (0.660, 0.351) | 70 |
| Example 54 | 212 | 4.15 | 24.9 | (0.661, 0.352) | 135 |
| Example 55 | 213 | 4.09 | 25.5 | (0.661, 0.352) | 141 |
| Example 56 | 214 | 4.17 | 23.5 | (0.660, 0.352) | 110 |
| Example 57 | 215 | 4.08 | 23.7 | (0.660, 0.352) | 711 |
| Example 58 | 217 | 4.35 | 19.1 | (0.660, 0.352) | 95 |
| Example 59 | 220 | 4.26 | 23.5 | (0.661, 0.351) | 72 |
| Example 60 | 224 | 4.17 | 25.1 | (0.662, 0.352) | 140 |
| Example 61 | 227 | 4.25 | 23.2 | (0.662, 0.352) | 111 |
| Example 62 | 228 | 4.14 | 23.9 | (0.662, 0.349) | 74 |
| Example 63 | 230 | 4.40 | 15.8 | (0.663, 0.352) | 80 |
| Example 64 | 235 | 4.30 | 23.5 | (0.662, 0.351) | 70 |
| Example 65 | 239 | 4.18 | 23.7 | (0.661, 0.352) | 110 |
| Example 66 | 241 | 4.40 | 15.5 | (0.661, 0.351) | 82 |
| Example 67 | 244 | 4.29 | 19.1 | (0.663, 0.352) | 72 |
| Example 68 | 248 | 4.30 | 23.4 | (0.662, 0.351) | 75 |
| Example 69 | 249 | 4.17 | 24.9 | (0.661, 0.352) | 139 |
| Example 70 | 252 | 4.19 | 22.9 | (0.661, 0.351) | 115 |
| Example 71 | 96 | 3.99 | 23.5 | (0.662, 0.352) | 120 |
| Example 72 | 97 | 3.89 | 24.0 | (0.662, 0.351) | 125 |

-continued
A
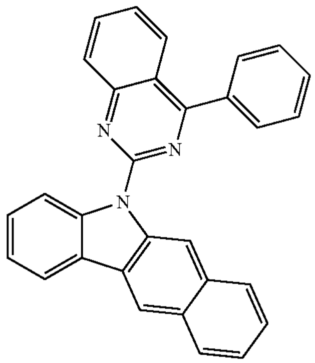
D
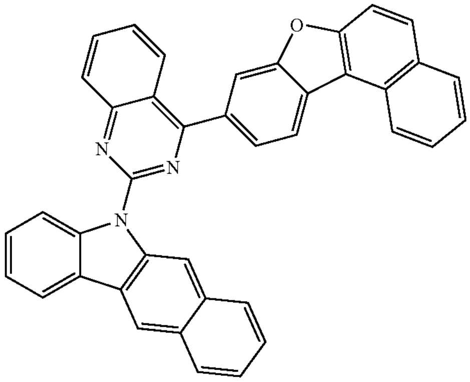
B
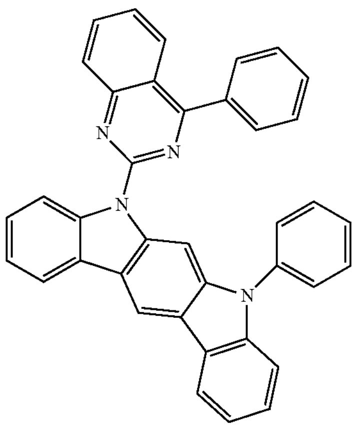
E
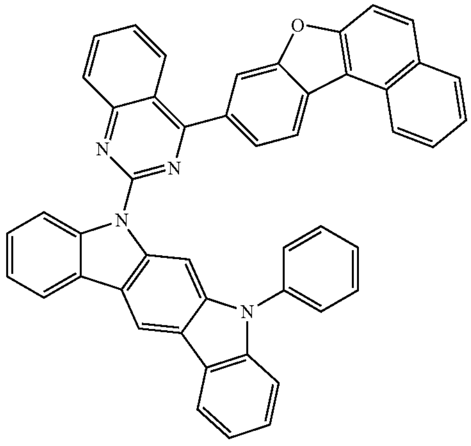
C
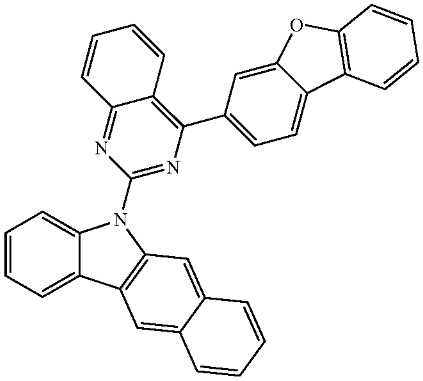
F
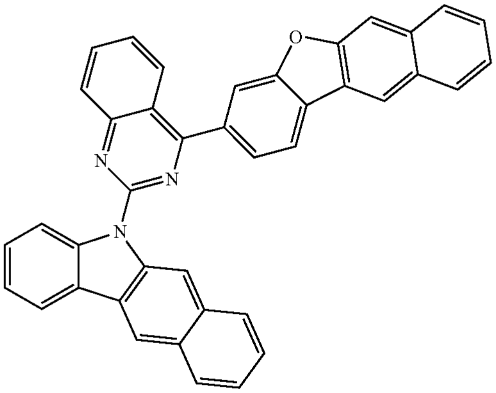

As seen from Table 7, it was identified that, when the compound corresponding to Chemical Formula 1 was used in the light emitting layer of the organic light emitting device, superior effects were obtained in the properties of lifetime, efficiency and driving voltage compared to when the compound was not used.

<Experimental Example 2>—Manufacture of Organic Light Emitting Device (Red N+P Mixed Host)

A glass substrate on which ITO was coated as a thin film to a thickness of 1,500 Å was cleaned with distilled water ultrasonic waves. After the cleaning with distilled water was finished, the substrate was ultrasonic cleaned with solvents such as acetone, methanol and isopropyl alcohol, then dried, and UVO treatment was conducted for 5 minutes using UV in a UV cleaner. After that, the substrate was transferred to a plasma cleaner (PT), and after conducting plasma treatment under vacuum for ITO work function and residual film removal, the substrate was transferred to a thermal deposition apparatus for organic deposition.

On the transparent ITO electrode (anode), a hole injection layer 2-TNATA (4,4',4"-tris[2-naphthyl(phenyl)amino]triphenylamine) and a hole transfer layer NPB (N,N'-di(1-naphthyl)-N,N'-diphenyl-(1,1'-biphenyl)-4,4'-diamine), which are common layers, were formed.

A light emitting layer was thermal vacuum deposited thereon as follows. As the light emitting layer, two types of compounds were pre-mixed as described in the following Table 8 and deposited to 400 Å in one source of supply as a red host, and (piq)2(Ir) (acac) was doped thereto by 3% as a red phosphorescent dopant and deposited. After that, BCP was deposited to 60 Å as a hole blocking layer, and $Alq_3$ was deposited to 200 Å thereon as an electron transfer layer. Lastly, an electron injection layer was formed on the electron transfer layer by depositing lithium fluoride (LiF) to a thickness of 10 Å, and then a cathode was formed on the electron injection layer by depositing an aluminum (Al) cathode to a thickness of 1,200 Å, and as a result, an organic electroluminescent device was manufactured.

Meanwhile, a11 the organic compounds required to manufacture the OLED were vacuum sublimation purified under $10^{-8}$ torr to $10^{-6}$ torr for each material to be used in the OLED manufacture.

For each of the organic electroluminescent devices manufactured as above, electroluminescent (EL) properties were measured using M7000 manufactured by McScience Inc., and with the measurement results, $T_{90}$ was measured when standard luminance was 6,000 cd/$m^2$ through a lifetime measurement system (M6000) manufactured by McScience Inc.

TABLE 8

| | Light Emitting Layer Compound | Ratio (N:P) | Driving Voltage (V) | Efficiency (cd/A) | Color Coordinate (x, y) | Lifetime ($T_{90}$) |
|---|---|---|---|---|---|---|
| Example 1 | I31: P-Host H | 1:3 | 4.20 | 27.5 | 0.672, 0.326 | 149 |
| Example 2 | | 1:2 | 3.90 | 30.8 | 0.678, 0.322 | 155 |
| Example 3 | | 1:1 | 3.78 | 36.2 | 0.674, 0.325 | 165 |
| Example 4 | | 2:1 | 3.75 | 35.8 | 0.679, 0.321 | 166 |
| Example 5 | | 3:1 | 3.76 | 35.0 | 0.678, 0.322 | 170 |
| Example 6 | I31: P-Host I | 1:3 | 4.05 | 27.7 | 0.674, 0.325 | 150 |
| Example 7 | | 1:2 | 3.92 | 30.1 | 0.687, 0.313 | 159 |
| Example 8 | | 1:1 | 3.82 | 36.5 | 0.681, 0.319 | 166 |
| Example 9 | | 2:1 | 3.88 | 35.5 | 0.680, 0.319 | 168 |
| Example 10 | | 3:1 | 3.99 | 35.4 | 0.682, 0.317 | 170 |
| Example 11 | P31: P-Host J | 1:3 | 3.99 | 33.9 | 0.671, 0.326 | 155 |
| Example 12 | | 1:2 | 3.85 | 37.2 | 0.677, 0.322 | 157 |
| Example 13 | | 1:1 | 3.79 | 40.1 | 0.675, 0.325 | 160 |
| Example 14 | | 2:1 | 3.78 | 39.8 | 0.678, 0.321 | 163 |
| Example 15 | | 3:1 | 3.78 | 39.0 | 0.678, 0.322 | 166 |
| Example 16 | I31: P-Host M | 1:1 | 3.90 | 34.9 | 0.680, 0.319 | 175 |
| Example 17 | I8: P-Host A | 1:1 | 3.89 | 33.2 | 0.682, 0.317 | 80 |
| Example 18 | I10: P-Host B | 1:1 | 3.85 | 34.0 | 0.682, 0.317 | 81 |
| Example 19 | I13: P-Host C | 1:1 | 3.76 | 37.0 | 0.685, 0.315 | 155 |
| Example 20 | I18: P-Host D | 1:1 | 4.10 | 22.9 | 0.680, 0.319 | 95 |
| Example 21 | I32: P-Host E | 1:1 | 3.90 | 31.5 | 0.678, 0.322 | 115 |
| Example 22 | I36: P-Host F | 1:1 | 3.88 | 34.2 | 0.680, 0.319 | 75 |
| Example 23 | I41: P-Host G | 1:1 | 4.05 | 33.9 | 0.682, 0.317 | 71 |
| Example 24 | I54: P-Host K | 1:1 | 3.99 | 33.5 | 0.679, 0.321 | 130 |
| Example 25 | I64: P-Host L | 1:1 | 4.10 | 31.9 | 0.685, 0.315 | 65 |
| Example 26 | I70: P-Host M | 1:1 | 4.00 | 30.5 | 0.680, 0.319 | 109 |

P-Host A
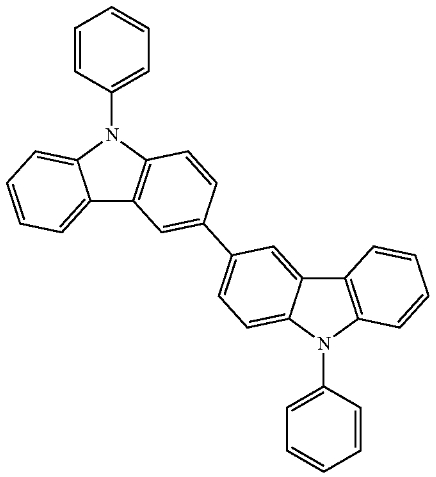
P-Host B
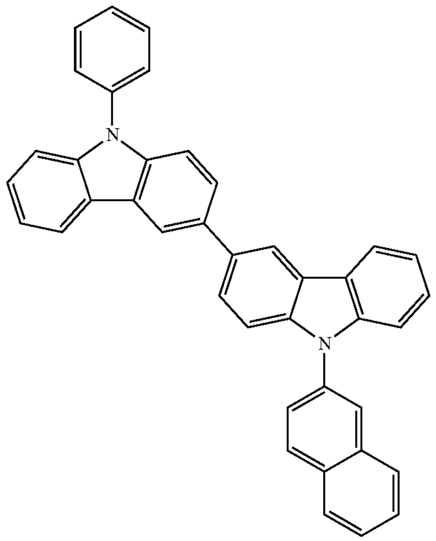
-continued
P-Host C
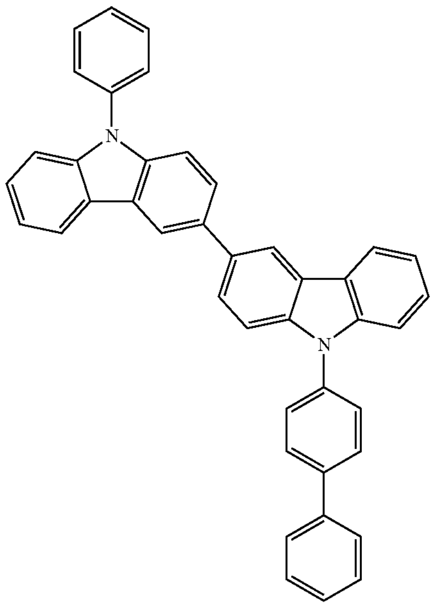
P-Host D
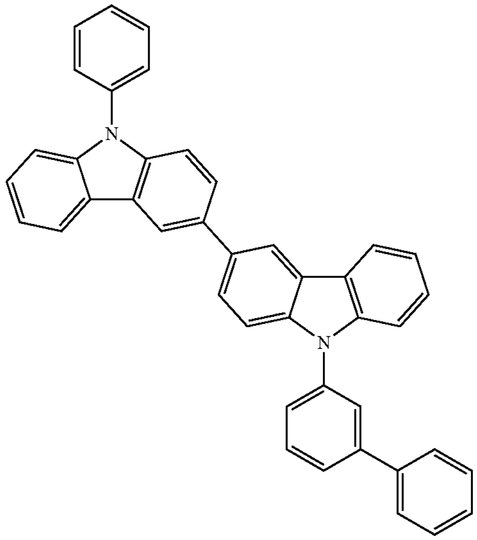

-continued
P-Host E
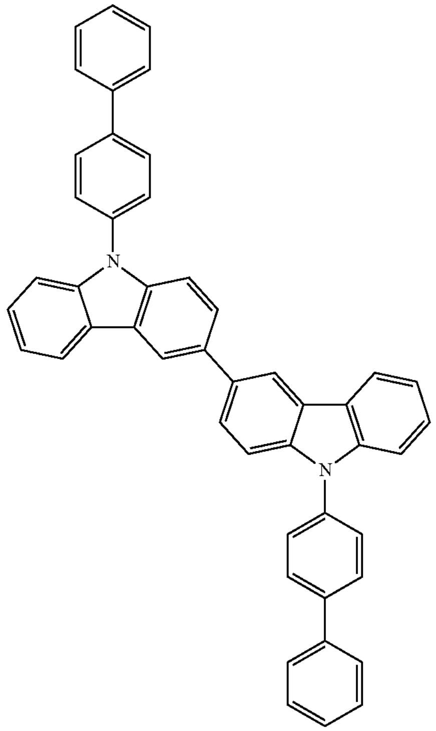
P-Host F
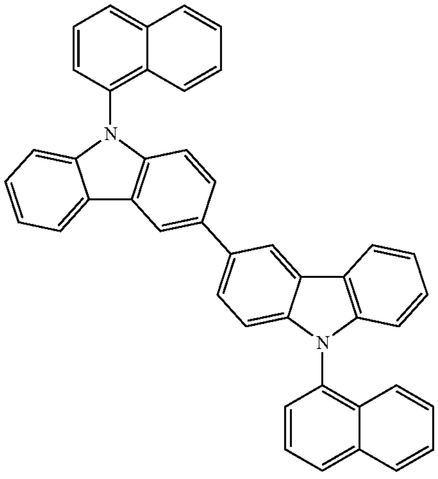
-continued
P-Host G
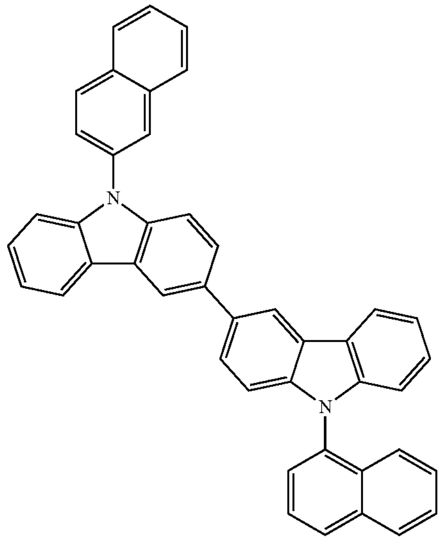
P-Host H
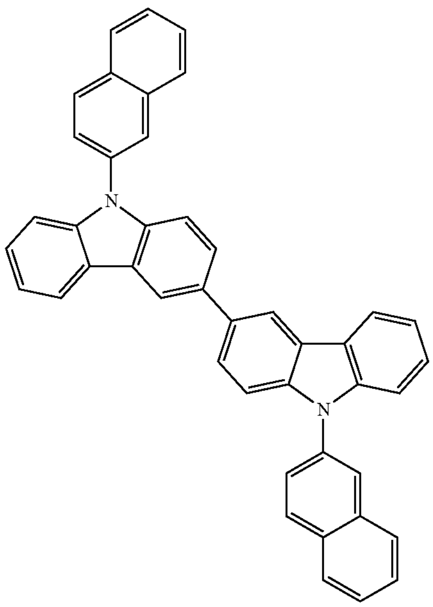

-continued
P-Host I
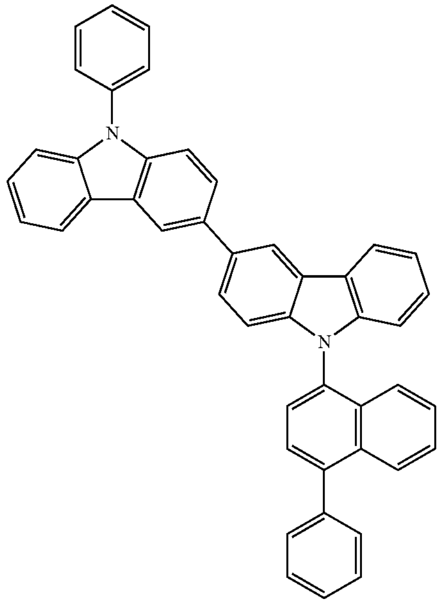
P-Host J
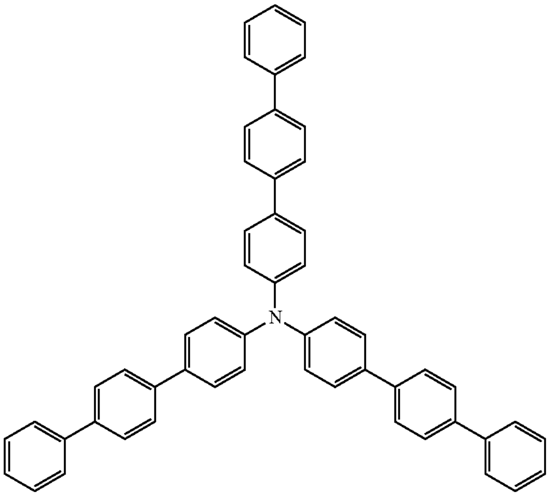
-continued
P-Host K
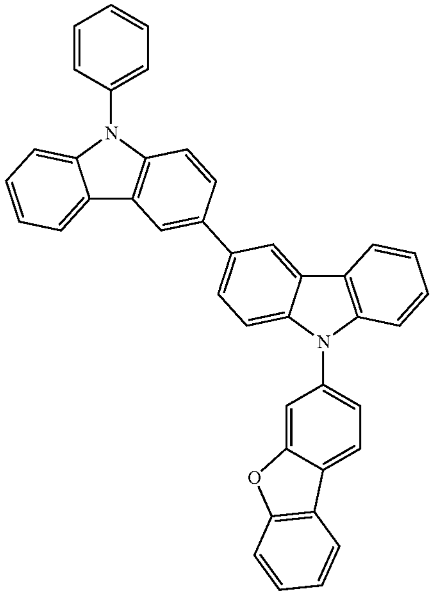
P-Host L
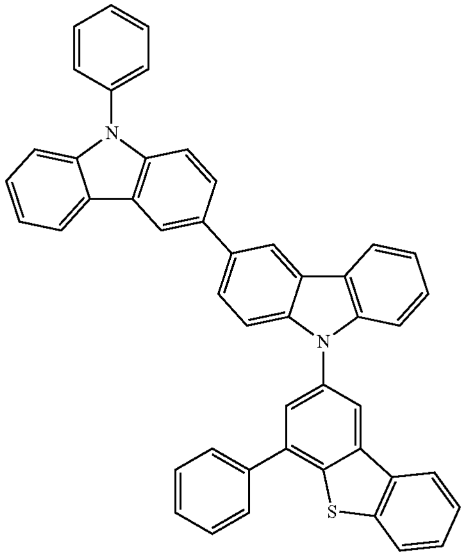

-continued

P-Host M

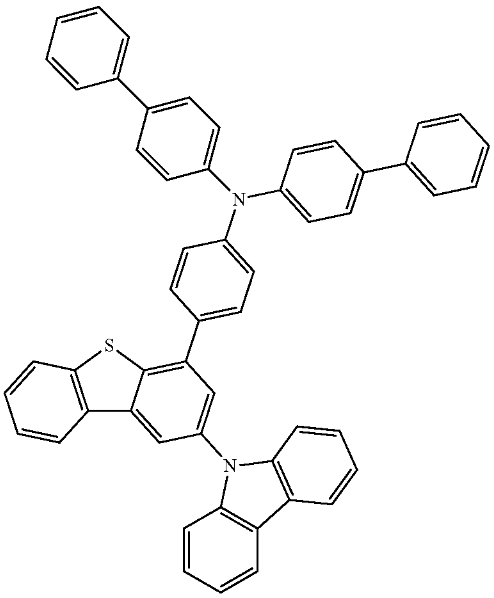

As seen from Table 8, effects of more superior efficiency and lifetime were obtained when comprising both the N-type compound and the P-type compound in the organic material layer of the organic light emitting device. Such results may lead to a forecast that an exciplex phenomenon occurs when comprising the two compounds at the same time. Particularly, the exciplex phenomenon of the N+P compounds is a phenomenon of releasing energy having sizes of a donor (p-host) HOMO level and an acceptor (n-host) LUMO level due to electron exchanges between two molecules. When a donor (p-host) having a favorable hole transfer ability and an acceptor (n-host) having a favorable electron transfer ability are used as a host of a light emitting layer, holes are injected to the p-host and electrons are injected to the n-host, and therefore, a driving voltage may be lowered, which resultantly helps with enhancement in the lifetime.

The invention claimed is:

1. A heterocyclic compound represented by the following Chemical Formula 2 or Chemical Formula 3:

[Chemical Formula 2]

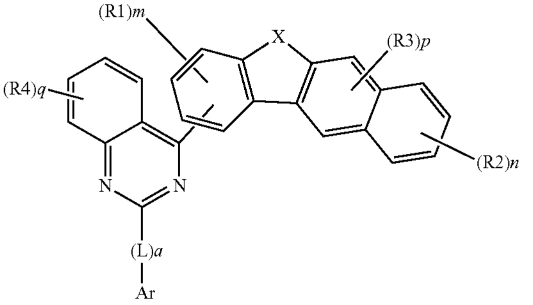

-continued

[Chemical Formula 3]

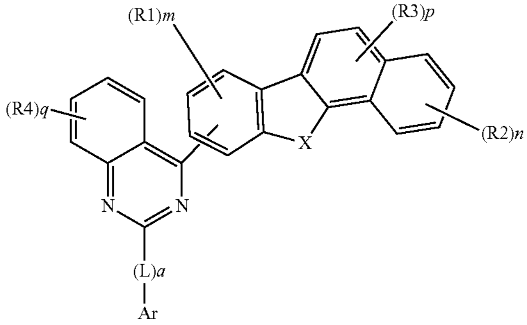

wherein, in Chemical Formulae 2 and 3,

X is O; or S;

L is a direct bond; a substituted or unsubstituted C6 to C60 arylene group; or a substituted or unsubstituted C2 to C60 heteroarylene group;

R1 to R4 are the same as or different from each other, and each independently selected from the group consisting of hydrogen; deuterium; halogen; a cyano group; a substituted or unsubstituted C1 to C60 alkyl group; a substituted or unsubstituted C2 to C60 alkenyl group; a substituted or unsubstituted C2 to C60 alkynyl group; a substituted or unsubstituted C1 to C60 alkoxy group; a substituted or unsubstituted C3 to C60 cycloalkyl group; a substituted or unsubstituted C2 to C60 heterocycloalkyl group; a substituted or unsubstituted C6 to C60 aryl group; a substituted or unsubstituted C2 to C60 heteroaryl group; —P(═O) RR'; —SiRR'R" and —NRR', or two or more groups adjacent to each other bond to each other to form a substituted or unsubstituted C6 to C60 aliphatic or aromatic hydrocarbon ring or a substituted or unsubstituted $C_2$ to C60 aliphatic or aromatic heteroring;

q and n are the same as or different from each other, and are each an integer of 0 to 4;

m is an integer of 0 to 3;

p is an integer of 0 to 2;

a is an integer of 0 to 4; and

Ar is represented by any one of the following Chemical Formula 1-1 to Chemical Formula 1-6,

[Chemical Formula 1-1]

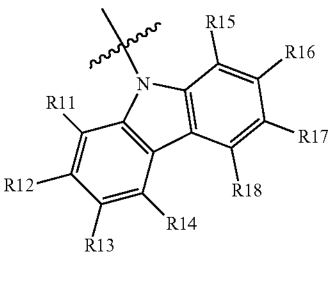

-continued

[Chemical Formula 1-2]

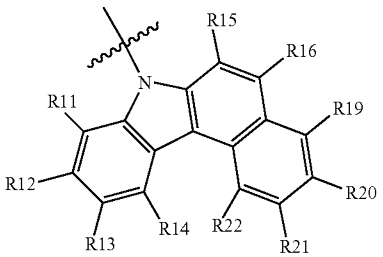

[Chemical Formula 1-3]

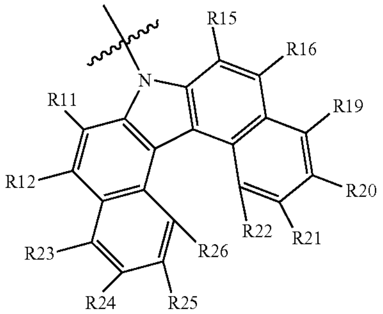

[Chemical Formula 1-4]

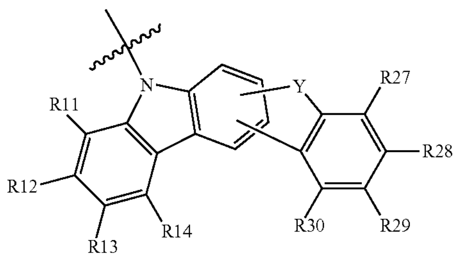

[Chemical Formula 1-5]

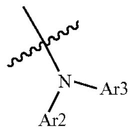

[Chemical Formula 1-6]

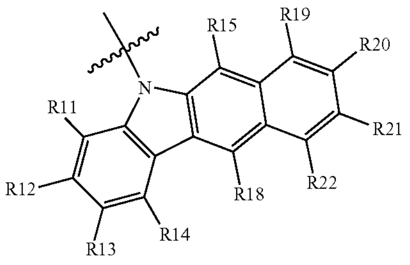

in Chemical Formulae 1-1 to 1-6,

means a position linked to L of Chemical Formulae 2 and 3;

R11 to R30 are the same as or different from each other, and each independently selected from the group consisting of hydrogen; deuterium; a substituted or unsubstituted C1 to C60 alkyl group; a substituted or unsubstituted C6 to C60 aryl group; a substituted or unsubstituted C2 to C60 heteroaryl group; —P(═O)RR'; —SiRR'R" and —NRR';

Ar2 and Ar3 are the same as or different from each other, and each independently a substituted or unsubstituted C6 to C60 aryl group; or a substituted or unsubstituted C2 to C60 heteroaryl group;

Y is O; S; NRa; or CRbRc; and

R, R', R" and Ra to Rc are the same as or different from each other, and each independently a substituted or unsubstituted C1 to C60 alkyl group; a substituted or unsubstituted C6 to C60 aryl group; or a substituted or unsubstituted C2 to C60 heteroaryl group.

2. The heterocyclic compound of claim 1, wherein Chemical Formula 2 or 3 is represented by any one of the following compounds:

1

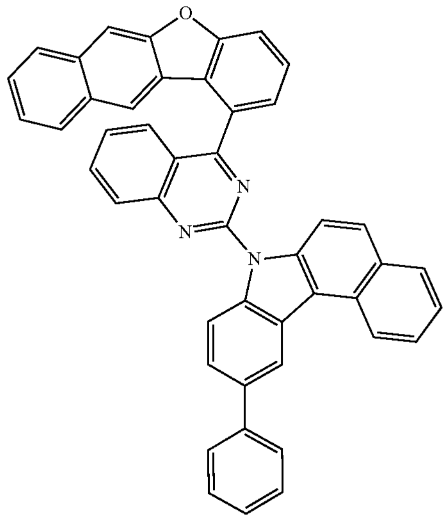

2

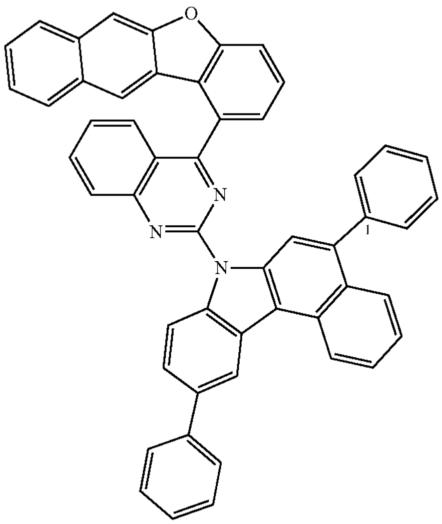

-continued
3
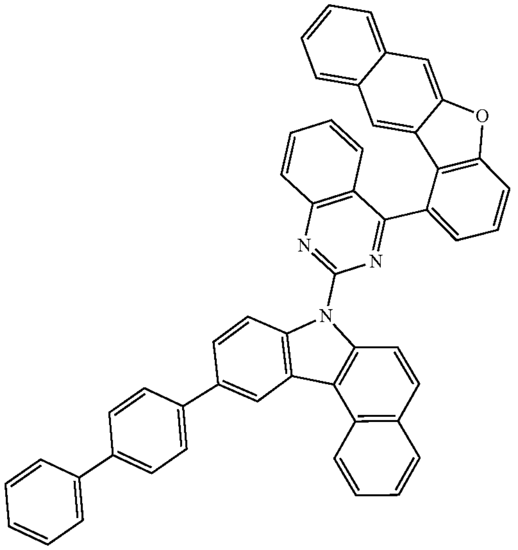
4
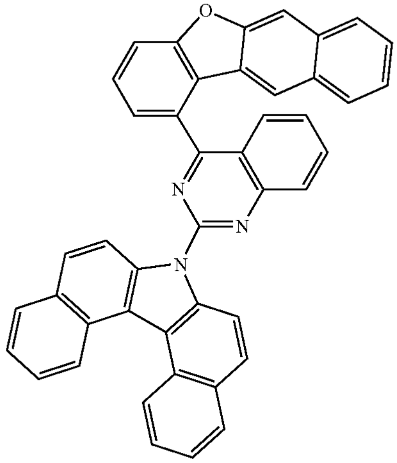
5
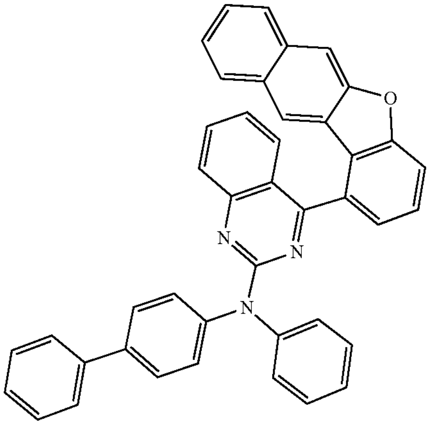
-continued
6
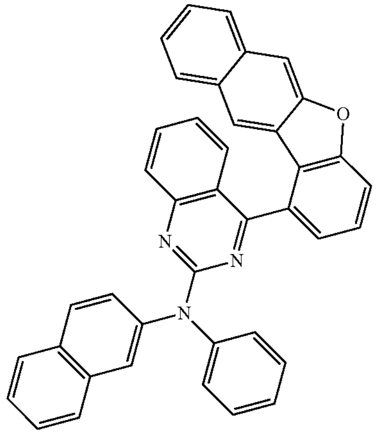
7
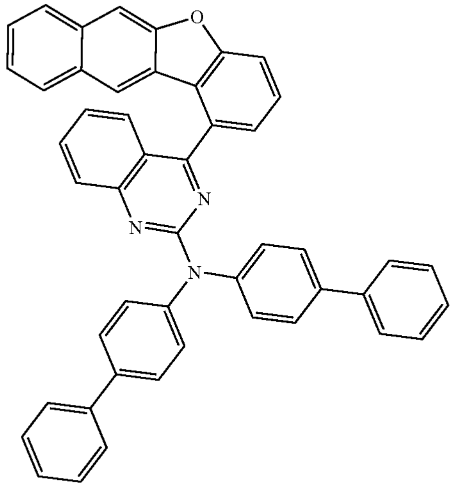
8
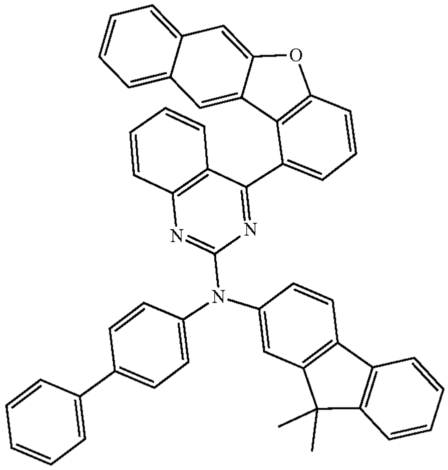

-continued
9
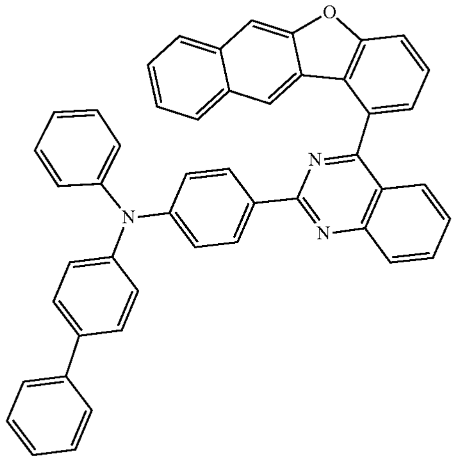
10
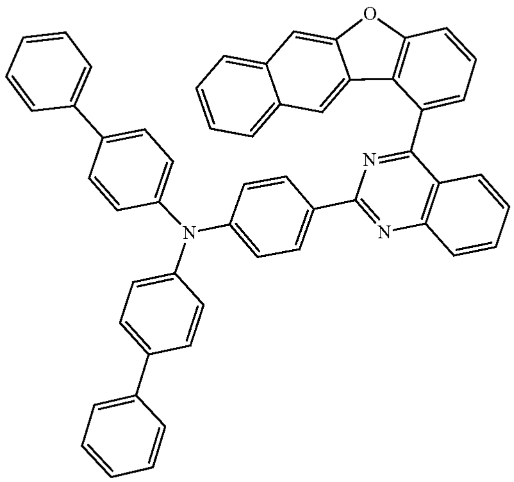
11
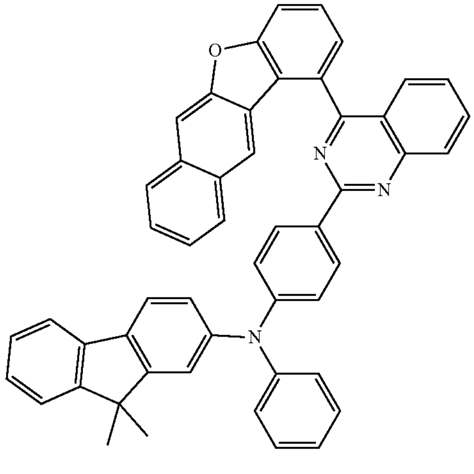
-continued
12
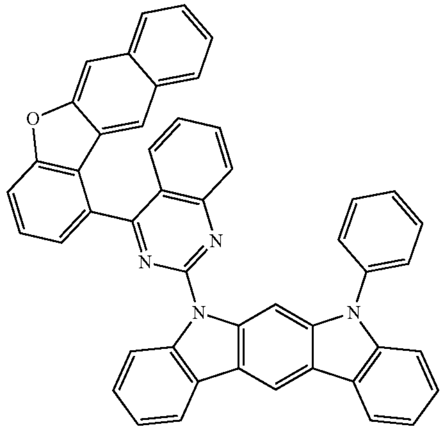
13
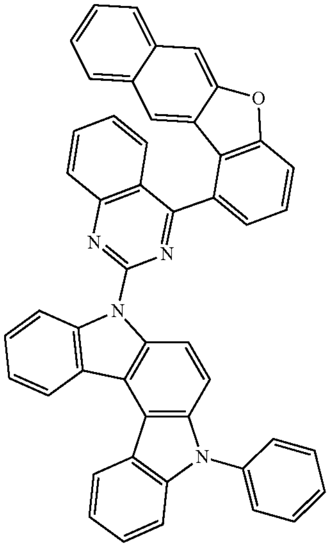
14
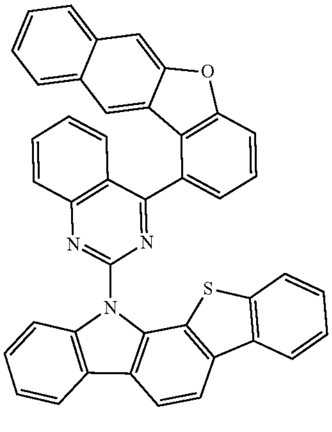

-continued
15
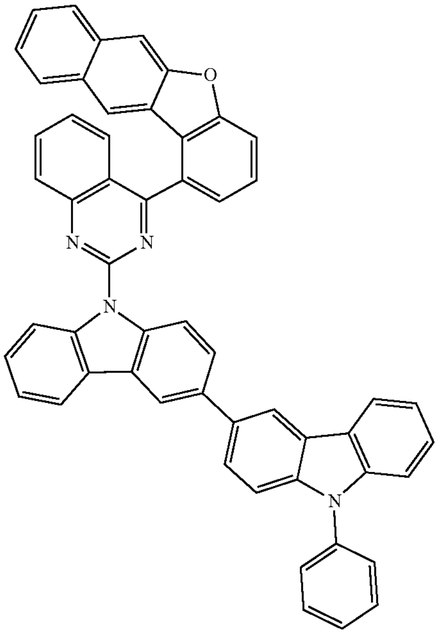
16
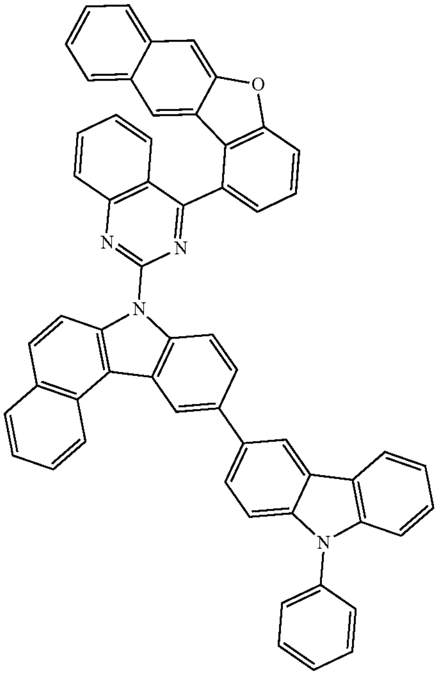
-continued
17
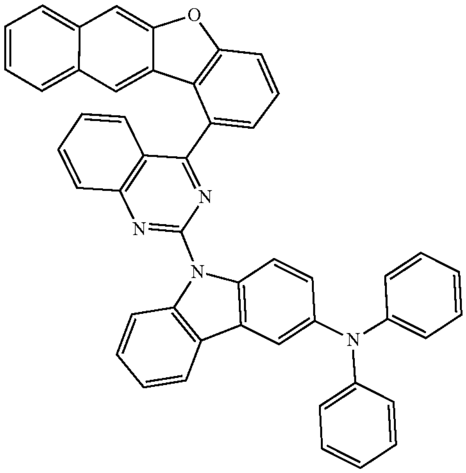
18
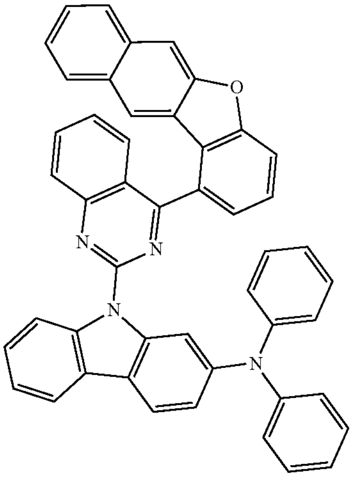
19
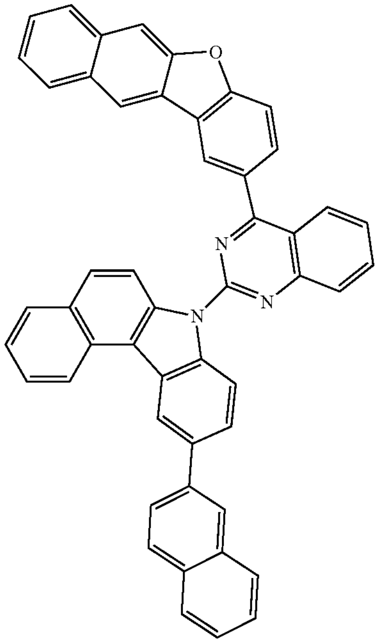

-continued
20
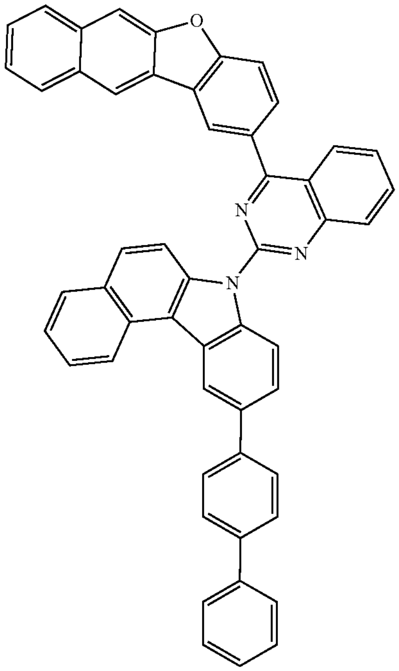
21
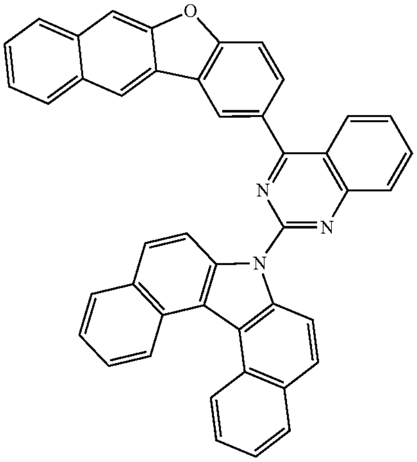
22
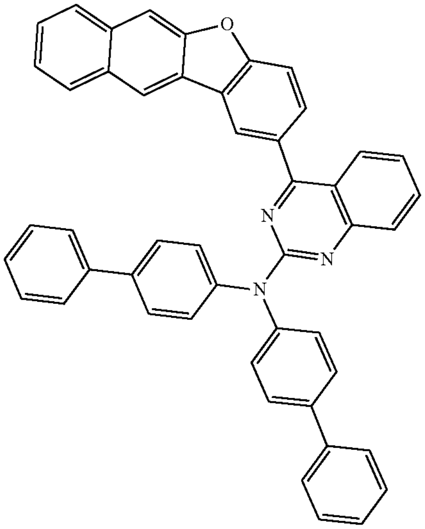
-continued
23
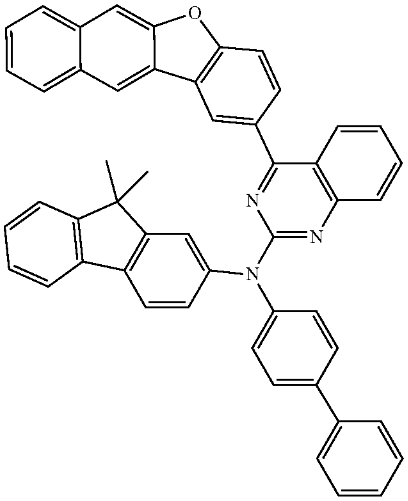
24
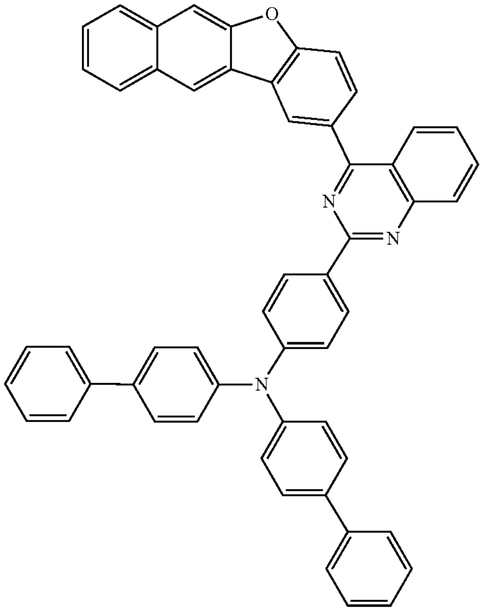
25
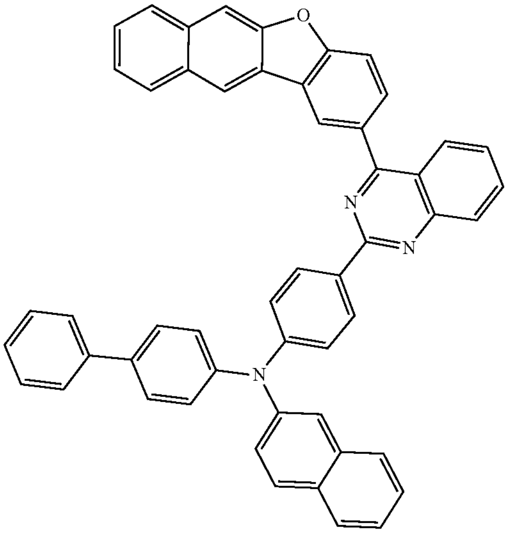

-continued
26
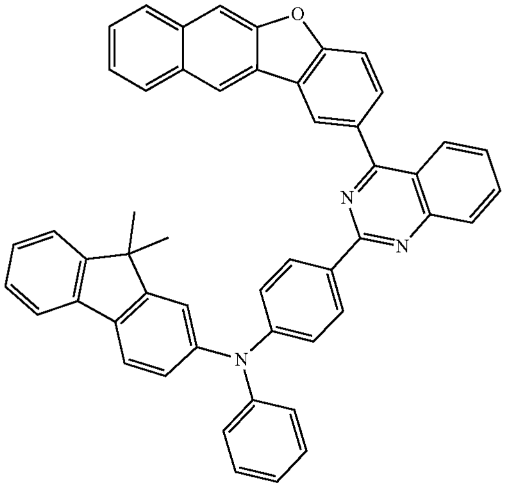
27
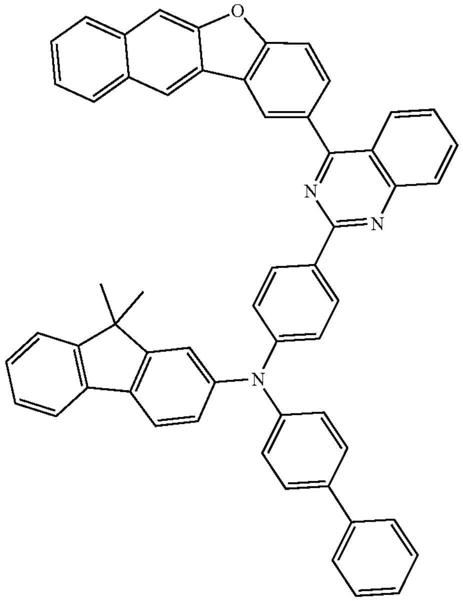
28
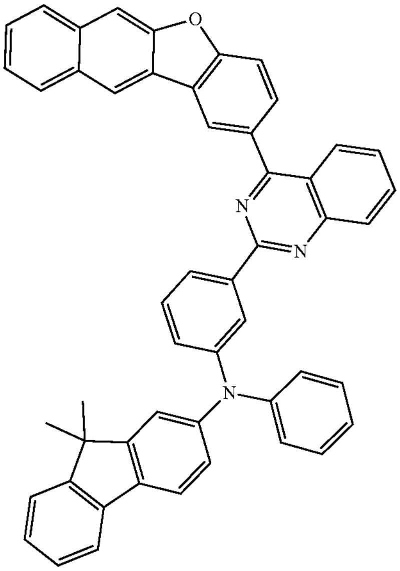
-continued
29
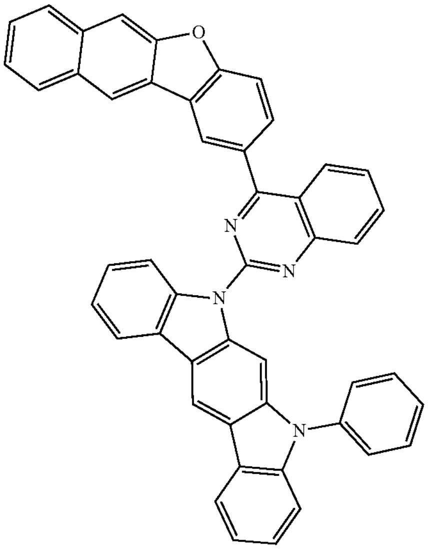
30
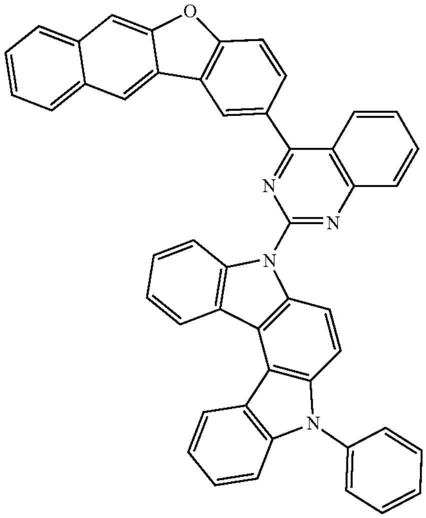
31
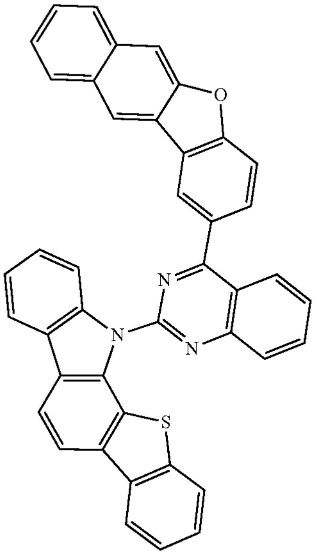

-continued
32
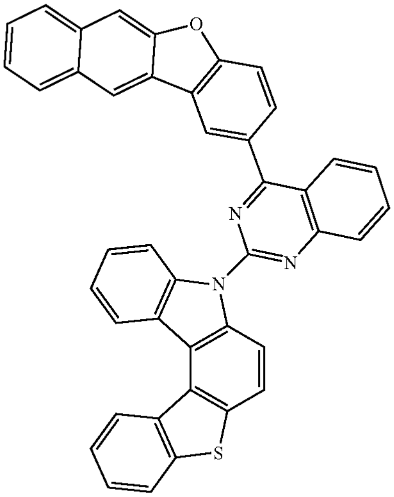
33
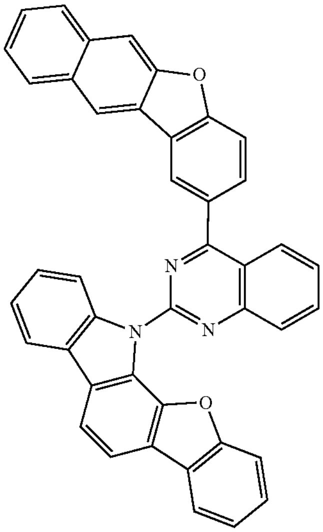
34
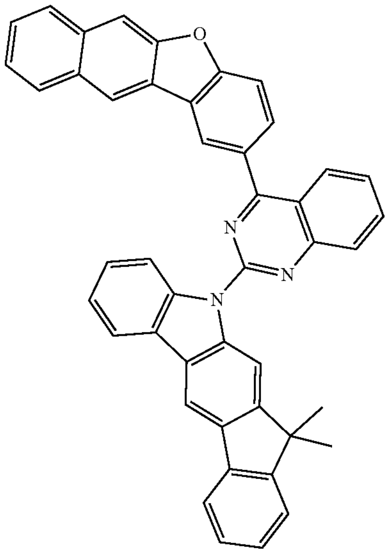
-continued
35
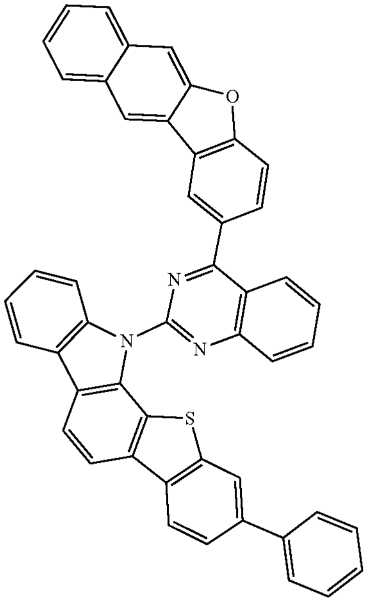
36
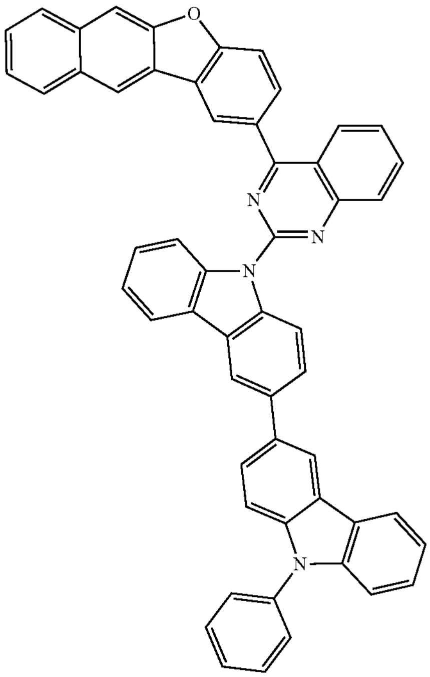

-continued
37
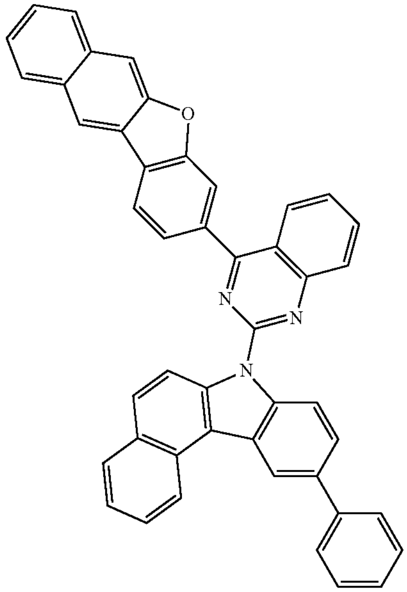
38
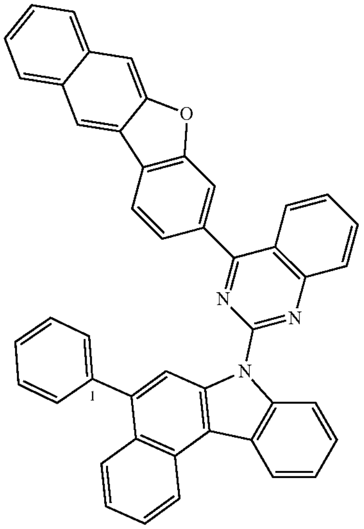
-continued
39
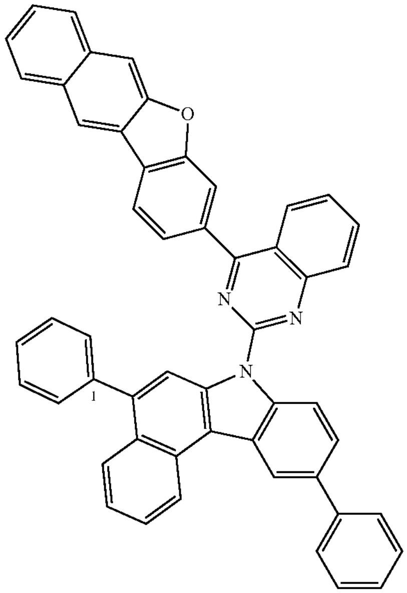
40
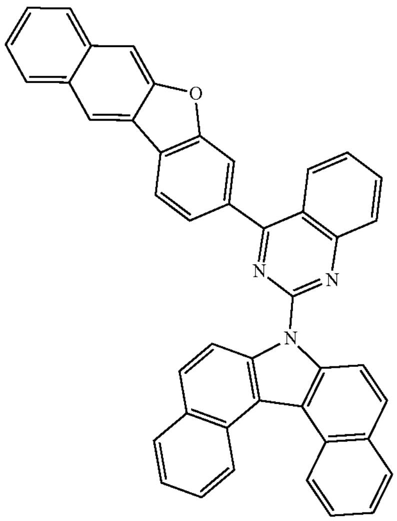

-continued
41
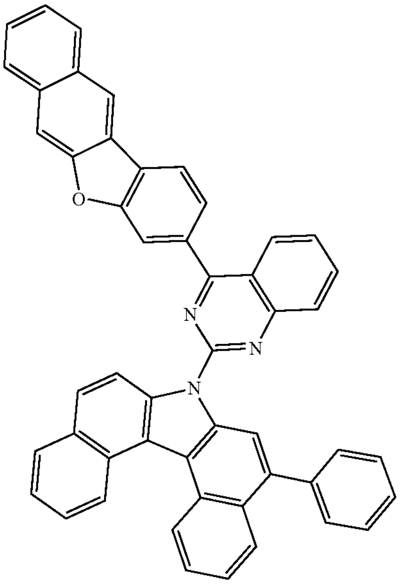
-continued
43
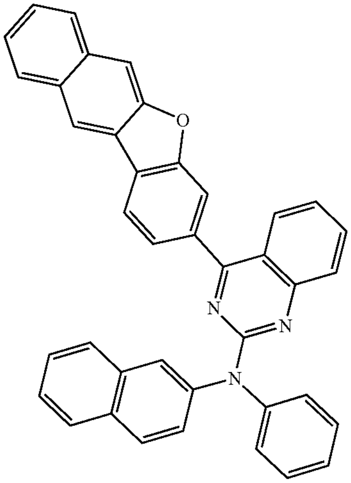
42
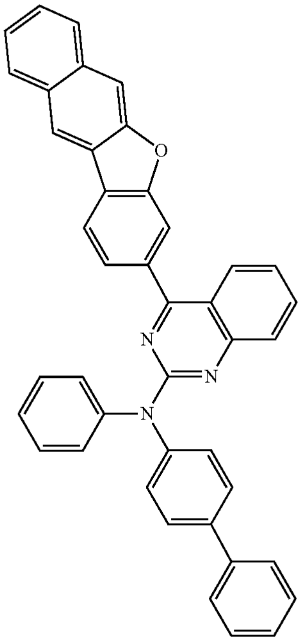
44
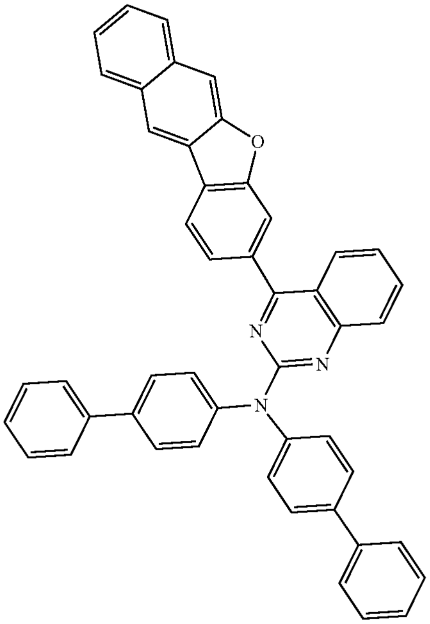

-continued
45
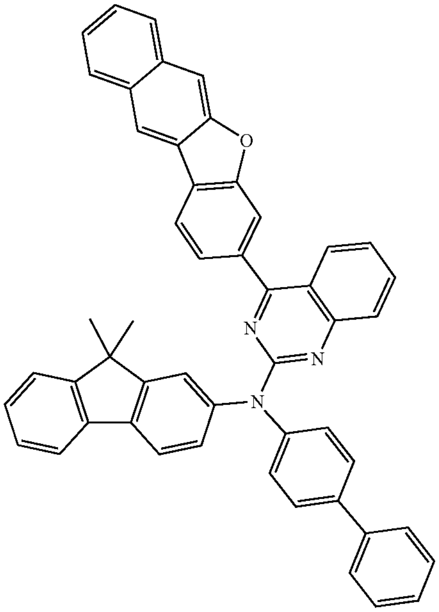
46
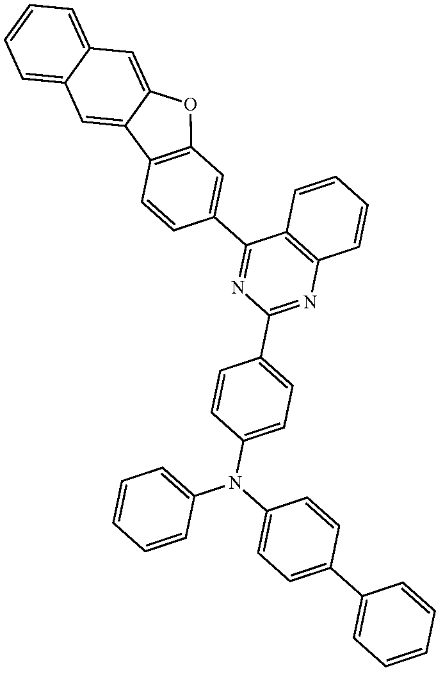
-continued
47
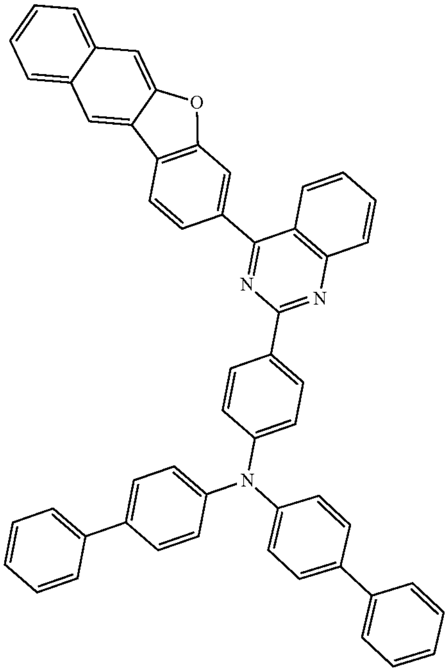
48
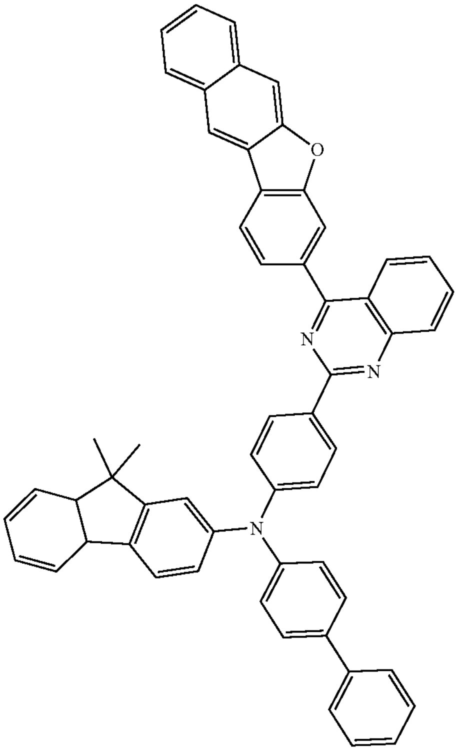

-continued
49
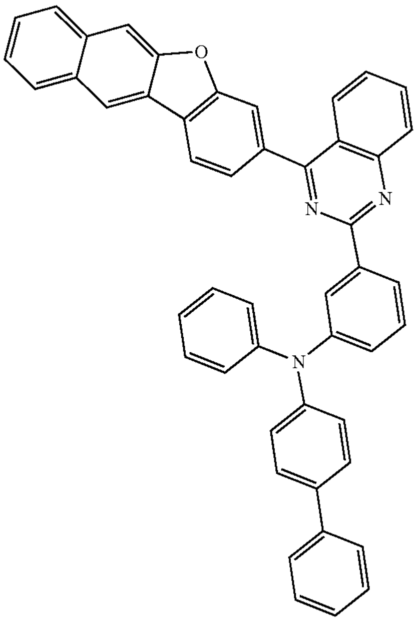
50
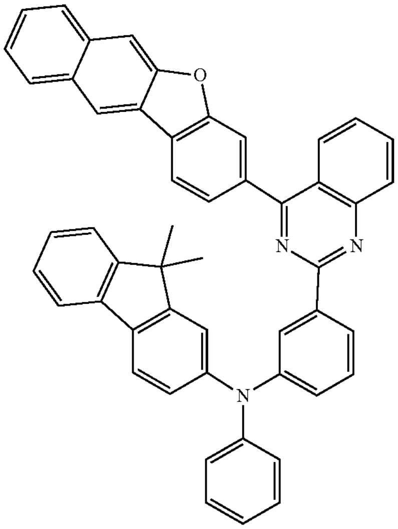
-continued
51
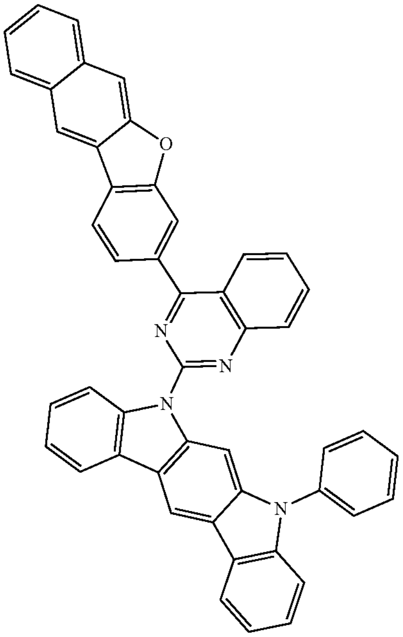
52
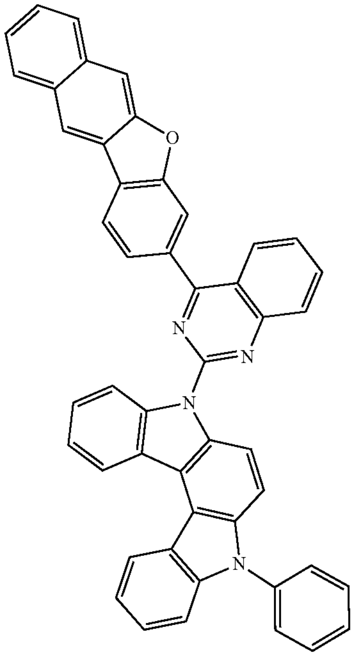

-continued
53
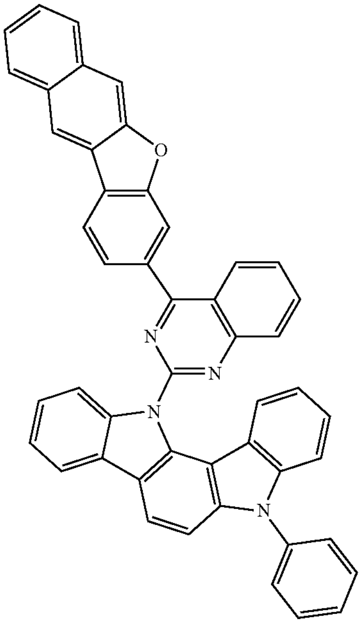
54
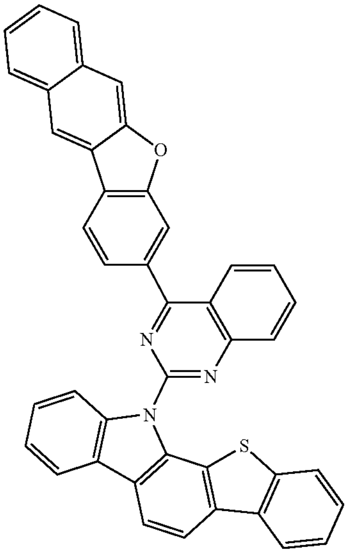
-continued
55
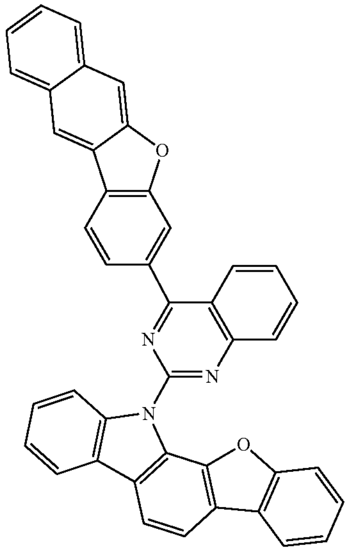
56
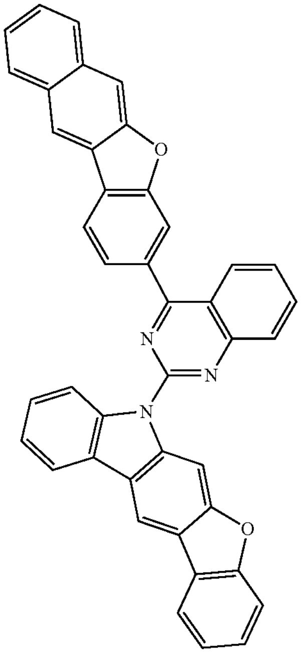

-continued
57
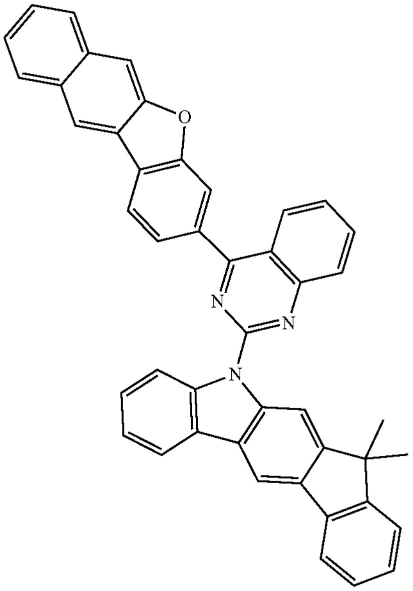
58
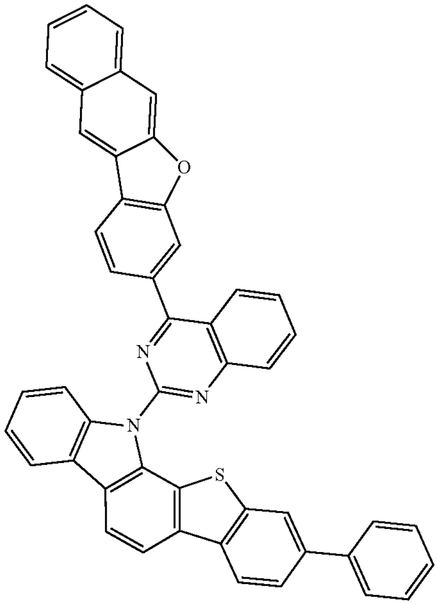
-continued
59
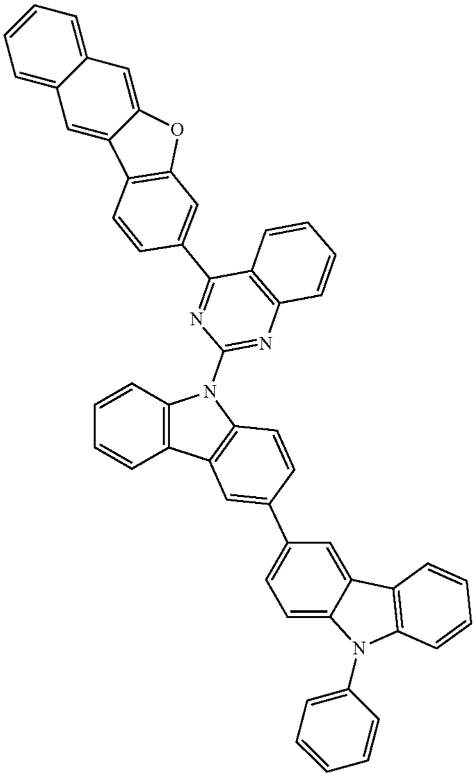
60
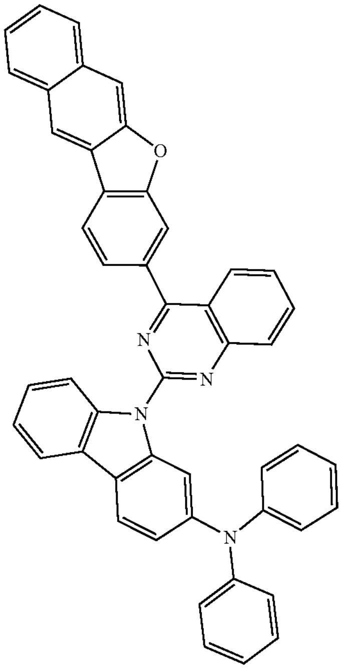

-continued
61
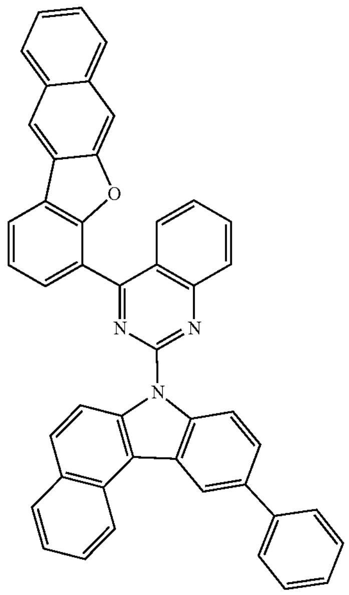
62
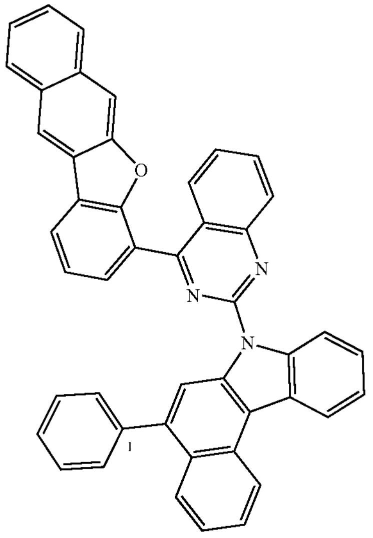
-continued
63
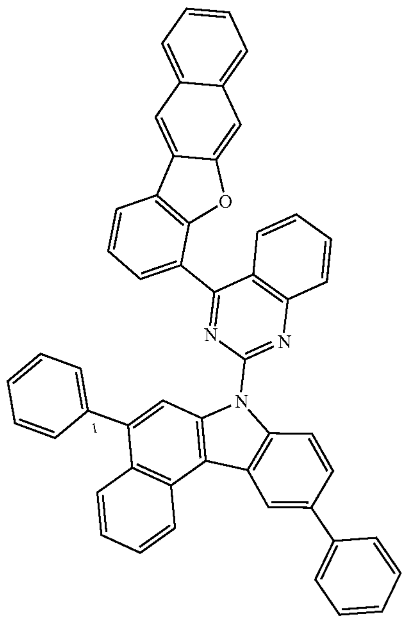
64
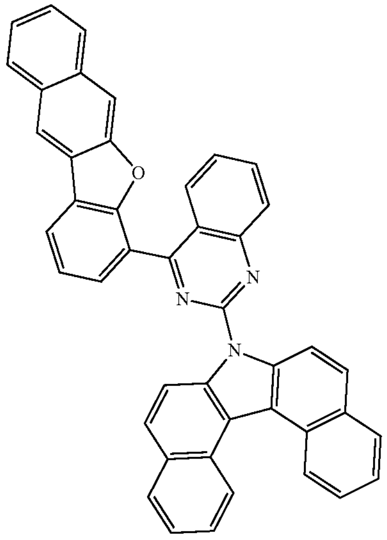

-continued
65
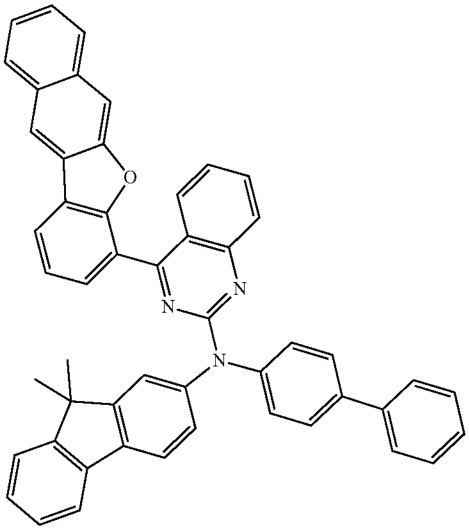
67
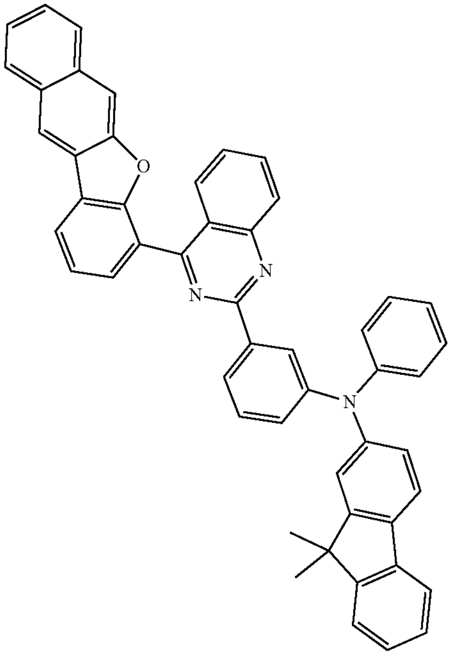
66
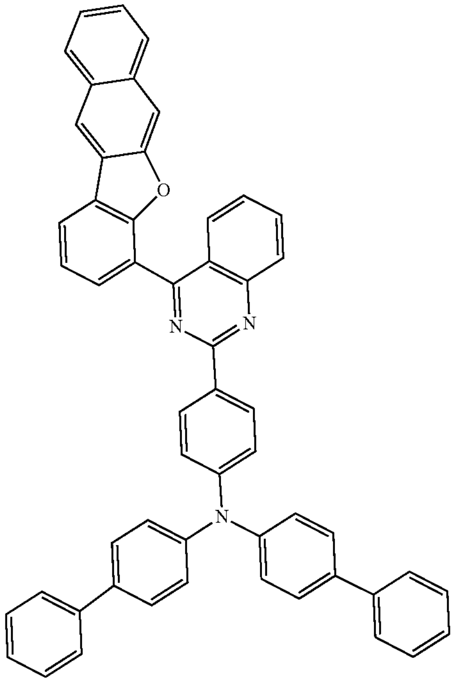
68
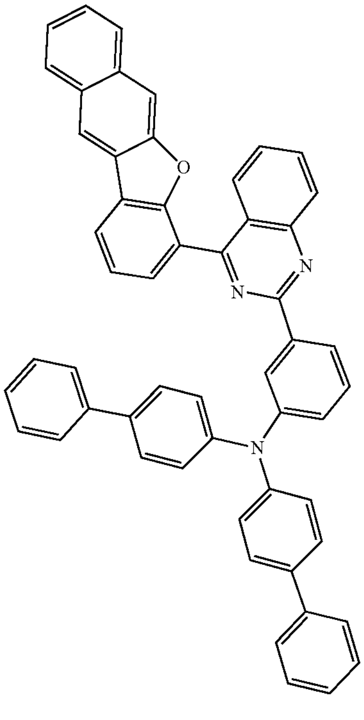

-continued
69
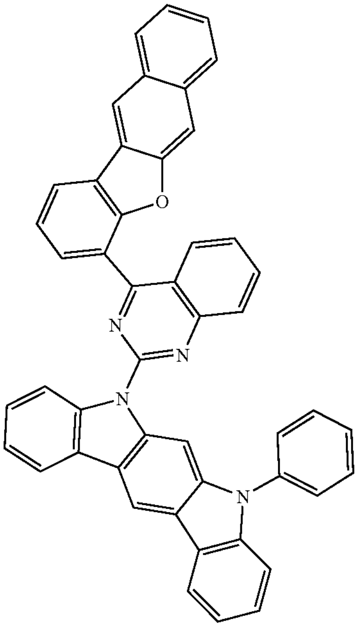
70
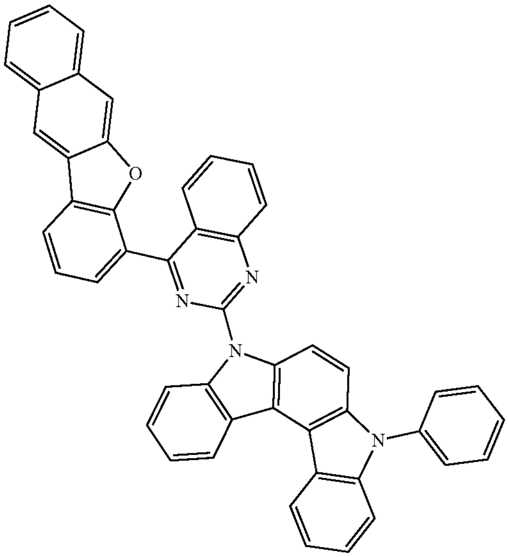
-continued
71
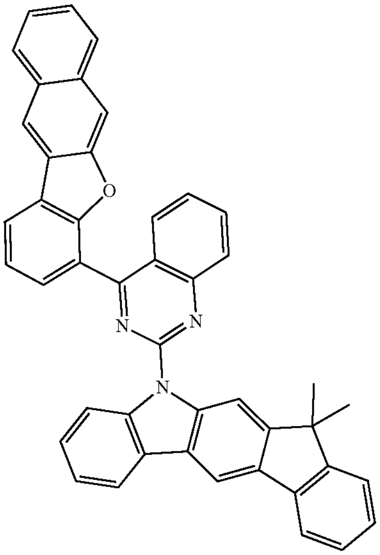
72
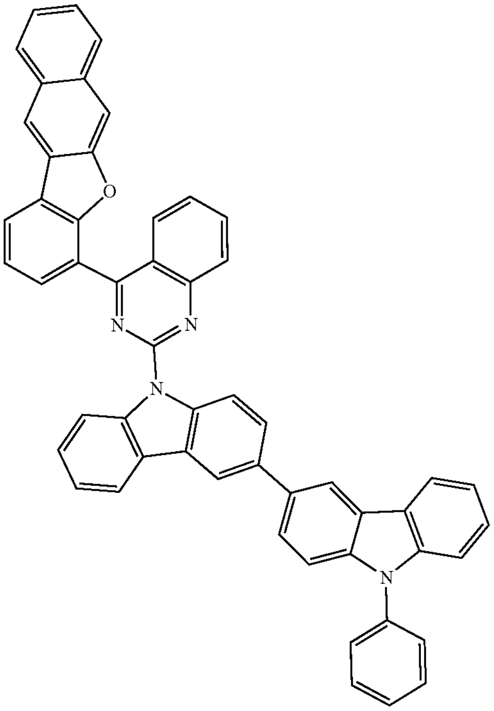

-continued
73
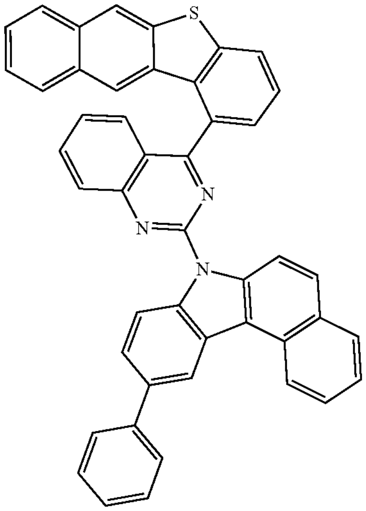
74
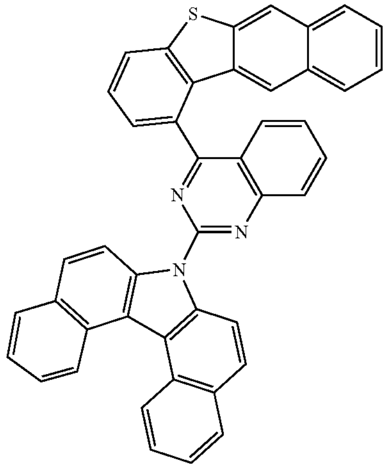
75
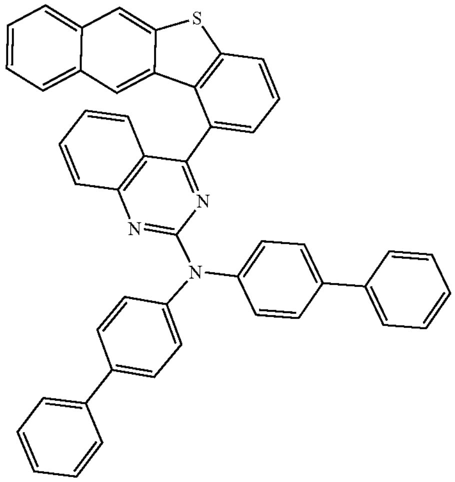
-continued
76
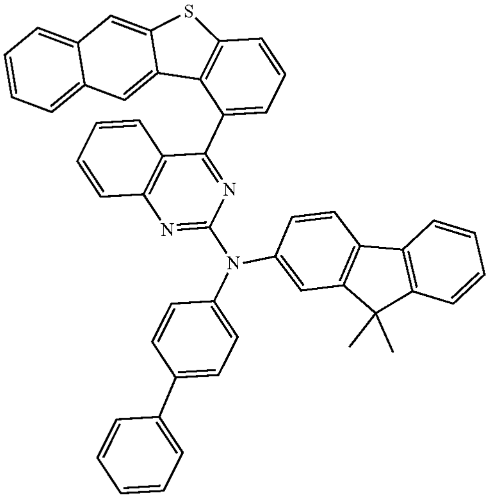
77
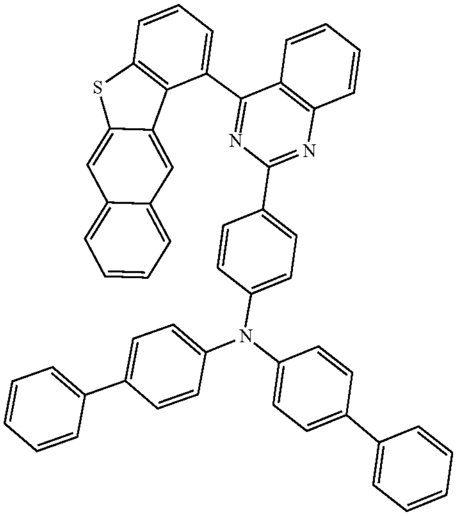
78
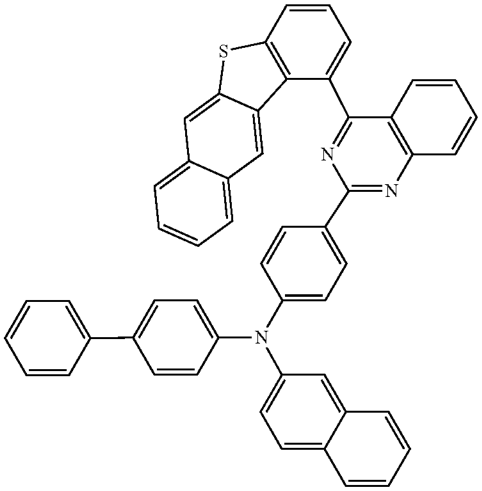

-continued
79
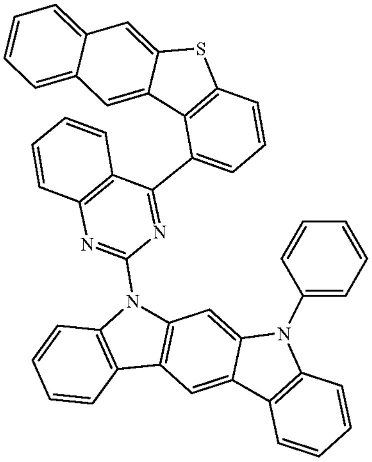
80
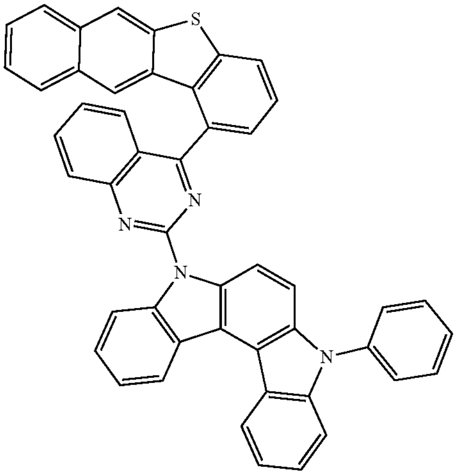
81
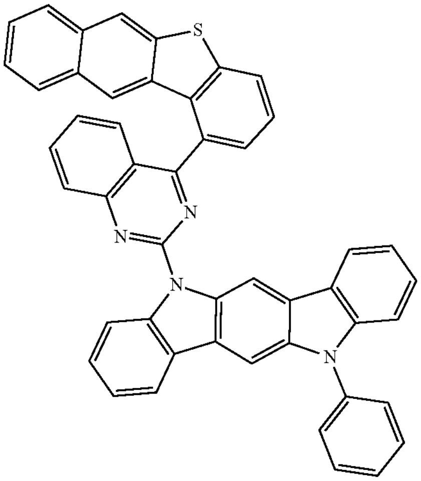
-continued
82
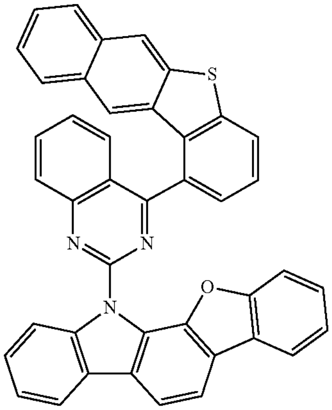
83
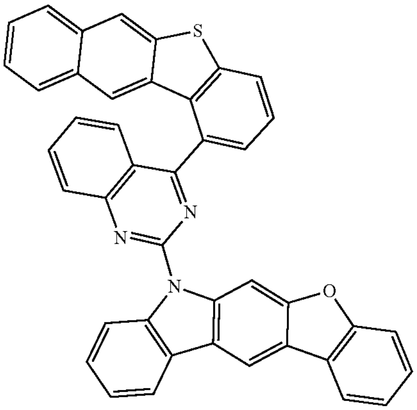
84
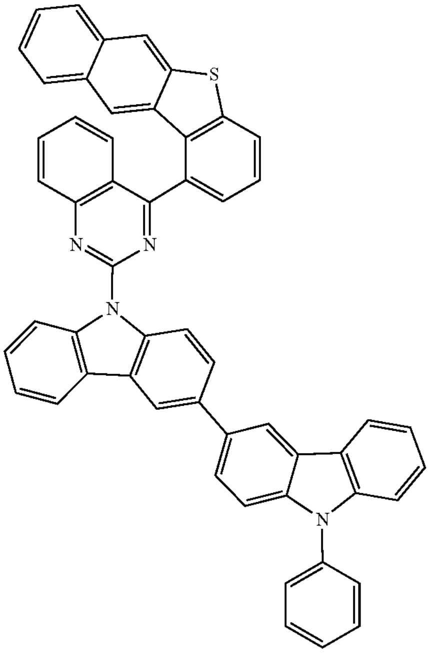

-continued
85
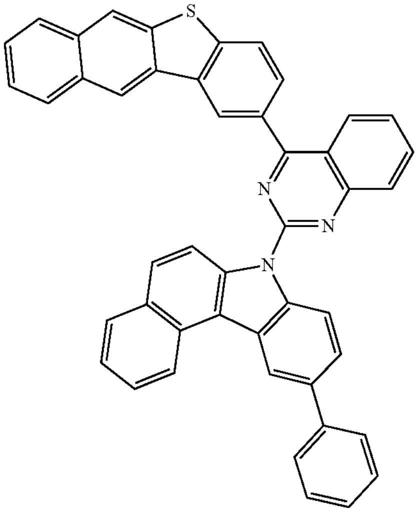
86
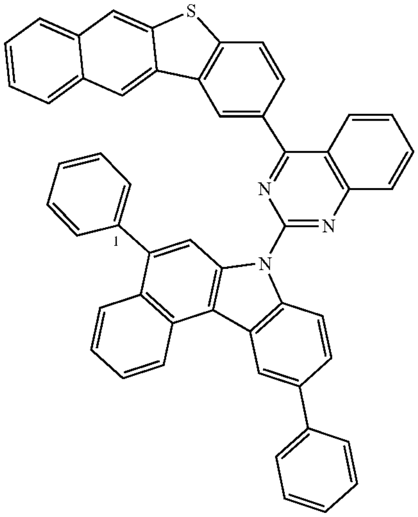
87
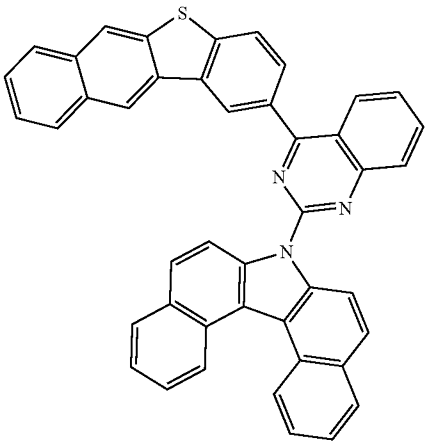
-continued
88
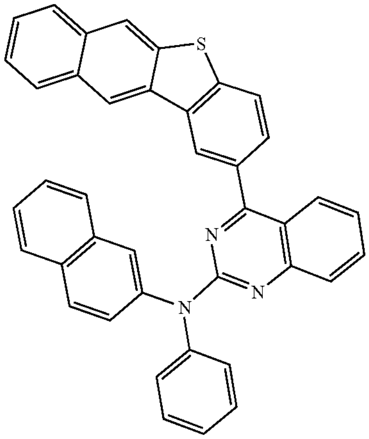
89
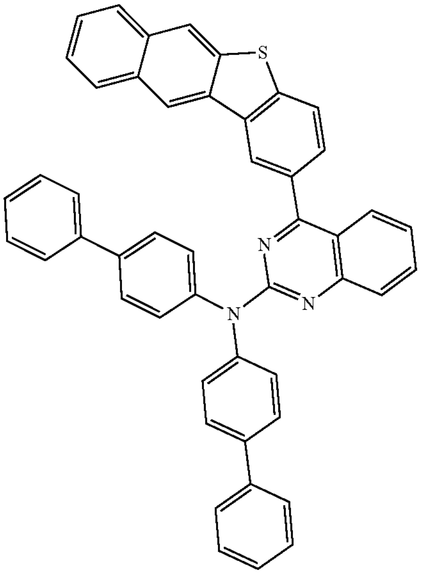
90
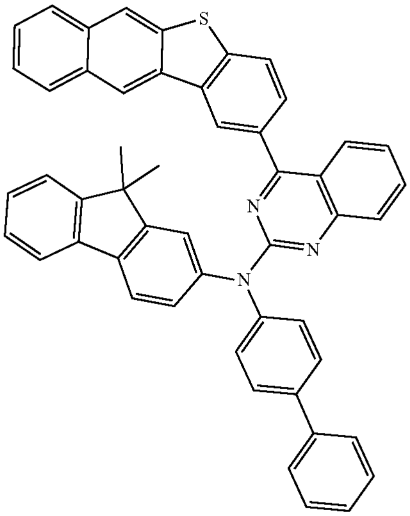

-continued
91
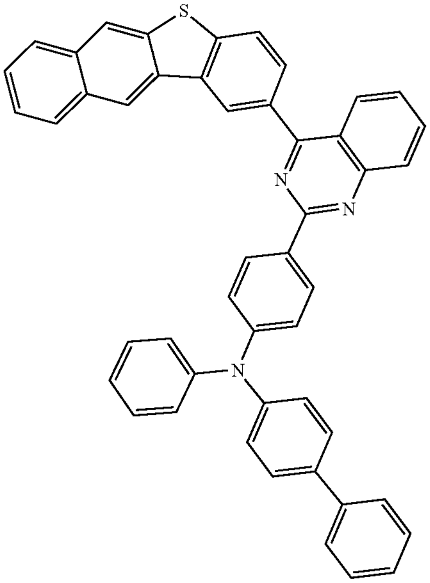
92
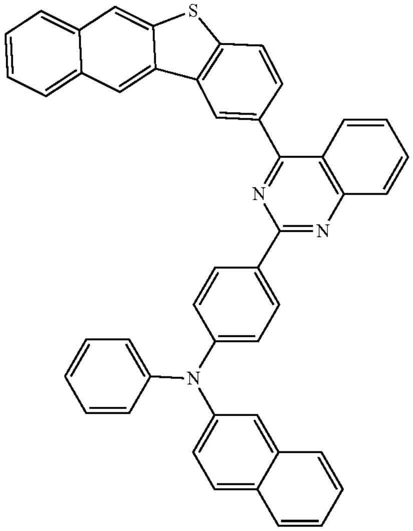
-continued
93
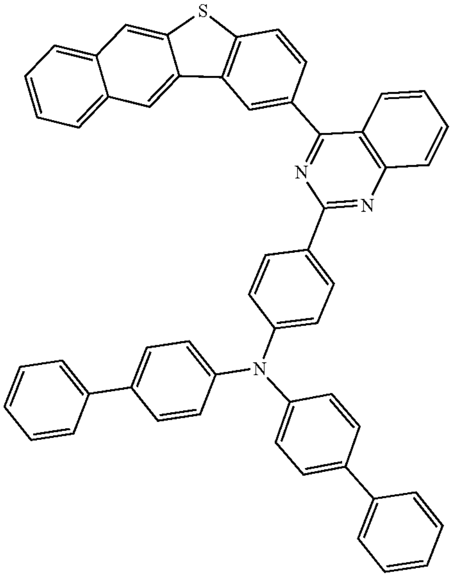
94
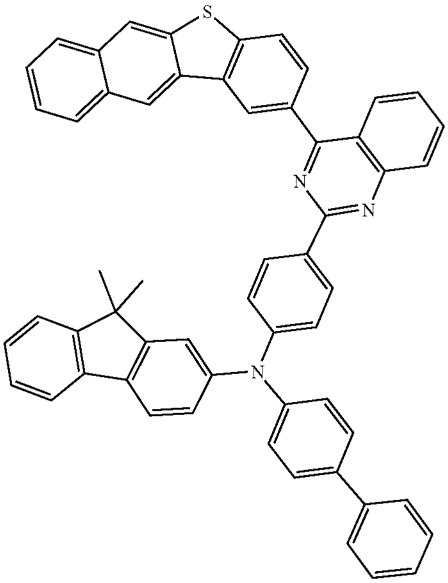

-continued
95
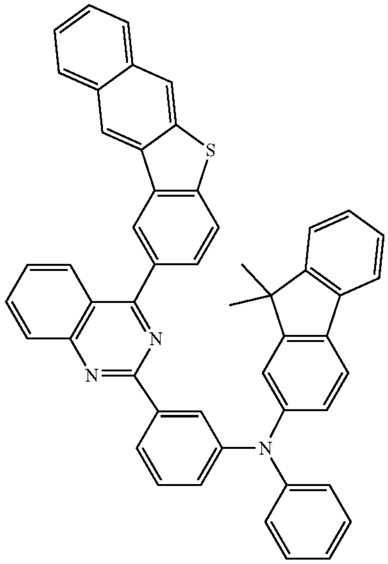
96
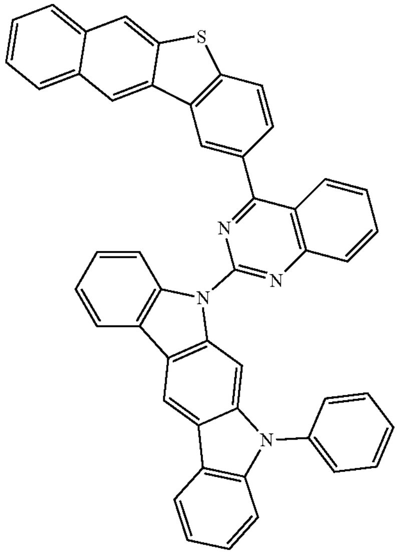
97
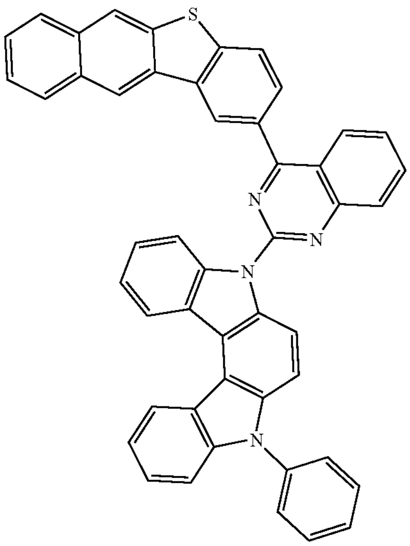
-continued
98
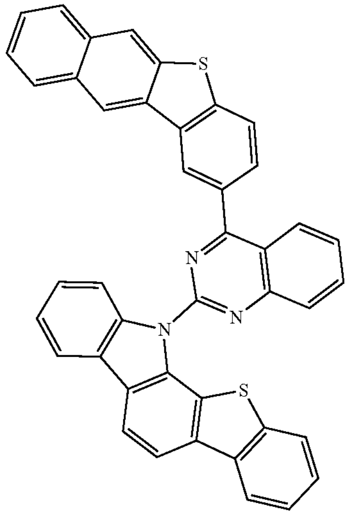
99
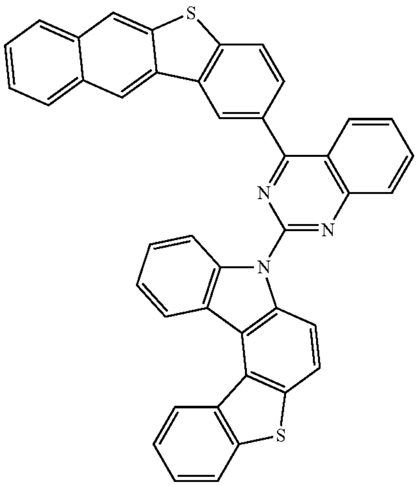
100
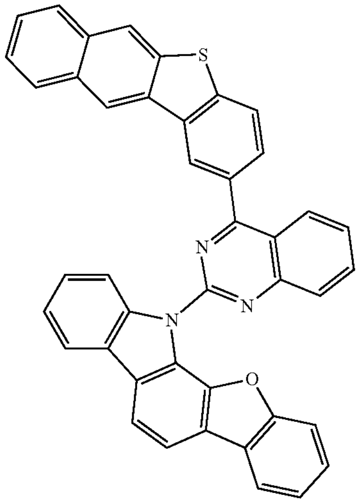

101
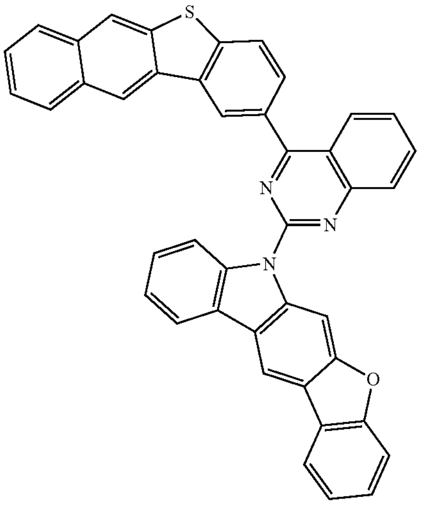
102
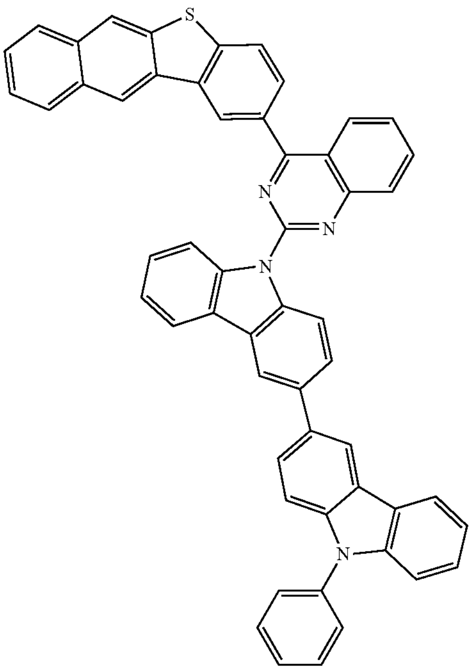
103
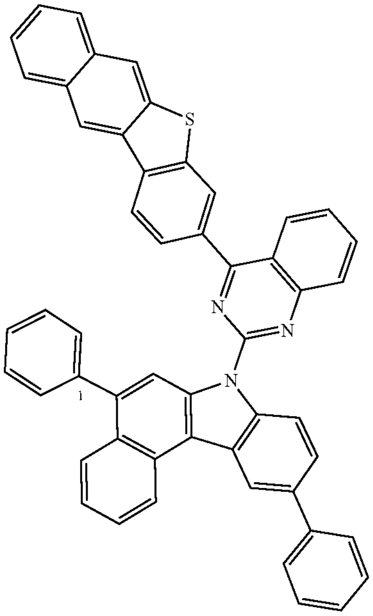
104
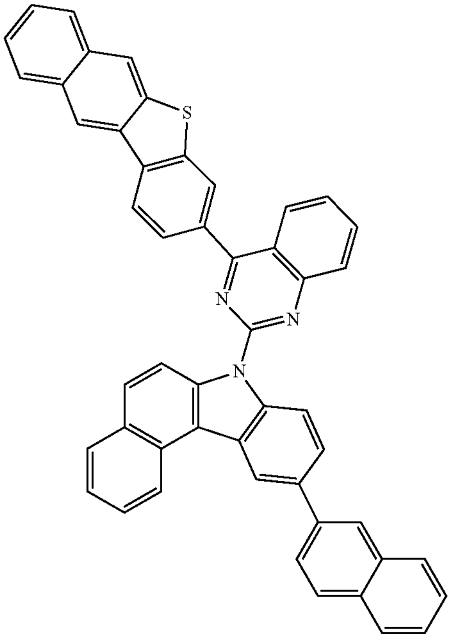

-continued
105
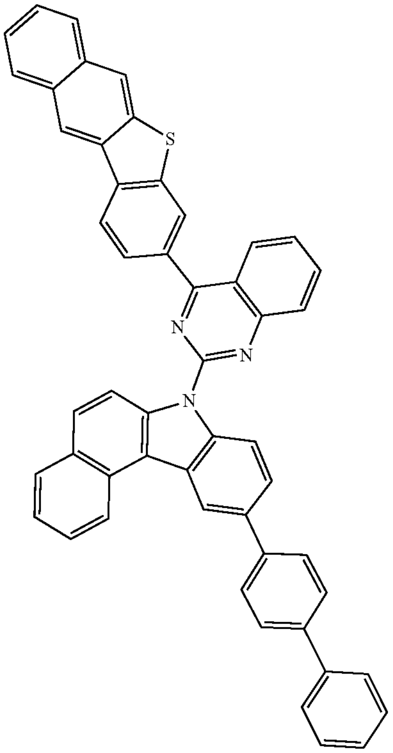
106
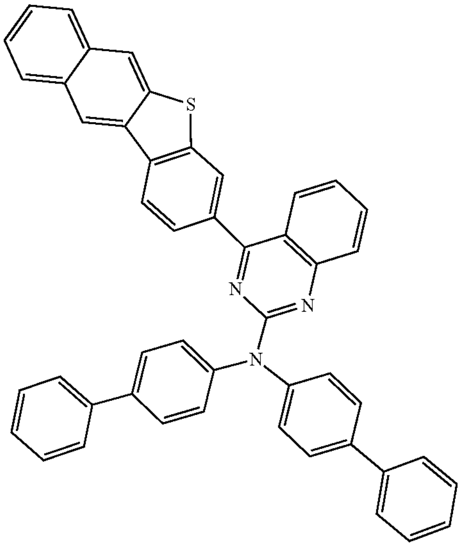
-continued
107
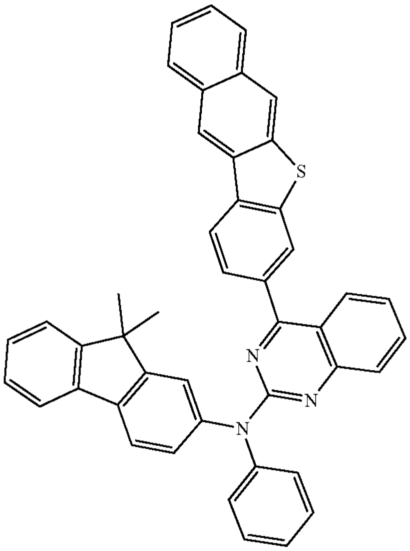
108
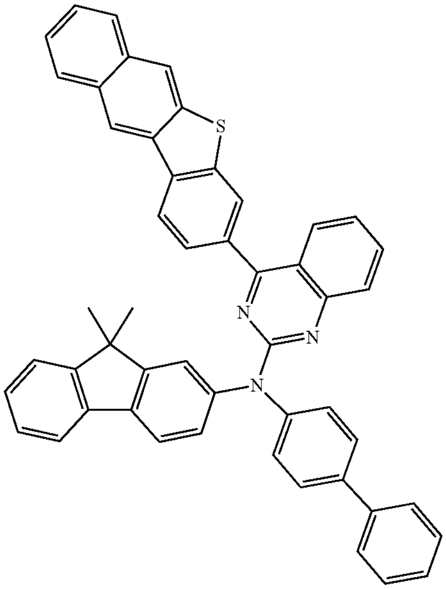

-continued
109
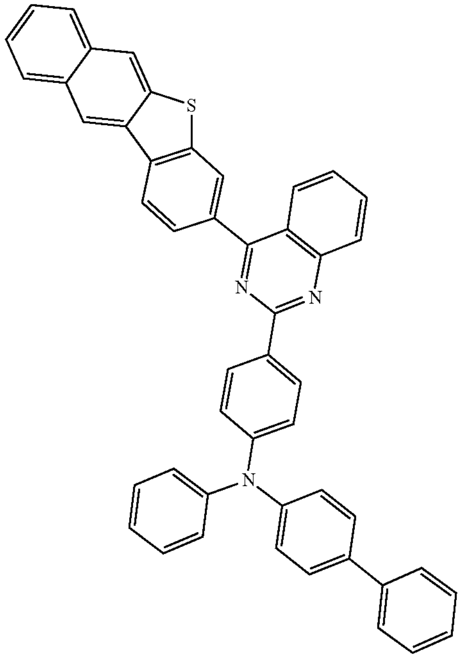
110
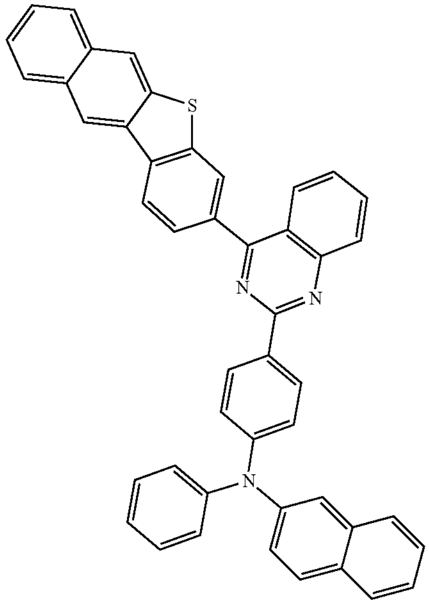
-continued
111
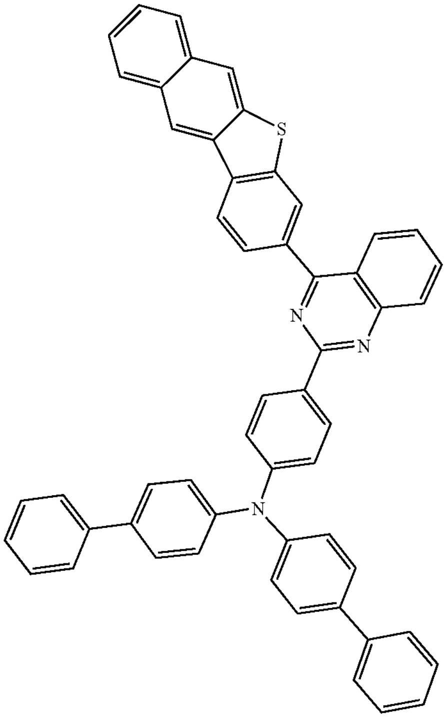
112
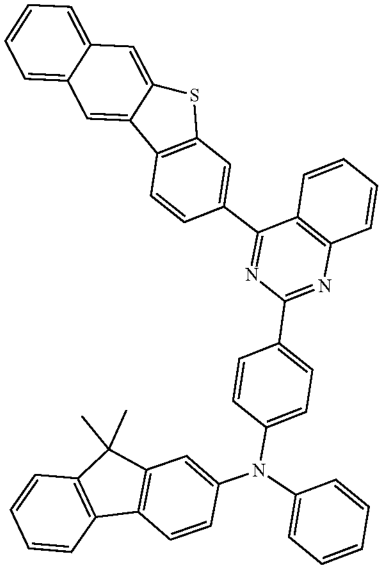

-continued
113
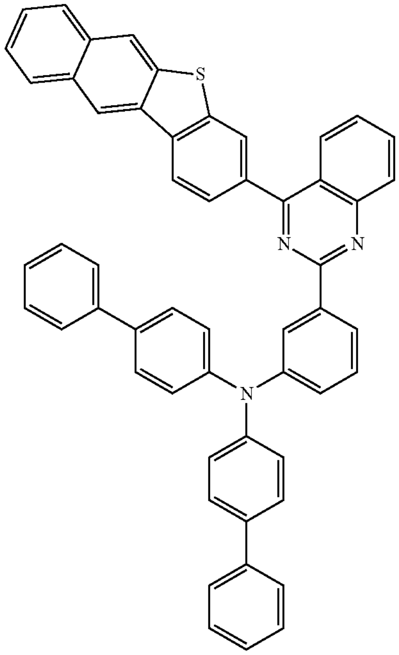
115
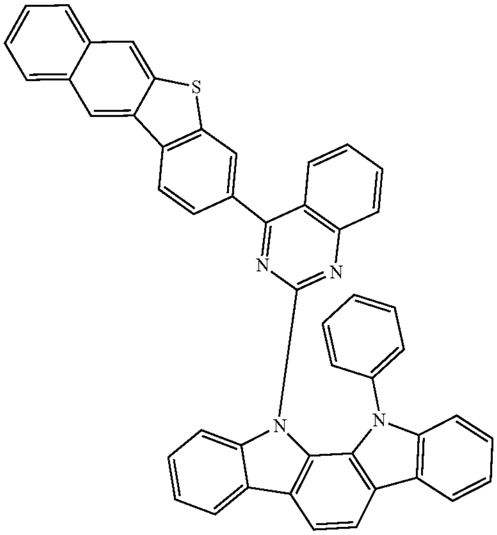
114
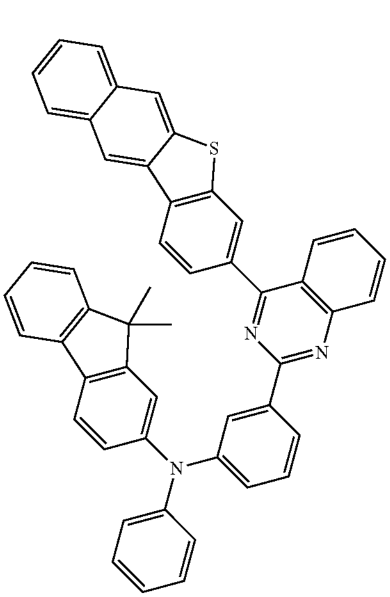
116
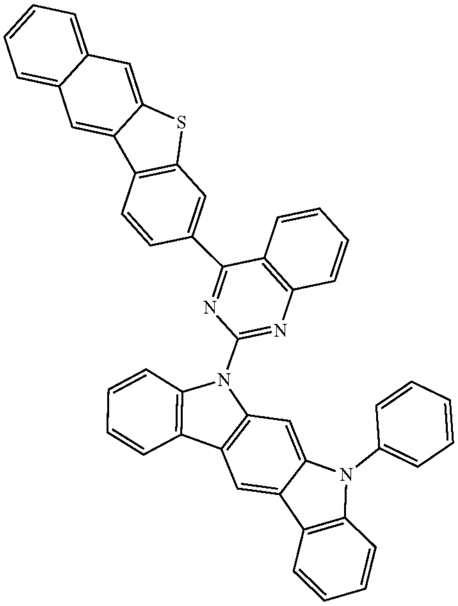

-continued
117
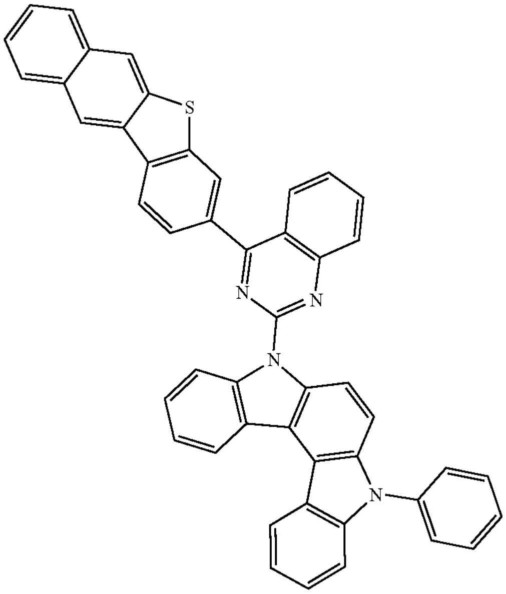
118
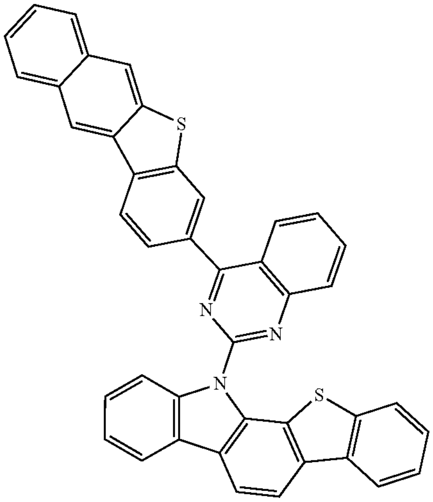
119
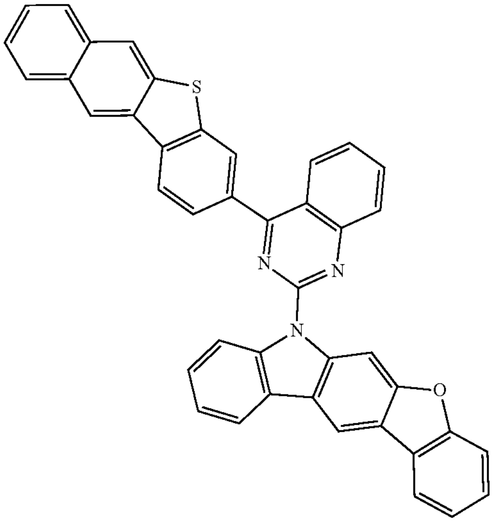
-continued
120
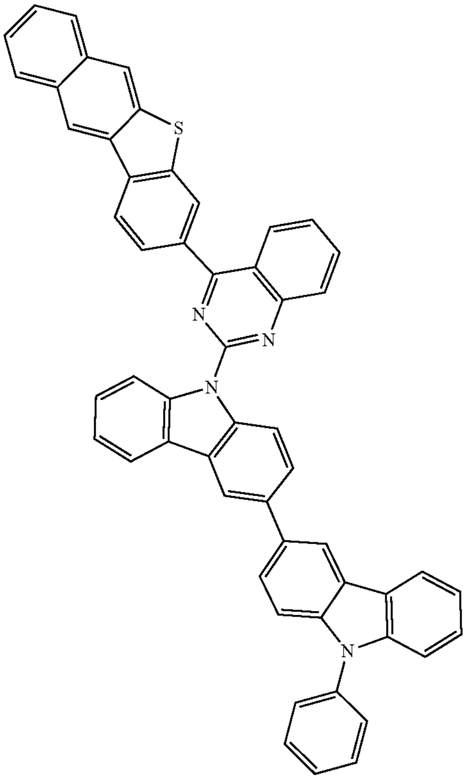
121
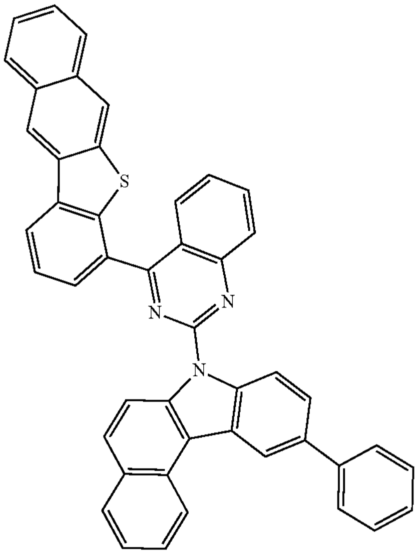

-continued
122
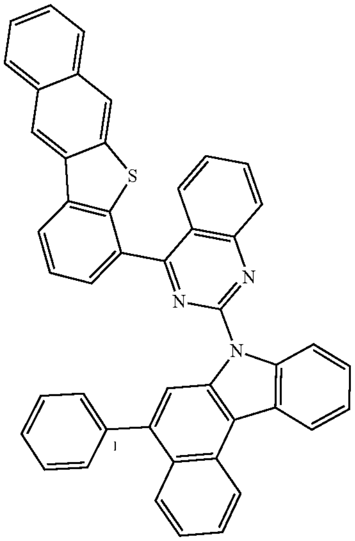
123
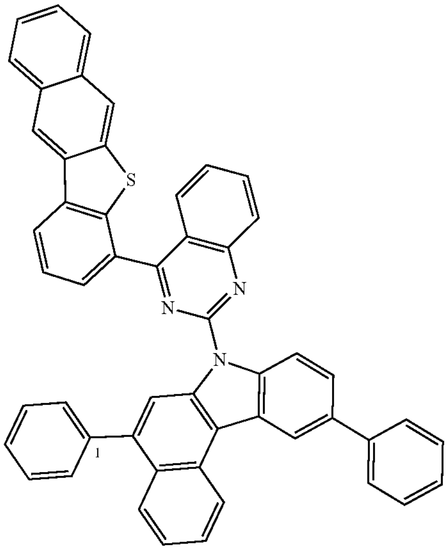
124
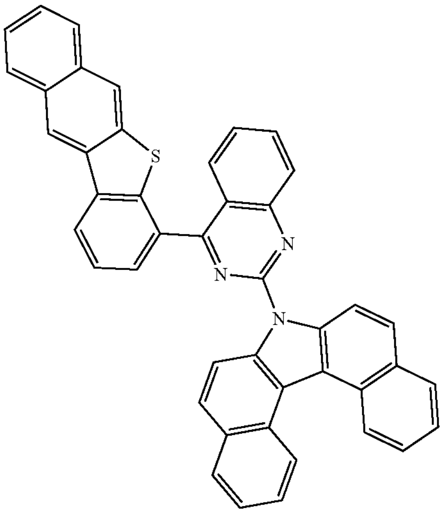
-continued
125
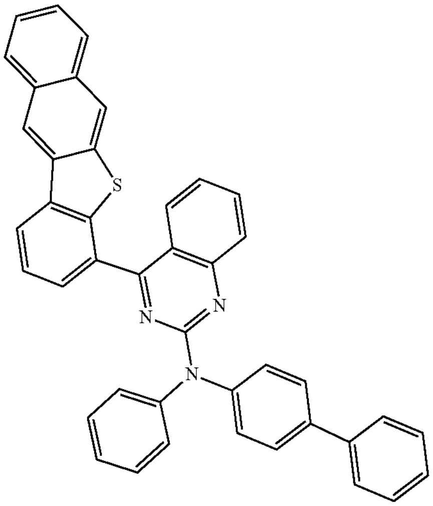
126
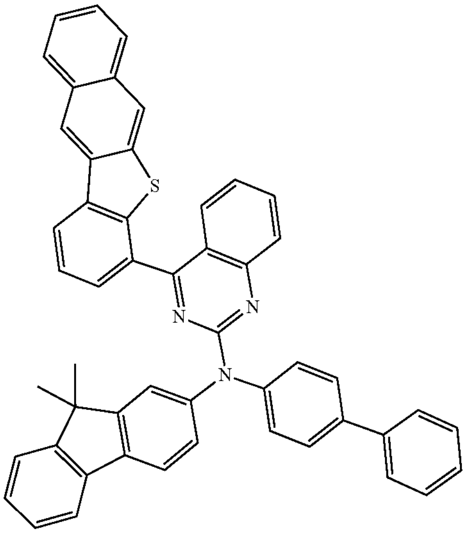

-continued
127
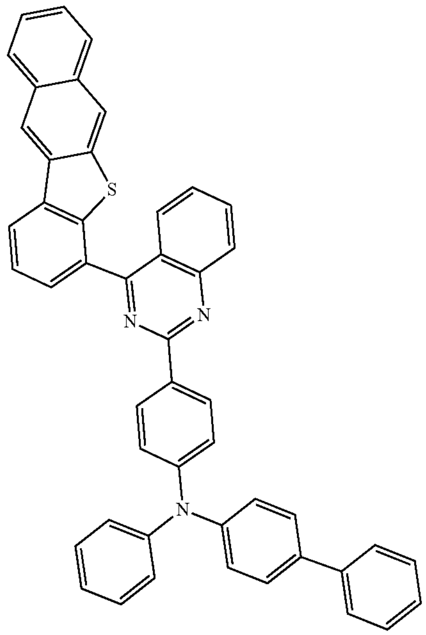
128
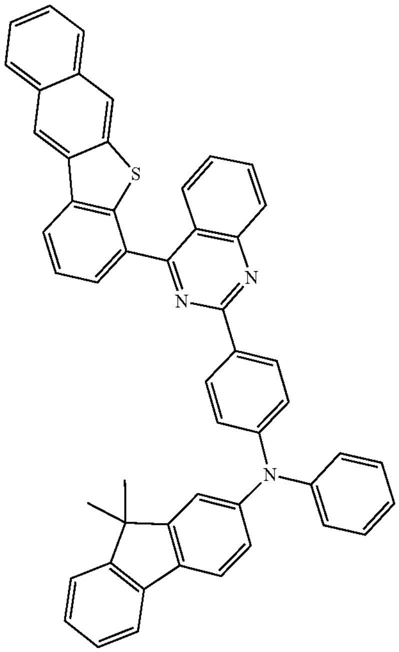
-continued
129
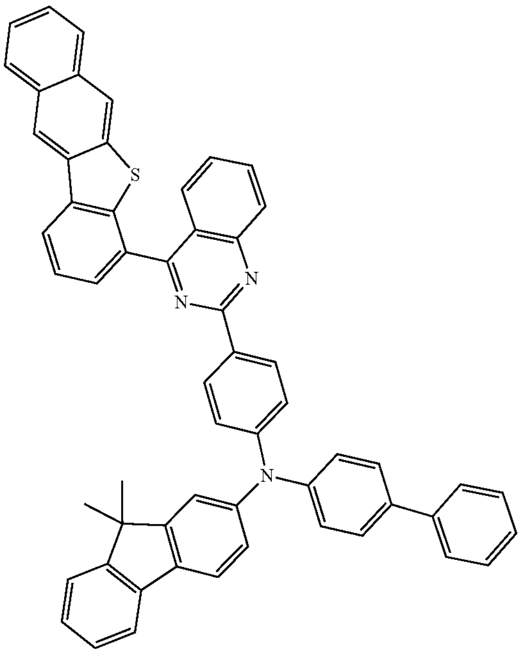
130
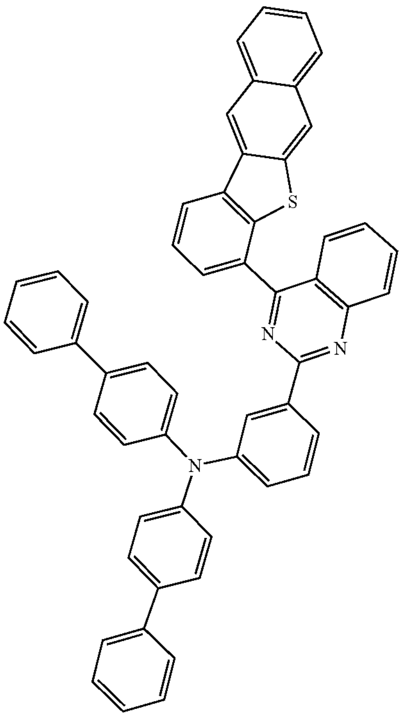

-continued
131
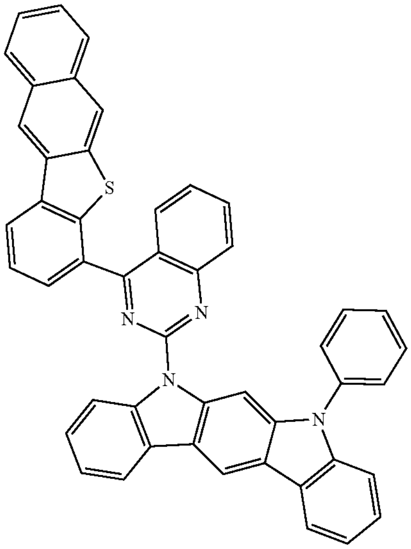
132
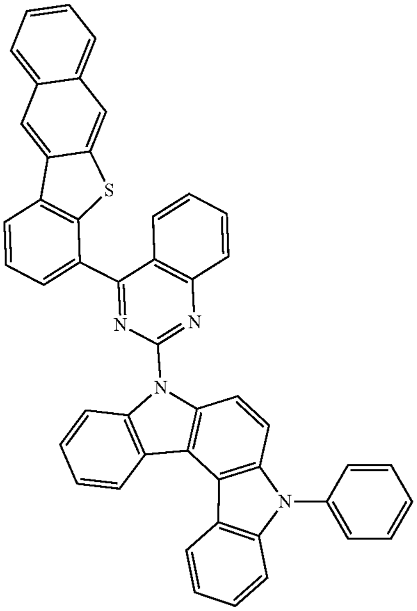
-continued
133
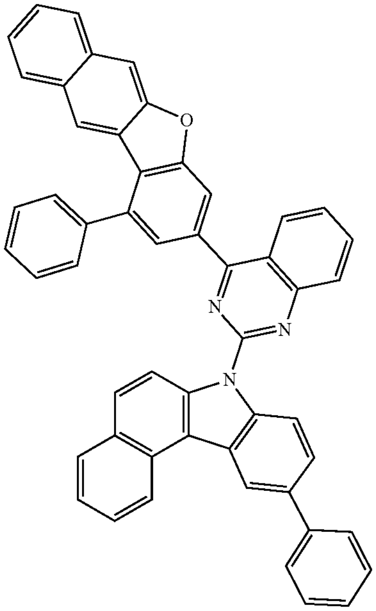
134
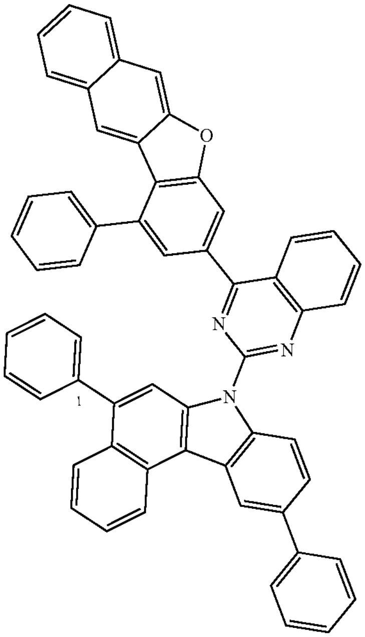

-continued
135
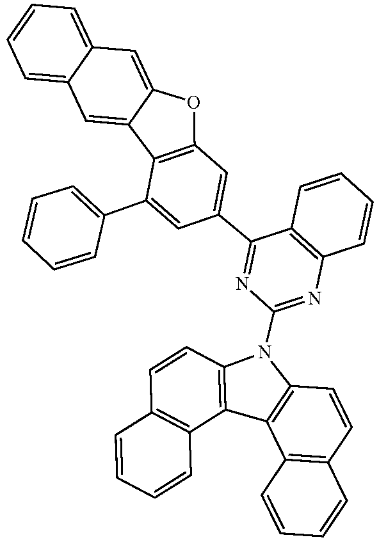
136
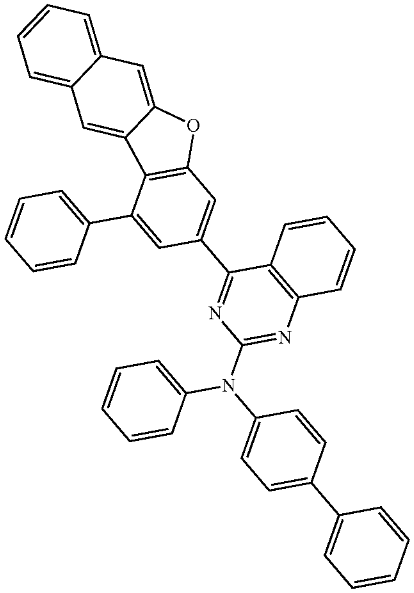
-continued
137
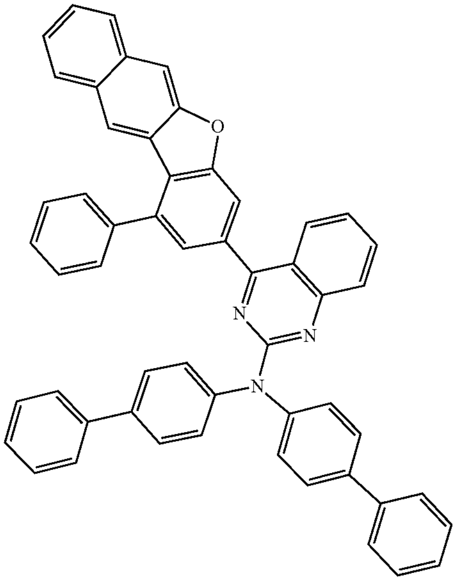
138
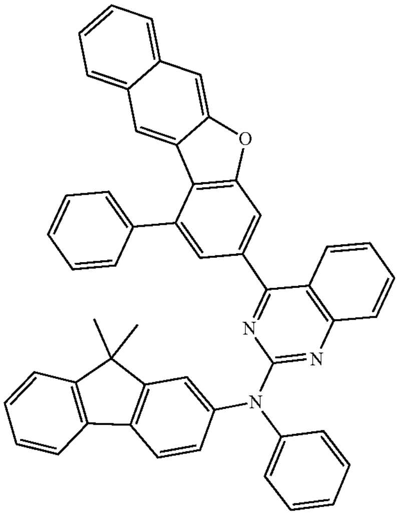

139
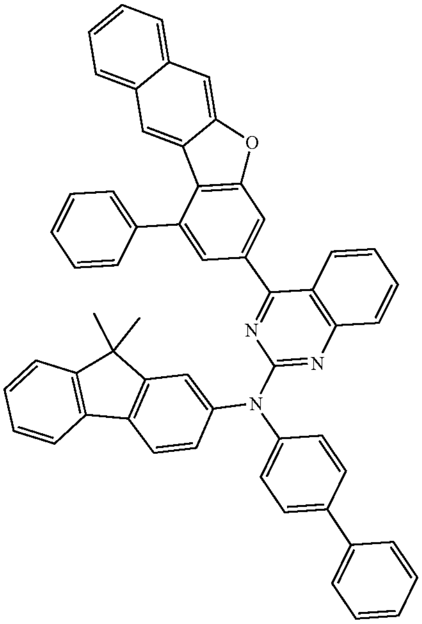
141
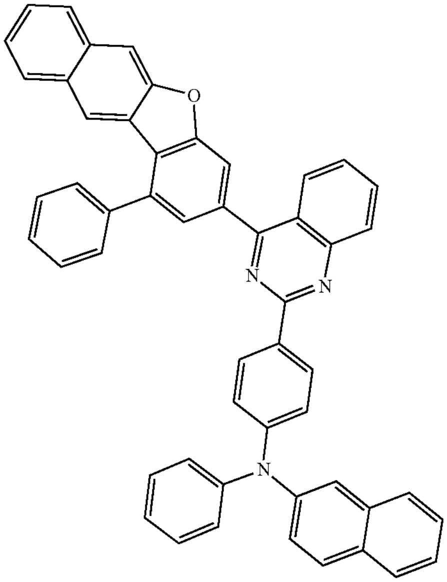
140
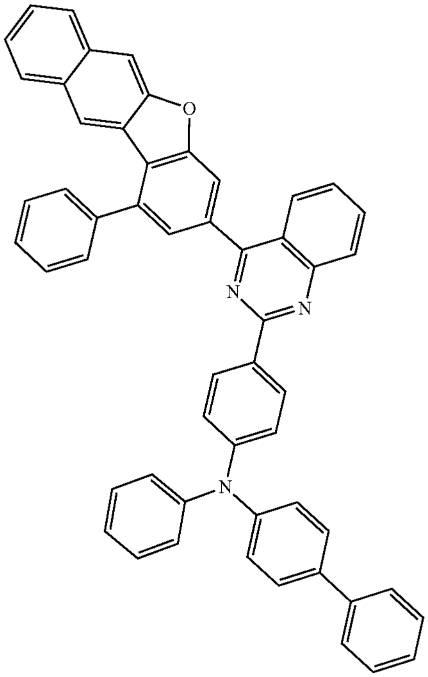
142
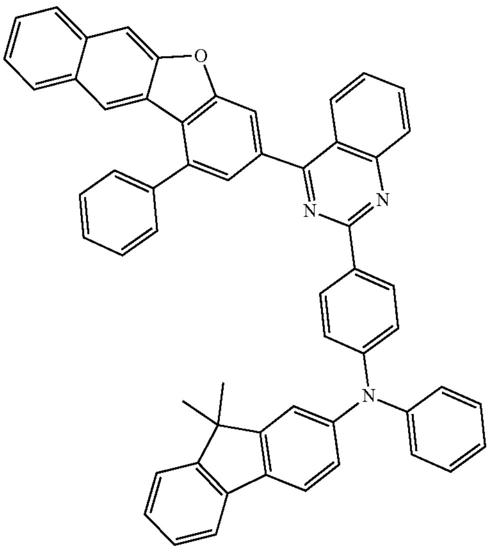

-continued
143
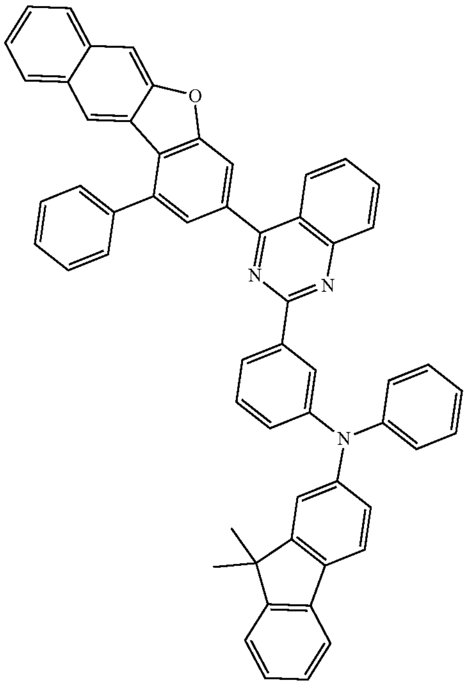
144
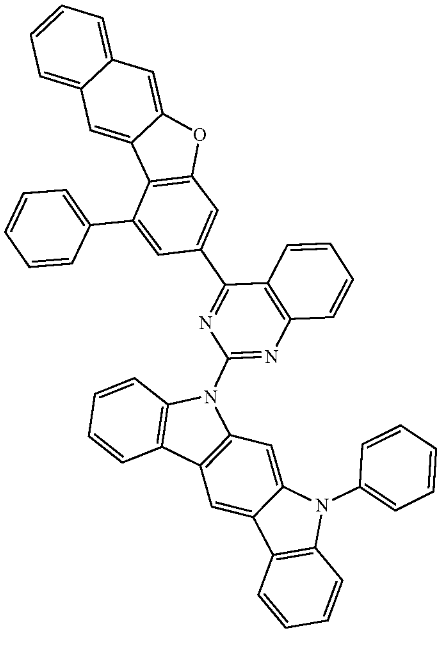
-continued
145
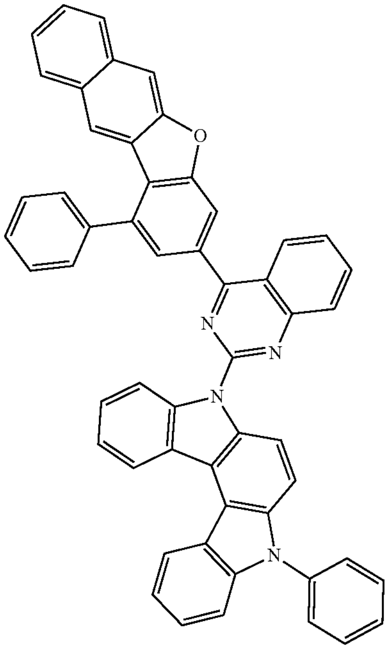
146
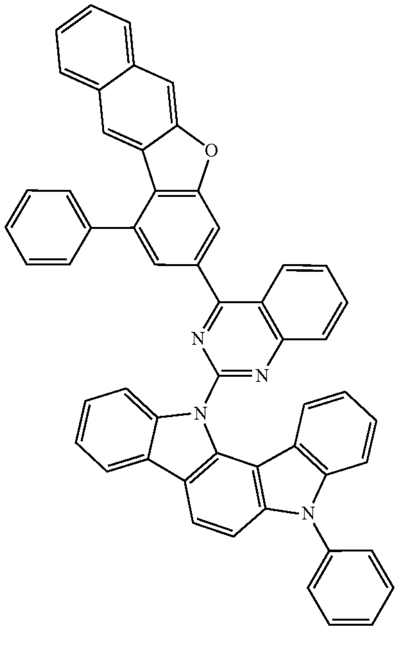

147
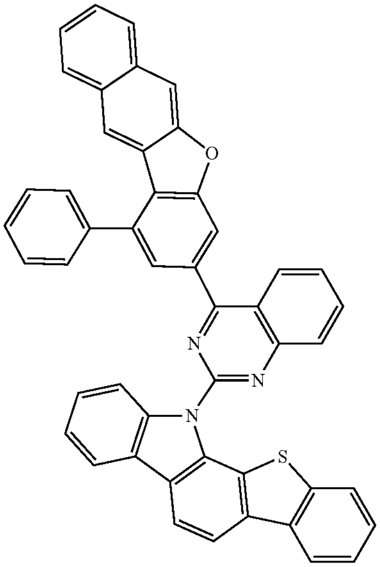
148
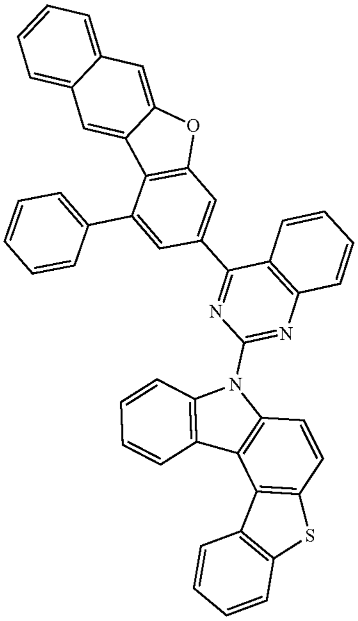
149
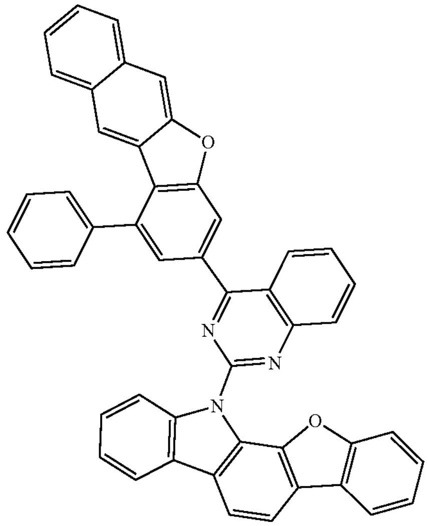
150
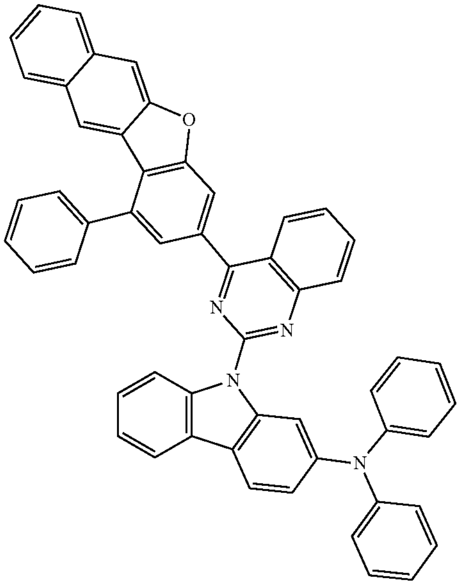

-continued
151
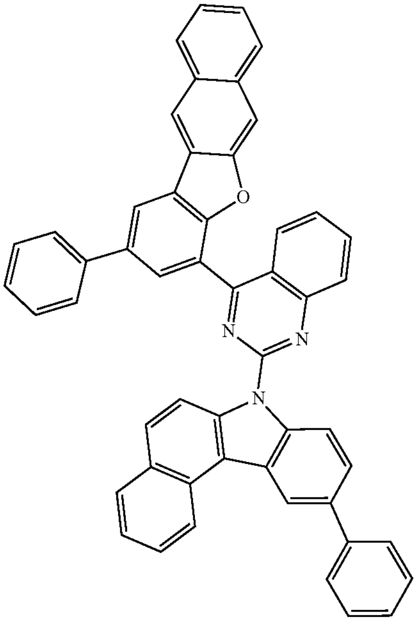
152
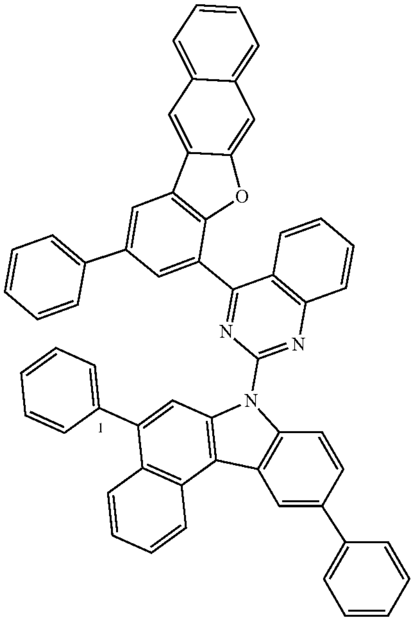
-continued
153
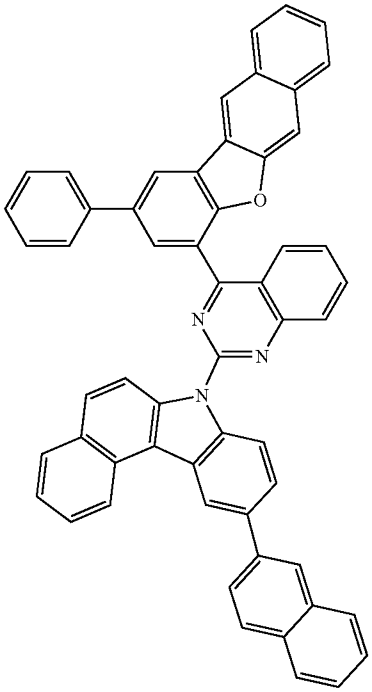
154
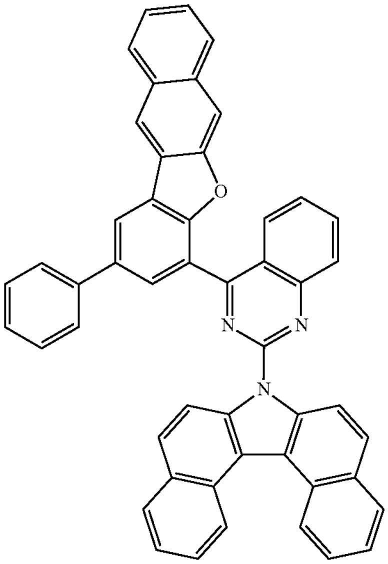

-continued
155
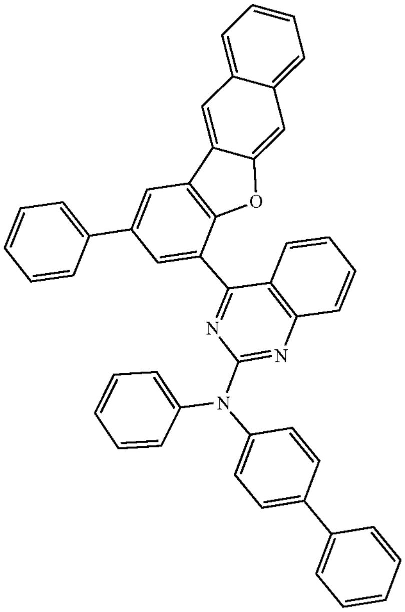
156
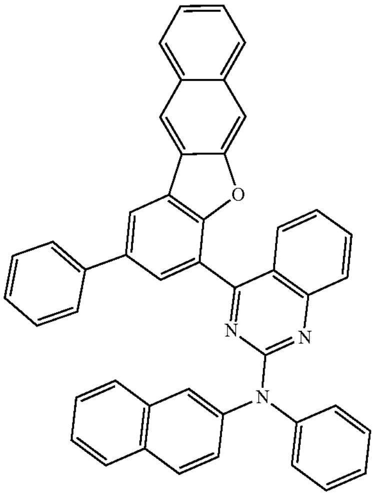
157
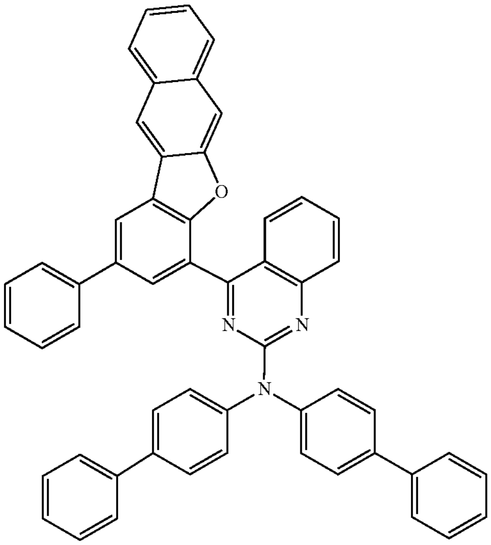
-continued
158
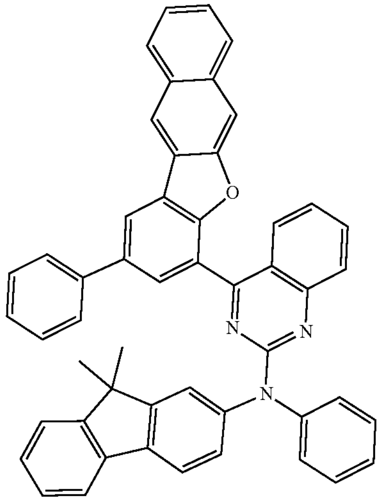
159
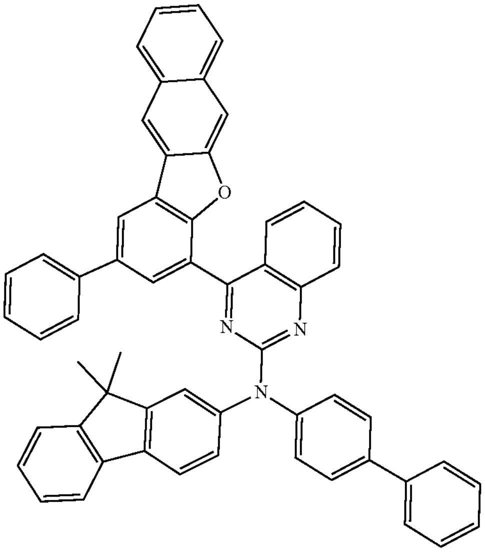

-continued
160
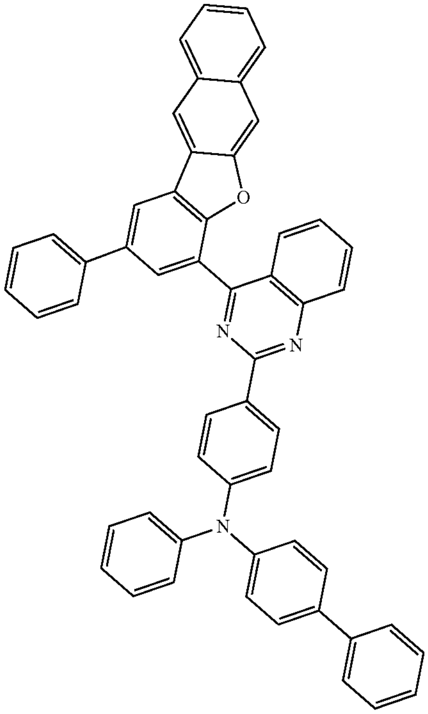
162
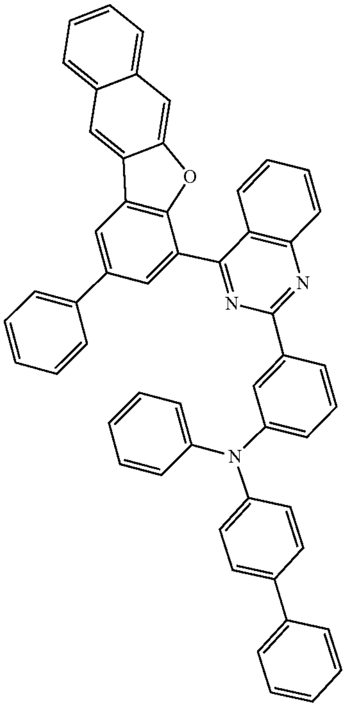
161
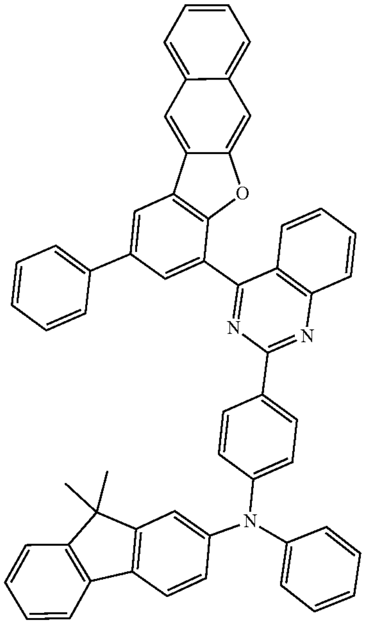
163
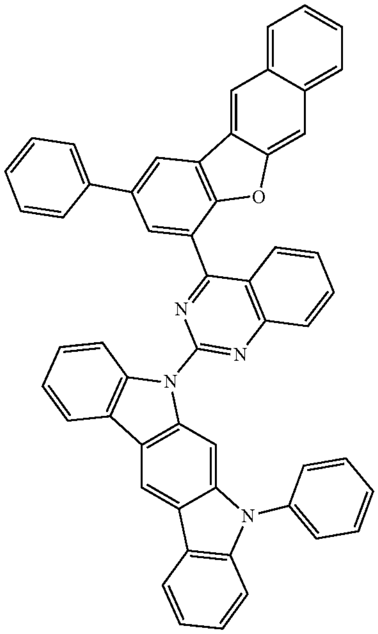

-continued
164
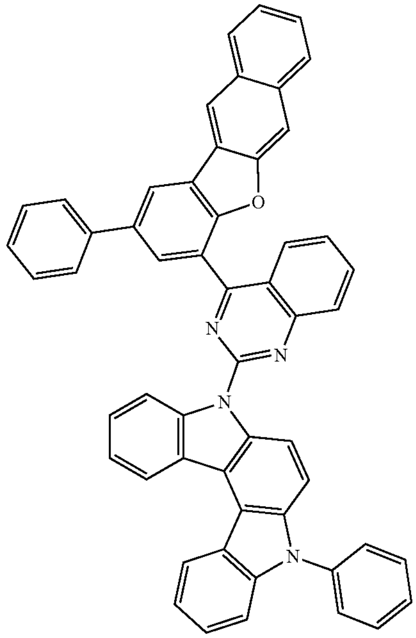
165
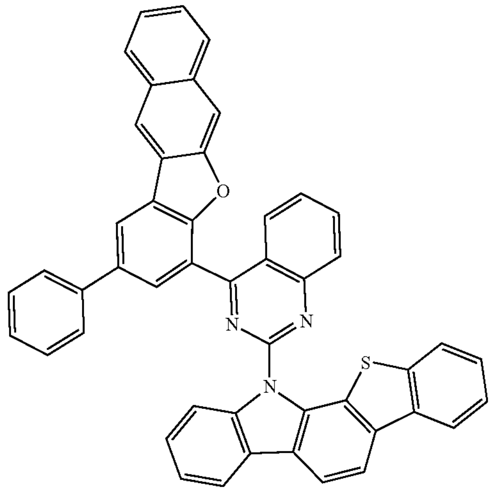
-continued
166
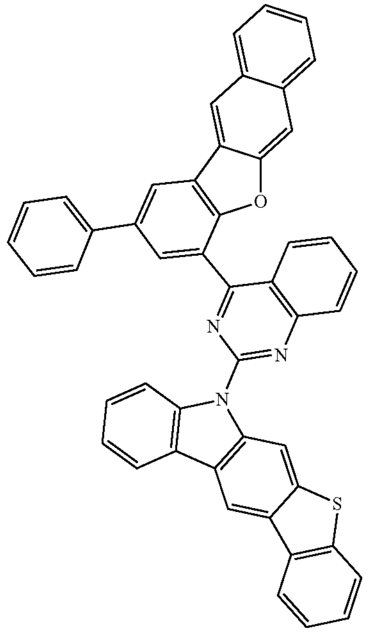
167
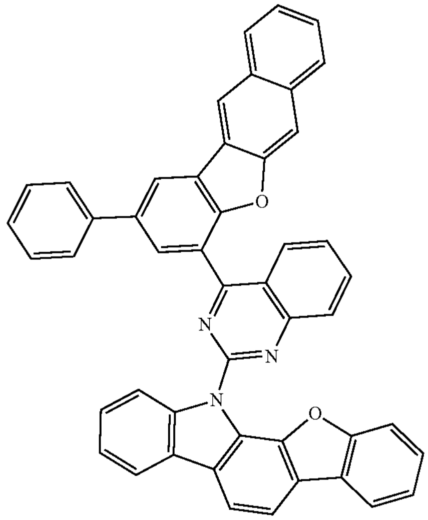

-continued
168
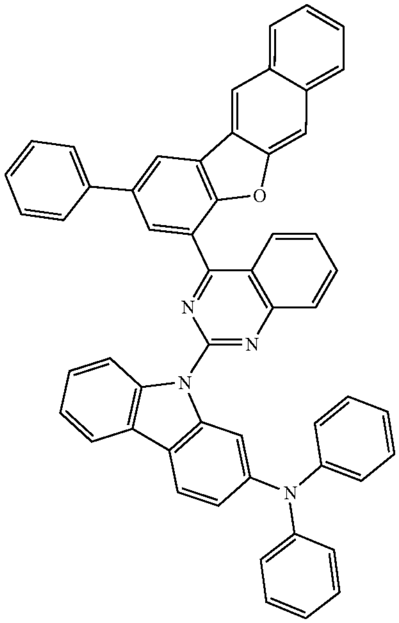
169
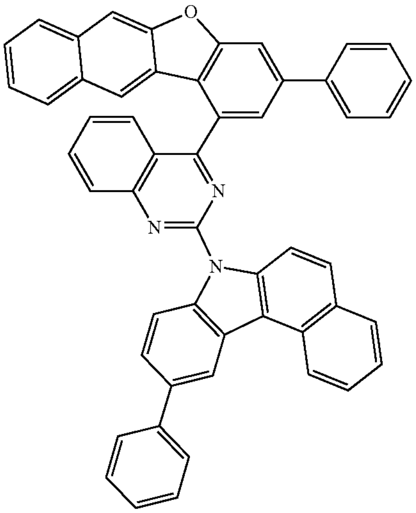
170
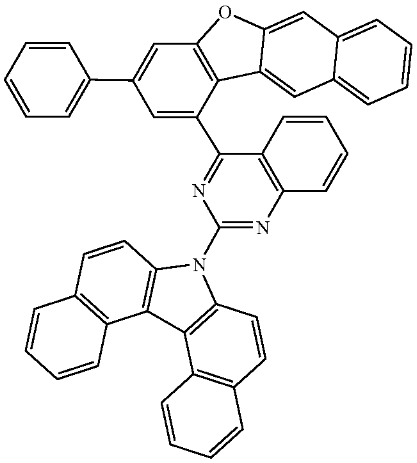
-continued
171
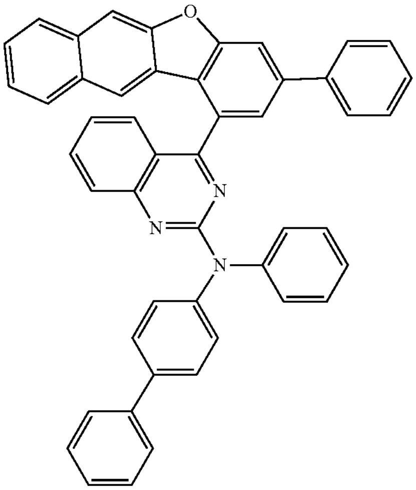
172
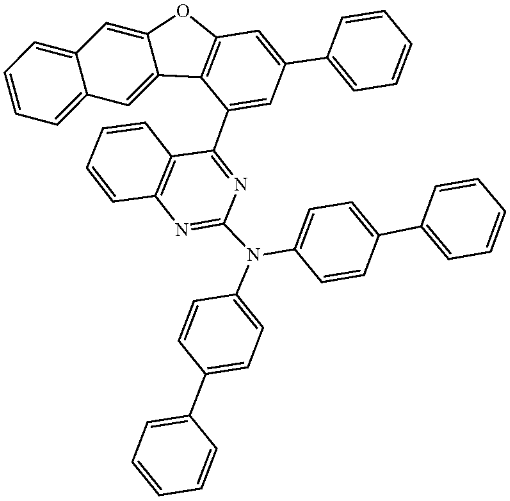
173
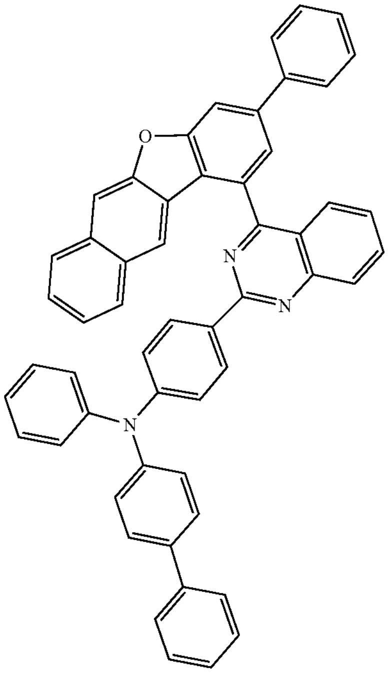

-continued
174
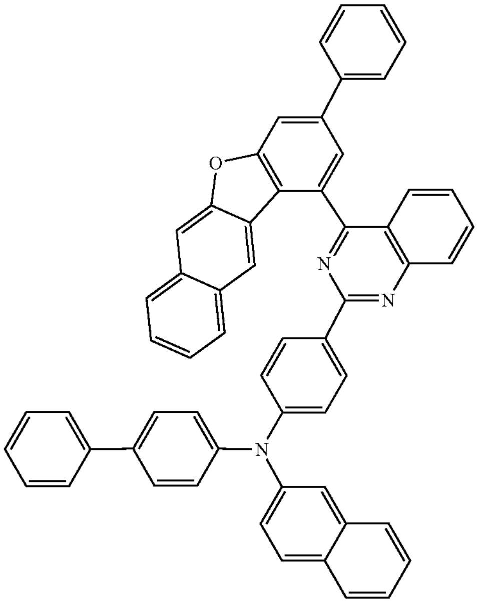
175
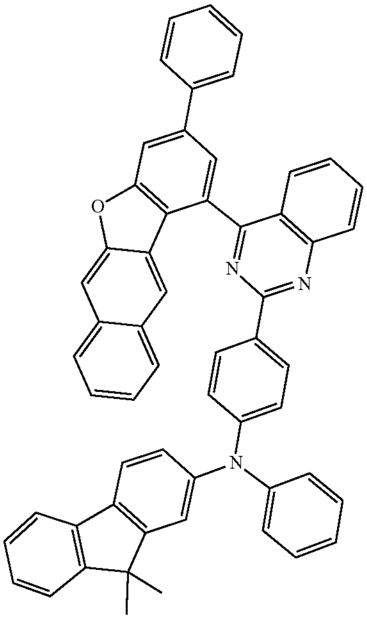
-continued
176
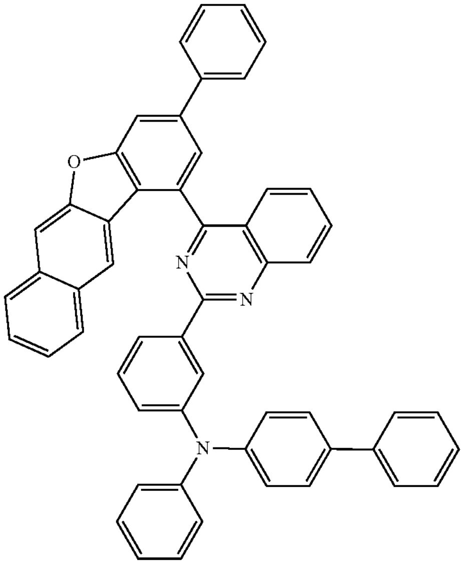
177
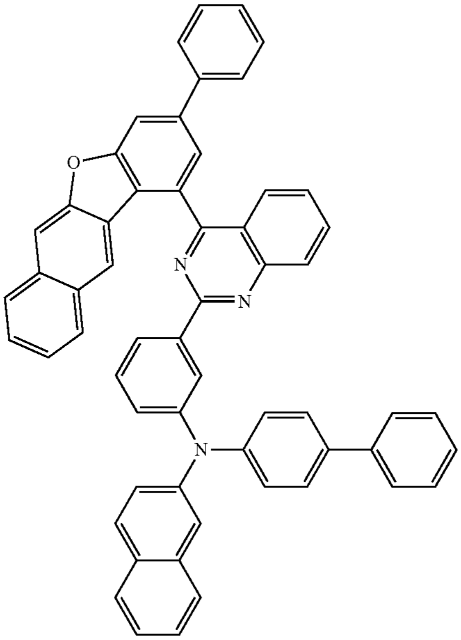

-continued
178
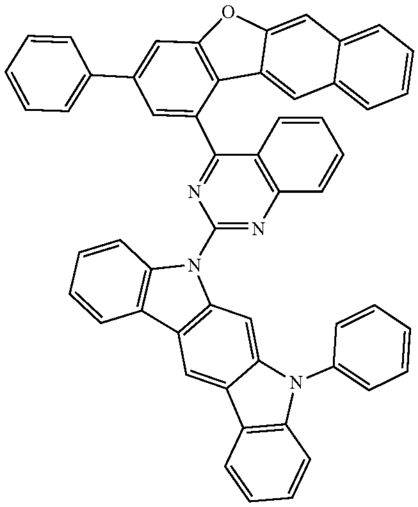
179
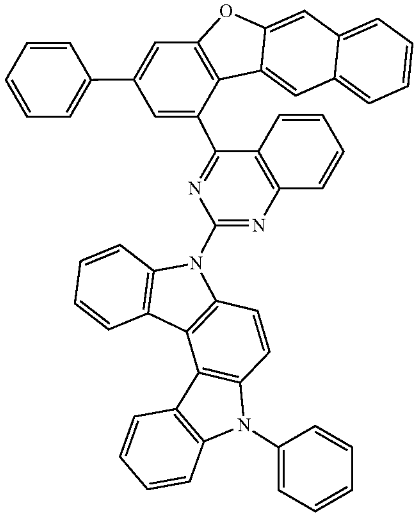
180
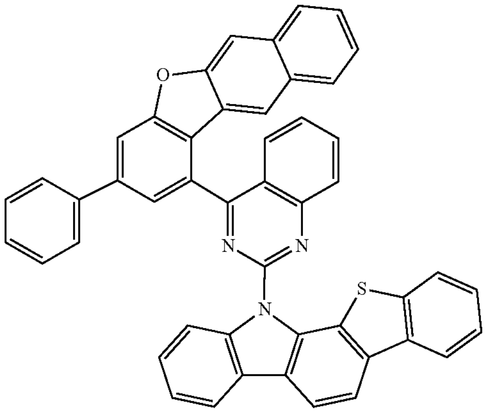
-continued
181
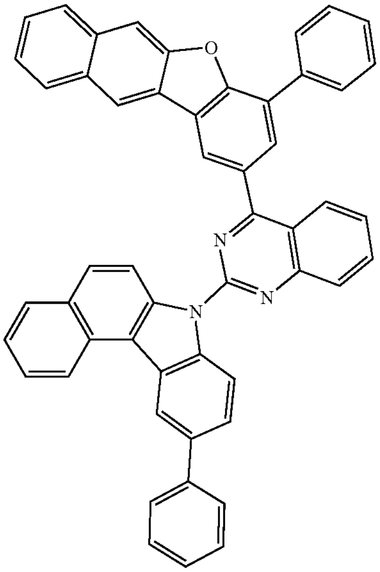
182
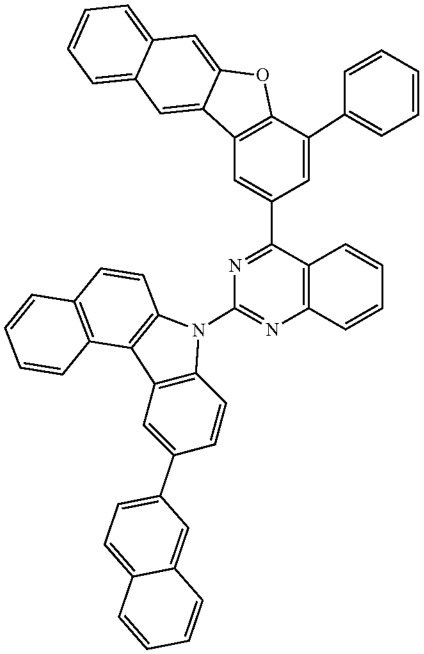

183
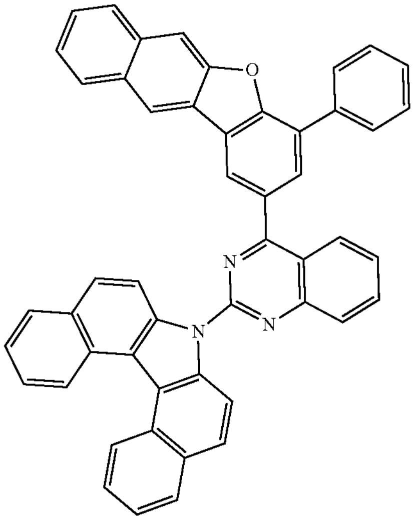
184
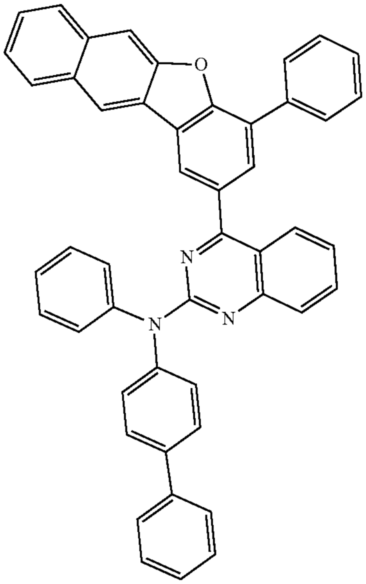
185
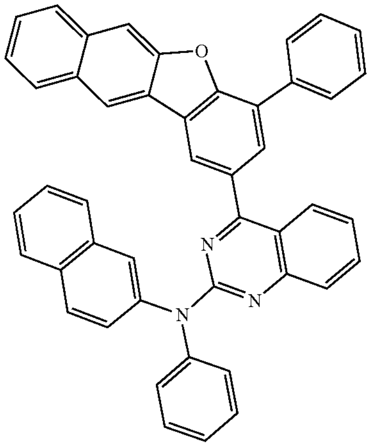
186
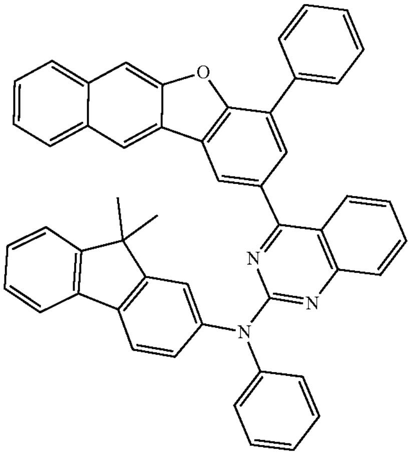
187
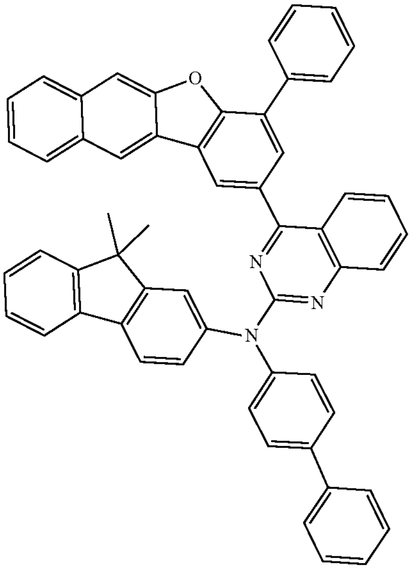

-continued
188
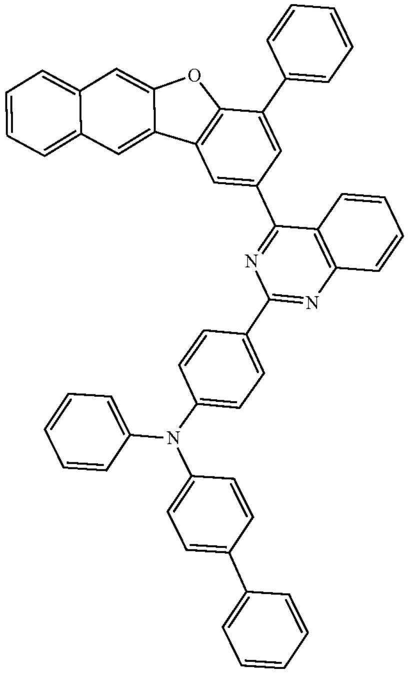
190
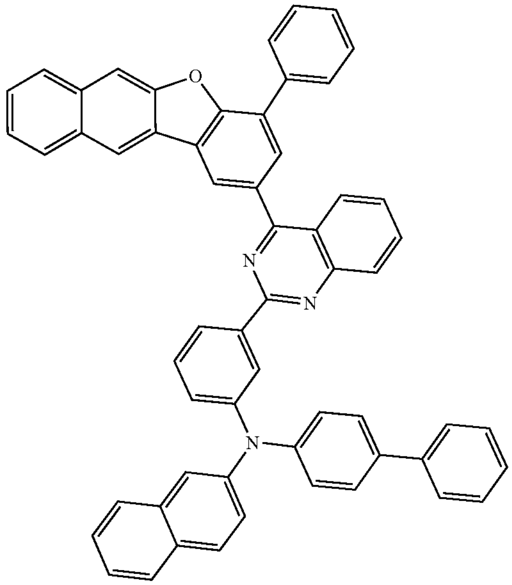
189
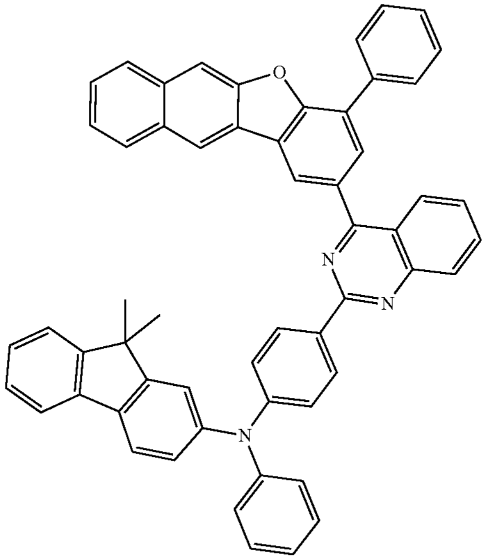
191
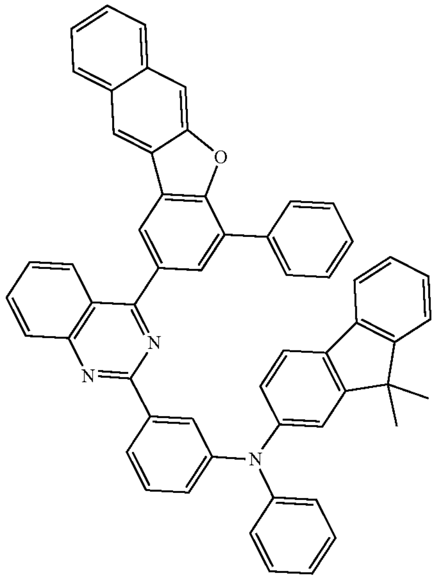
-continued -continued
192
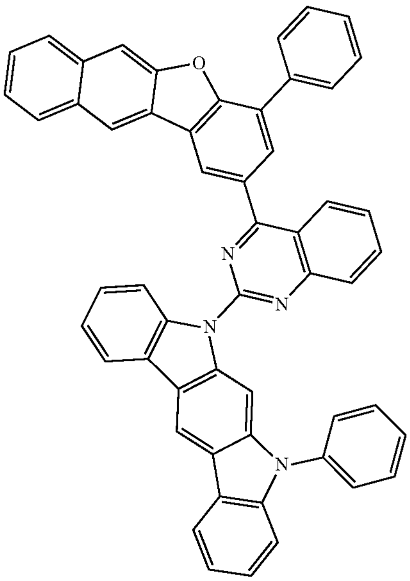
193
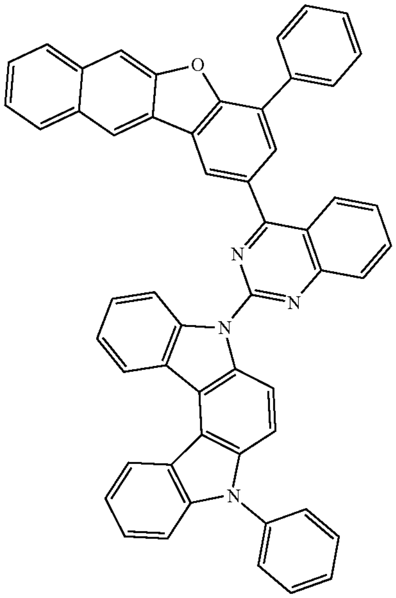
-continued
194
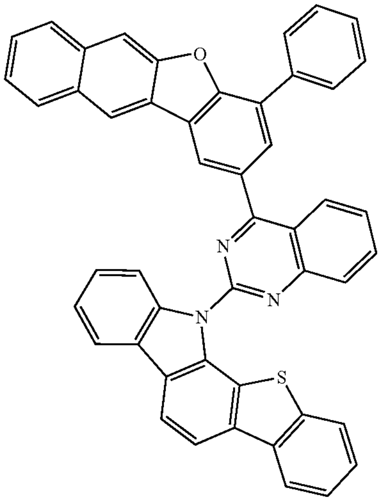
195
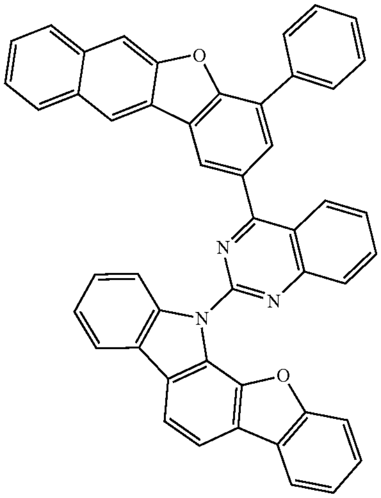
196
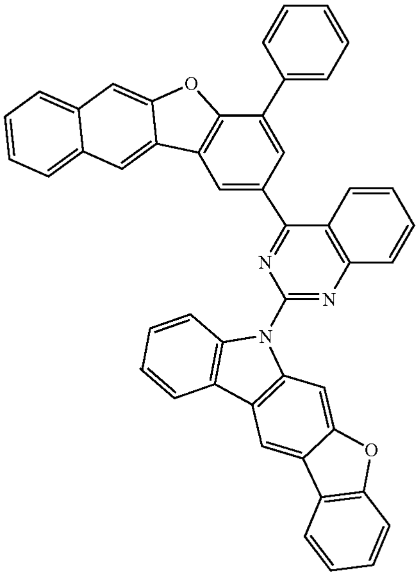

-continued
197
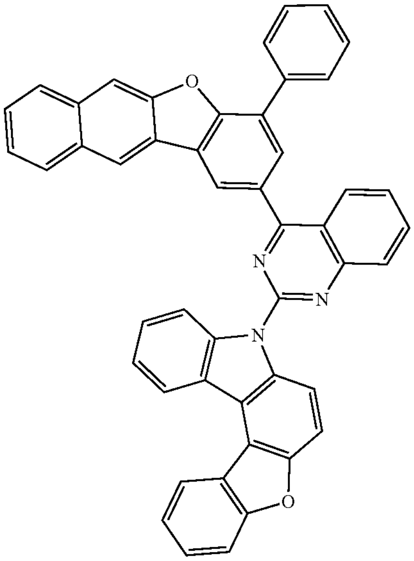
198
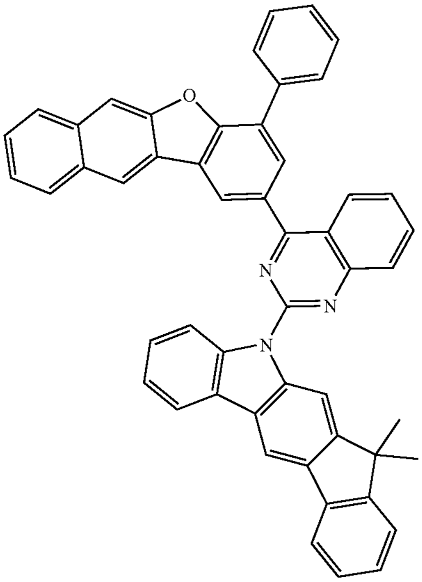
199
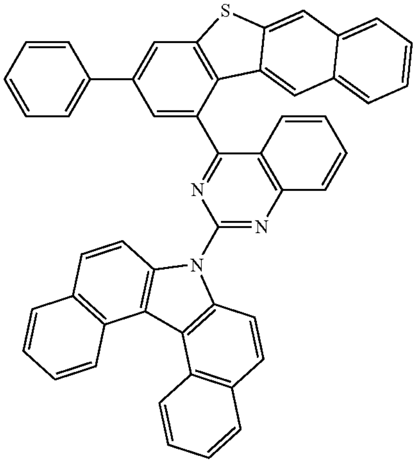
-continued
200
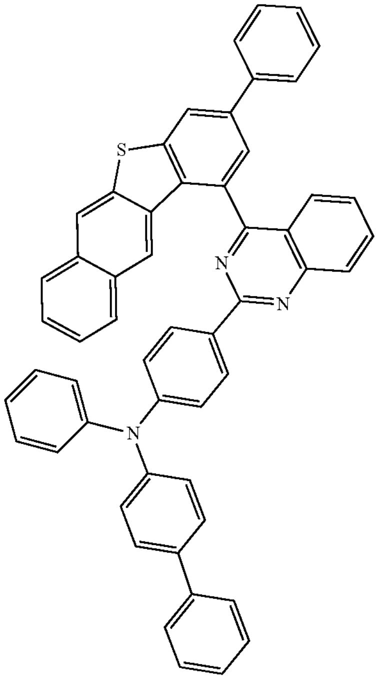
201
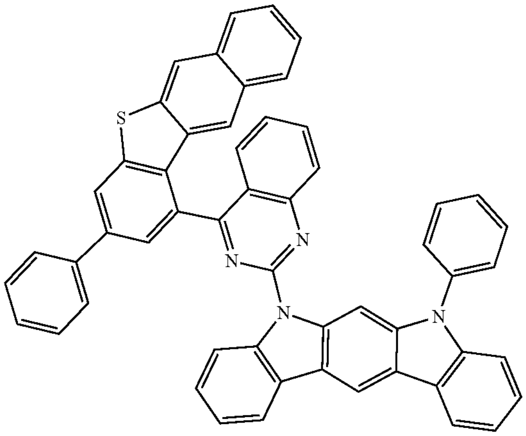

-continued
202
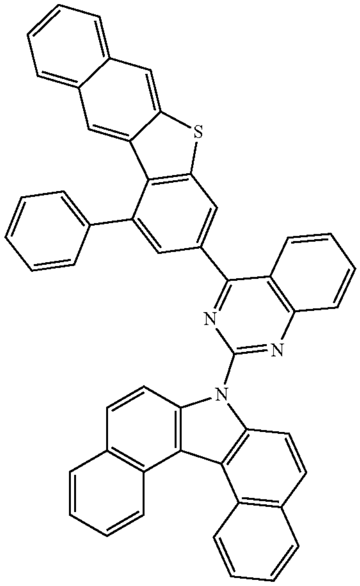
203
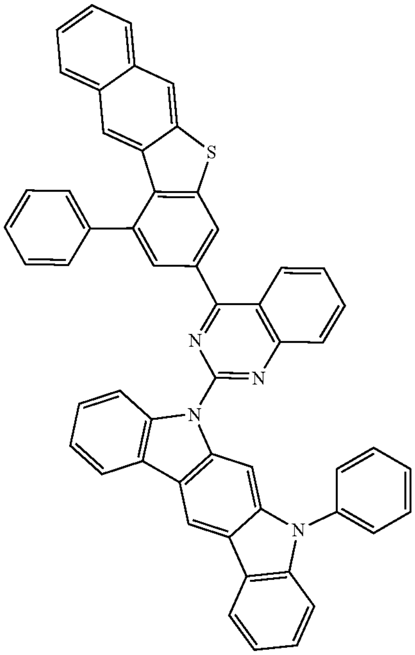
-continued
204
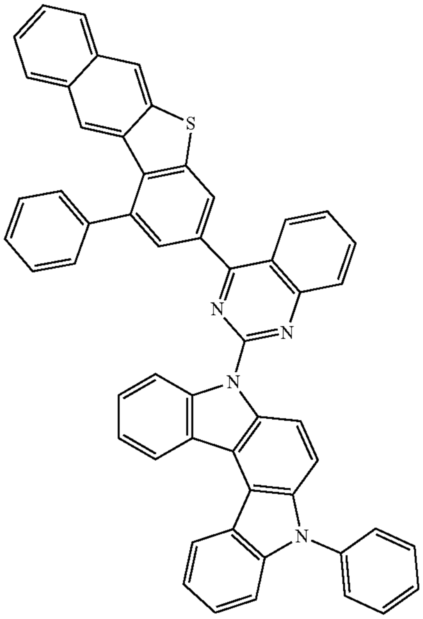
205
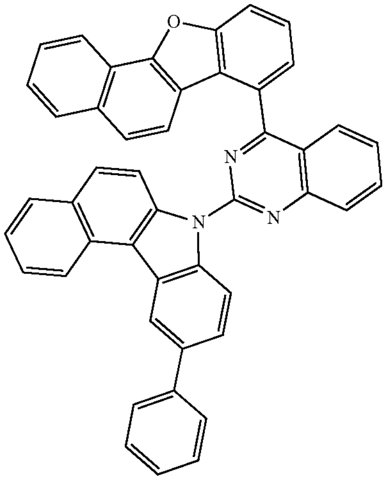
206
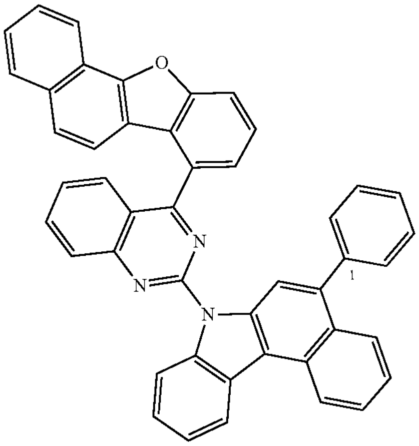

-continued
207
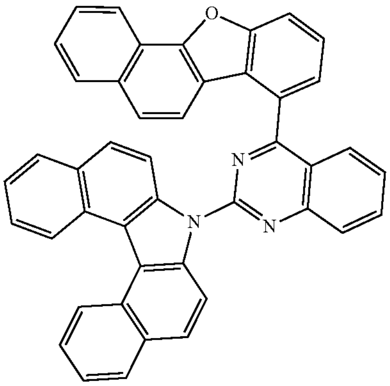
208
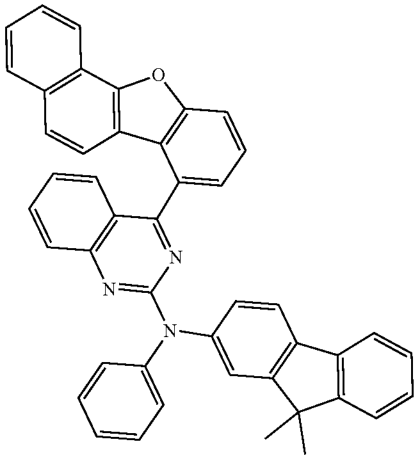
209
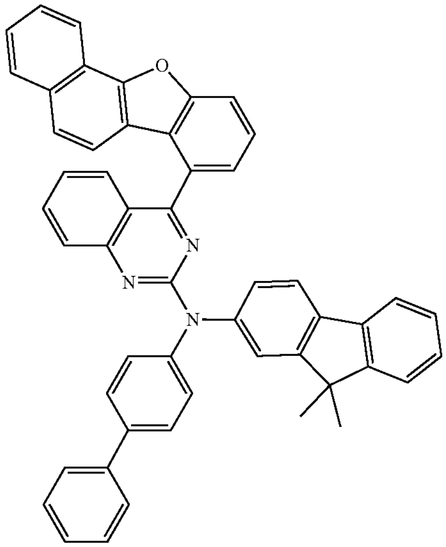
-continued
210
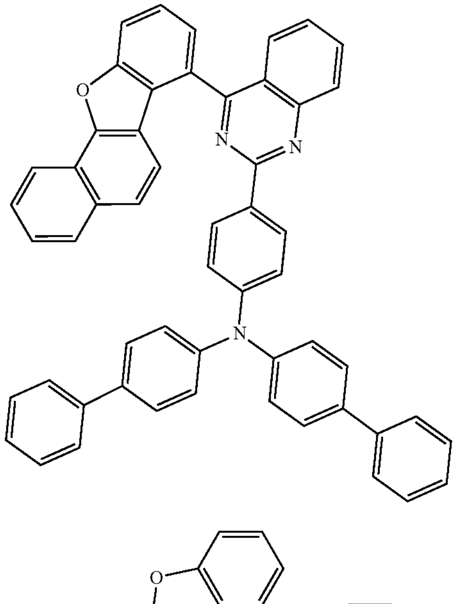
211
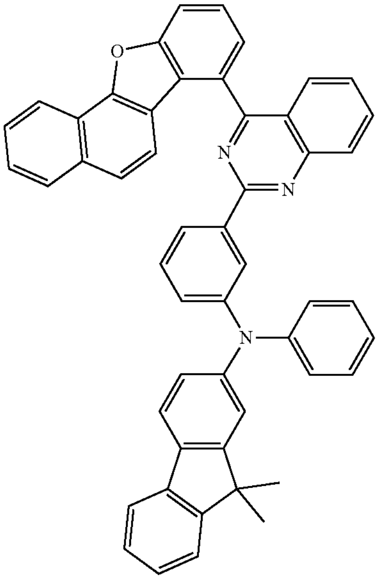
212
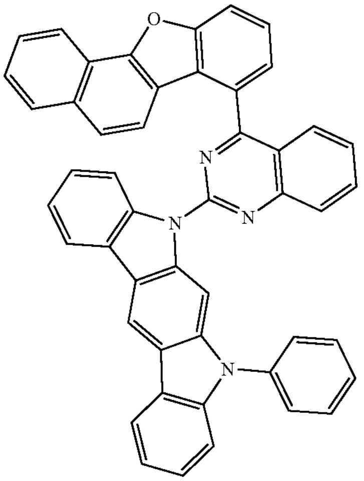

-continued
213
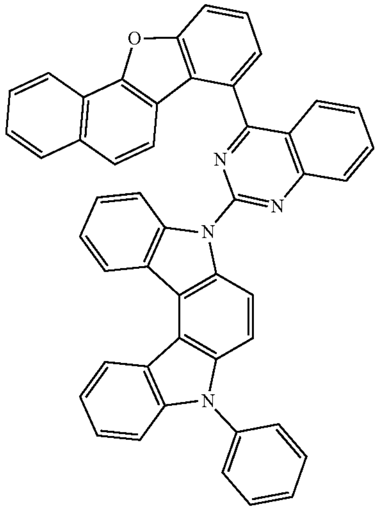
214
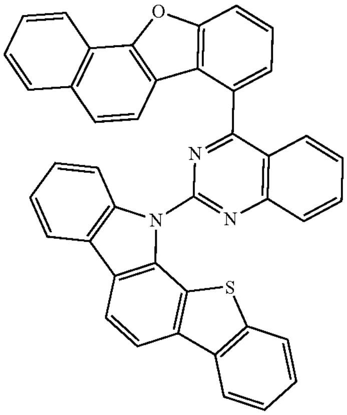
215
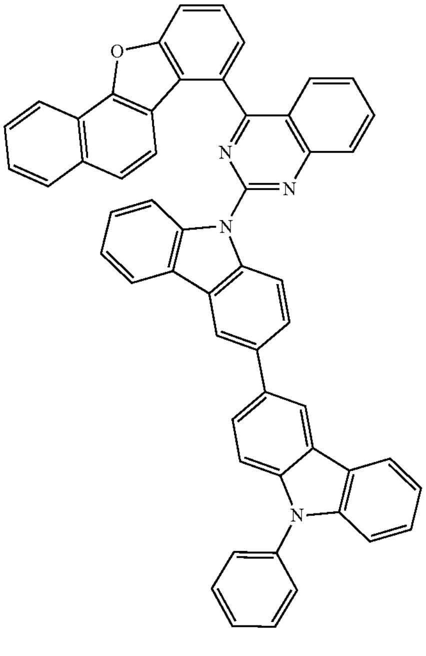
-continued
216
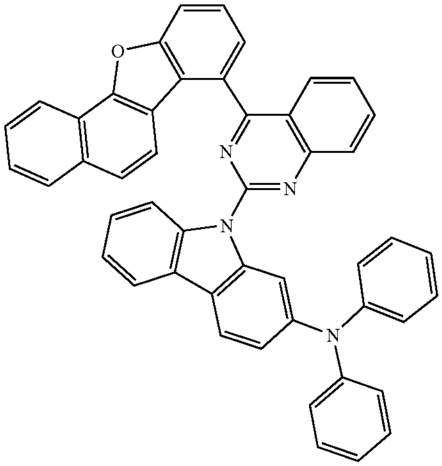
217
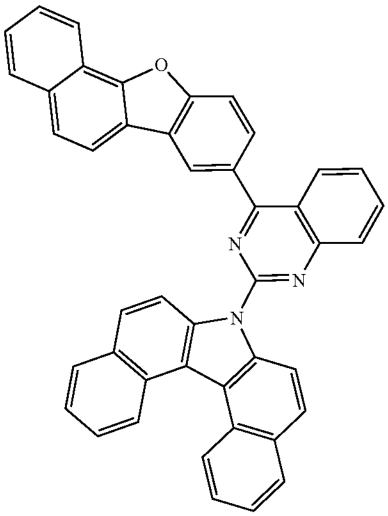
218
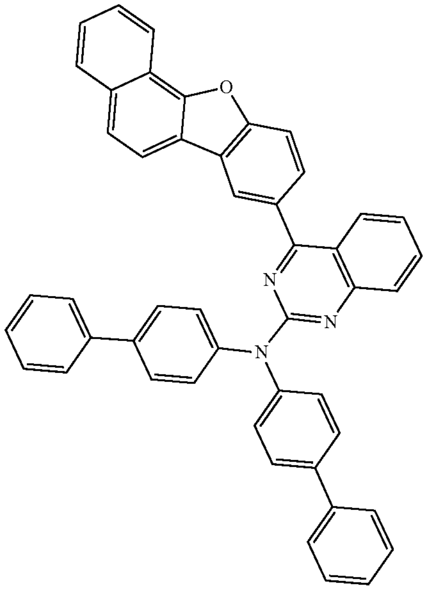

219
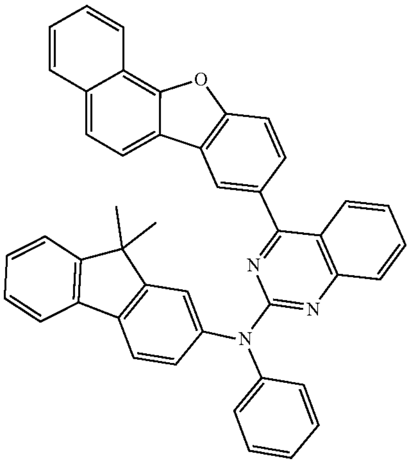
220
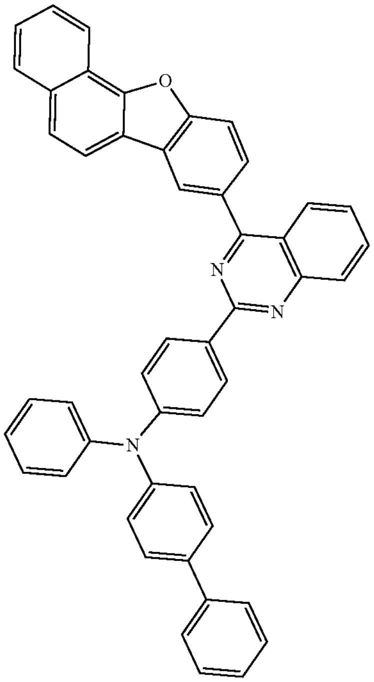
221
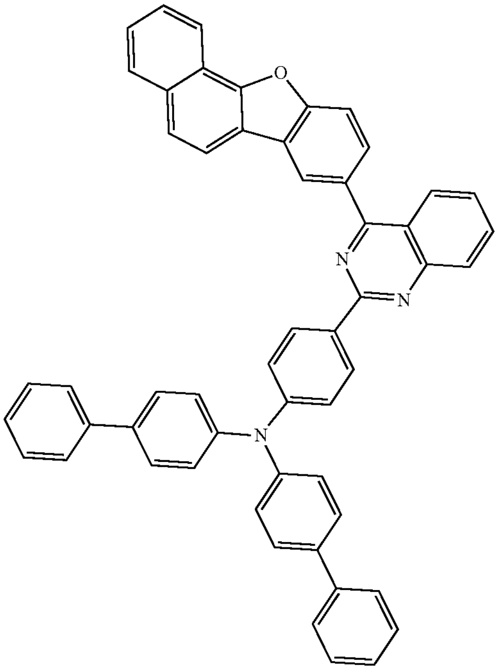
222
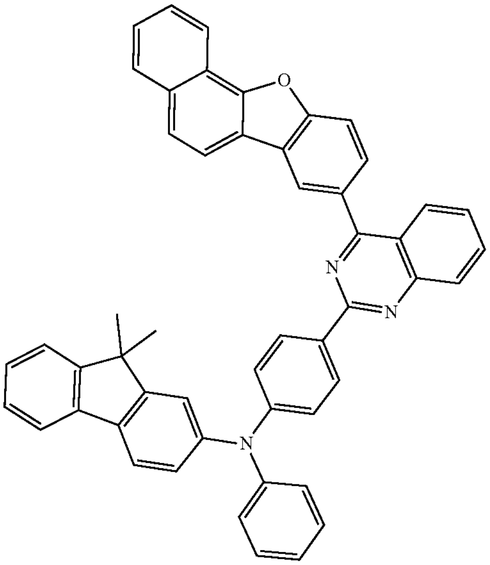

223
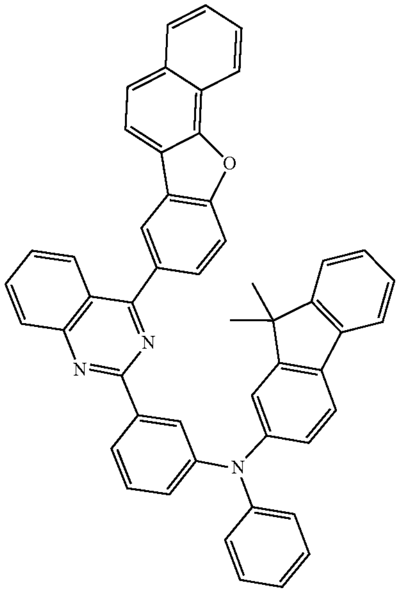
224
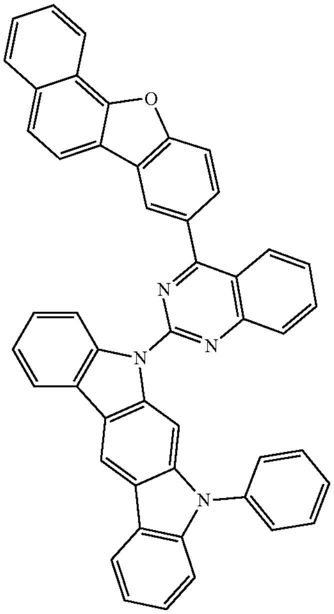
225
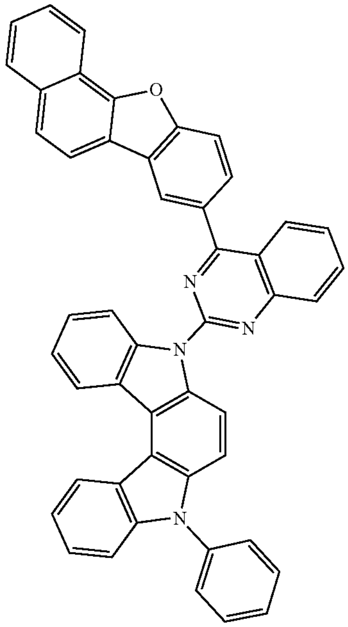
226
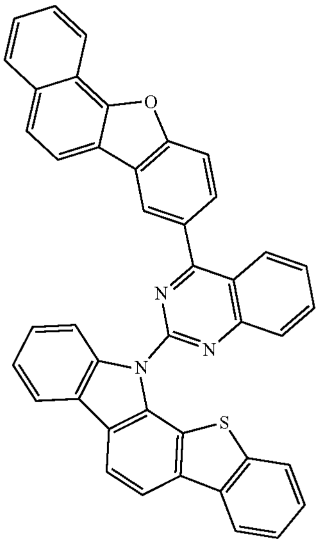

-continued
227
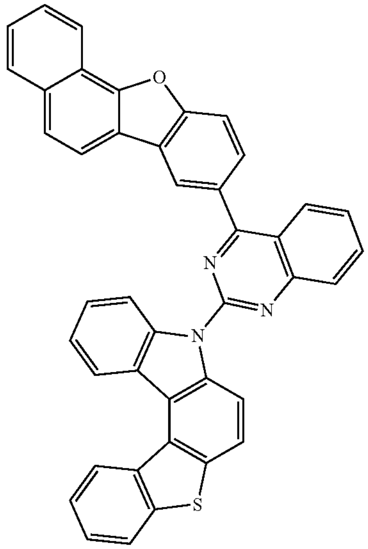
228
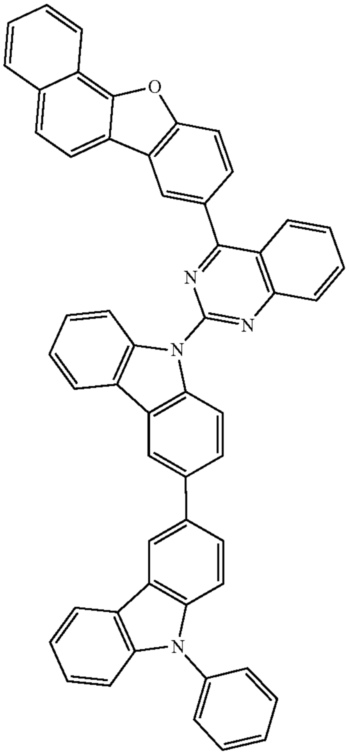
-continued
229
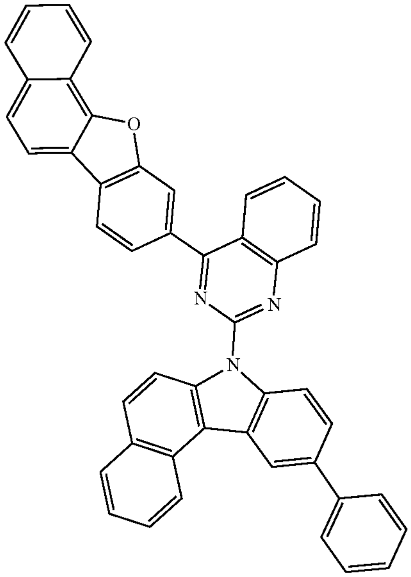
230
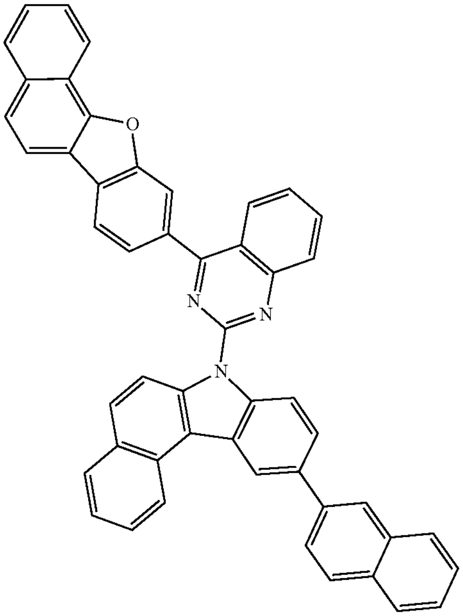

-continued
231
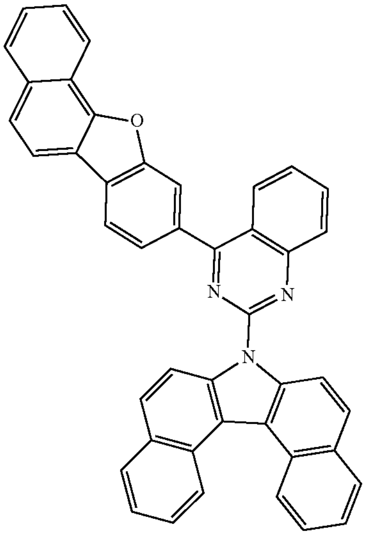
232
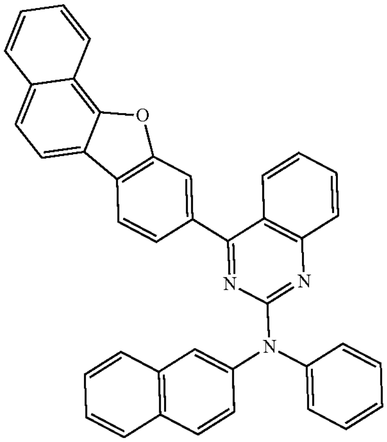
233
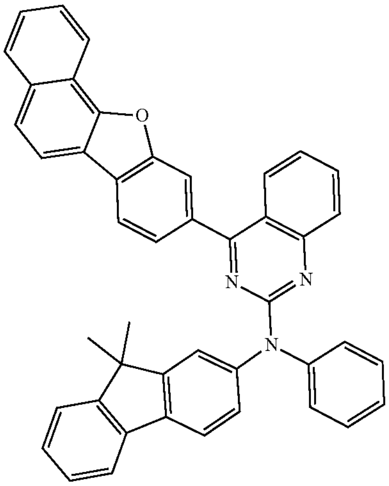
-continued
234
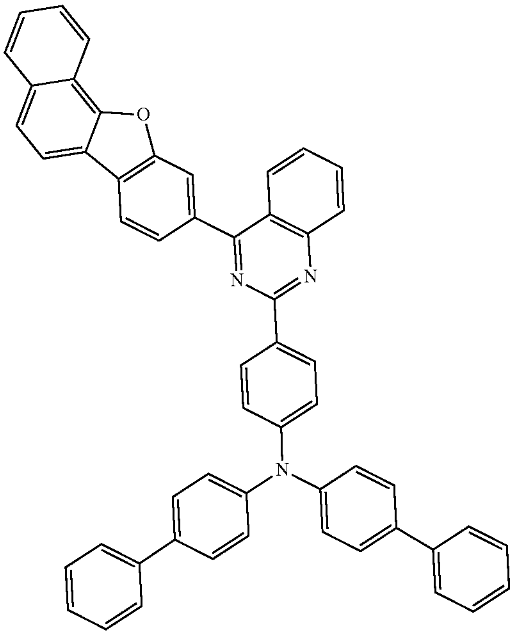
235
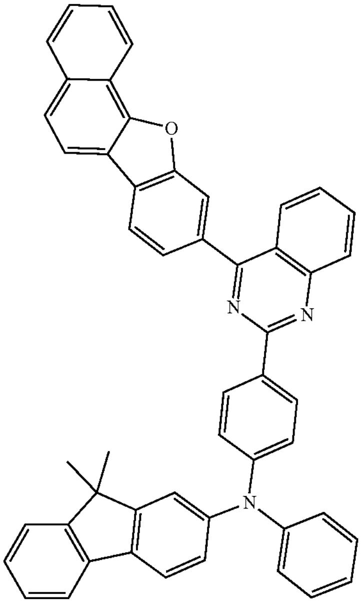

-continued
236
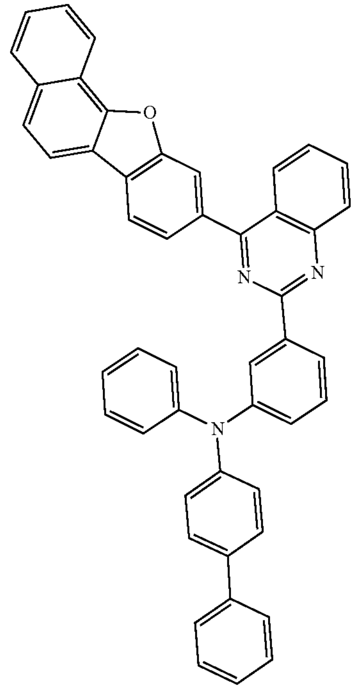
237
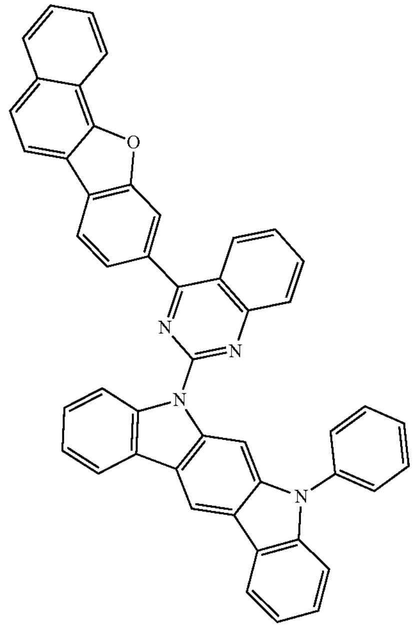
-continued
238
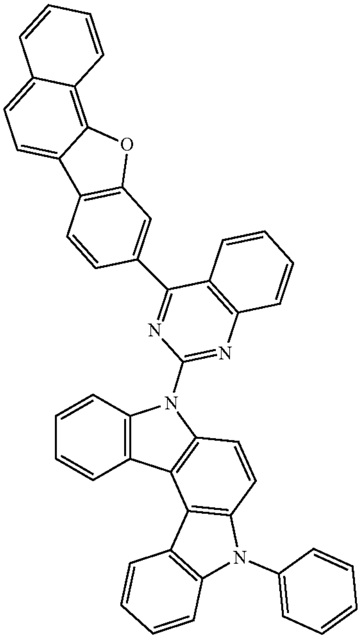
239
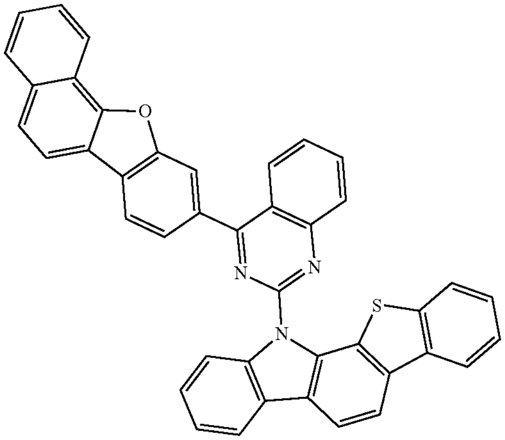

240
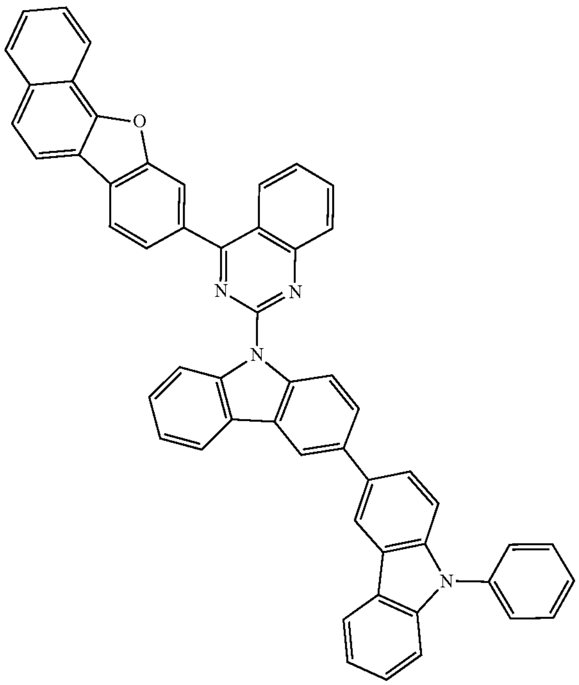
241
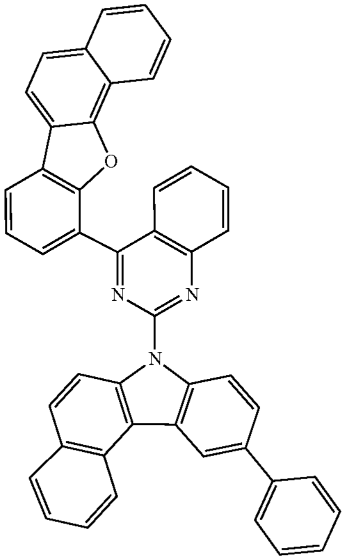
242
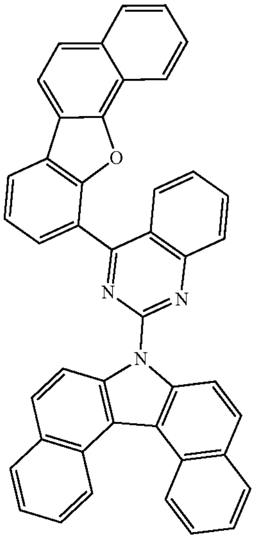
243
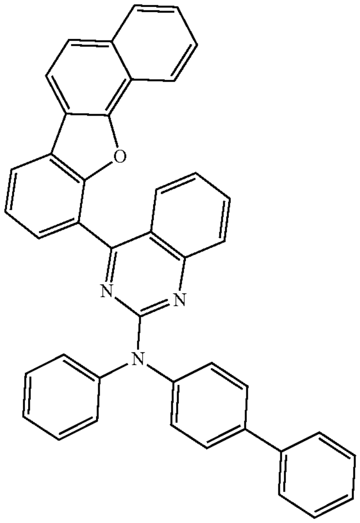
244
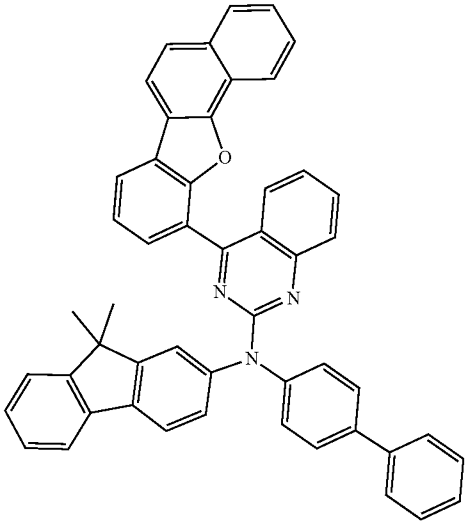

-continued
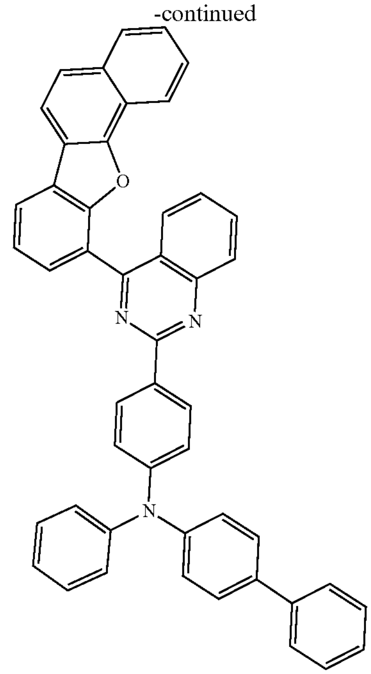
-continued
247
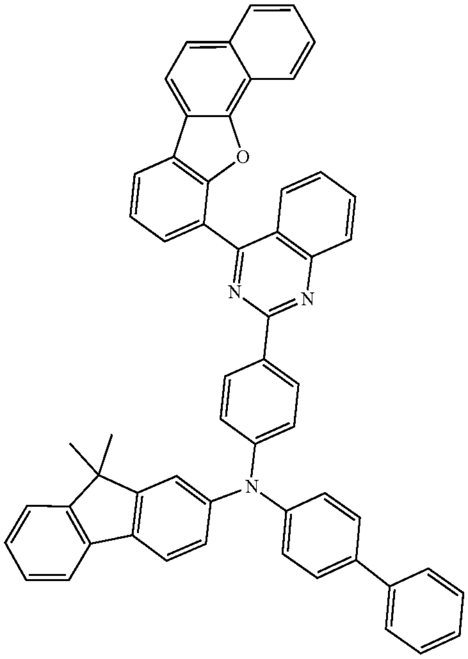
246
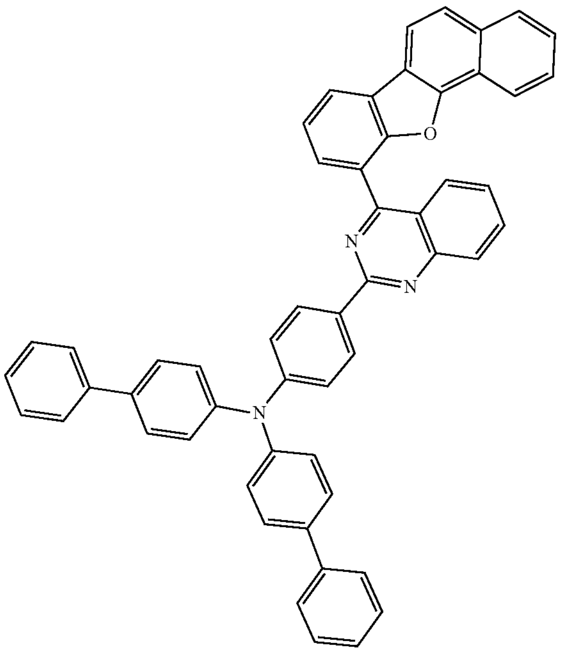
248
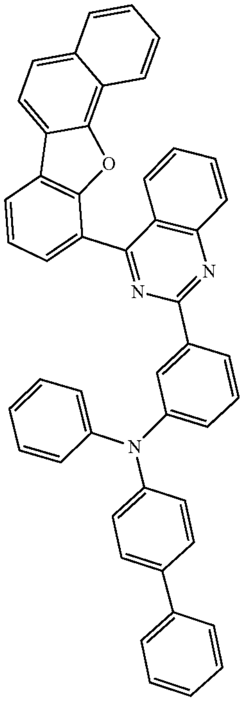

-continued
249
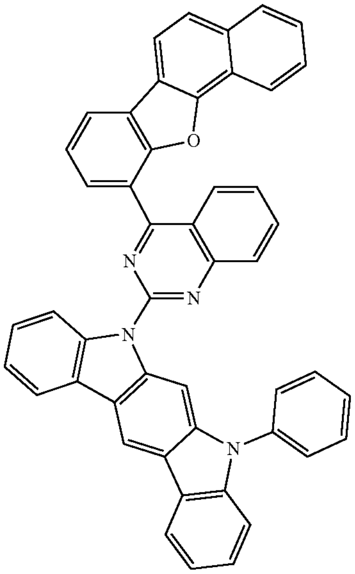
250
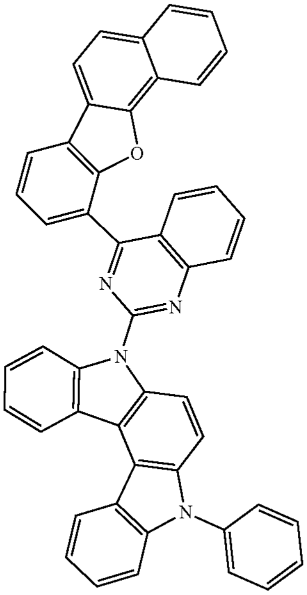
251
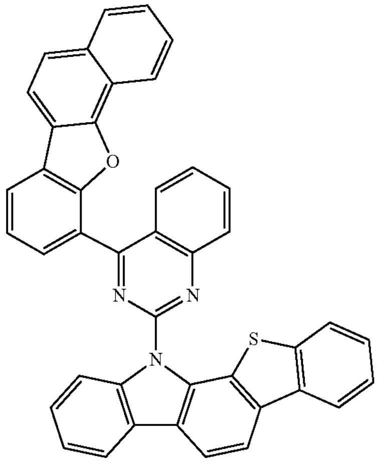
-continued
252
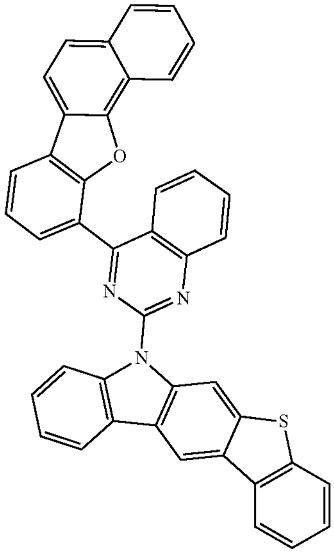
253
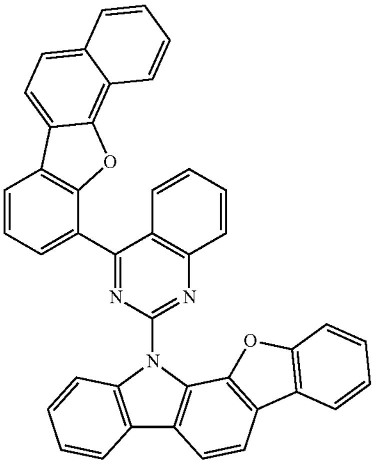
254
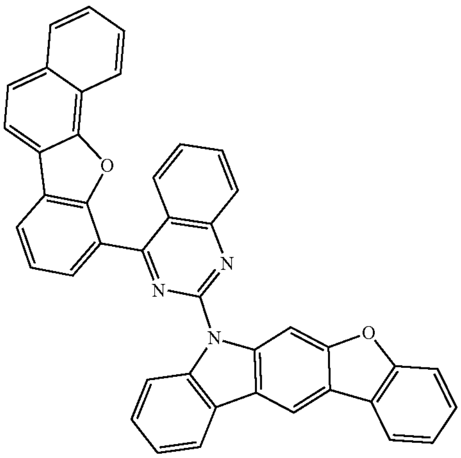

-continued
255
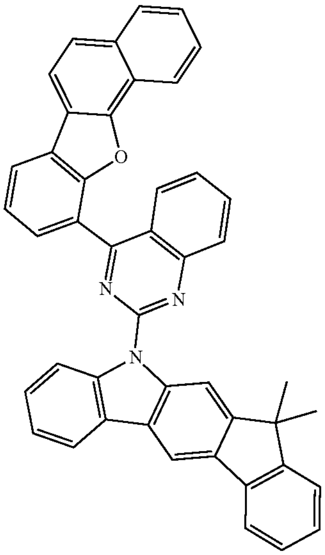
256
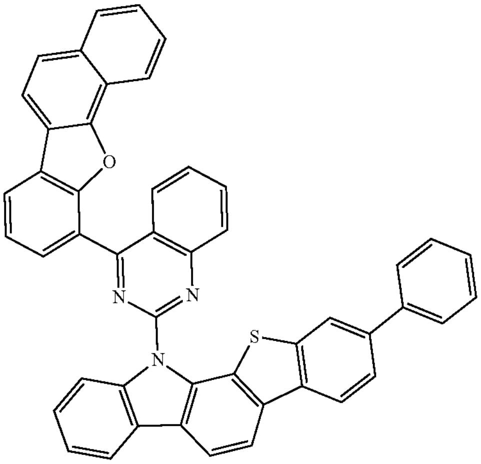
-continued
257
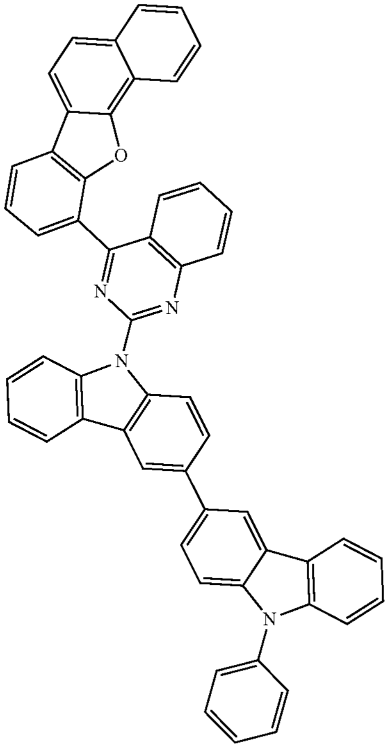
258
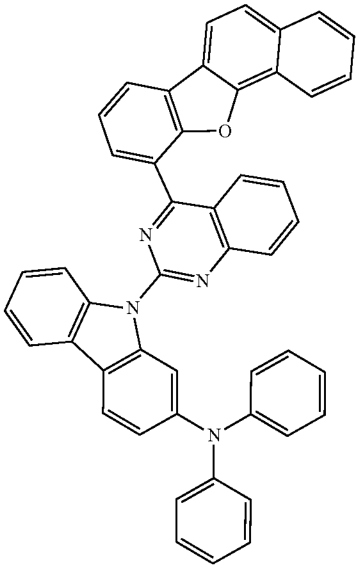

-continued
259
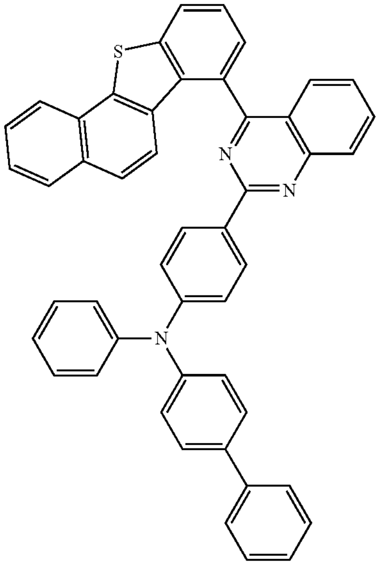
260
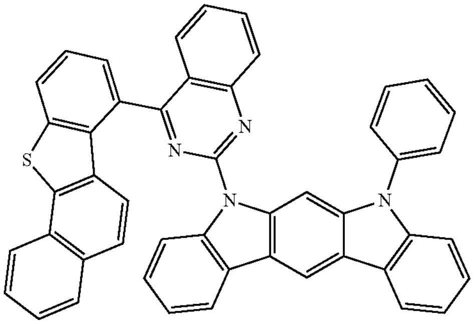
261
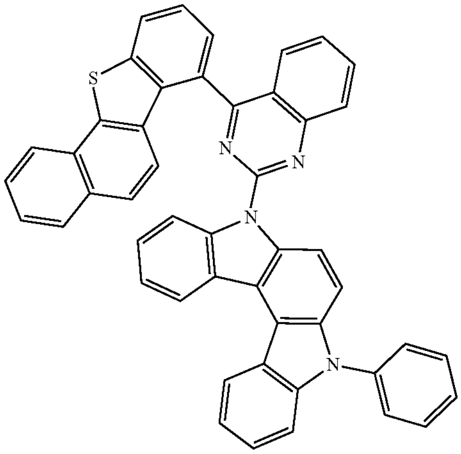
-continued
262
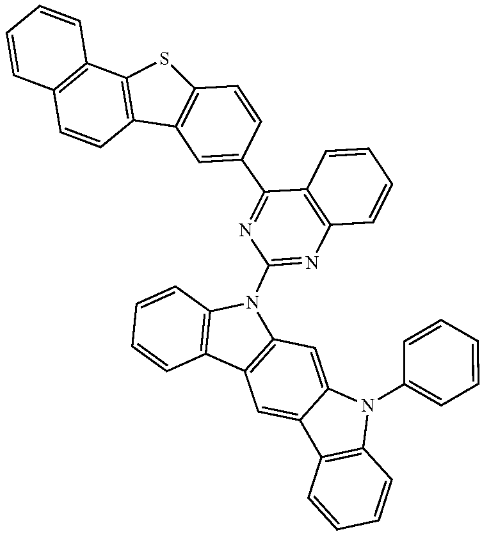
263
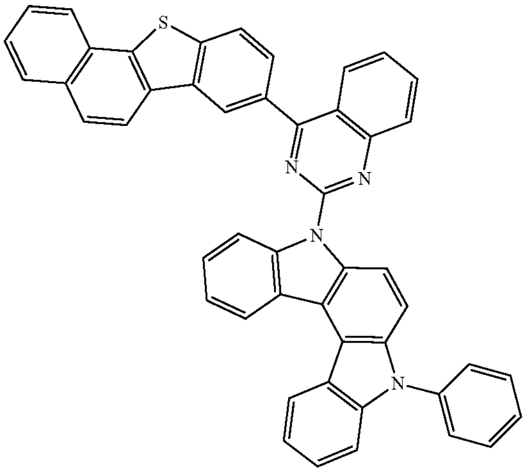
264
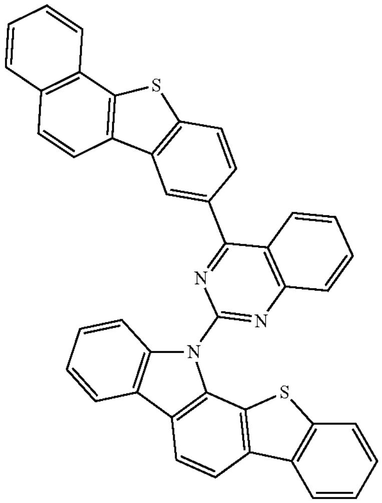

-continued
265
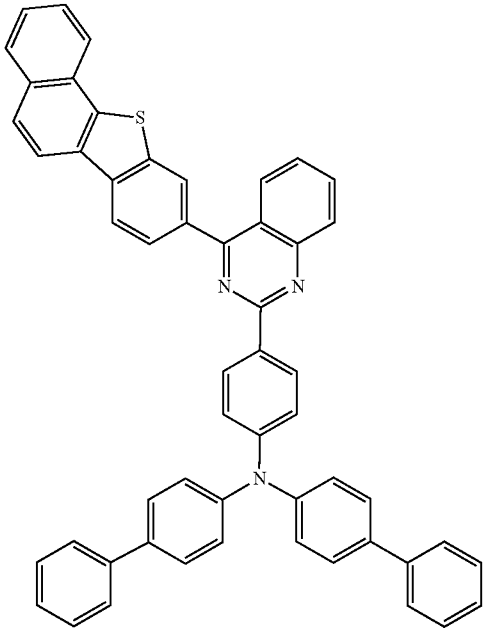
266
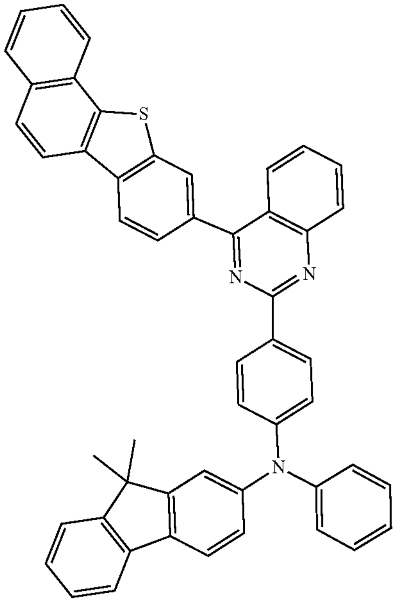
-continued
267
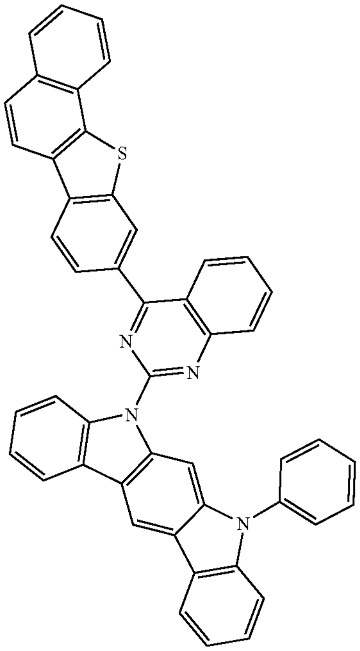
268
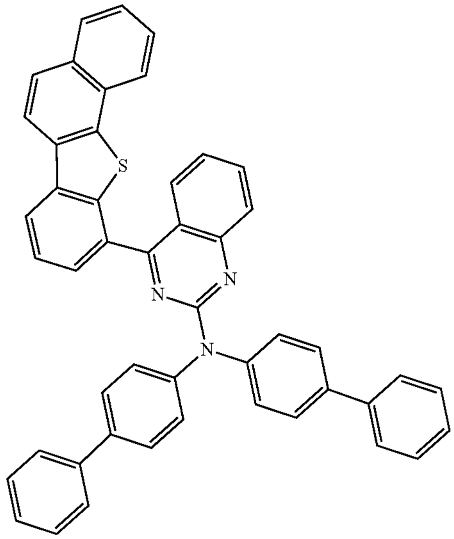
269
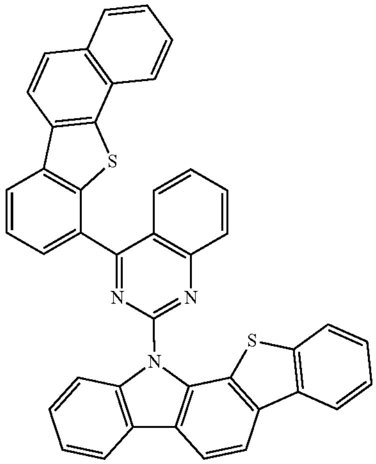

-continued
270
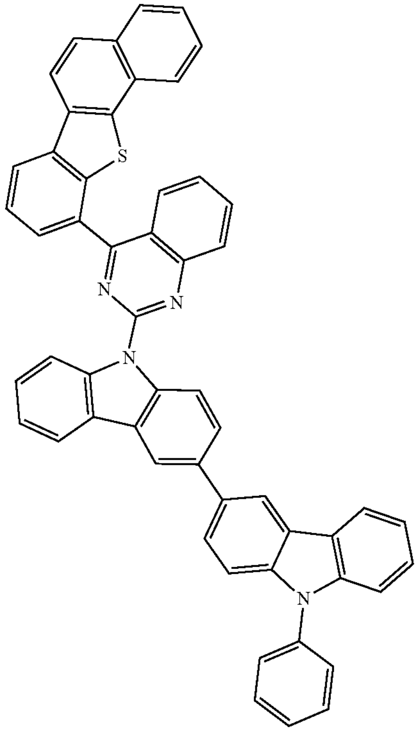
271
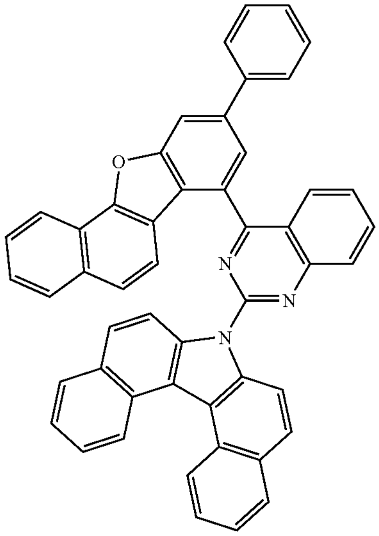
-continued
272
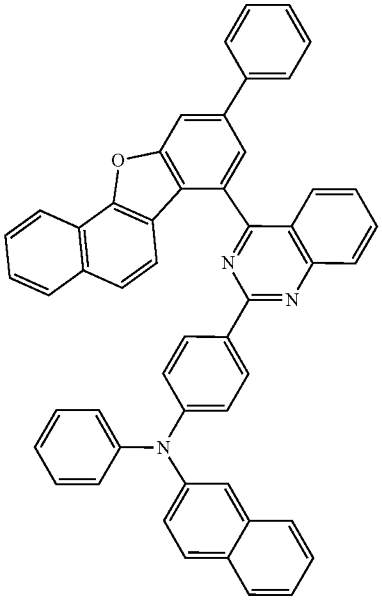
273
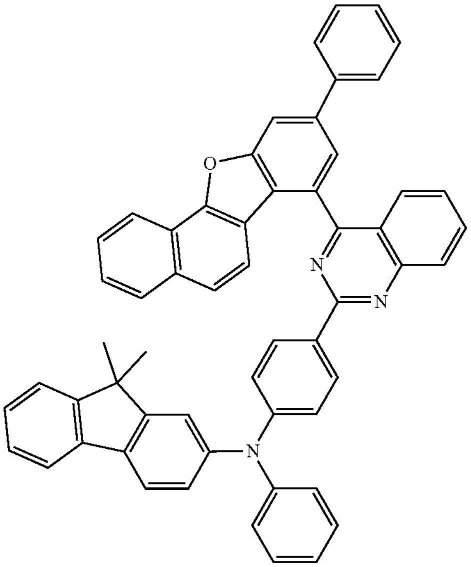

-continued
274
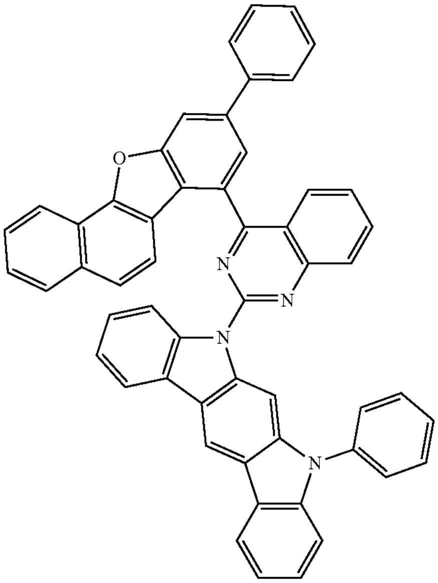
275
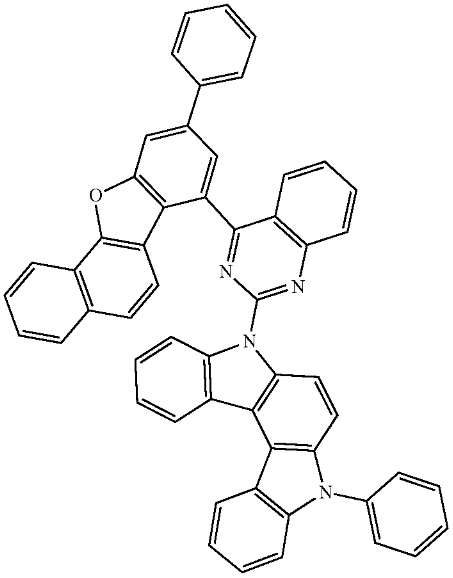
276
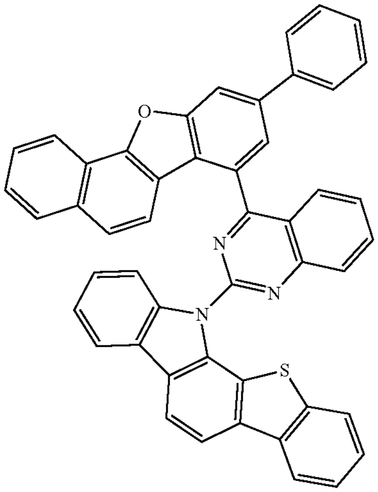
-continued
277
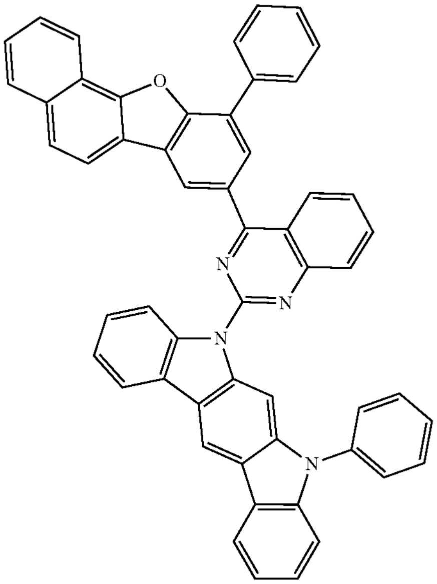
278
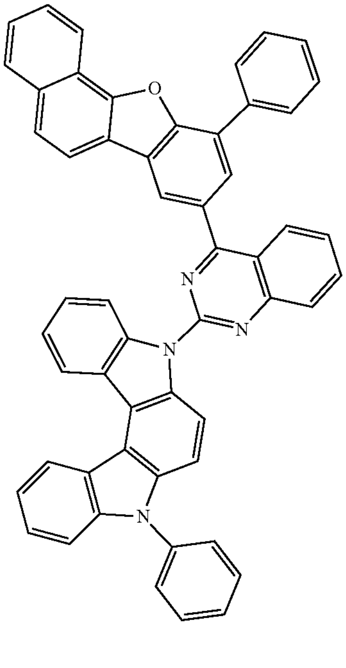

-continued
279
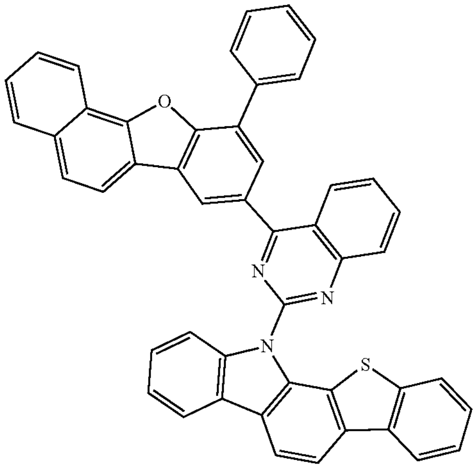
280
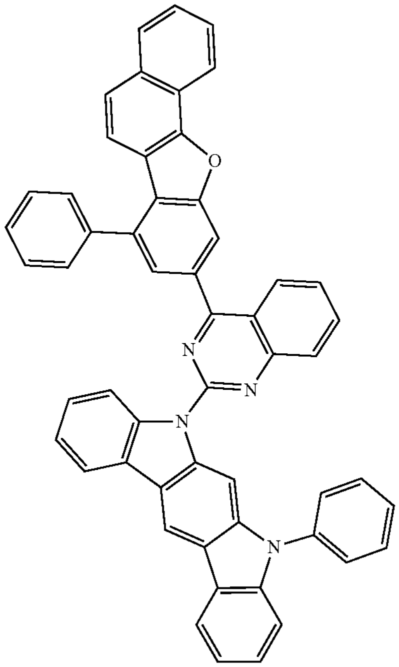
-continued
281
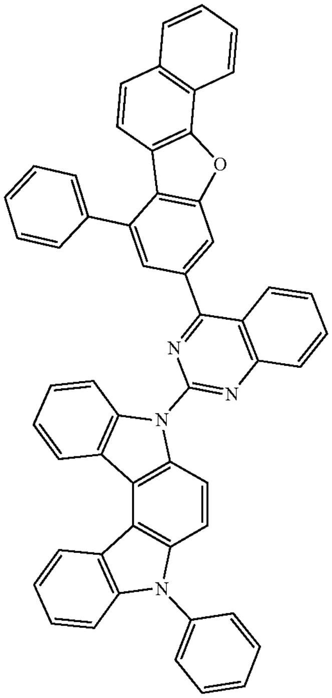
282
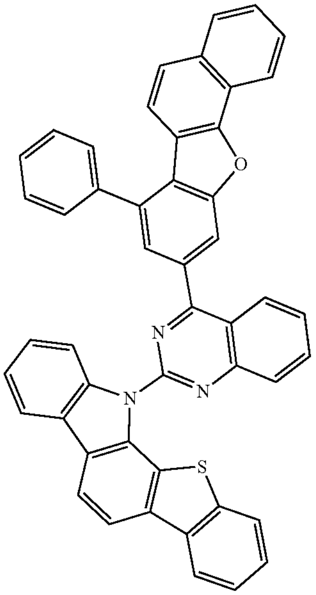

-continued
283
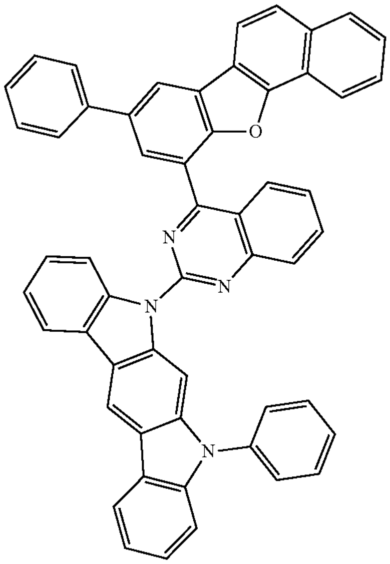
284
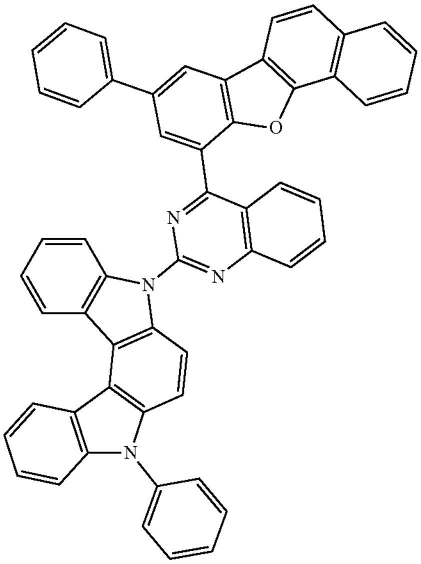
285
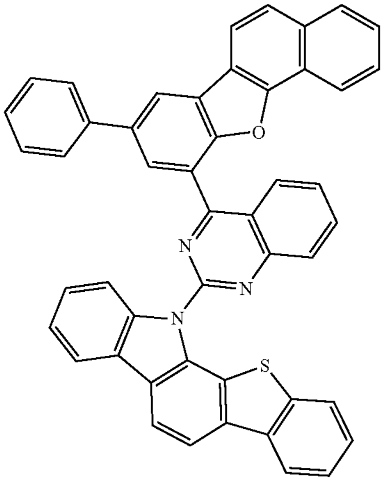
-continued
286
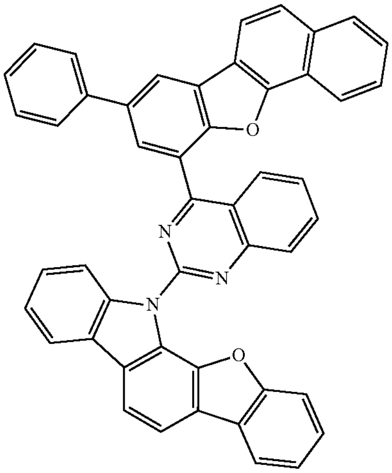
287
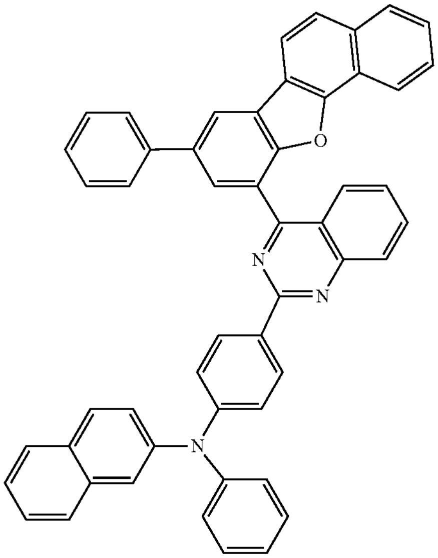

-continued
288
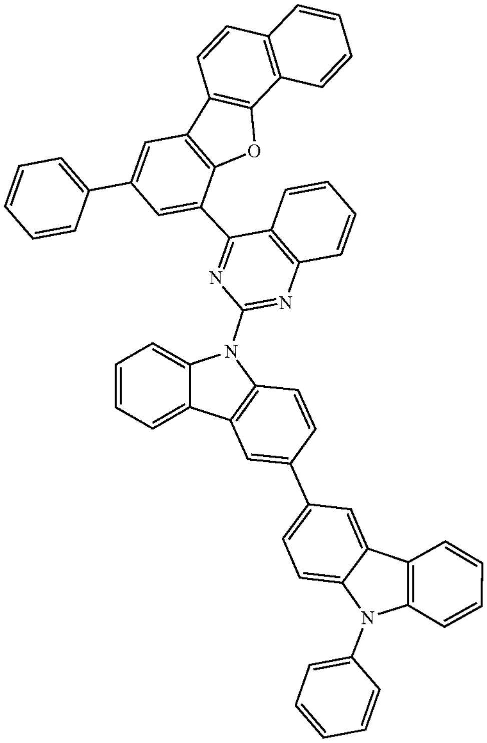
-continued
290
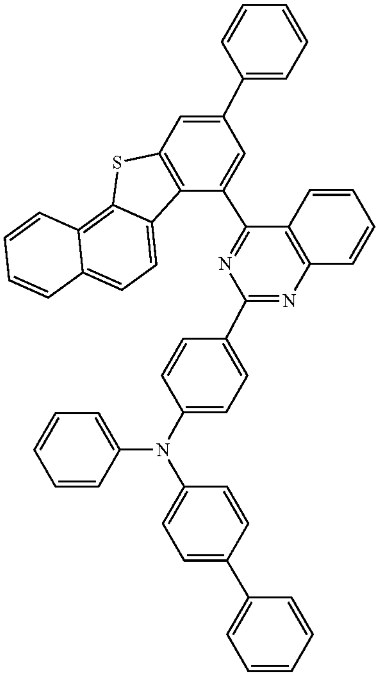
289
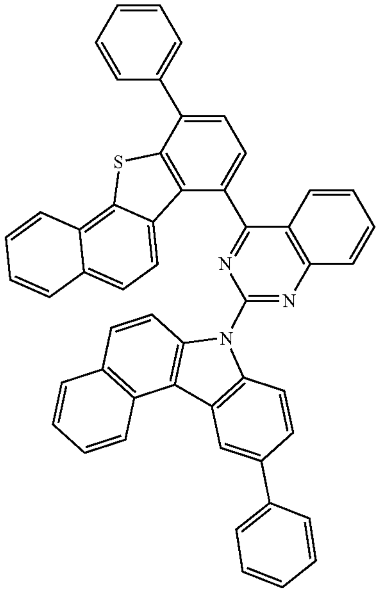
291
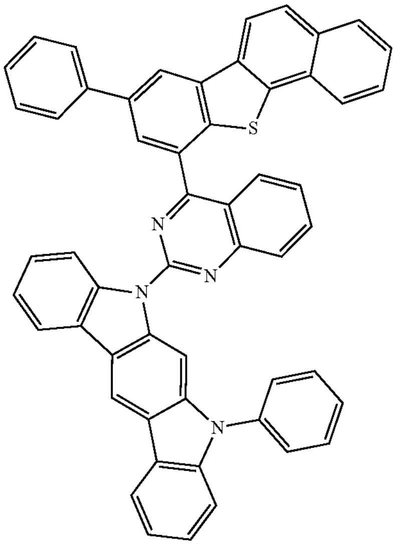

-continued
292
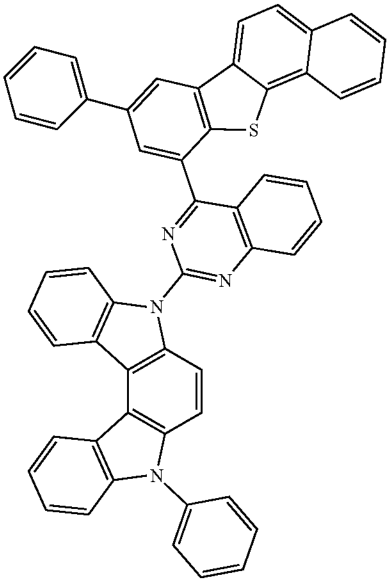
293
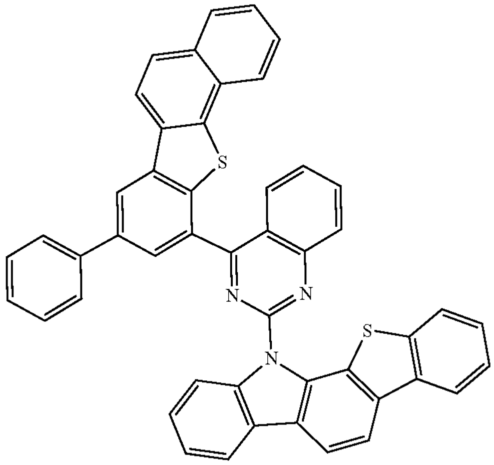
-continued
294
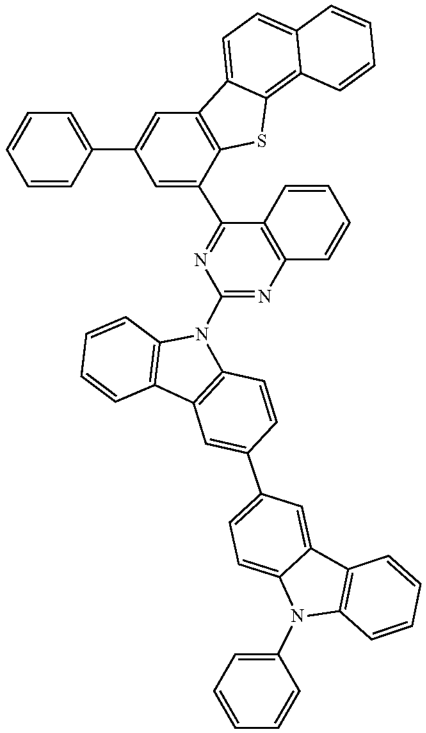
295
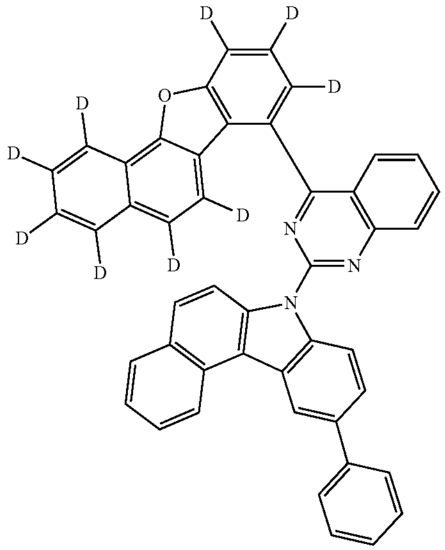

-continued
296
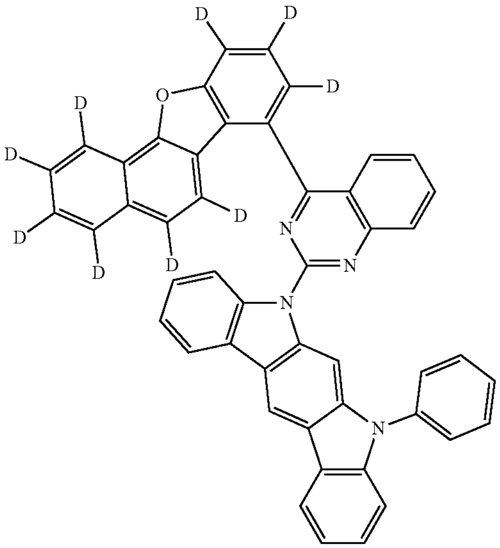
297
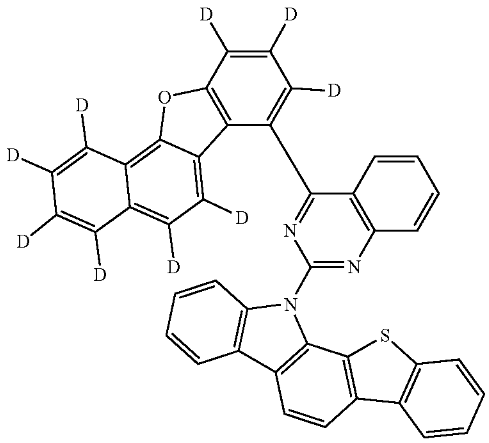
298
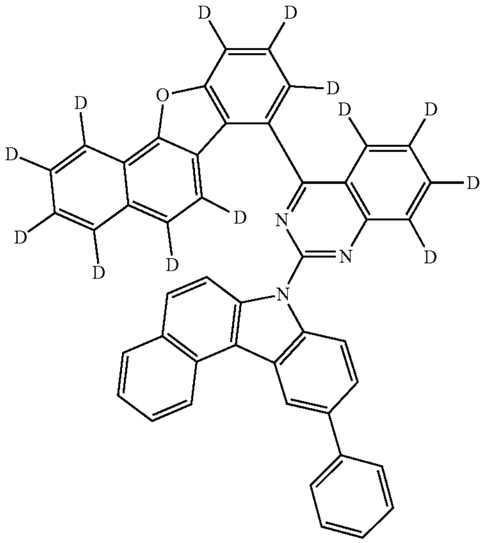
-continued
299
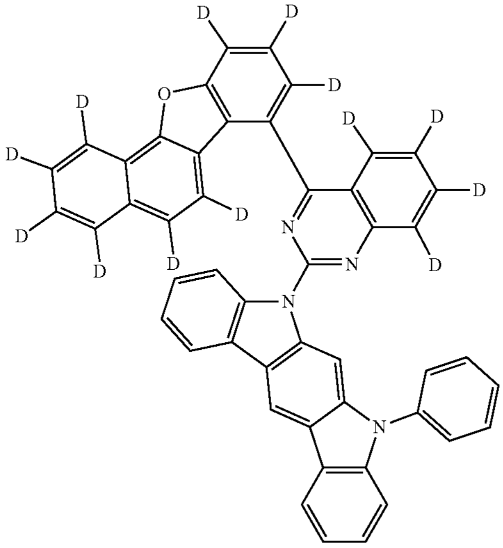
300
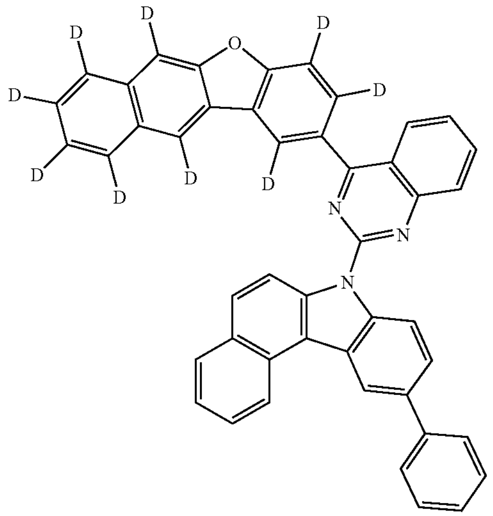
301
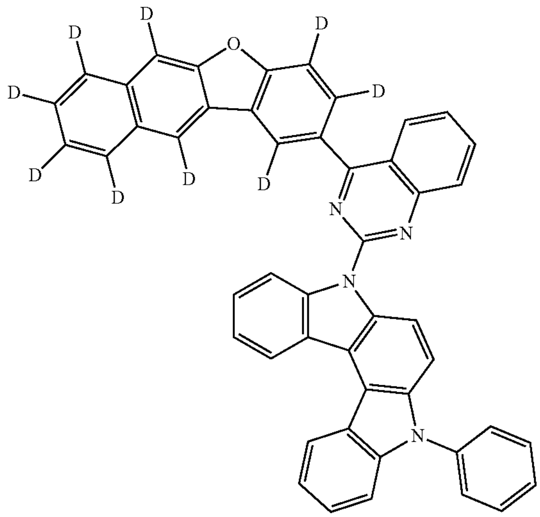

-continued
302
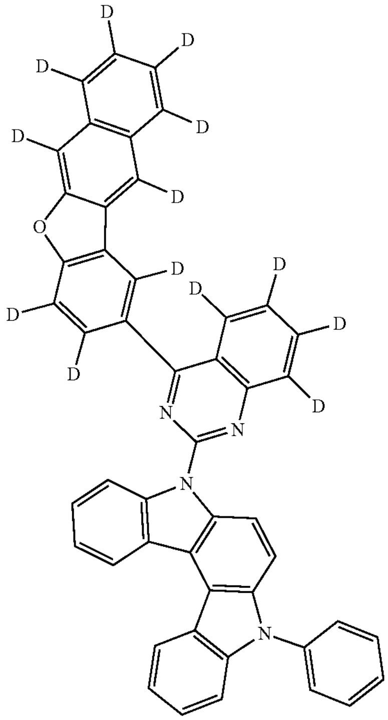
303
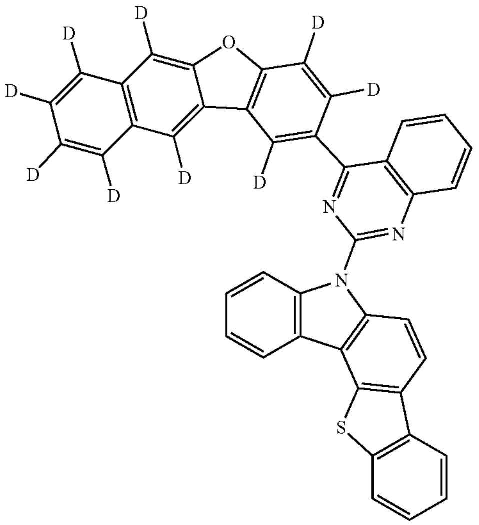
-continued
304
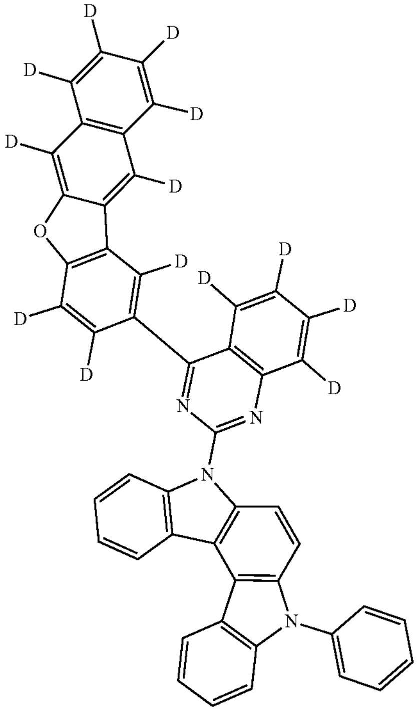
305
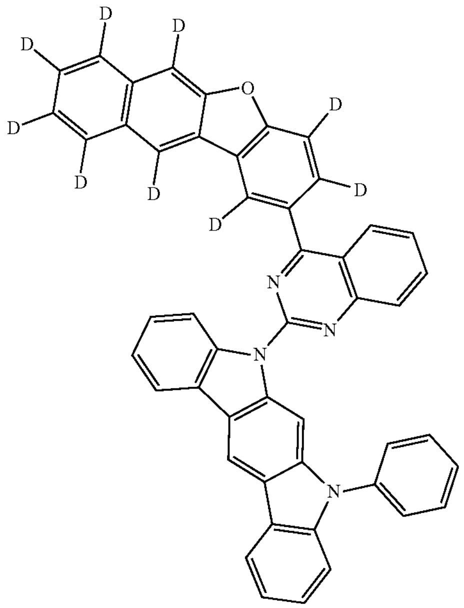

-continued
306
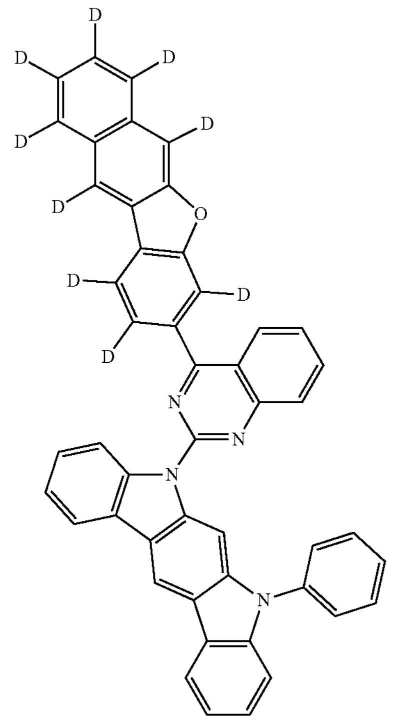
307
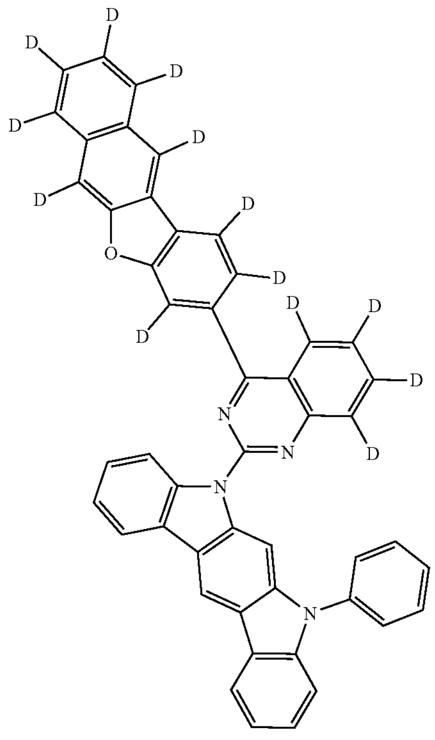
-continued
308
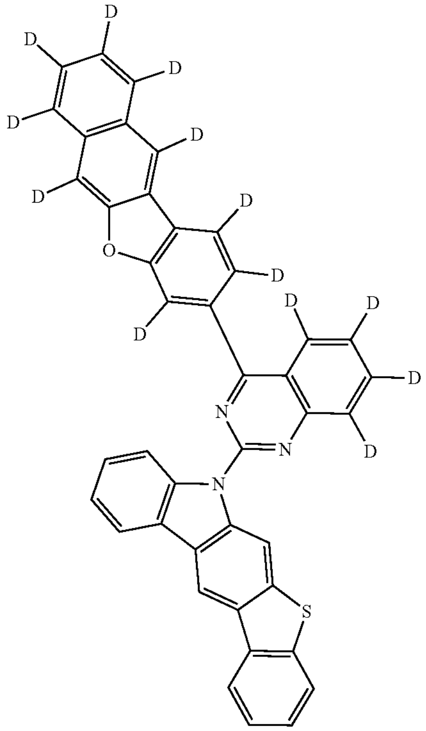
309
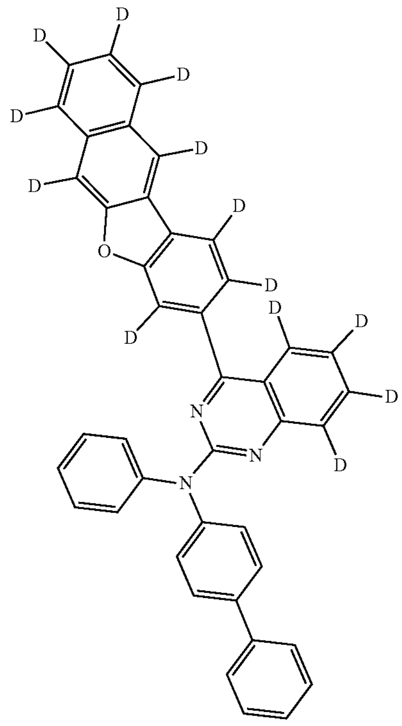

-continued
310
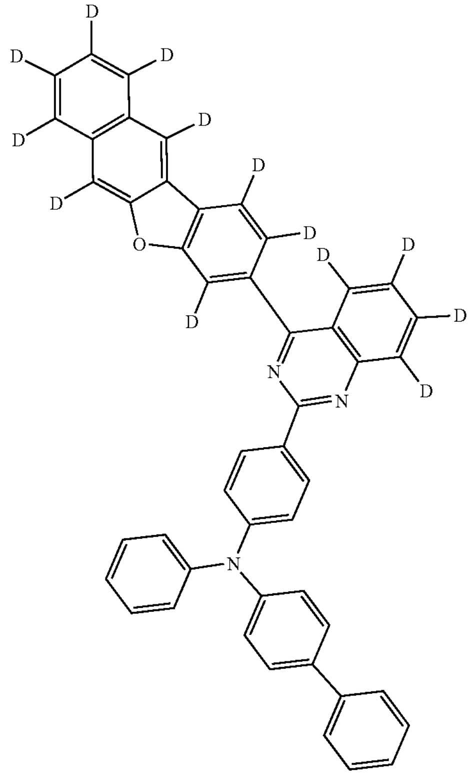
311
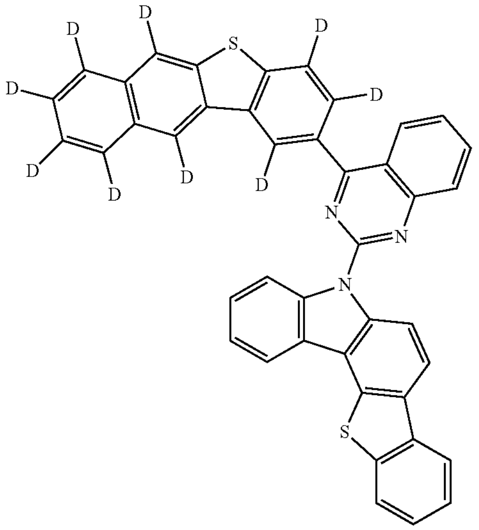
-continued
312
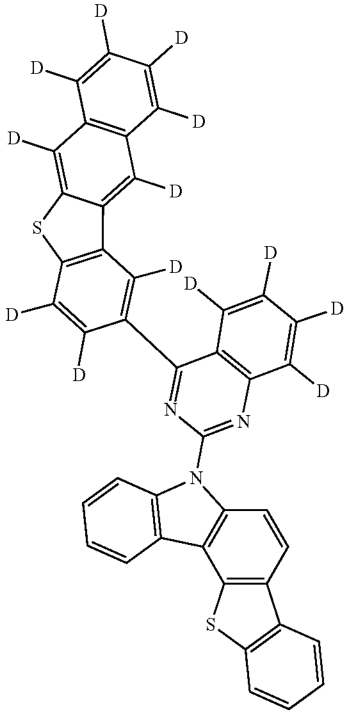
313
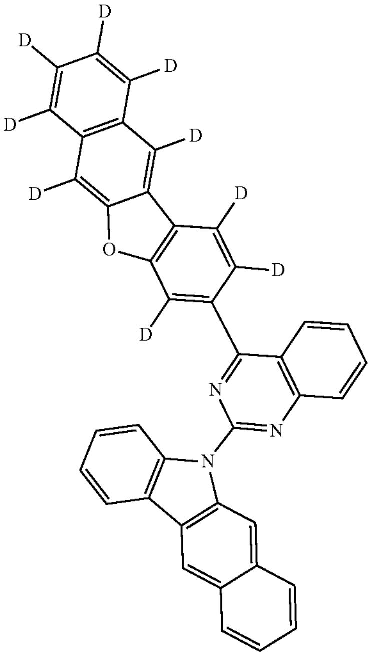

-continued
314
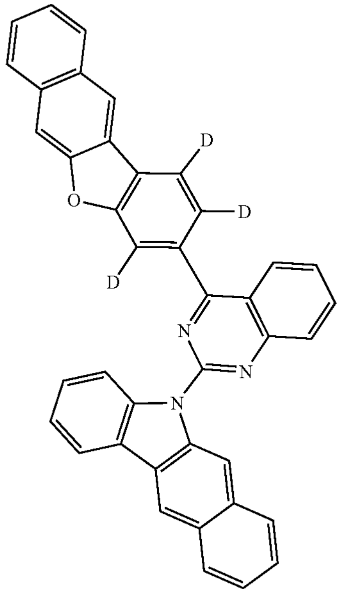
315
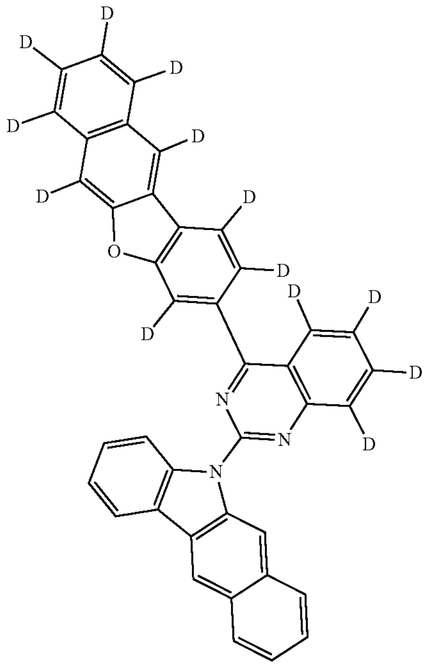
-continued
316
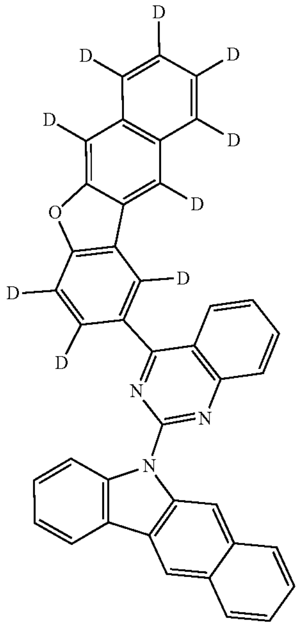
317
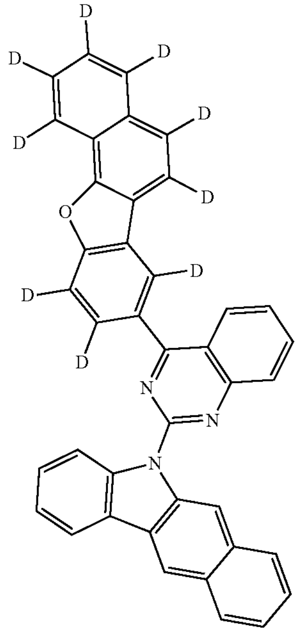
318
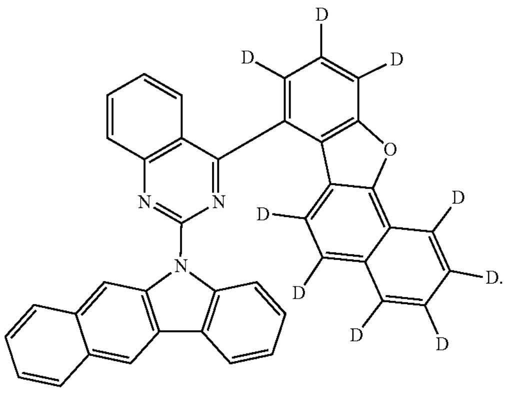
.

3. An organic light emitting device comprising:
- a first electrode;
- a second electrode provided opposite to the first electrode; and
- one or more organic material layers provided between the first electrode and the second electrode,
- wherein the one or more organic material layers comprise the heterocyclic compound of claim 1.

4. The organic light emitting device of claim 3, wherein the one or more organic material layers further comprise a heterocyclic compound represented by the following Chemical Formula 7:

[Chemical Formula 7]

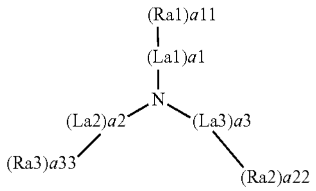

in Chemical Formula 7,
- La1 to La3 are the same as or different from each other, and each independently a direct bond; a substituted or unsubstituted C6 to C60 arylene group; or a substituted or unsubstituted C2 to C60 heteroarylene group;
- Ra1 is a substituted or unsubstituted C6 to C60 aryl group;
- Ra2 and Ra3 are the same as or different from each other, and each independently selected from the group consisting of hydrogen; deuterium; halogen; a cyano group; a substituted or unsubstituted C1 to C60 alkyl group; a substituted or unsubstituted C2 to C60 alkenyl group; a substituted or unsubstituted C2 to C60 alkynyl group; a substituted or unsubstituted $C_1$ to C60 alkoxy group; a substituted or unsubstituted C3 to C60 cycloalkyl group; a substituted or unsubstituted C2 to C60 heterocycloalkyl group; a substituted or unsubstituted C6 to C60 aryl group; a substituted or unsubstituted C2 to C60 heteroaryl group; and —NRR', or two or more groups adjacent to each other bond to each other to form a substituted or unsubstituted C6 to C60 aliphatic or aromatic hydrocarbon ring or a substituted or unsubstituted C2 to C60 aliphatic or aromatic heteroring;
- R and R' are the same as or different from each other, and each independently a substituted or unsubstituted C1 to C60 alkyl group; a substituted or unsubstituted C6 to C60 aryl group; or a substituted or unsubstituted C2 to C60 heteroaryl group;
- a1 to a3 are an integer of 0 to 4;
- a11, a22 and a33 are an integer of 1 to 6; and
- when a1 to a3, a11, a22 and a33 are 2 or greater, substituents in the parentheses are the same as or different from each other.

5. The organic light emitting device of claim 3, wherein the one or more organic material layers comprise a light emitting layer, and the light emitting layer comprises the heterocyclic compound.

6. The organic light emitting device of claim 3, wherein the one or more organic material layers comprise a light emitting layer, the light emitting layer comprises a host material, and the host material comprises the heterocyclic compound.

7. The organic light emitting device of claim 3, further comprising one, two or more layers selected from the group consisting of a light emitting layer, a hole injection layer, a hole transfer layer, an electron injection layer, an electron transfer layer, an electron blocking layer and a hole blocking layer.

8. A composition for an organic material layer of an organic light emitting device, the composition comprising:
- the heterocyclic compound of claim 1; and
- a heterocyclic compound represented by the following Chemical Formula 7:

[Chemical Formula 7]

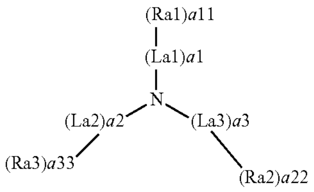

wherein, in Chemical Formula 7,
- La1 to La3 are the same as or different from each other, and each independently a direct bond; a substituted or unsubstituted C6 to C60 arylene group; or a substituted or unsubstituted $C_2$ to C60 heteroarylene group;
- Ra1 is a substituted or unsubstituted C6 to C60 aryl group;
- Ra2 and Ra3 are the same as or different from each other, and each independently selected from the group consisting of hydrogen; deuterium; halogen; a cyano group; a substituted or unsubstituted C1 to C60 alkyl group; a substituted or unsubstituted C2 to C60 alkenyl group; a substituted or unsubstituted C2 to C60 alkynyl group; a substituted or unsubstituted C1 to C60 alkoxy group; a substituted or unsubstituted C3 to C60 cycloalkyl group; a substituted or unsubstituted C2 to C60 heterocycloalkyl group; a substituted or unsubstituted C6 to C60 aryl group; a substituted or unsubstituted C2 to C60 heteroaryl group; and —NRR', or two or more groups adjacent to each other bond to each other to form a substituted or unsubstituted C6 to C60 aliphatic or aromatic hydrocarbon ring or a substituted or unsubstituted C2 to C60 aliphatic or aromatic heteroring;
- R and R' are the same as or different from each other, and each independently a substituted or unsubstituted C1 to C60 alkyl group; a substituted or unsubstituted C6 to C60 aryl group; or a substituted or unsubstituted C2 to C60 heteroaryl group;
- a1 to a3 are an integer of 0 to 4;
- a11, a22 and a33 are an integer of 1 to 6; and
- when a1 to a3, a11, a22 and a33 are 2 or greater, substituents in the parentheses are the same as or different from each other.

9. The composition of claim 8, wherein the heterocyclic compound represented by Chemical Formula 2 or 3 and the heterocyclic compound represented by Chemical Formula 7 have a weight ratio of 1:10 to 10:1 in the composition.

10. A method for manufacturing an organic light emitting device, the method comprising:
- preparing a substrate;
- forming a first electrode on the substrate;
- forming one or more organic material layers on the first electrode; and
- forming a second electrode on the one or more organic material layers,
- wherein the forming of the one or more organic material layers is performed by using the composition of claim 8.

11. The method of claim 10, wherein the forming of the one or more organic material layers is performed by using a thermal vacuum deposition method after pre-mixing the heterocyclic compound of Chemical Formula 2 or 3 and the heterocyclic compound of Chemical Formula 7.

* * * * *